US012760305B2

(12) United States Patent
Maguire et al.

(10) Patent No.: US 12,760,305 B2
(45) Date of Patent: Oct. 13, 2026

(54) OLIGONUCLEOTIDE COMPOSITIONS AND METHODS THEREOF

(71) Applicant: WAVE LIFE SCIENCES, LTD., Singapore (SG)

(72) Inventors: Abbie Madeline Maguire, Bolton, MA (US); Priyanka Shiva Prakasha, Cambridge, MA (US); Naoki Iwamoto, Boston, MA (US); Kenneth Allan Longo, Cambridge, MA (US); Chandra Vargeese, Schwenksville, PA (US); Kevin Kim, Quincy, MA (US); Elena Dale, Concord, MA (US); Pachamuthu Kandasamy, Lexington, MA (US); Mamoru Shimizu, Arlington, MA (US)

(73) Assignee: WAVE LIFE SCIENCES, INC., Cambridge, MA (US)

( * ) Notice: Subject to any disclaimer, the term of this patent is extended or adjusted under 35 U.S.C. 154(b) by 826 days.

(21) Appl. No.: 17/907,895

(22) PCT Filed: Feb. 26, 2021

(86) PCT No.: PCT/US2021/019874

§ 371 (c)(1),
(2) Date: Aug. 29, 2022

(87) PCT Pub. No.: WO2021/178237

PCT Pub. Date: Sep. 10, 2021

(65) Prior Publication Data

US 2023/0295619 A1 Sep. 21, 2023

Related U.S. Application Data

(60) Provisional application No. 63/111,071, filed on Nov. 8, 2020, provisional application No. 62/983,742, filed on Mar. 1, 2020.

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/14* (2013.01); *C12N 2310/314* (2013.01); *C12N 2310/315* (2013.01); *C12N 2310/321* (2013.01); *C12N 2310/322* (2013.01)

(58) Field of Classification Search
None
See application file for complete search history.

(56) References Cited

U.S. PATENT DOCUMENTS

| | | | |
|---|---|---|---|
| 8,470,987 | B2 | 6/2013 | Wada et al. |
| 8,822,671 | B2 | 9/2014 | Shimizu et al. |
| 8,859,755 | B2 | 10/2014 | Wada et al. |
| 9,394,333 | B2 | 7/2016 | Wada et al. |
| 9,598,458 | B2 | 3/2017 | Shimizu et al. |
| 9,605,019 | B2 | 3/2017 | Verdine et al. |
| 9,617,547 | B2 | 4/2017 | Gemba |
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,428,019 | B2 | 10/2019 | Wada et al. |
| 10,450,568 | B2 | 10/2019 | Butler et al. |
| 10,479,995 | B2 | 11/2019 | Vargeese et al. |
| 10,590,413 | B2 | 3/2020 | Butler et al. |
| 10,696,711 | B2 | 6/2020 | Shimizu et al. |
| 10,724,035 | B2 | 7/2020 | Vargeese et al. |
| 10,815,482 | B2 | 10/2020 | Meena et al. |
| 11,013,757 | B2 | 5/2021 | Zhang et al. |
| 11,136,346 | B2 | 10/2021 | Shimizu et al. |

(Continued)

FOREIGN PATENT DOCUMENTS

| | | |
|---|---|---|
| JP | 2003-238586 A | 8/2003 |
| JP | 2011-184318 A | 9/2011 |

(Continued)

OTHER PUBLICATIONS

Dyudeeva et al. (Russian Journal of Bioorganic Chemistry, vol. 45, pp. 709-718 (Year: 2019).*

Kang et al. Nucleic Acids Research 53, W39-W44, pp. 1-6 (Year: 2025).*

Devos, S. L. et al., Tau Reduction Prevents Neuronal Loss and Reverses Pathological Tau Deposition and Seeding in Mice with Tauopathy, Sci. Transl. Med., 9(374):1-30 (2017).

(Continued)

*Primary Examiner* — Brian Whiteman
(74) *Attorney, Agent, or Firm* — Choate, Hall & Stewart LLP; Xiaodong Li

(57) ABSTRACT

Among other things, the present disclosure provides oligonucleotides, compositions, and methods for preventing and/or treating various conditions, disorders or diseases. In some embodiments, provided technologies comprise nucleobase modifications, sugar modifications, internucleotidic linkage modifications and/or patterns thereof, and have improved properties, activities and/or selectivities. In some embodiments, provided technologies target MAPT. In some embodiments, the present disclosure provides MAPT oligonucleotides, compositions and methods for preventing and/or treating MAPT-associated conditions, disorders or diseases, such as Alzheimer's Disease (AD) or Frontotemporal Dementia (FTD).

20 Claims, No Drawings

Specification includes a Sequence Listing.

(56) References Cited

U.S. PATENT DOCUMENTS

| | | | |
|---|---|---|---|
| 11,279,929 | B2 * | 3/2022 | Hagedorn ............ C12N 15/113 |
| 11,407,775 | B2 | 8/2022 | Butler et al. |
| 11,596,646 | B2 | 3/2023 | Zhang et al. |
| 11,597,927 | B2 | 3/2023 | Vargeese et al. |
| 11,603,532 | B2 | 3/2023 | Vargeese et al. |
| 11,608,355 | B2 | 3/2023 | Bowman et al. |
| 11,634,710 | B2 | 4/2023 | Frank-Kamenetsky et al. |
| 11,643,657 | B2 | 5/2023 | Butler et al. |
| 11,718,638 | B2 | 8/2023 | Butler et al. |
| 11,739,325 | B2 | 8/2023 | Vargeese et al. |
| 11,873,316 | B2 | 1/2024 | Butler et al. |
| 12,391,942 | B2 | 8/2025 | Zhang et al. |
| 12,428,442 | B2 | 9/2025 | Butler et al. |
| 12,435,105 | B2 | 10/2025 | Bowman et al. |
| 12,473,321 | B2 | 11/2025 | Butler et al. |
| 12,486,505 | B2 | 12/2025 | Frank-Kamenetsky et al. |
| 12,552,743 | B2 | 2/2026 | Zhang et al. |
| 2011/0178284 | A1 | 7/2011 | Wada et al. |
| 2011/0294124 | A1 | 12/2011 | Wada et al. |
| 2012/0316224 | A1 | 12/2012 | Verdine et al. |
| 2013/0184450 | A1 | 7/2013 | Wada et al. |
| 2013/0253178 | A1 | 9/2013 | Shimizu et al. |
| 2014/0194610 | A1 | 7/2014 | Verdine et al. |
| 2015/0166999 | A1 | 6/2015 | Gemba |
| 2015/0197540 | A1 | 7/2015 | Shimizu et al. |
| 2016/0347780 | A1 | 12/2016 | Wada et al. |
| 2016/0347784 | A1 | 12/2016 | Verdine et al. |
| 2017/0029445 | A1 | 2/2017 | Shimizu et al. |
| 2017/0037399 | A1 | 2/2017 | Meena et al. |
| 2017/0275621 | A1 | 9/2017 | Butler et al. |
| 2018/0111958 | A1 | 4/2018 | Wada et al. |
| 2018/0119145 | A1 | 5/2018 | Kordasiewicz |
| 2018/0216108 | A1 | 8/2018 | Vargeese et al. |
| 2018/0222936 | A1 | 8/2018 | Verdine et al. |
| 2019/0008986 | A1 | 1/2019 | Butler et al. |
| 2019/0127733 | A1 | 5/2019 | Butler et al. |
| 2019/0209604 | A1 | 7/2019 | Zhang et al. |
| 2019/0249173 | A1 | 8/2019 | Vargeese et al. |
| 2019/0264267 | A1 | 8/2019 | Yang et al. |
| 2019/0375774 | A1 | 12/2019 | Butler et al. |
| 2020/0157545 | A1 | 5/2020 | Vargeese et al. |
| 2020/0190515 | A1 | 6/2020 | Vargeese et al. |
| 2020/0231620 | A1 | 7/2020 | Bowman et al. |
| 2020/0299692 | A1 | 9/2020 | Frank-Kamenetsky et al. |
| 2020/0362337 | A1 | 11/2020 | Dodart et al. |
| 2020/0385420 | A1 | 12/2020 | Shimizu et al. |
| 2021/0032620 | A1 | 2/2021 | Vargeese et al. |
| 2021/0115444 | A1 | 4/2021 | Meena et al. |
| 2021/0130821 | A1 | 5/2021 | Butler et al. |
| 2021/0198305 | A1 | 7/2021 | Vargeese et al. |
| 2021/0228615 | A1 | 7/2021 | Zhang et al. |
| 2021/0254062 | A1 | 8/2021 | Zhang et al. |
| 2022/0098585 | A1 | 3/2022 | Brown et al. |
| 2022/0127301 | A1 | 4/2022 | Shimizu et al. |
| 2022/0145300 | A1 | 5/2022 | Liu et al. |
| 2022/0162598 | A1 | 5/2022 | Vargeese et al. |
| 2022/0186217 | A1 | 6/2022 | Zhang et al. |
| 2022/0195429 | A1 | 6/2022 | Vargeese et al. |
| 2022/0306573 | A1 | 9/2022 | Zhang et al. |
| 2022/0307019 | A1 | 9/2022 | Yokota et al. |
| 2022/0356204 | A1 | 11/2022 | Butler et al. |
| 2022/0401467 | A1 | 12/2022 | Zhang et al. |
| 2023/0089442 | A1 | 3/2023 | Kandasamy et al. |
| 2023/0136645 | A1 | 5/2023 | Butler et al. |
| 2023/0145795 | A1 | 5/2023 | Byrne et al. |
| 2023/0203087 | A1 | 6/2023 | Kandasamy et al. |
| 2023/0220384 | A1 | 7/2023 | Monian et al. |
| 2023/0295617 | A1 | 9/2023 | Vargeese et al. |
| 2023/0329201 | A1 | 10/2023 | Yang et al. |
| 2023/0348524 | A1 | 11/2023 | Bowman et al. |
| 2023/0392137 | A1 | 12/2023 | Monian et al. |
| 2024/0026358 | A1 | 1/2024 | Monian et al. |
| 2024/0109931 | A1 | 4/2024 | Vargeese et al. |
| 2024/0117347 | A1 | 4/2024 | Butler et al. |
| 2024/0132894 | A1 | 4/2024 | Vargeese et al. |
| 2024/0150756 | A1 | 5/2024 | Frank-Kamenetsky et al. |
| 2024/0174710 | A1 | 5/2024 | Butler et al. |
| 2024/0175016 | A1 | 5/2024 | Liu et al. |
| 2024/0175018 | A1 | 5/2024 | Vargeese et al. |
| 2024/0229026 | A1 | 7/2024 | Butler et al. |
| 2024/0368207 | A1 | 11/2024 | Butler et al. |
| 2025/0051778 | A1 | 2/2025 | Byrne et al. |
| 2025/0066775 | A1 | 2/2025 | Vargeese et al. |
| 2025/0135036 | A1 | 5/2025 | Acker et al. |
| 2025/0154190 | A1 | 5/2025 | Kandasamy et al. |
| 2025/0197857 | A1 | 6/2025 | Hu et al. |
| 2025/0262235 | A1 | 8/2025 | Lu et al. |
| 2025/0270628 | A1 | 8/2025 | Yang et al. |
| 2025/0302995 | A1 | 10/2025 | Shivalila et al. |
| 2025/0313836 | A1 | 10/2025 | Meena et al. |
| 2025/0333740 | A1 | 10/2025 | Monian et al. |
| 2026/0008806 | A1 | 1/2026 | Bowman et al. |
| 2026/0055133 | A1 | 2/2026 | Butler et al. |
| 2026/0055402 | A1 | 2/2026 | Lake et al. |
| 2026/0062435 | A1 | 3/2026 | Vargeese et al. |
| 2026/0076989 | A1 | 3/2026 | Zhang et al. |

FOREIGN PATENT DOCUMENTS

| | | | |
|---|---|---|---|
| WO | WO-2005/014609 | A2 | 2/2005 |
| WO | WO-2005/023828 | A1 | 3/2005 |
| WO | WO-2005/028494 | A1 | 3/2005 |
| WO | WO-2005/070859 | A1 | 8/2005 |
| WO | WO-2005/085272 | A1 | 9/2005 |
| WO | WO-2005/092909 | A1 | 10/2005 |
| WO | WO-2010/064146 | A2 | 6/2010 |
| WO | WO-2011/005761 | A1 | 1/2011 |
| WO | WO-2011/034072 | A1 | 3/2011 |
| WO | WO-2011/108682 | A1 | 9/2011 |
| WO | WO-2012/039448 | A1 | 3/2012 |
| WO | WO-2012/073857 | A1 | 6/2012 |
| WO | WO-2013/012758 | A1 | 1/2013 |
| WO | WO-2013/148260 | A1 | 10/2013 |
| WO | WO-2014/010250 | A1 | 1/2014 |
| WO | WO-2014/010718 | A1 | 1/2014 |
| WO | WO-2014/012081 | A2 | 1/2014 |
| WO | WO-2015/010135 | A2 | 1/2015 |
| WO | WO-2015/107425 | A2 | 7/2015 |
| WO | WO-2015/108046 | A1 | 7/2015 |
| WO | WO-2015/108047 | A1 | 7/2015 |
| WO | WO-2015/108048 | A1 | 7/2015 |
| WO | WO-2016/019063 | A1 | 2/2016 |
| WO | WO-2016/028187 | A1 | 2/2016 |
| WO | WO-2016/126995 | A1 | 8/2016 |
| WO | WO-2017/015555 | A1 | 1/2017 |
| WO | WO-2017/015575 | A1 | 1/2017 |
| WO | WO-2017/062862 | A2 | 4/2017 |
| WO | WO-2017/160741 | A1 | 9/2017 |
| WO | WO-2017/192664 | A1 | 11/2017 |
| WO | WO-2017/192679 | A1 | 11/2017 |
| WO | WO-2017/210647 | A1 | 12/2017 |
| WO | WO-2018/022473 | A1 | 2/2018 |
| WO | WO-2018/064593 | A1 | 4/2018 |
| WO | WO-2018/067973 | A1 | 4/2018 |
| WO | WO-2018/098264 | A1 | 5/2018 |
| WO | WO-2018/223056 | A1 | 12/2018 |
| WO | WO-2018/223073 | A1 | 12/2018 |
| WO | WO-2018/223081 | A1 | 12/2018 |
| WO | WO-2018/237194 | A1 | 12/2018 |
| WO | WO-2019/032607 | A1 | 2/2019 |
| WO | WO-2019/032612 | A1 | 2/2019 |
| WO | WO-2019/055951 | A1 | 3/2019 |
| WO | WO-2019/075357 | A1 | 4/2019 |
| WO | WO-2019/200185 | A1 | 10/2019 |
| WO | WO-2019/217784 | A1 | 11/2019 |
| WO | WO-2020/007892 | A1 | 1/2020 |
| WO | WO-2020/118246 | A1 | 6/2020 |
| WO | WO-2020/160336 | A1 | 8/2020 |
| WO | WO-2020/191252 | A1 | 9/2020 |
| WO | WO-2020/196662 | A1 | 10/2020 |
| WO | WO-2020/219981 | A2 | 10/2020 |
| WO | WO-2020/219983 | A2 | 10/2020 |
| WO | WO-2020/227691 | A2 | 11/2020 |
| WO | WO-2021/071788 | A2 | 4/2021 |

(56) References Cited

FOREIGN PATENT DOCUMENTS

| | | | |
|---|---|---|---|
| WO | WO-2021/071858 | A1 | 4/2021 |
| WO | WO-2021/178237 | A2 | 9/2021 |
| WO | WO-2021/234459 | A2 | 11/2021 |
| WO | WO-2021/237223 | A1 | 11/2021 |
| WO | WO-2022/046667 | A1 | 3/2022 |
| WO | WO-2022/046723 | A1 | 3/2022 |
| WO | WO-2022/099159 | A1 | 5/2022 |
| WO | WO-2023/004390 | A1 | 1/2023 |
| WO | WO-2023/049475 | A1 | 3/2023 |
| WO | WO-2023/049477 | A2 | 3/2023 |
| WO | WO-2023/064707 | A1 | 4/2023 |
| WO | WO-2023/075766 | A1 | 5/2023 |
| WO | WO-2023/076352 | A2 | 5/2023 |
| WO | WO-2023/154528 | A1 | 8/2023 |
| WO | WO-2023/168014 | A2 | 9/2023 |
| WO | WO-2023/201095 | A2 | 10/2023 |
| WO | WO-2023/220440 | A1 | 11/2023 |
| WO | WO-2024/035946 | A1 | 2/2024 |
| WO | WO-2025/030155 | A1 | 2/2025 |
| WO | WO-2025/072685 | A1 | 4/2025 |
| WO | WO-2025/072862 | A1 | 4/2025 |
| WO | WO-2025/072879 | A1 | 4/2025 |
| WO | WO-2025/072881 | A2 | 4/2025 |
| WO | WO-2025/072883 | A2 | 4/2025 |
| WO | WO-2025/072886 | A1 | 4/2025 |
| WO | WO-2025/151895 | A1 | 7/2025 |
| WO | WO-2025/160090 | A1 | 7/2025 |
| WO | WO-2025/212958 | A1 | 10/2025 |
| WO | WO-2025/213136 | A1 | 10/2025 |
| WO | WO-2025/213142 | A2 | 10/2025 |
| WO | WO-2026/006477 | A1 | 1/2026 |
| WO | WO-2026/055273 | A1 | 3/2026 |

OTHER PUBLICATIONS

Mummery, C. J. et al., Tau-targeting antisense oligonucleotide $MAPT_{RX}$ in mild Alzheimer's disease: a phase 1b, randomized, placebo-controlled trial, Nat. Med., 20 pages (2023).
Crooke, S. T. et al., Antisense technology: A review, J. Biol. Chem., 296 (100416):1-39 (2021).
GenBank Accession No. NG_007398, *Homo sapiens* microtubule associated protein tau (MAPT), RefSeqGene on chromosome 17, PRI: Dec. 27, 2019.
International Search Report for PCT/US2021/019874, 5 pages (mailed Sep. 8, 2021).
Invitation to Pay Additional Fees for PCT/US2021/019874, 3 pages (mailed Jun. 15, 2021).
Kupryushkin, M. S. Phosphoryl Guanidines: A New Type of Nucleic Acid Analogues, Acta Naturae, 6(4): 116-118 (2014).
Pavlova, A. S. et al., SDS-PAGE procedure: Application for characterization of new entirely uncharged nucleic acids analogs, Electrophor., 39:670-674 (2018).
Written Opinion for PCT/US2021/019874, 8 pages (mailed Sep. 8, 2021).
Devos, S. L. et al., Antisense Reduction of Tau in Adult Mice Protects against Seizures, Jrnl. Neurosci., 33(31):12887-12897 (2013).
Kandasamy, P. et al., Impact of guanidine-containing backbone linkages on stereopure antisense oligonucleotides in the CNS, Nucl. Acids Res., 50(10):5401-5423 (2022).
Zhang, C-C et al., The Role of MAPT in Neurodegenerative Diseases: Genetics, Mechanisms and Therapy, Mole. Neurobio., 53(7):4893-4904 (2016).
U.S. Appl. No. 18/185,901, filed Mar. 17, 2023, Bowman et al.
U.S. Appl. No. 18/204,895, filed Jun. 1, 2023, Vargeese et al.
U.S. Appl. No. 18/316,932, filed May 12, 2023, Butler et al.
U.S. Appl. No. 18/704,629, filed Apr. 25, 2024, Byrne et al.
U.S. Appl. No. 18/864,863, filed Nov. 11, 2024, Liu et al.
U.S. Appl. No. 19/217,825, filed May 23, 2025, Vargeese et al.
U.S. Appl. No. 19/241,178, filed Jun. 17, 2025, Zhang et al.
U.S. Appl. No. 19/276,854, filed Jul. 22, 2025, Zhang et al.
U.S. Appl. No. 19/281,441, filed Jul. 25, 2025, Butler et al.
U.S. Appl. No. 19/281,453, filed Jul. 25, 2025, Liu et al.
U.S. Appl. No. 19/284,561, filed Jul. 29, 2025, Butler et al.
U.S. Appl. No. 19/297,725, filed Aug. 12, 2025, Stetsenko et al.
U.S. Appl. No. 19/367,099, filed Oct. 23, 2025, Frank-Kamenetsky et al.
U.S. Appl. No. 19/434,730, filed Dec. 29, 2025, Zhang et al.
U.S. Appl. No. 19/458,525, filed Jan. 23, 2026, Shimizu et al.
U.S. Appl. No. 19/462,715, filed Jan. 28, 2026, Kandasamy et al.
U.S. Appl. No. 19/517,442, filed Mar. 6, 2026, Liu et al.
U.S. Appl. No. 19/562,646, filed Mar. 10, 2026, Liu et al.

* cited by examiner

SEQUENCE LISTING

```
<160> NUMBER OF SEQ ID NOS: 280

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 1

acgttgcagt gttccacuau                                                  20


<210> SEQ ID NO 2
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 2

actatcctcc ttcagcuccu                                                  20


<210> SEQ ID NO 3
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 3

agtgttccac tatccuccuu                                                  20


<210> SEQ ID NO 4
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 4

atcctccttc agctccugca                                                  20


<210> SEQ ID NO 5
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 5
```

```
cacgttgcag tgttccacua                                                20


<210> SEQ ID NO 6
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 6

cactatcctc cttcagcucc                                                20


<210> SEQ ID NO 7
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 7

cagtgttcca ctatccuccu                                                20


<210> SEQ ID NO 8
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 8

ccacgttgca gtgttccacu                                                20


<210> SEQ ID NO 9
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 9

ccactatcct ccttcagcuc                                                20


<210> SEQ ID NO 10
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa
```

```
<400> SEQUENCE: 10

cgttgcagtg ttccacuauc                                                20


<210> SEQ ID NO 11
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 11

ctatcctcct tcagcuccug                                                20


<210> SEQ ID NO 12
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 12

gcagtgttcc actatccucc                                                20


<210> SEQ ID NO 13
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 13

gtgttccact atcctccuuc                                                20


<210> SEQ ID NO 14
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa

<400> SEQUENCE: 14

gttccactat cctccuucag                                                20


<210> SEQ ID NO 15
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U
      and vice versa
```

<400> SEQUENCE: 15
guguuccact atcctccttc 20

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U and vice versa

<400> SEQUENCE: 16
tatcctcctt cagctccugc 20

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U and vice versa

<400> SEQUENCE: 17
tccactatcc tccttcagcu 20

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U and vice versa

<400> SEQUENCE: 18
tgcagtgttc cactauccuc 20

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U and vice versa

<400> SEQUENCE: 19
tgttccacta tcctccuuca 20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U and vice versa

<400> SEQUENCE: 20
ttccactatc ctcctucagc 20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA/RNA oligonucleotide
<220> FEATURE:
<221> NAME/KEY: misc_feature
<223> OTHER INFORMATION: each T can be independently substituted with U and vice versa

<400> SEQUENCE: 21
ttgcagtgtt ccactauccu 20

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA/RNA oligonucleotide

<400> SEQUENCE: 22
gcauagcgag cgagggaaaa c 21

<210> SEQ ID NO 23
<211> LENGTH: 21
<212> TYPE: DNA
<213> ORGANISM: Artificial Sequence
<220> FEATURE:
<223> OTHER INFORMATION: Synthetic DNA/RNA oligonucleotide

<400> SEQUENCE: 23
guuuucccuc gcucgcuaug c 21

<210> SEQ ID NO 24
<211> LENGTH: 18
<212> TYPE: DNA
<213> ORGANISM: Artificial Sequence
<220> FEATURE:
<223> OTHER INFORMATION: Synthetic DNA/RNA oligonucleotide

<400> SEQUENCE: 24
ccgttttctt accaccct 18

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 25
gtgttccact atcctccuuc 20

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 26
gtgttccact atcctccuuc 20

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 27
gtgttccact atcctccuuc 20

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 28
gtgttccact atcctccuuc 20

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 29
gtgttccact atcctccuuc 20

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 30
gtgttccact atcctccuuc 20

<210> SEQ ID NO 31
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 31
gtgttccact atcctccuuc 20

<210> SEQ ID NO 32
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 32
gtgttccact atcctccuuc 20

<210> SEQ ID NO 33
<211> LENGTH: 20
<212> TYPE: DNA

<213> ORGANISM: Artificial Sequence
<220> FEATURE:
<223> OTHER INFORMATION: Synthetic DNA/RNA oligonucleotide

<400> SEQUENCE: 33
gtgttccact atcctccuuc 20

<210> SEQ ID NO 34
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 34
gtgttccact atcctccuuc 20

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 35
gtgttccact atcctccuuc 20

<210> SEQ ID NO 36
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 36
gtgttccact atcctccuuc 20

<210> SEQ ID NO 37
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 37
gtgttccact atcctccuuc 20

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 38
gtgttccact atcctccuuc 20

<210> SEQ ID NO 39
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 39
gtgttccact atcctccuuc 20

<210> SEQ ID NO 40
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 40
gtgttccact atcctccuuc 20

<210> SEQ ID NO 41
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 41
gtgttccact atcctccuuc 20

<210> SEQ ID NO 42
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 42
gtgttccact atcctccuuc 20

<210> SEQ ID NO 43
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 43
gtgttccact atcctccuuc 20

<210> SEQ ID NO 44
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 44
atcctccttc agctccugca 20

<210> SEQ ID NO 45
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 45
atcctccttc agctccugca 20

<210> SEQ ID NO 46
<211> LENGTH: 20
<212> TYPE: DNA
<213> ORGANISM: Artificial Sequence
<220> FEATURE:

<223> OTHER INFORMATION: Synthetic DNA/RNA oligonucleotide

<400> SEQUENCE: 46
atcctccttc agctccugca 20

<210> SEQ ID NO 47
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 47
atcctccttc agctccugca 20

<210> SEQ ID NO 48
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 48
tatcctcctt cagctccugc 20

<210> SEQ ID NO 49
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 49
tatcctcctt cagctccugc 20

<210> SEQ ID NO 50
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 50
tatcctcctt cagctccugc 20

<210> SEQ ID NO 51
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 51
tatcctcctt cagctccugc 20

<210> SEQ ID NO 52
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 52
ctatcctcct tcagcuccug 20

<210> SEQ ID NO 53
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 53
ctatcctcct tcagcuccug 20

<210> SEQ ID NO 54
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 54
ctatcctcct tcagcuccug 20

<210> SEQ ID NO 55
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 55
ctatcctcct tcagcuccug 20

<210> SEQ ID NO 56
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 56
actatcctcc ttcagcuccu 20

<210> SEQ ID NO 57
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 57
actatcctcc ttcagcuccu 20

<210> SEQ ID NO 58
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 58
actatcctcc ttcagcuccu 20

<210> SEQ ID NO 59
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 59
actatcctcc ttcagcuccu 20

<210> SEQ ID NO 60
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 60
cactatcctc cttcagcucc 20

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 61
cactatcctc cttcagcucc 20

<210> SEQ ID NO 62
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 62
cactatcctc cttcagcucc 20

<210> SEQ ID NO 63
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 63
cactatcctc cttcagcucc 20

<210> SEQ ID NO 64
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 64
ccactatcct ccttcagcuc 20

<210> SEQ ID NO 65
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 65
ccactatcct ccttcagcuc 20

<210> SEQ ID NO 66
<211> LENGTH: 20

<212> TYPE: DNA
<213> ORGANISM: Artificial Sequence
<220> FEATURE:
<223> OTHER INFORMATION: Synthetic DNA/RNA oligonucleotide

<400> SEQUENCE: 66
ccactatcct ccttcagcuc 20

<210> SEQ ID NO 67
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 67
ccactatcct ccttcagcuc 20

<210> SEQ ID NO 68
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 68
tccactatcc tccttcagcu 20

<210> SEQ ID NO 69
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 69
tccactatcc tccttcagcu 20

<210> SEQ ID NO 70
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 70
tccactatcc tccttcagcu 20

<210> SEQ ID NO 71
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 71
tccactatcc tccttcagcu 20

<210> SEQ ID NO 72
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 72

-continued

```
ttccactatc ctcctucagc                                              20


<210> SEQ ID NO 73
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 73

ttccactatc ctcctucagc                                              20


<210> SEQ ID NO 74
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 74

ttccactatc ctcctucagc                                              20


<210> SEQ ID NO 75
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 75

ttccactatc ctcctucagc                                              20


<210> SEQ ID NO 76
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 76

gttccactat cctccuucag                                              20


<210> SEQ ID NO 77
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 77

gttccactat cctccuucag                                              20


<210> SEQ ID NO 78
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 78

gttccactat cctccuucag                                              20


<210> SEQ ID NO 79
<211> LENGTH: 20
<212> TYPE: DNA
<213> ORGANISM: Artificial Sequence
```

<220> FEATURE:
<223> OTHER INFORMATION: Synthetic DNA/RNA oligonucleotide

<400> SEQUENCE: 79
gttccactat cctccuucag 20

<210> SEQ ID NO 80
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 80
tgttccacta tcctccuuca 20

<210> SEQ ID NO 81
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 81
tgttccacta tcctccuuca 20

<210> SEQ ID NO 82
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 82
tgttccacta tcctccuuca 20

<210> SEQ ID NO 83
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 83
tgttccacta tcctccuuca 20

<210> SEQ ID NO 84
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 84
gtgttccact atcctccuuc 20

<210> SEQ ID NO 85
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 85
gtgttccact atcctccuuc 20

<210> SEQ ID NO 86
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 86
gtgttccact atcctccuuc 20

<210> SEQ ID NO 87
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 87
agtgttccac tatccuccuu 20

<210> SEQ ID NO 88
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 88
agtgttccac tatccuccuu 20

<210> SEQ ID NO 89
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 89
agtgttccac tatccuccuu 20

<210> SEQ ID NO 90
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 90
agtgttccac tatccuccuu 20

<210> SEQ ID NO 91
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 91
cagtgttcca ctatccuccu 20

<210> SEQ ID NO 92
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 92
cagtgttcca ctatccuccu 20

<210> SEQ ID NO 93
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 93
cagtgttcca ctatccuccu 20

<210> SEQ ID NO 94
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 94
cagtgttcca ctatccuccu 20

<210> SEQ ID NO 95
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 95
gcagtgttcc actatccucc 20

<210> SEQ ID NO 96
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 96
gcagtgttcc actatccucc 20

<210> SEQ ID NO 97
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 97
gcagtgttcc actatccucc 20

<210> SEQ ID NO 98
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 98
gcagtgttcc actatccucc 20

<210> SEQ ID NO 99

<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 99
tgcagtgttc cactauccuc 20

<210> SEQ ID NO 100
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 100
tgcagtgttc cactauccuc 20

<210> SEQ ID NO 101
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 101
tgcagtgttc cactauccuc 20

<210> SEQ ID NO 102
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 102
tgcagtgttc cactauccuc 20

<210> SEQ ID NO 103
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 103
ttgcagtgtt ccactauccu 20

<210> SEQ ID NO 104
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 104
ttgcagtgtt ccactauccu 20

<210> SEQ ID NO 105
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 105
ttgcagtgtt ccactauccu 20

<210> SEQ ID NO 106
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 106
ttgcagtgtt ccactauccu 20

<210> SEQ ID NO 107
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 107
gttgcagtgt tccacuaucc 20

<210> SEQ ID NO 108
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 108
gttgcagtgt tccacuaucc 20

<210> SEQ ID NO 109
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 109
gttgcagtgt tccacuaucc 20

<210> SEQ ID NO 110
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 110
gttgcagtgt tccacuaucc 20

<210> SEQ ID NO 111
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 111
cgttgcagtg ttccacuauc 20

<210> SEQ ID NO 112
<211> LENGTH: 20
<212> TYPE: DNA

<213> ORGANISM: Artificial Sequence
<220> FEATURE:
<223> OTHER INFORMATION: Synthetic DNA/RNA oligonucleotide

<400> SEQUENCE: 112
cgttgcagtg ttccacuauc 20

<210> SEQ ID NO 113
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 113
cgttgcagtg ttccacuauc 20

<210> SEQ ID NO 114
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 114
cgttgcagtg ttccacuauc 20

<210> SEQ ID NO 115
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 115
acgttgcagt gttccacuau 20

<210> SEQ ID NO 116
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 116
acgttgcagt gttccacuau 20

<210> SEQ ID NO 117
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 117
acgttgcagt gttccacuau 20

<210> SEQ ID NO 118
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 118
acgttgcagt gttccacuau 20

-continued

<210> SEQ ID NO 119
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 119
cacgttgcag tgttccacua 20

<210> SEQ ID NO 120
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 120
cacgttgcag tgttccacua 20

<210> SEQ ID NO 121
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 121
cacgttgcag tgttccacua 20

<210> SEQ ID NO 122
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 122
ccacgttgca gtgttccacu 20

<210> SEQ ID NO 123
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 123
ccacgttgca gtgttccacu 20

<210> SEQ ID NO 124
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 124
ccacgttgca gtgttccacu 20

<210> SEQ ID NO 125
<211> LENGTH: 20
<212> TYPE: DNA
<213> ORGANISM: Artificial Sequence
<220> FEATURE:

<223> OTHER INFORMATION: Synthetic DNA/RNA oligonucleotide

<400> SEQUENCE: 125
ccacgttgca gtgttccacu 20

<210> SEQ ID NO 126
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 126
gtgttccact atcctccuuc 20

<210> SEQ ID NO 127
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 127
gtgttccact atcctccuuc 20

<210> SEQ ID NO 128
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 128
gtgttccact atcctccuuc 20

<210> SEQ ID NO 129
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 129
gtgttccact atcctccuuc 20

<210> SEQ ID NO 130
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 130
gtgttccact atcctccuuc 20

<210> SEQ ID NO 131
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 131
gtgttccact atcctccuuc 20

<210> SEQ ID NO 132
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 132
gtgttccact atcctccuuc 20

<210> SEQ ID NO 133
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 133
gtgttccact atcctccuuc 20

<210> SEQ ID NO 134
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 134
gtgttccact atcctccuuc 20

<210> SEQ ID NO 135
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 135
gtgttccact atcctccuuc 20

<210> SEQ ID NO 136
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 136
gtgttccact atcctccuuc 20

<210> SEQ ID NO 137
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 137
gtgttccact atcctccuuc 20

<210> SEQ ID NO 138
<211> LENGTH: 20
<212> TYPE: DNA
<213> ORGANISM: Artificial Sequence
<220> FEATURE:
<223> OTHER INFORMATION: Synthetic DNA/RNA oligonucleotide -continued

<400> SEQUENCE: 138
gtgttccact atcctccuuc 20

<210> SEQ ID NO 139
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 139
gtgttccact atcctccuuc 20

<210> SEQ ID NO 140
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 140
gtgttccact atcctccuuc 20

<210> SEQ ID NO 141
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 141
gtgttccact atcctccuuc 20

<210> SEQ ID NO 142
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 142
gtgttccact atcctccuuc 20

<210> SEQ ID NO 143
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 143
gtgttccact atcctccuuc 20

<210> SEQ ID NO 144
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 144
gtgttccact atcctccuuc 20

<210> SEQ ID NO 145
<211> LENGTH: 20

<212> TYPE: DNA
<213> ORGANISM: Artificial Sequence
<220> FEATURE:
<223> OTHER INFORMATION: Synthetic DNA/RNA oligonucleotide

<400> SEQUENCE: 145
gtgttccact atcctccuuc 20

<210> SEQ ID NO 146
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 146
atcctccttc agctccugca 20

<210> SEQ ID NO 147
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 147
atcctccttc agctccugca 20

<210> SEQ ID NO 148
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 148
atcctccttc agctccugca 20

<210> SEQ ID NO 149
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 149
atcctccttc agctccugca 20

<210> SEQ ID NO 150
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 150
tatcctcctt cagctccugc 20

<210> SEQ ID NO 151
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 151
tatcctcctt cagctccugc 20

<210> SEQ ID NO 152
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 152
tatcctcctt cagctccugc 20

<210> SEQ ID NO 153
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 153
tatcctcctt cagctccugc 20

<210> SEQ ID NO 154
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 154
ctatcctcct tcagcuccug 20

<210> SEQ ID NO 155
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 155
ctatcctcct tcagcuccug 20

<210> SEQ ID NO 156
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 156
ctatcctcct tcagcuccug 20

<210> SEQ ID NO 157
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 157
ctatcctcct tcagcuccug 20

<210> SEQ ID NO 158
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 158
actatcctcc ttcagcuccu 20

<210> SEQ ID NO 159
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 159
actatcctcc ttcagcuccu 20

<210> SEQ ID NO 160
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 160
actatcctcc ttcagcuccu 20

<210> SEQ ID NO 161
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 161
actatcctcc ttcagcuccu 20

<210> SEQ ID NO 162
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 162
cactatcctc cttcagcucc 20

<210> SEQ ID NO 163
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 163
cactatcctc cttcagcucc 20

<210> SEQ ID NO 164
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 164
cactatcctc cttcagcucc 20

<210> SEQ ID NO 165
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 165
cactatcctc cttcagcucc 20

<210> SEQ ID NO 166
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 166
ccactatcct ccttcagcuc 20

<210> SEQ ID NO 167
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 167
ccactatcct ccttcagcuc 20

<210> SEQ ID NO 168
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 168
ccactatcct ccttcagcuc 20

<210> SEQ ID NO 169
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 169
ccactatcct ccttcagcuc 20

<210> SEQ ID NO 170
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 170
tccactatcc tccttcagcu 20

<210> SEQ ID NO 171
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 171
tccactatcc tccttcagcu 20

<210> SEQ ID NO 172
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 172
tccactatcc tccttcagcu 20

<210> SEQ ID NO 173
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 173
tccactatcc tccttcagcu 20

<210> SEQ ID NO 174
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 174
ttccactatc ctcctucagc 20

<210> SEQ ID NO 175
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 175
ttccactatc ctcctucagc 20

<210> SEQ ID NO 176
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 176
ttccactatc ctcctucagc 20

<210> SEQ ID NO 177
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 177
ttccactatc ctcctucagc 20

<210> SEQ ID NO 178

<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 178
gttccactat cctccuucag 20

<210> SEQ ID NO 179
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 179
gttccactat cctccuucag 20

<210> SEQ ID NO 180
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 180
gttccactat cctccuucag 20

<210> SEQ ID NO 181
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 181
gttccactat cctccuucag 20

<210> SEQ ID NO 182
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 182
tgttccacta tcctccuuca 20

<210> SEQ ID NO 183
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 183
tgttccacta tcctccuuca 20

<210> SEQ ID NO 184
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 184
tgttccacta tcctccuuca 20

<210> SEQ ID NO 185
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 185
tgttccacta tcctccuuca 20

<210> SEQ ID NO 186
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 186
gtgttccact atcctccuuc 20

<210> SEQ ID NO 187
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 187
gtgttccact atcctccuuc 20

<210> SEQ ID NO 188
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 188
gtgttccact atcctccuuc 20

<210> SEQ ID NO 189
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 189
agtgttccac tatccuccuu 20

<210> SEQ ID NO 190
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 190
agtgttccac tatccuccuu 20

<210> SEQ ID NO 191
<211> LENGTH: 20
<212> TYPE: DNA

<213> ORGANISM: Artificial Sequence
<220> FEATURE:
<223> OTHER INFORMATION: Synthetic DNA/RNA oligonucleotide

<400> SEQUENCE: 191
agtgttccac tatccuccuu 20

<210> SEQ ID NO 192
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 192
agtgttccac tatccuccuu 20

<210> SEQ ID NO 193
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 193
cagtgttcca ctatccuccu 20

<210> SEQ ID NO 194
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 194
cagtgttcca ctatccuccu 20

<210> SEQ ID NO 195
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 195
cagtgttcca ctatccuccu 20

<210> SEQ ID NO 196
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 196
cagtgttcca ctatccuccu 20

<210> SEQ ID NO 197
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 197
gcagtgttcc actatccucc 20

<210> SEQ ID NO 198
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 198
gcagtgttcc actatccucc 20

<210> SEQ ID NO 199
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 199
gcagtgttcc actatccucc 20

<210> SEQ ID NO 200
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 200
gcagtgttcc actatccucc 20

<210> SEQ ID NO 201
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 201
tgcagtgttc cactauccuc 20

<210> SEQ ID NO 202
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 202
tgcagtgttc cactauccuc 20

<210> SEQ ID NO 203
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 203
tgcagtgttc cactauccuc 20

<210> SEQ ID NO 204
<211> LENGTH: 20
<212> TYPE: DNA
<213> ORGANISM: Artificial Sequence
<220> FEATURE:

<223> OTHER INFORMATION: Synthetic DNA/RNA oligonucleotide

<400> SEQUENCE: 204
tgcagtgttc cactauccuc 20

<210> SEQ ID NO 205
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 205
ttgcagtgtt ccactauccu 20

<210> SEQ ID NO 206
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 206
ttgcagtgtt ccactauccu 20

<210> SEQ ID NO 207
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 207
ttgcagtgtt ccactauccu 20

<210> SEQ ID NO 208
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 208
ttgcagtgtt ccactauccu 20

<210> SEQ ID NO 209
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 209
gttgcagtgt tccacuaucc 20

<210> SEQ ID NO 210
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 210
gttgcagtgt tccacuaucc 20

<210> SEQ ID NO 211
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 211
gttgcagtgt tccacuaucc 20

<210> SEQ ID NO 212
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 212
gttgcagtgt tccacuaucc 20

<210> SEQ ID NO 213
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 213
cgttgcagtg ttccacuauc 20

<210> SEQ ID NO 214
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 214
cgttgcagtg ttccacuauc 20

<210> SEQ ID NO 215
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 215
cgttgcagtg ttccacuauc 20

<210> SEQ ID NO 216
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 216
cgttgcagtg ttccacuauc 20

<210> SEQ ID NO 217
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 217
acgttgcagt gttccacuau 20

<210> SEQ ID NO 218
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 218
acgttgcagt gttccacuau 20

<210> SEQ ID NO 219
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 219
acgttgcagt gttccacuau 20

<210> SEQ ID NO 220
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 220
acgttgcagt gttccacuau 20

<210> SEQ ID NO 221
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 221
cacgttgcag tgttccacua 20

<210> SEQ ID NO 222
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 222
cacgttgcag tgttccacua 20

<210> SEQ ID NO 223
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 223
cacgttgcag tgttccacua 20

<210> SEQ ID NO 224
<211> LENGTH: 20

<212> TYPE: DNA
<213> ORGANISM: Artificial Sequence
<220> FEATURE:
<223> OTHER INFORMATION: Synthetic DNA/RNA oligonucleotide

<400> SEQUENCE: 224
cacgttgcag tgttccacua 20

<210> SEQ ID NO 225
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 225
ccacgttgca gtgttccacu 20

<210> SEQ ID NO 226
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 226
ccacgttgca gtgttccacu 20

<210> SEQ ID NO 227
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 227
ccacgttgca gtgttccacu 20

<210> SEQ ID NO 228
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 228
ccacgttgca gtgttccacu 20

<210> SEQ ID NO 229
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 229
gtgttccact atcctccuuc 20

<210> SEQ ID NO 230
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 230

-continued gtgttccact atcctccuuc 20

<210> SEQ ID NO 231
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 231
gtgttccact atcctccuuc 20

<210> SEQ ID NO 232
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 232
guguuccact atcctccttc 20

<210> SEQ ID NO 233
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 233
guguuccact atcctccttc 20

<210> SEQ ID NO 234
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 234
guguuccact atcctccttc 20

<210> SEQ ID NO 235
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 235
guguuccact atcctccttc 20

<210> SEQ ID NO 236
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 236
guguuccact atcctccttc 20

<210> SEQ ID NO 237
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 237
guguuccact atcctccttc 20

<210> SEQ ID NO 238
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 238
guguuccact atcctccttc 20

<210> SEQ ID NO 239
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 239
gtccactttc tgacagcucc 20

<210> SEQ ID NO 240
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 240
gtccactttc tgacagcucc 20

<210> SEQ ID NO 241
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 241
gtccactttc tgacagcucc 20

<210> SEQ ID NO 242
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 242
gtccactttc tgacagcucc 20

<210> SEQ ID NO 243
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 243
gtccactttc tgacagcucc 20

<210> SEQ ID NO 244
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 244
gtccactttc tgacagcucc 20

<210> SEQ ID NO 245
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 245
gtccactttc tgacagcucc 20

<210> SEQ ID NO 246
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 246
guccactttc tgacagctcc 20

<210> SEQ ID NO 247
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 247
guccactttc tgacagctcc 20

<210> SEQ ID NO 248
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 248
guccactttc tgacagctcc 20

<210> SEQ ID NO 249
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 249
guccactttc tgacagctcc 20

<210> SEQ ID NO 250
<211> LENGTH: 20
<212> TYPE: DNA
<213> ORGANISM: Artificial Sequence
<220> FEATURE:
<223> OTHER INFORMATION: Synthetic DNA/RNA oligonucleotide -continued

<400> SEQUENCE: 250
guccactttc tgacagctcc 20

<210> SEQ ID NO 251
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 251
guccactttc tgacagctcc 20

<210> SEQ ID NO 252
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 252
guccactttc tgacagctcc 20

<210> SEQ ID NO 253
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 253
gtccactttc tgacagcucc 20

<210> SEQ ID NO 254
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 254
gtccactttc tgacagcucc 20

<210> SEQ ID NO 255
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 255
gtccactttc tgacagcucc 20

<210> SEQ ID NO 256
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 256
gtccactttc tgacagcucc 20

<210> SEQ ID NO 257

<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 257
gtccactttc tgacagcucc 20

<210> SEQ ID NO 258
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 258
gtccactttc tgacagcucc 20

<210> SEQ ID NO 259
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 259
gtccactttc tgacagcucc 20

<210> SEQ ID NO 260
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 260
guccactttc tgacagctcc 20

<210> SEQ ID NO 261
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 261
guccactttc tgacagctcc 20

<210> SEQ ID NO 262
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 262
guccactttc tgacagctcc 20

<210> SEQ ID NO 263
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 263
guccactttc tgacagctcc 20

<210> SEQ ID NO 264
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 264
guccactttc tgacagctcc 20

<210> SEQ ID NO 265
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 265
guccactttc tgacagctcc 20

<210> SEQ ID NO 266
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 266
guccactttc tgacagctcc 20

<210> SEQ ID NO 267
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 267
gtccactttc tgacagcucc 20

<210> SEQ ID NO 268
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 268
guccactttc tgacagctcc 20

<210> SEQ ID NO 269
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 269
guccactttc tgacagctcc 20

<210> SEQ ID NO 270
<211> LENGTH: 20
<212> TYPE: DNA

<213> ORGANISM: Artificial Sequence
<220> FEATURE:
<223> OTHER INFORMATION: Synthetic DNA/RNA oligonucleotide

<400> SEQUENCE: 270
gtccactttc tgacagcucc 20

<210> SEQ ID NO 271
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 271
gtccactttc tgacagcucc 20

<210> SEQ ID NO 272
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 272
guccactttc tgacagctcc 20

<210> SEQ ID NO 273
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 273
guccactttc tgacagctcc 20

<210> SEQ ID NO 274
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 274
gtgttccact atcctccuuc 20

<210> SEQ ID NO 275
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 275
gtccactttc tgacagcucc 20

<210> SEQ ID NO 276
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 276
gtccactttc tgacagcucc 20

-continued

<210> SEQ ID NO 277
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 277
gtgttccact atcctccuuc 20

<210> SEQ ID NO 278
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 278
gtccactttc tgacagcucc 20

<210> SEQ ID NO 279
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 279
gtccactttc tgacagcucc 20

<210> SEQ ID NO 280
<211> LENGTH: 20
<212> TYPE: DNA
<213> ORGANISM: Artificial Sequence
<220> FEATURE:
<223> OTHER INFORMATION: Synthetic DNA/RNA oligonucleotide

<400> SEQUENCE: 280
ccttccctga aggttccucc 20

OLIGONUCLEOTIDE COMPOSITIONS AND METHODS THEREOF

CROSS-REFERENCE TO RELATED APPLICATIONS

This application is the National Stage of International Application No. PCT/US2021/019874, filed Feb. 19, 2021, which claims priority to U.S. Provisional Application Ser. No. 62/983,742, filed Mar. 1, 2020, and 63/111,071, filed Nov. 8, 2020, the entirety of each of which is incorporated herein by reference.

SEQUENCE LISTING

The instant application contains a Sequence Listing, which has been submitted electronically as a .txt file named "2010581-0899_SL.txt" The .txt file was created on Apr. 13, 2021, and is 60,536 bytes in size. The entire contents of the Sequence Listing are herein incorporated by reference.

TECHNICAL FIELD

Among other things, the present disclosure provides oligonucleotides, compositions and methods (e.g., of preparation, use, etc.) thereof. In some embodiments, provided technologies are useful for preventing and/or treating various conditions, disorders or diseases including various neurodegenerative disorders.

BACKGROUND

Oligonucleotides are useful in various applications, e.g., therapeutic, diagnostic, and/or research applications. For example, oligonucleotides targeting various genes can be useful for treatment of conditions, disorders or diseases related to such target genes.

SUMMARY

In some embodiments, the present disclosure provides MAPT oligonucleotides and compositions thereof that have significantly improved properties and/or high activities. Among other things, the present disclosure provides technologies for designing, manufacturing and utilizing such oligonucleotides and compositions. Particularly, in some embodiments, the present disclosure provides oligonucleotides comprising useful patterns of internucleotidic linkages and/or patterns of sugar modifications, which, when combined with one or more other structural elements, e.g., base sequence (or portion thereof), nucleobase modifications (and patterns thereof), additional chemical moieties, etc., can provide MAPT oligonucleotides and compositions thereof with high activities and/or desired properties, including but not limited to effective and efficient reduction of expression, levels and/or activities of MAPT transcripts and products encoded thereby. In some embodiments, MAPT oligonucleotides and compositions reduce levels of a MAPT transcript, and are useful for treating and/or preventing MAPT-associated condition, disorder or disease, e.g., Alzheimer's Disease (AD) and Frontotemporal Dementia (FTD).

In some embodiments, a MAPT oligonucleotide is capable of mediating knockdown of MAPT, wherein the level, expression and/or activity of MAPT or a product thereof are decreased. In some embodiments, a MAPT oligonucleotide is capable of mediating pan-specific knockdown of MAPT, wherein the level, expression and/or activity of multiple or all MAPT alleles are decreased. In some embodiments, a MAPT oligonucleotide has a base sequence that is complementary to a sequence which is common in multiple or all MAPT alleles.

In some embodiments, the base sequence of a MAPT oligonucleotide is, comprises, or comprises a span (e.g., 10-20, or 10, 11, 12, 13, 14, 15, 16, 17, 18, 19, 20 contiguous bases) of ACGTTGCAGTGTTCCACUAU (SEQ ID NO: 1), ACTATCCTCCTTCAGCUCCU (SEQ ID NO: 2), AGTGTTCCACTATCCUCCUU (SEQ ID NO: 3), ATCCTCCTTCAGCTCCUGCA (SEQ ID NO: 4), CACGTTGCAGTGTTCCACUA (SEQ ID NO: 5), CACTATCCTCCTTCAGCUCC (SEQ ID NO: 6), CAGTGTTCCACTATCCUCCU (SEQ ID NO: 7), CCACGTTGCAGTGTTCCACU (SEQ ID NO: 8), CCACTATCCTCCTTCAGCUC (SEQ ID NO: 9), CGTTGCAGTGTTCCACUAUC (SEQ ID NO: 10), CTATCCTCCTTCAGCUCCUG (SEQ ID NO: 11), GCAGTGTTCCACTATCCUCC (SEQ ID NO: 12), GTGTTCCACTATCCTCCUUC (SEQ ID NO: 13), GTTCCACTATCCTCCUUCAG (SEQ ID NO: 14), GUGUUCCACTATCCTCCTTC (SEQ ID NO: 15), TATCCTCCTTCAGCTCCUGC (SEQ ID NO: 16), TCCACTATCCTCCTTCAGCU (SEQ ID NO: 17), TGCAGTGTTCCACTAUCCUC (SEQ ID NO: 18), TGTTCCACTATCCTCCUUCA (SEQ ID NO: 19), TTCCACTATCCTCCTUCAGC (SEQ ID NO: 20), or TTGCAGTGTTCCACTAUCCU (SEQ ID NO: 21), or wherein each T can be independently substituted with U and vice versa. In some embodiments, the base sequence of a MAPT oligonucleotide is such a sequence.

Among other things, the present disclosure demonstrates that controlling structural elements of MAPT oligonucleotides can have a significant impact on oligonucleotide properties and/or activities, including knockdown (e.g., a decrease in the activity, expression and/or level) of MAPT (or a product thereof). In some embodiments, knockdown of MAPT is mediated by RNase H and/or steric hindrance affecting translation, and/or interference with mRNA maturation. In some embodiments, knockdown of MAPT is mediated by a mechanism involving RNA interference or modulation of splicing. In some embodiments, knockdown of MAPT may be through multiple mechanisms. In some embodiments, controlled structural elements of oligonucleotides include but are not limited to: base sequence, chemical modifications (e.g., modifications of a sugar, base and/or internucleotidic linkage) or patterns thereof, alterations in stereochemistry (e.g., stereochemistry of linkage phosphorus in a chiral internucleotidic linkage) or patterns thereof, structure of a first or second wing or core, and/or conjugation with an additional chemical moiety (e.g., a carbohydrate moiety, a targeting moiety, etc.). Particularly, in some embodiments, the present disclosure demonstrates that control of stereochemistry of backbone chiral centers (stereochemistry of linkage phosphorus), optionally with controlling other aspects of oligonucleotide design, can greatly improve properties and/or activities of MAPT oligonucleotides.

In some embodiments, the present disclosure pertains to any MAPT oligonucleotide which operates through any mechanism, and which comprises any sequence, structure or format (or portion thereof) described herein, wherein the oligonucleotide comprises at least one non-naturally-occurring modification of a base, sugar or internucleotidic linkage.

In some embodiments, an oligonucleotide composition comprises a plurality of oligonucleotides, wherein the oligonucleotides comprise at least one chirally controlled internucleotidic linkage, e.g., an internucleotidic linkage whose linkage phosphorus is in or is enriched for the Rp or Sp configuration (e.g., about 70-100% (e.g., about 85%-100%, 90%-100%, 95-100%, or about 80%, 85%, 90%, 91%, 92%, 93%, 94%, 95%, 96%, 97%, 98%, 99% or more) of all oligonucleotides of the same base sequence in the composition share the same stereochemistry at the linkage phosphorus) rather than a random mixture of the Rp and Sp. In some embodiments, such an internucleotidic linkage is also referred to as a "stereodefined (or stereocontrolled or chirally controlled) internucleotidic linkage." In some embodiments, such an oligonucleotide composition is referred to as a "stereodefined (or stereocontrolled or chirally controlled) oligonucleotide composition". In some embodiments, at least 1 internucleotidic linkage is chirally controlled internucleotidic linkage and is Sp. In some embodiments, at least 1 internucleotidic linkage is chirally controlled internucleotidic linkage and is Rp. In some embodiments, at least 1-20, e.g., 5, 6, 7, 8, 9, 10, 11, 12, 13, 14, 15, 16, 17, 18, 19, 20 internucleotidic linkages are each independently a chirally controlled internucleotidic linkage. In some embodiments, each phosphorothioate internucleotidic linkage is independently a chirally controlled internucleotidic linkage. In some embodiments, each internucleotidic linkage comprising a chiral linkage phosphorus is independently a chirally controlled internucleotidic linkage.

In some embodiments, the present disclosure provides an oligonucleotide, wherein the base sequence of the oligonucleotide comprises at least 10 contiguous bases of a base sequence that is identical to or complementary to a base sequence of a MAPT gene or a transcript thereof, wherein the oligonucleotide comprises at least one modified internucleotidic linkage (an internucleotidic linkage that is not a natural phosphate linkage (which may exist in various salt forms)), and wherein the oligonucleotide is capable of decreasing the level, expression and/or activity of a MAPT target gene or a gene product thereof.

In some embodiments, the present disclosure pertains to a MAPT oligonucleotide composition wherein the MAPT oligonucleotides comprise at least one chiral internucleotidic linkage which is not chirally controlled (e.g., the internucleotidic linkage is stereorandom). In some embodiments, an internucleotidic linkage which is not chirally controlled is a phosphorothioate internucleotidic linkage. In some embodiments, an internucleotidic linkage which is not chirally controlled is a non-negatively charged internucleotidic linkage, e.g., n001.

In some embodiments, a MAPT oligonucleotide comprises a non-negatively charged or neutral internucleotidic linkage.

In some embodiments, provided oligonucleotides comprise additional chemical moieties, such as carbohydrate moieties, targeting moieties, etc. In some embodiments, when incorporated into oligonucleotides, such moieties may improve one or more properties and/or activities.

In some embodiments, the present disclosure provides a chirally controlled MAPT oligonucleotide composition comprising a plurality of oligonucleotides which share:

1) a common base sequence;
2) a common pattern of backbone linkages; and
3) a common pattern of backbone chiral centers, which composition is a substantially pure preparation of a single oligonucleotide in that a non-random or controlled level of the oligonucleotides in the composition have the common base sequence, the common pattern of backbone linkages, and the common pattern of backbone chiral centers. In some embodiments, the plurality of oligonucleotides comprises a common pattern of sugar modifications, a common pattern of base modifications (if any), and a common additional chemical moiety (if any).

In some embodiments, a MAPT oligonucleotide composition is a chirally controlled oligonucleotide composition comprising a plurality of oligonucleotides of a particular oligonucleotide type, which composition is chirally controlled in that it is enriched, relative to a substantially racemic preparation of oligonucleotides having the same base sequence, for oligonucleotides of the particular oligonucleotide type. In some embodiments, a MAPT oligonucleotide (e.g., a MAPT having a base sequence which is, comprises, or comprises a span of at least 15 contiguous bases of a base sequence disclosed herein) is stereorandom (or not chirally controlled).

In some embodiments, a provided oligonucleotide comprises one or more blocks. In some embodiments, a block comprises one or more consecutive nucleosides, and/or nucleotides, and/or sugars, or bases, and/or internucleotidic linkages which share a common chemistry (e.g., at least one common modification of sugar, base or internucleotidic linkage, or combination or pattern thereof, or pattern of stereochemistry) which is not present in an adjacent block, or vice versa. In some embodiments, a block is a wing or a core.

In some embodiments, an oligonucleotide comprises two or more portions, e.g., at least one wing and at least one core. In some embodiments, a wing differs structurally from a core in that a wing of an oligonucleotide comprises a structure [e.g., stereochemistry, or chemical modification at a sugar, base or internucleotidic linkage (or pattern thereof), etc.] not present in the core, or vice versa. In some embodiments, the structure of an oligonucleotide comprises a wing-core-wing structure. In some embodiments, the structure of an oligonucleotide comprises a wing-core-wing structure, wherein one wing differs in structure [e.g., stereochemistry, additional chemical moiety, or chemical modification at a sugar, base or internucleotidic linkage (or pattern thereof)] from the other wing and the core (for example, an asymmetrical oligonucleotide). In some embodiments, the structure of an oligonucleotide has or comprises a wing-core, core-wing, or wing-core-wing structure, and a block is a wing or core. In some embodiments, a core is referred to as a gap.

In some embodiments, a wing comprises a sugar modification or a pattern thereof that is absent from a core. In some embodiments, a wing comprises a sugar modification that is absent from a core. In some embodiments, each sugar in a wing is the same. In some embodiments, at least one sugar in a wing is different from another sugar in the wing. In some embodiments, one or more sugar modifications and/or patterns of sugar modifications in a first wing of an oligonucleotide (e.g., a 5'-wing) is/are different from one or more sugar modifications and/or patterns of sugar modifications in a second wing of the oligonucleotide (e.g., a 3'-wing). In some embodiments, a modification is a 2'-OR modification, wherein R is as described herein. In some embodiments, R is optionally substituted $C_{1-4}$ alkyl. In some embodiments, a modification is 2'-OMe. In some embodiments, a modification is a 2'-MOE. In some embodiments, a modified sugar is a high-affinity sugar, e.g., a bicyclic sugar (e.g., a LNA sugar), 2'-MOE, etc. In some embodiments, a 5'-wing comprises 2-MOE modifications. In some embodiments, each 5'-wing sugar is 2'-MOE modified. In some embodiments, a 3'-wing comprises 2-OMe modifications. In some embodiments, each 3'-wing sugar is 2'-OMe modified.

In some embodiments, an internucleotidic linkage linking a wing nucleoside and a core nucleoside is considered part of the core. In some embodiments, an internucleotidic linkage linking a wing nucleoside and a core nucleoside is considered part of the wing.

In some embodiments, a wing comprises one or more (e.g., 1, 2, 3, 4, 5, 6, 7, 8, 9, or 10) non-negatively charged internucleotidic linkages. In some embodiments, a non-negatively charged internucleotidic linkage is a neutral internucleotidic linkage. In some embodiments, as demonstrated herein, oligonucleotides that comprise wings comprising non-negatively charged internucleotidic linkages can deliver high activities and/or selectivities.

In some embodiments, a core sugar is a natural DNA sugar which comprises no substitution at the 2' position (two —H at 2'-carbon). In some embodiments, each core sugar is a natural DNA sugar which comprises no substitution at the 2' position (two —H at 2'-carbon).

In some embodiments, a MAPT oligonucleotide or MAPT oligonucleotide composition is useful for prevention or treatment of a MAPT-associated condition, disorder or disease, in a subject in need thereof. In some embodiments, the present disclosure provides a method for preventing or treating a MAPT-associated condition, disorder or disease, comprising administering to a subject suffering therefrom or subject thereto a therapeutically effective amount of a provided oligonucleotide or a pharmaceutical composition that can deliver or comprise a therapeutically effective amount of a provided oligonucleotide. In some embodiments, the present disclosure provides pharmaceutical compositions which comprise a provided MAPT oligonucleotide and a pharmaceutically acceptable carrier. In some embodiments, oligonucleotides in a pharmaceutical composition are in one or more pharmaceutically acceptable salt forms, e.g., a sodium salt form, an ammonium salt form, etc.

In some embodiments, an oligonucleotide or oligonucleotide composition is useful for the manufacture of a medicament for prevention or treatment of a MAPT-associated condition, disorder or disease, such as Alzheimer's Disease (AD) and Frontotemporal Dementia (FTD), in a subject in need thereof.

Various MAPT-associated conditions, disorders or diseases may be prevented and/or treated utilizing provided technologies (e.g., oligonucleotide, compositions, methods, etc.). In some embodiments, a condition, disorder or disease is Alzheimer's Disease (AD). In some embodiments, a condition, disorder or disease is Frontotemporal Dementia (FTD).

DETAILED DESCRIPTION OF CERTAIN EMBODIMENTS

Technologies of the present disclosure may be understood more readily by reference to the following detailed description of certain embodiments.

Definitions

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein in the present disclosure, unless otherwise clear from context, (i) the term "a" or "an" may be understood to mean "at least one"; (ii) the term "or" may be understood to mean "and/or"; (iii) the terms "comprising", "comprise", "including" (whether used with "not limited to" or not), and "include" (whether used with "not limited to" or not) may be understood to encompass itemized components or steps whether presented by themselves or together with one or more additional components or steps; (iv) the term "another" may be understood to mean at least an additional/second one or more; (v) the terms "about" and "approximately" may be understood to permit standard variation as would be understood by those of ordinary skill in the art; and (vi) where ranges are provided, endpoints are included.

Unless otherwise specified, description of oligonucleotides and elements thereof (e.g., base sequence, sugar modifications, internucleotidic linkages, linkage phosphorus stereochemistry, patterns thereof, etc.) is from 5' to 3'. As those skilled in the art will appreciate, in some embodiments, oligonucleotides may be provided and/or utilized as salt forms, particularly pharmaceutically acceptable salt forms, e.g., sodium salts. Unless otherwise indicated, oligonucleotides include various forms of the oligonucleotides. As those skilled in the art will also appreciate, in some embodiments, individual oligonucleotides within a composition may be considered to be of the same constitution and/or structure even though, within such composition (e.g., a liquid composition), particular such oligonucleotides might be in different salt form(s) (and may be dissolved and the oligonucleotide chain may exist as an anion form when, e.g., in a liquid composition) at a particular moment in time. For example, those skilled in the art will appreciate that, at a given pH, individual internucleotidic linkages along an oligonucleotide chain may be in an acid (H) form, or in one of a plurality of possible salt forms (e.g., a sodium salt, or a salt of a different cation, depending on which ions might be present in the preparation or composition), and will understand that, so long as their acid forms (e.g., replacing all cations, if any, with $H^+$) are of the same constitution and/or structure, such individual oligonucleotides may properly be considered to be of the same constitution and/or structure.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Antisense: The term "antisense", as used herein, refers to a characteristic of an oligonucleotide or other nucleic acid having a base sequence complementary or substantially complementary to a target nucleic acid to which it is capable of hybridizing. In some embodiments, a target nucleic acid is a target gene mRNA. In some embodiments, hybridization is required for or results in at one activity, e.g., a decrease in the level, expression or activity of the target nucleic acid or a gene product thereof. The term "antisense oligonucleotide", as used herein, refers to an oligonucleotide complementary to a target nucleic acid. In some embodiments, an antisense oligonucleotide is capable of directing a decrease in the level, expression or activity of a target nucleic acid or a product thereof. In some embodiments, an antisense oligonucleotide is capable of directing a decrease in the level, expression or activity of the target nucleic acid or a product thereof, via a mechanism that involves RNase H, steric hindrance and/or RNA interference.

Chiral control: As used herein, "chiral control" refers to control of the stereochemical designation of the chiral linkage phosphorus in a chiral internucleotidic linkage within an oligonucleotide. As used herein, a chiral internucleotidic linkage is an internucleotidic linkage whose linkage phosphorus is chiral. In some embodiments, a control is achieved through a chiral element that is absent from the sugar and base moieties of an oligonucleotide, for example, in some embodiments, a control is achieved through use of one or more chiral auxiliaries during oligonucleotide preparation as described in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in each chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same linkage phosphorus stereochemistry at one or more chiral internucleotidic linkages (chirally controlled or stereodefined internucleotidic linkages, whose chiral linkage phosphorus is Rp or Sp in the composition ("stereodefined"), not a random Rp and Sp mixture as non-chirally controlled internucleotidic linkages). Level of the plurality of oligonucleotides (or nucleic acids) in a chirally controlled oligonucleotide composition is pre-determined/controlled (e.g., through chirally controlled oligonucleotide preparation to stereoselectively form one or more chiral internucleotidic linkages). In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%0, 1%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a level is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications. In some embodiments, the plurality of oligonucleotides share the same stereochemistry at about 1-50 chiral internucleotidic linkages. In some embodiments, the plurality of oligonucleotides share the same stereochemistry at about 1%-100% of chiral internucleotidic linkages. In some embodiments, oligonucleotides (or nucleic acids) of a plurality are of the same constitution (as appreciated by those skilled in the art, in some embodiments may exist in one or more forms, e.g., acid forms, salt forms, etc.). In some embodiments, level of the oligonucleotides (or nucleic acids) of the plurality is about 1%-100% of all oligonucleotides (or nucleic acids) in a composition that share the same constitution as the oligonucleotides (or nucleic acids) of the plurality. In some embodiments, each chiral internucleotidic linkage is a chiral controlled internucleotidic linkage, and the composition is a completely chirally controlled oligonucleotide composition. In some embodiments, oligonucleotides (or nucleic acids) of a plurality are structurally identical. In some embodiments, a chirally controlled internucleotidic linkage has a diastereopurity of at least 80%, 85%, 90%, 91%, 92%, 93%, 94%, 95%, 96%, 97%, 98%, 99% or 99.5%, typically at least 90%, 91%, 92%, 93%, 94%, 95%, 96%, 97%, 98%, 99% or 99.5%. In some embodiments, a chirally controlled internucleotidic linkage has a diastereopurity of at least 95%. In some embodiments, a chirally controlled internucleotidic linkage has a diastereopurity of at least 96%. In some embodiments, a chirally controlled internucleotidic linkage has a diastereopurity of at least 97%. In some embodiments, a chirally controlled internucleotidic linkage has a diastereopurity of at least 98%. In some embodiments, a chirally controlled internucleotidic linkage has a diastereopurity of at least 99%. In some embodiments, a percentage (e.g., a level as described herein) is or is at least $(DS)^{nc}$, wherein DS is a diastereopurity as described in the present disclosure (e.g., 90%, 91%, 92%, 93%, 94%, 95%, 96%, 97%, 98%, 99% or 99.5% or more) and nc is the number of chirally controlled internucleotidic linkages as described in the present disclosure (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more). In some embodiments, a percentage (e.g., a level as described herein) is or is at least $(DS)^{nc}$, wherein DS is 95%-100%. For example, when DS is 99% and nc is 10, the percentage is or is at least 90% ($(99\%)^{10}\approx0.90=90\%$). In some embodiments, level of a plurality of oligonucleotides in a composition is represented as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions (e.g., for the linkage between Nx and Ny in an oligonucleotide . . . NxNy . . . , the dimer is NxNy). In some embodiments, not all chiral internucleotidic linkages are chiral controlled internucleotidic linkages, and the composition is a partially chirally controlled oligonucleotide composition. In some embodiments, a non-chirally controlled internucleotidic linkage has a diastereopurity of less than about 80%, 75%, 70%, 65%, 60%, 55%, or of about 50%, as typically observed in stereorandom oligonucleotide compositions (e.g., as appreciated by those skilled in the art, from traditional oligonucleotide synthesis, e.g., the phosphoramidite method). In some embodiments, oligonucleotides (or nucleic acids) of a plurality are of the same type. In some embodiments, a chirally controlled oligonucleotide composition comprises non-random or controlled levels of individual oligonucleotide or nucleic acids types. For instance, in some embodiments a chirally controlled oligonucleotide composition comprises one and no more than one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, a chirally controlled oligonucleotide composition is a composition of oligonucleotides of an oligonucleotide type, which composition comprises a non-random or controlled level of a plurality of oligonucleotides of the oligonucleotide type.

Internucleotidic linkage: As used herein, the phrase "internucleotidic linkage" refers generally to a linkage linking nucleoside units of an oligonucleotide or a nucleic acid. In some embodiments, an internucleotidic linkage is a phosphodiester linkage, as extensively found in naturally occurring DNA and RNA molecules (natural phosphate linkage (—OP(═O)(OH)O—), which as appreciated by those skilled in the art may exist as a salt form). In some embodiments, an internucleotidic linkage is a modified internucleotidic linkage (not a natural phosphate linkage). In some embodiments, an internucleotidic linkage is a "modified internucleotidic linkage" wherein at least one oxygen atom or —OH of a phosphodiester linkage is replaced by a different organic or inorganic moiety. In some embodiments, such an organic or inorganic moiety is selected from ═S, ═Se, ═NR', —SR', —SeR', $—N(R')_2$, $B(R')_3$, —S—, —Se—, and —N(R')—, wherein each R' is independently as defined and described in the present disclosure. In some embodiments, an internucleotidic linkage is a phosphotriester linkage, phosphorothioate linkage (or phosphorothioate diester linkage, —OP(═O)(SH)O—, which as appreciated by those skilled in the art may exist as a salt form), or phosphorothioate triester linkage. In some embodiments, a modified internucleotidic linkage is a phosphorothioate linkage. In some embodiments, an internucleotidic linkage is one of, e.g., PNA (peptide nucleic acid) or PMO (phosphorodiamidate Morpholino oligomer) linkage. In some embodiments, a modified internucleotidic linkage is a non-negatively charged internucleotidic linkage. In some embodiments, a modified internucleotidic linkage is a neutral internucleotidic linkage (e.g., n001 in certain provided oligonucleotides). It is understood by a person of ordinary skill in the art that an internucleotidic linkage may exist as an anion or cation at a given pH due to the existence of acid or base moieties in the linkage. In some embodiments, a modified internucleotidic linkages is a modified internucleotidic linkages designated as s, s1, s2, s3, s4, s5, s6, s7, s8, s9, s10, s 11, s12, s13, s14, s15, s16, s17 and s18 as described in WO 2017/210647.

In vitro: As used herein, the term "in vitro" refers to events that occur in an artificial environment, e.g., in a test tube or reaction vessel, in cell culture, etc., rather than within an organism (e.g., animal, plant and/or microbe).

In vivo: As used herein, the term "in vivo" refers to events that occur within an organism (e.g., animal, plant and/or microbe).

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is the P of Formula I as described herein. In some embodiments, a linkage phosphorus atom is chiral. In some embodiments, a linkage phosphorus atom is achiral (e.g., as in natural phosphate linkages).

Linker: The terms "linker", "linking moiety" and the like refer to any chemical moiety which connects one chemical moiety to another. As appreciated by those skilled in the art, a linker can be bivalent or trivalent or more, depending on the number of chemical moieties the linker connects. In some embodiments, a linker is a moiety which connects one oligonucleotide to another oligonucleotide in a multimer. In some embodiments, a linker is a moiety optionally positioned between the terminal nucleoside and the solid support or between the terminal nucleoside and another nucleoside, nucleotide, or nucleic acid. In some embodiments, in an oligonucleotide a linker connects a chemical moiety (e.g., a targeting moiety, a lipid moiety, a carbohydrate moiety, etc.) with an oligonucleotide chain (e.g., through its 5'-end, 3'-end, nucleobase, sugar, internucleotidic linkage, etc.)

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases. In some embodiments, a modified nucleobase is substituted A, T, C, G, or U, or a substituted tautomer of A, T, C, G, or U. In some embodiments, a modified nucleobase in the context of oligonucleotides refer to a nucleobase that is not A, T, C, G or U.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Modified sugar: The term "modified sugar" refers to a moiety that can replace a sugar. A modified sugar mimics the spatial arrangement, electronic properties, or some other physicochemical property of a sugar. In some embodiments, as described in the present disclosure, a modified sugar is substituted ribose or deoxyribose. In some embodiments, a modified sugar comprises a 2'-modification. Examples of useful 2'-modification are widely utilized in the art and described herein. In some embodiments, a 2'-modification is 2'-OR, wherein R is optionally substituted $C_{1-10}$ aliphatic. In some embodiments, a 2'-modification is 2'-OMe. In some embodiments, a 2'-modification is 2'-MOE. In some embodiments, a modified sugar is a bicyclic sugar (e.g., a sugar used in LNA, BNA, etc.). In some embodiments, in the context of oligonucleotides, a modified sugar is a sugar that is not ribose or deoxyribose as typically found in natural RNA or DNA.

Nucleic acid: The term "nucleic acid", as used herein, includes any nucleotides and polymers thereof. The term "polynucleotide", as used herein, refers to a polymeric form of nucleotides of any length, either ribonucleotides (RNA) or deoxyribonucleotides (DNA) or a combination thereof. These terms refer to the primary structure of the molecules and, thus, include double- and single-stranded DNA, and double- and single-stranded RNA. These terms include, as equivalents, analogs of either RNA or DNA comprising modified nucleotides and/or modified polynucleotides, such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified internucleotidic linkages. The term encompasses nucleic acids containing any combinations of nucleobases, modified nucleobases, sugars, modified sugars, phosphate bridges or modified internucleotidic linkages. Examples include, and are not limited to, nucleic acids containing ribose moieties, nucleic acids containing deoxy-ribose moieties, nucleic acids containing both ribose and deoxyribose moieties, nucleic acids containing ribose and modified ribose moieties. Unless otherwise specified, the prefix poly- refers to a nucleic acid containing 2 to about 10,000 nucleotide monomer units and wherein the prefix oligo- refers to a nucleic acid containing 2 to about 200 nucleotide monomer units.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, a naturally-occurring nucleobases are modified adenine, guanine, uracil, cytosine, or thymine. In some embodiments, a naturally-occurring nucleobases are methylated adenine, guanine, uracil, cytosine, or thymine. In some embodiments, a nucleobase comprises a heteroaryl ring wherein a ring atom is nitrogen, and when in a nucleoside, the nitrogen is bonded to a sugar moiety. In some embodiments, a nucleobase comprises a heterocyclic ring wherein a ring atom is nitrogen, and when in a nucleoside, the nitrogen is bonded to a sugar moiety. In some embodiments, a nucleobase is a "modified nucleobase," a nucleobase other than adenine (A), guanine (G), uracil (U), cytosine (C), and thymine (T). In some embodiments, a modified nucleobase is substituted A, T, C, G or U. In some embodiments, a modified nucleobase is a substituted tautomer of A, T, C, G, or U. In some embodiments, a modified nucleobases is methylated adenine, guanine, uracil, cytosine, or thymine. In some embodiments, a modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs. In some embodiments, a nucleobase is optionally substituted A, T, C, G, or U, or an optionally substituted tautomer of A, T, C, G, or U. In some embodiments, a "nucleobase" refers to a nucleobase unit in an oligonucleotide or a nucleic acid (e.g., A, T, C, G or U as in an oligonucleotide or a nucleic acid).

Nucleoside: The term "nucleoside" refers to a moiety wherein a nucleobase or a modified nucleobase is covalently bound to a sugar or a modified sugar. In some embodiments, a nucleoside is a natural nucleoside, e.g., adenosine, deoxyadenosine, guanosine, deoxyguanosine, thymidine, uridine, cytidine, or deoxycytidine. In some embodiments, a nucleoside is a modified nucleoside, e.g., a substituted natural nucleoside selected from adenosine, deoxyadenosine, guanosine, deoxyguanosine, thymidine, uridine, cytidine, and deoxycytidine. In some embodiments, a nucleoside is a modified nucleoside, e.g., a substituted tautomer of a natural nucleoside selected from adenosine, deoxyadenosine, guanosine, deoxyguanosine, thymidine, uridine, cytidine, and deoxycytidine. In some embodiments, a "nucleoside" refers to a nucleoside unit in an oligonucleotide or a nucleic acid.

Nucleotide: The term "nucleotide" as used herein refers to a monomeric unit of a polynucleotide that consists of a nucleobase, a sugar, and one or more internucleotidic linkages (e.g., phosphate linkages in natural DNA and RNA). The naturally occurring bases [guanine, (G), adenine, (A), cytosine, (C), thymine, (T), and uracil (U)] are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs. In some embodiments, a "nucleotide" refers to a nucleotide unit in an oligonucleotide or a nucleic acid.

Oligonucleotide: The term "oligonucleotide" refers to a polymer or oligomer of nucleotides, and may contain any combination of natural and non-natural nucleobases, sugars, and internucleotidic linkages.

Oligonucleotides can be single-stranded or double-stranded. A single-stranded oligonucleotide can have double-stranded regions (formed by two portions of the single-stranded oligonucleotide) and a double-stranded oligonucleotide, which comprises two oligonucleotide chains, can have single-stranded regions for example, at regions where the two oligonucleotide chains are not complementary to each other. Example oligonucleotides include, but are not limited to structural genes, genes including control and termination regions, self-replicating systems such as viral or plasmid DNA, single-stranded and double-stranded RNAi agents and other RNA interference reagents (RNAi agents or iRNA agents), shRNA, antisense oligonucleotides, ribozymes, microRNAs, microRNA mimics, supermirs, aptamers, antimirs, antagomirs, Ul adaptors, triplex-forming oligonucleotides, G-quadruplex oligonucleotides, RNA activators, immuno-stimulatory oligonucleotides, and decoy oligonucleotides.

Oligonucleotides of the present disclosure can be of various lengths. In particular embodiments, oligonucleotides can range from about 2 to about 200 nucleosides in length. In various related embodiments, oligonucleotides, single-stranded, double-stranded, or triple-stranded, can range in length from about 4 to about 10 nucleosides, from about 10 to about 50 nucleosides, from about 20 to about 50 nucleosides, from about 15 to about 30 nucleosides, from about 20 to about 30 nucleosides in length. In some embodiments, the oligonucleotide is from about 9 to about 39 nucleosides in length. In some embodiments, the oligonucleotide is at least 4, 5, 6, 7, 8, 9, 10, 11, 12, 13, 14, 15, 16, 17, 18, 19, 20, 21, 22, 23, 24, or 25 nucleosides in length. In some embodiments, the oligonucleotide is at least 19 nucleosides in length. In some embodiments, the oligonucleotide is at least 20 nucleosides in length. In some embodiments, the oligonucleotide is at least 25 nucleosides in length. In some embodiments, the oligonucleotide is at least 30 nucleosides in length. In some embodiments, the oligonucleotide is a duplex of complementary strands of at least 18 nucleosides in length. In some embodiments, the oligonucleotide is a duplex of complementary strands of at least 21 nucleosides in length. In some embodiments, each nucleoside counted in an oligonucleotide length independently comprises A, T, C, G, or U, or optionally substituted A, T, C, G, or U, or an optionally substituted tautomer of A, T, C, G or U.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, phosphorothioate triester, etc.), pattern of backbone chiral centers [i.e., pattern of linkage phosphorus stereochemistry (Rp/Sp)], and pattern of backbone phosphorus modifications (e.g., pattern of "-$XLR^1$" groups in Formula I as described herein). In some embodiments, oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In some embodiments, however, provided compositions comprise a plurality of oligonucleotides of different types, typically in pre-determined relative amounts.

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-1}Ph$ which may be substituted with $R^\circ$; $-CH{=}CHPh$, which may be substituted with R°; $-(CH_2)_{0-4}O(CH_2)_{0-1}$-pyridyl which may be substituted with R°; $-NO_2$; —CN; $-N_3$; $-(CH_2)_{0-4}N(R°)_2$; $-(CH_2)_{0-4}N(R°)C(O)R°$; —N(R°)C(S)R°; $-(CH_2)_{0-4}N(R°)C(O)NR°_2$; $-N(R°)C(S)NR°_2$; $-(CH_2)_{0-4}N(R°)C(O)OR°$; —N(R°)N(R°)C(O)R°; $-N(R°)N(R=°)C(O)NR°_2$; —N(R°)N(R°)C(O)OR°; $-(CH_2)_{0-4}C(O)R°$; —C(S)R°; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR°$, —SC(S)SR°; $-(CH_2)_{0-4}SC(O)R°$; $-(CH_2)_{0-4}C(O)NR°_2$; $-C(S)NR°_2$; —C(S)SR°; $-(CH_2)_{0-4}OC(O)NR°_2$; —C(O)N(OR°)R°; —C(O)C(O)R°; $-C(O)CH_2C(O)R°$; —C(NOR°)R°; $-(CH_2)_{0-4}SSR°$; $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R=°$; —N(OR°)R°; $-C(NH)NR°_2$; $-Si(R°)_3$; $-OSi(R°)_3$; $-B(R°)_2$; $-OB(R°)_2$; $-OB(OR°)_2$; $-P(R°)_2$; $-P(OR°)_2$; —P(R°)(OR°); $-OP(R°)_2$; $-OP(OR°)_2$; —OP(R°)(OR°); $-P(O)(R°)_2$; $-P(O)(OR°)_2$; $-OP(O)(R°)_2$; $-OP(O)(OR°)_2$; —OP(O)(OR°)(SR°); $-SP(O)(R°)_2$; $-SP(O)(OR°)_2$; $-N(R°)P(O)(R°)_2$; $-N(R°)P(O)(OR°)_2$; $-P(R°)_2[B(R°)_3]$; $-P(OR°)_2[B(R°)_3]$; $-OP(R°)_2[B(R°)_3]$; $-OP(OR°)_2[B(R°)_3]$; $-(C_{1-4}$ straight or branched alkylene)O—$N(R°)_2$; or $-(C_{1-4}$ straight or branched alkylene)C(O)O—$N(R°)_2$, wherein each R° may be substituted as defined herein and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R°, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R° (or the ring formed by taking two independent occurrences of R° together with their intervening atoms), are independently halogen, $-(CH_2)_{0-2}R^●$, -(haloR$^●$), $-(CH_2)_{0-2}OH$, $-(CH_2)_{0-2}OR^●$, $-(CH_2)_{0-2}CH(OR^●)_2$; —O(haloR$^●$), —CN, $-N_3$, $-(CH_2)_{0-2}C(O)R^●$, $-(CH_2)_{0-2}C(O)OH$, $-(CH_2)_{0-2}C(O)OR^●$, $-(CH_2)_{0-2}SR^●$, $-(CH_2)_{0-2}SH$, $-(CH_2)_{0-2}NH_2$, $-(CH_2)_{0-2}NHR^●$, $-(CH_2)_{0-2}NR^●_2$, $-NO_2$, $-SiR^●_3$, $-OSiR^●_3$, $-C(O)SR^●$, $-(C_{1-4}$ straight or branched alkylene)C(O)OR$^●$, or —SSR$^●$ wherein each R$^●$ is unsubstituted or where preceded by "halo" is substituted only with one or more halogens, and is independently selected from $C_{1-4}$ aliphatic, $-CH_2Ph$, $-O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents, e.g., on a suitable carbon atom, are independently the following: =O, =S, $=NNR^*_2$, =NNHC(O)R*, =NNHC(O)OR*, $=NNHS(O)_2R^*$, =NR*, =NOR*, $-O(C(R^*_2))_{2-3}O-$, or-$S(C(R^*_2))_{2-3}S-$, wherein each independent occurrence of R* is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of R* are independently halogen, —R$^●$, -(haloR$^●$), —OH, —OR$^●$, —O(haloR$^●$), —CN, —C(O)OH, —C(O)OR$^●$, $-NH_2$, —NHR$^●$, $-NR^●_2$, or $-NO_2$, wherein each R$^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently $-R^†$, $-NR^†_2$, $-C(O)R^†$, $-C(O)OR^†$, $-C(O)C(O)R^†$, $-C(O)CH_2C(O)R^†$, $-S(O)_2R^†$, $-S(O)_2NR^†_2$, $-C(S)NR^†_2$, $-C(NH)NR^†_2$, or $-N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of RT are independently halogen, —R$^●$, -(haloR$^●$), —OH, —OR$^●$, —O(haloR$^●$), —CN, —C(O)OH, —C(O)OR$^●$, $-NH_2$, -NHRv, $-NR^●_2$, or $-NO_2$, wherein each R$^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase “pharmaceutically acceptable” refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term “pharmaceutically acceptable carrier” means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be “acceptable” in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; pH buffered solutions; polyesters, polycarbonates and/or polyanhydrides; and other non-toxic compatible substances employed in pharmaceutical formulations.

Pharmaceutically acceptable salt: The term “pharmaceutically acceptable salt”, as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups, e.g., an oligonucleotide, and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, an oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen (e.g., in an aqueous solution with a pKa no more than about 11, 10, 9, 8, 7, 6, 5, 4, 3, or 2; in some embodiments, no more than about 7; in some embodiments, no more than about 6; in some embodiments, no more than about 5; in some embodiments, no more than about 4; in some embodiments, no more than about 3) in the acidic groups are replaced with cations. In some embodiments, each phosphorothioate and phosphate group independently exists in its salt form (e.g., if sodium salt, —O—P(O)(SNa)—O— and —O—P(O)(ONa)—O—, respectively). In some embodiments, each phosphorothioate and phosphate internucleotidic linkage independently exists in its salt form (e.g., if sodium salt, —O—P(O)(SNa)—O— and —O—P(O)(ONa)—O—, respectively). In some embodiments, a pharmaceutically acceptable salt is a sodium salt of an oligonucleotide. In some embodiments, a pharmaceutically acceptable salt is a sodium salt of an oligonucleotide, wherein each acidic phosphate and modified phosphate group (e.g., phosphorothioate, phosphate, etc.), if any, exists as a salt form (all sodium salt).

Protecting group: The term “protecting group,” as used herein, is well known in the art and includes those described in detail in *Protecting Groups in Organic Synthesis*, T. W. Greene and P. G. M. Wuts, $3^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. 06/2012, the entirety of Chapter 2 is incorporated herein by reference. Suitable amino-protecting groups include but are not limited to described herein and/or in: WO 2018/022473, WO 2018/098264, WO 2018/223056, WO 2018/223073, WO 2018/223081, WO 2018/237194, WO 2019/032607, WO 2019/055951, and/or WO 2019/075357, or U.S. Provisional patent applications 62/825,766 and 62/911339, the description of the protecting groups of each of which is independently incorporated herein by reference.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secreations, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Subject: As used herein, the term "subject" or "test subject" refers to any organism to which a provided compound (e.g., a provided oligonucleotide) or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject is a human. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. A base sequence which is substantially complementary to a second sequence is not identical to the second sequence, but is mostly or nearly identical to the second sequence. In addition, one of ordinary skill in the biological and/or chemical arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars. In some embodiments, a sugar is a RNA or DNA sugar (ribose or deoxyribose). In some embodiments, a sugar is a modified ribose or deoxyribose sugar, e.g., 2'-modified, 5'-modified, etc. As described herein, in some embodiments, when used in oligonucleotides and/or nucleic acids, modified sugars may provide one or more desired properties, activities, etc. In some embodiments, a sugar is optionally substituted ribose or deoxyribose. In some embodiments, a "sugar" refers to a sugar unit in an oligonucleotide or a nucleic acid.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition is predisposed to have that disease, disorder and/or condition. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the term "therapeutic agent" in general refers to any agent that elicits a desired effect (e.g., a desired biological, clinical, or pharmacological effect) when administered to a subject. In some embodiments, an agent is considered to be a therapeutic agent if it demonstrates a statistically significant effect across an appropriate population. In some embodiments, an appropriate population is a population of subjects suffering from and/or susceptible to a disease, disorder or condition. In some embodiments, an appropriate population is a population of model organisms. In some embodiments, an appropriate population may be defined by one or more criterion such as age group, gender, genetic background, preexisting clinical conditions, prior exposure to therapy. In some embodiments, a therapeutic agent is a substance that alleviates, ameliorates, relieves, inhibits, prevents, delays onset of, reduces severity of, and/or reduces incidence of one or more symptoms or features of a disease, disorder, and/or condition in a subject when administered to the subject in an effective amount. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, a therapeutic agent is a provided compound, e.g., a provided oligonucleotide.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

As those skilled in the art will appreciate, methods and compositions described herein relating to provided compounds (e.g., oligonucleotides) generally also apply to pharmaceutically acceptable salts of such compounds.

Description of Certain Embodiments

Oligonucleotides are useful tools for a wide variety of applications. For example, MAPT oligonucleotides are useful in therapeutic, diagnostic, and research applications, including the treatment of a variety of MAPT-associated conditions, disorders, and diseases, including but not limited to Alzheimer's Disease (AD) and Frontotemporal Dementia (FTD). The use of naturally occurring nucleic acids (e.g., unmodified DNA or RNA) is limited, for example, by their susceptibility to endo- and exo-nucleases. As such, various synthetic counterparts have been developed to circumvent these shortcomings and/or to further improve various properties and activities. These include synthetic oligonucleotides that contain chemical modifications, e.g., base modifications, sugar modifications, backbone modifications, etc., which, among other things, render these molecules less susceptible to degradation and improve other properties and/or activities. From a structural point of view, modifications to internucleotidic linkages can introduce chirality, and certain properties may be affected by configurations of linkage phosphorus atoms of oligonucleotides. For example, binding affinity, sequence specific binding to complementary RNA, stability against nucleases, cleavage of target nucleic acids, delivery, pharmacokinetics, etc., can be affected by, inter alia, chirality of backbone linkage phosphorus atoms.

In some embodiments, a MAPT oligonucleotide comprises a sequence that is completely or substantially identical to or is completely or substantially complementary to 10 or more (e.g., 10, 11, 12, 13, 14, 15, 16, 17, 18, 19, 20 or more) contiguous bases of a MAPT genomic sequence or a transcript therefrom (e.g., mRNA (e.g., pre-mRNA, mRNA after splicing, etc.)). In some embodiments, a MAPT oligonucleotide comprises a sequence that is completely complementary to 10 or more (e.g., 10, 11, 12, 13, 14, 15, 16, 17, 18, 19, 20 or more) contiguous bases of a MAPT transcript. In some embodiments, the number of contiguous bases is about 15-20. In some embodiments, the number of contiguous bases is about 20. In some embodiments, an oligonucleotide that targets MAPT can hybridize with a MAPT transcript (e.g., pre-mRNA, RNA, etc.) and can reduce the level of the MAPT transcript and/or a protein encoded by the MAPT transcript.

In some embodiments, the present disclosure provides a MAPT oligonucleotide as disclosed herein, e.g., in a Table. In some embodiments, the present disclosure provides a MAPT oligonucleotide having a base sequence disclosed herein, e.g., in a Table, or a portion thereof comprising at least 10 (e.g., 10, 11, 12, 13, 14, 15, 16, 17, 18, 19, 20 or more) contiguous bases, wherein the MAPT oligonucleotide is stereorandom or not chirally controlled, and wherein each T can be independently substituted with U and vice versa.

In some embodiments, internucleotidic linkages of an oligonucleotide comprise or consist of 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more chirally controlled internucleotidic linkages. In some embodiments, the present disclosure provides a MAPT oligonucleotide composition wherein the MAPT oligonucleotides comprise at least one chirally controlled internucleotidic linkage. In some embodiments, the present disclosure provides a MAPT oligonucleotide composition wherein the MAPT oligonucleotides are stereorandom or not chirally controlled. In some embodiments, in a MAPT oligonucleotide, at least one internucleotidic linkage is stereorandom and at least one internucleotidic linkage is chirally controlled.

In some embodiments, internucleotidic linkages of an oligonucleotide comprise or consist of one or more negatively charged internucleotidic linkages (e.g., phosphorothioate internucleotidic linkages, natural phosphate linkages, etc.). In some embodiments, the present disclosure pertains to a MAPT oligonucleotide which comprises at least one neutral or non-negatively charged internucleotidic linkage as described in the present disclosure.

Mapt

In some embodiments, MAPT refers to a gene or a gene product thereof (including but not limited to, a nucleic acid, including but not limited to a DNA or RNA, a transcript, a protein encoded thereby; can be from any form of MAPT, e.g., wide-type or mutant alleles) from any species, which may be known as: MAPT, TAU, MSTD, PPND, DDPAC, MAPTL, MTBT1, MTBT2, FTDP-17, or PPP1R103. In some embodiments, it refers to the gene and product thereof in human. In some embodiments, it refers to the gene and product thereof in a non-human primate. Various MAPT sequences, including variants thereof, from human, mouse, rat, monkey, etc., are readily available to those of skill in the art. In some embodiments, MAPT is a human or mouse MAPT, which is wild-type or mutant. It has been reported that MAPT can have a number of functions. Various technologies, e.g., assays, cells, animal models, etc., have also been reported and can be utilized for characterization and/or assessment of provided technologies (e.g., oligonucleotides, compositions, methods, etc.) in accordance with the present disclosure.

In some embodiments, a MAPT gene, transcript (e.g., mRNA before or after splicing), or protein variant or isoform comprises a mutation. In some embodiments, a MAPT gene, transcript or protein is or a transcription or translation product of an alternatively spliced variant or isoform.

MAPT-Associated Conditions, Disorders or Diseases

Various conditions, disorders or diseases are reported to be associated with MAPT. Generally, a disease, disorder, or condition is associated with MAPT if the presence, level, activity, and/or form of MAPT and/or products (e.g., transcripts, encoded proteins, etc.) thereof correlates with incidence of and/or susceptibility to the disease, disorder, or condition (e.g., across a relevant population). In some embodiments, a condition, disorder or disease associated with MAPT may be treated and/or prevented by reducing expression, level and/or activity of MAPT transcripts and/or proteins.

Various MAPT-associated conditions, disorders or diseases are reported. In some embodiments, a MAPT-associated condition, disorder or disease is Alzheimer's Disease (AD). In some embodiments, a MAPT-associated condition, disorder or disease is Frontotemporal Dementia (FTD).

Among other things, provided technologies are useful for treating or preventing a condition, disorder or disease associated with MAPT, e.g., Alzheimer's Disease (AD), Frontotemporal Dementia (FTD), etc. In some embodiments, the present disclosure pertains to the use of a MAPT oligonucleotide or a composition thereof in the treatment of a MAPT-associated disorder, disease or condition, e.g., Alzheimer's Disease (AD), Frontotemporal Dementia (FTD), etc.

The Alzheimer's Association has reported that by its estimation, 1 in 10 people age 65 or older have AD, and that nearly 6 million individuals in the USA may suffer from this disease. AD reportedly leads to progressive loss of cognitive abilities, loss of independence, and eventual death. AD has reported to be characterized by extracellular amyloid plaques as well as intracellular accumulation of tau aggregates. In addition to AD, tau is also reported to be involved in the pathophysiology of Frontotemporal Dementia (FTD). FTD is reported to be a heterogeneous group of disorders with a prevalence of about 20 in 100,000 individuals. It is reported that FTD is characterized by degeneration of the frontal, temporal and other cortical regions as well as the basal ganglia, thalamus, and other regions and is associated with Tau pathology in approximately one half of cases. It is reported that FTD subtypes that are associated with tau pathology include behavioral variant FTD (bvFTD) characterized by neuropsychiatric symptoms, non-fluent variant primary progressive aphasia (nfvPPA) characterized by reduced word output and word finding difficulties, and sometimes also motor syndromes including Corticobasal Degeneration (CBD) and Primary Progressive Aphasia (PSP). It is also reported that in contrast to AD which mainly affects older individuals, FTD typically presents at an earlier age and therefore is more likely to affect individuals who are still working than AD and like AD is eventually fatal.

While not wishing to be bound by any theory, it is noted that there are, according to certain reports, genetic, and histological evidences (in genetic and sporadic disease) to the importance of tau in causing AD and FTD pathology, disability and death. Although MAPT is reported to be not genome-wide significant for AD itself in some cases, it is reported to be genome-wide significant for shared AD/PD risk (Desikan et al., 2015). It is reported that MAPT has been unequivocally demonstrated to be causative in forms of FTD with underlying tau pathology based mainly on family-based genetic studies (Greaves and Rohrer, 2019). In some cases, tau pathology is reported to be very well established.

Tau is reported to be a neuronal scaffolding protein which in disease states aggregates intracellularly to form neurofibrillary tangles (NFT), a key reportedly defining pathology in AD. It is reported that Tau pathology can spread from one neuron to the next via a prion-like mechanism and NFTs are typically found in pyramidal neurons of the hippocampus, of the entorhinal cortex and of layers III and V of the isocortex, leaving interneurons largely unaffected (Braak et al., 2016). Furthermore, it has been reported that tau isolated from AD brain is pathogenic when injected into rodent brain (Goedert et al., 2017).

In some embodiments, provided technologies (e.g., oligonucleotides, compositions, methods, etc.) reduce expression, level, functions, and/or activities of tau transcripts and proteins encoded thereby. In some embodiments, such reduction addresses intracellular aggregation. In some embodiments, such reduction addresses tau spreading. In some embodiments, such reduction addresses intracellular aggregation and tau spreading.

In some embodiments, the present disclosure provides methods for reducing a level, function and/or activity of a tau protein, comprising contacting the protein with an oligonucleotide or a composition of the present disclosure. In some embodiments, the present disclosure provides methods for reducing tau intracellular aggregation, comprising contacting the protein with an oligonucleotide or a composition of the present disclosure. In some embodiments, the present disclosure provides methods for reducing tau spreading, comprising contacting the protein with an oligonucleotide or a composition of the present disclosure. In some embodiments, the present disclosure provides methods for reducing tau intracellular aggregation and spreading, comprising contacting the protein with an oligonucleotide or a composition of the present disclosure. In some embodiments, the present disclosure provides methods for reducing a level, function and/or activity of a tau protein in a system, comprising administering to the system an effective amount of an oligonucleotide or composition of the present disclosure. In some embodiments, the present disclosure provides methods for reducing tau intracellular aggregation in a system, comprising administering to the system an effective amount of an oligonucleotide or composition of the present disclosure. In some embodiments, the present disclosure provides methods for reducing tau spreading in a system, comprising administering to the system an effective amount of an oligonucleotide or composition of the present disclosure. In some embodiments, the present disclosure provides methods for reducing tau intracellular aggregation and spreading in a system, comprising administering to the system an effective amount of an oligonucleotide or composition of the present disclosure. In some embodiments, a system is in vitro. In some embodiments, a system is in vivo. In some embodiments, a system is or comprises a cell. In some embodiments, a system is or comprises a tissue. In some embodiments, a system is or comprises an organ. In some embodiments, a system is or comprises a sample. In some embodiments, a system is or comprises a subject. In some embodiments, a system is or comprises a mouse. In some embodiments, a system is or comprises a non-human primate. In some embodiments, a system is or comprises a human.

In some embodiments, treatment or prevention with provided technologies reduces rate of tau production and reduces or halts or reverses accumulation of aggregates and further spreading. In some embodiments, treatment or prevention with provided technologies reduces the rate of clinical decline, or delays or prevents onset of a condition, disorder or disease.

As appreciated by those skilled in the art, mechanisms, genotypes, symptoms, biomarkers, etc. of such conditions, disorders or diseases may be utilized in accordance with the present disclosure to characterize/assess provided technologies.

Oligonucleotides

Among other things, the present disclosure provides oligonucleotides of various designs, which may comprises various nucleobases and patterns thereof, sugars and patterns thereof, internucleotidic linkages and patterns thereof, and/or additional chemical moieties and patterns thereof as described in the present disclosure. In some embodiments, provided MAPT oligonucleotides can direct a decrease in the expression, level and/or activity of a MAPT gene and/or one or more of its products (e.g., transcripts, mRNA, proteins, etc.). In some embodiments, provided MAPT oligonucleotides can direct a decrease in the expression, level and/or activity of a MAPT gene and/or one or more of its products in a cell of a subject or patient. In some embodiments, a cell normally expresses MAPT or produces MAPT protein. In some embodiments, provided MAPT oligonucleotides can direct a decrease in the expression, level and/or activity of a MAPT target gene or a gene product and has a base sequence which consists of, comprises, or comprises a portion (e.g., a span of 10, 11, 12, 13, 14, 15, 16, 17, 18, 19, 20 or more contiguous bases) of the base sequence of a MAPT oligonucleotide disclosed herein, wherein each T can be independently substituted with U and vice versa, and the oligonucleotide comprises at least one non-naturally-occurring modification of a base, sugar and/or internucleotidic linkage.

In some embodiments, MAPT oligonucleotides can direct a decrease in the expression, level and/or activity of a target gene, e.g., a MAPT target gene, or a product thereof. In some embodiments, MAPT oligonucleotides can direct a decrease in the expression, level and/or activity of a MAPT target gene or a product thereof via RNase H-mediated knockdown. In some embodiments, MAPT oligonucleotides can direct a decrease in the expression, level and/or activity of a MAPT target gene or a product thereof by sterically blocking translation after binding to a MAPT target gene mRNA, and/or by altering or interfering with mRNA splicing. Regardless, however, the present disclosure is not limited to any particular mechanism. In some embodiments, the present disclosure provides oligonucleotides, compositions, methods, etc., capable of operating via double-stranded RNA interference, single-stranded RNA interference, RNase H-mediated knock-down, steric hindrance of translation, or a combination of two or more such mechanisms.

In some embodiments, a MAPT oligonucleotide is capable of mediating a decrease in the expression, level and/or activity of MAPT. In some embodiments, a MAPT oligonucleotide is capable of mediating a decrease in the level of tau proteins. In some embodiments, a MAPT oligonucleotide is capable of mediating a decrease in the level of tau proteins. In some embodiments, a MAPT oligonucleotide is capable of mediating a decrease in the level of tau aggregation, e.g., in a neuron. In some embodiments, a MAPT oligonucleotide is capable of mediating a decrease in the level of tau spreading, e.g., from one neuron to another.

In some embodiments, a MAPT oligonucleotide is capable of mediating a decrease in the expression, level and/or activity of MAPT via a mechanism involving mRNA degradation and/or steric hindrance of translation of MAPT mRNA.

In some embodiments, a MAPT oligonucleotide is capable of mediating a decrease in the expression, level and/or activity of more than one MAPT allele.

In some embodiments, the present disclosure pertains to a method of treatment of a MAPT-associated disease, disorder or condition, wherein MAPT is overexpressed, comprising the step of administering a therapeutically effective amount of a MAPT oligonucleotide capable of mediating a decrease in the expression, level and/or activity of MAPT. In some embodiments, multiple forms, e.g., alleles, of MAPT may exist, and provided technologies can reduce expression, level and/or activity of two or more or all of the forms and products thereof.

In some embodiments, the present disclosure pertains to a method of treatment of a MAPT-associated disease, disorder or condition, comprising the step of administering a therapeutic amount of a MAPT oligonucleotide capable of mediating a decrease in the expression, level and/or activity of MAPT.

In some embodiments, a MAPT oligonucleotide is capable of mediating a decrease in the expression, level and/or activity of MAPT via a mechanism involving splicing modulation, e.g., exon skipping.

In some embodiments, a MAPT oligonucleotide comprises a structural element or a portion thereof described herein, e.g., in a Table. In some embodiments, a MAPT oligonucleotide comprises a base sequence (or a portion thereof) described herein, wherein each T can be independently substituted with U and vice versa, a chemical modification or a pattern of chemical modifications (or a portion thereof), and/or a format or a portion thereof described herein. In some embodiments, a MAPT oligonucleotide has a base sequence which comprises the base sequence (or a portion thereof) wherein each T can be independently substituted with U, pattern of chemical modifications (or a portion thereof), and/or a format of an oligonucleotide disclosed herein, e.g., in a Table, or otherwise disclosed herein. In some embodiments, such oligonucleotides, e.g., MAPT oligonucleotides reduce expression, level and/or activity of a gene, e.g., a MAPT gene, or a gene product thereof.

Among other things, MAPT oligonucleotides may hybridize to their target nucleic acids (e.g., pre-mRNA, mature mRNA, etc.). For example, in some embodiments, a MAPT oligonucleotide can hybridize to a MAPT nucleic acid derived from a DNA strand (either strand of the MAPT gene). In some embodiments, a MAPT oligonucleotide can hybridize to a MAPT transcript. In some embodiments, a MAPT oligonucleotide can hybridize to a MAPT nucleic acid in any stage of RNA processing, including but not limited to a pre-mRNA or a mature mRNA. In some embodiments, a MAPT oligonucleotide can hybridize to any element of a MAPT nucleic acid or its complement, including but not limited to: a promoter region, an enhancer region, a transcriptional stop region, a translational start signal, a translation stop signal, a coding region, a non-coding region, an exon, an intron, an intron/exon or exon/intron junction, the 5' UTR, or the 3' UTR. In some embodiments, MAPT oligonucleotides can hybridize to their targets with no more than 2 mismatches. In some embodiments, MAPT oligonucleotides can hybridize to their targets with no more than one mismatch. In some embodiments, MAPT oligonucleotides can hybridize to their targets with no mismatches (e.g., when all C-G and/or A-T/U base paring).

In some embodiments, an oligonucleotide can hybridize to two or more variants of transcripts. In some embodiments, a MAPT oligonucleotide can hybridize to two or more or all variants of MAPT transcripts. In some embodiments, a MAPT oligonucleotide can hybridize to two or more or all variants of MAPT transcripts derived from the sense strand.

In some embodiments, a MAPT target of a MAPT oligonucleotide is a MAPT RNA which is not a mRNA.

In some embodiments, oligonucleotides, e.g., MAPT oligonucleotides, contain increased levels of one or more isotopes. In some embodiments, oligonucleotides, e.g., MAPT oligonucleotides, are labeled, e.g., by one or more isotopes of one or more elements, e.g., hydrogen, carbon, nitrogen, etc. In some embodiments, oligonucleotides, e.g., MAPT oligonucleotides, in provided compositions, e.g., oligonucleotides of a plurality of a composition, comprise base modifications, sugar modifications, and/or internucleotidic linkage modifications, wherein the oligonucleotides contain an enriched level of deuterium. In some embodiments, oligonucleotides, e.g., MAPT oligonucleotides, are labeled with deuterium (replacing —$^1$H with —$^2$H) at one or more positions. In some embodiments, one or more $^1$H of an oligonucleotide chain or any moiety conjugated to the oligonucleotide chain (e.g., a targeting moiety, etc.) is substituted with $^2$H. Such oligonucleotides can be used in compositions and methods described herein.

In some embodiments, the present disclosure provides an oligonucleotide composition comprising a plurality of oligonucleotides which:

1) have a common base sequence complementary to a target sequence (e.g., a MAPT target sequence) in a transcript; and
2) comprise one or more modified sugar moieties and/or modified internucleotidic linkages.

In some embodiments, MAPT oligonucleotides having a common base sequence may have the same pattern of nucleoside modifications, e.g., sugar modifications, base modifications, etc. In some embodiments, a pattern of nucleoside modifications may be represented by a combination of locations and modifications. In some embodiments, a pattern of backbone linkages comprises locations and types (e.g., phosphate, phosphorothioate, substituted phosphorothioate, etc.) of each internucleotidic linkage.

In some embodiments, oligonucleotides of a plurality, e.g., in provided compositions, are of the same oligonucleotide type. In some embodiments, oligonucleotides of an oligonucleotide type have a common pattern of sugar modifications. In some embodiments, oligonucleotides of an oligonucleotide type have a common pattern of base modifications. In some embodiments, oligonucleotides of an oligonucleotide type have a common pattern of nucleoside modifications. In some embodiments, oligonucleotides of an oligonucleotide type have the same constitution. In some embodiments, oligonucleotides of an oligonucleotide type are identical. In some embodiments, oligonucleotides of a plurality are identical. In some embodiments, oligonucleotides of a plurality share the same constitution.

In some embodiments, as exemplified herein, MAPT oligonucleotides are chiral controlled, comprising one or more chirally controlled internucleotidic linkages. In some embodiments, MAPT oligonucleotides are stereochemically pure. In some embodiments, MAPT oligonucleotides are substantially separated from other stereoisomers.

In some embodiments, MAPT oligonucleotides comprise one or more modified nucleobases, one or more modified sugars, and/or one or more modified internucleotidic linkages.

In some embodiments, MAPT oligonucleotides comprise one or more modified sugars. In some embodiments, oligonucleotides of the present disclosure comprise one or more modified nucleobases. Various modifications can be introduced to a sugar and/or nucleobase in accordance with the present disclosure. For example, in some embodiments, a modification is a modification described in U.S. Pat. No. 9,006,198. In some embodiments, a modification is a modification described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the sugar, base, and internucleotidic linkage modifications of each of which are independently incorporated herein by reference.

As used in the present disclosure, in some embodiments, "one or more" is 1-200, 1-150, 1-100, 1-90, 1-80, 1-70, 1-60, 1-50, 1-40, 1-30, or 1, 2, 3, 4, 5, 6, 7, 8, 9, 10, 11, 12, 13, 14, 15, 16, 17, 18, 19, 20, 21, 22, 23, 24, or 25. In some embodiments, "one or more" is one. In some embodiments, "one or more" is two. In some embodiments, "one or more" is three. In some embodiments, "one or more" is four. In some embodiments, "one or more" is five. In some embodiments, "one or more" is six. In some embodiments, "one or more" is seven. In some embodiments, "one or more" is eight. In some embodiments, "one or more" is nine. In some embodiments, "one or more" is ten. In some embodiments, "one or more" is at least one. In some embodiments, "one or more" is at least two. In some embodiments, "one or more" is at least three. In some embodiments, "one or more" is at least four. In some embodiments, "one or more" is at least five. In some embodiments, "one or more" is at least six. In some embodiments, "one or more" is at least seven. In some embodiments, "one or more" is at least eight. In some embodiments, "one or more" is at least nine. In some embodiments, "one or more" is at least ten.

As used in the present disclosure, in some embodiments, "at least one" is 1-200, 1-150, 1-100, 1-90, 1-80, 1-70, 1-60, 1-50, 1-40, 1-30, or 1, 2, 3, 4, 5, 6, 7, 8, 9, 10, 11, 12, 13, 14, 15, 16, 17, 18, 19, 20, 21, 22, 23, 24, or 25. In some embodiments, "at least one" is one. In some embodiments, "at least one" is two. In some embodiments, "at least one" is three. In some embodiments, "at least one" is four. In some embodiments, "at least one" is five. In some embodiments, "at least one" is six. In some embodiments, "at least one" is seven. In some embodiments, "at least one" is eight. In some embodiments, "at least one" is nine. In some embodiments, "at least one" is ten.

In some embodiments, a MAPT oligonucleotide is or comprises a MAPT oligonucleotide described in a Table.

As demonstrated in the present disclosure, in some embodiments, a provided oligonucleotide (e.g., a MAPT oligonucleotide) is characterized in that, when it is contacted with the transcript in a knockdown system, knockdown of its target (e.g., a MAPT transcript for a MAPT oligonucleotide.

In some embodiments, oligonucleotides are provided as salt forms. In some embodiments, oligonucleotides are provided as salts comprising negatively-charged internucleotidic linkages (e.g., phosphorothioate internucleotidic linkages, natural phosphate linkages, etc.) existing as their salt forms. In some embodiments, oligonucleotides are provided as pharmaceutically acceptable salts. In some embodiments, oligonucleotides are provided as metal salts. In some embodiments, oligonucleotides are provided as sodium salts. In some embodiments, oligonucleotides are provided as metal salts, e.g., sodium salts, wherein each negatively-charged internucleotidic linkage is independently in a salt form (e.g., for sodium salts, —O—P(O)(SNa)—O— for a phosphorothioate internucleotidic linkage, —O—P(O)(ONa)—O— for a natural phosphate linkage, etc.).

Base Sequences

In some embodiments, a MAPT oligonucleotide comprises a base sequence described herein or a portion (e.g., a span of 5-50, 5-40, 5-30, 5-20, or 5, 6, 7, 8, 9, 10, 11, 12, 13, 14, 15, 16, 17, 18, 19, 20, or at least 10, at least 15, contiguous nucleobases) thereof with 0-5 (e.g., 0, 1, 2, 3, 4 or 5) mismatches, wherein each T can be independently substituted with U and vice versa. In some embodiments, a MAPT oligonucleotide comprises a base sequence described herein, or a portion thereof, wherein a portion is a span of at least 10 contiguous nucleobases, or a span of at least 15 contiguous nucleobases with 1-5 mismatches. In some embodiments, MAPT oligonucleotides comprise abase sequence described herein, or a portion thereof, wherein a portion is a span of at least 10 contiguous nucleobases, or a span of at least 10 contiguous nucleobases with 1-5 mismatches, wherein each T can be independently substituted with U and vice versa. In some embodiments, base sequences of oligonucleotides comprise or consists of 10-50 (e.g., about or at least 10, 11, 12, 13, 14, 15, 16, 17, 18, 19, 20, 21, 22, 23, 24, 25, 30, 35, 40, 45; in some embodiments, at least 15; in some embodiments, at least 16; in some embodiments, at least 17; in some embodiments, at least 18; in some embodiments, at least 19; in some embodiments, at least 20; in some embodiments, at least 21; in some embodiments, at least 22; in some embodiments, at least 23; in some embodiments, at least 24; in some embodiments, at least 25) contiguous bases of a base sequence that is identical to or complementary to a base sequence of a MAPT gene or a transcript (e.g., mRNA) thereof (e.g., in an intron, e.g., intron 11).

Base sequences of MAPT oligonucleotides, as appreciated by those skilled in the art, typically have sufficient length and complementarity to their targets, e.g., RNA transcripts (e.g., pre-mRNA, mature mRNA, etc.) to mediate target-specific knockdown. In some embodiments, the base sequence of a MAPT oligonucleotide has a sufficient length and identity to a MAPT transcript target to mediate target-specific knockdown. In some embodiments, the MAPT oligonucleotide is complementary to a portion of a MAPT transcript (a MAPT transcript target sequence). In some embodiments, the base sequence of a MAPT oligonucleotide has 90% or more identity with the base sequence of an oligonucleotide disclosed in a Table, wherein each T can be independently substituted with U and vice versa. In some embodiments, the base sequence of a MAPT oligonucleotide has 95% or more identity with the base sequence of an oligonucleotide disclosed in a Table, wherein each T can be independently substituted with U and vice versa. In some embodiments, the base sequence of a MAPT oligonucleotide comprises a continuous span of 15 or more bases of an oligonucleotide disclosed in a Table, wherein each T can be independently substituted with U and vice versa, except that one or more bases within the span are abasic (e.g., a nucleobase is absent from a nucleotide). In some embodiments, the base sequence of a MAPT oligonucleotide comprises a continuous span of 19 or more bases of a MAPT oligonucleotide disclosed herein, except that one or more bases within the span are abasic (e.g., a nucleobase is absent from a nucleotide). In some embodiments, the base sequence of a MAPT oligonucleotide comprises a continuous span of 19 or more bases of an oligonucleotide disclosed herein, wherein each T can be independently substituted with U and vice versa, except for a difference in the 1 or 2 bases at the 5' end and/or 3' end of the base sequences.

In some embodiments, a base sequence of an oligonucleotide is, comprises, or comprises 10-20, e.g., 10, 11, 12, 13, 14, 15, 16, 17, 18, 19 or 20 contiguous bases of ACGTTGCAGTGTTCCACUAU (SEQ ID NO: 1), ACTATCCTCCTTCAGCUCCU (SEQ ID NO: 2), AGTGTTCCACTATCCUCCUU (SEQ ID NO: 3), ATCCTCCTTCAGCTCCUGCA (SEQ ID NO: 4), CACGTTGCAGTGTTCCACUA (SEQ ID NO: 5), CACTATCCTCCTTCAGCUCC (SEQ ID NO: 6), CAGTGTTCCACTATCCUCCU (SEQ ID NO: 7), CCACGTTGCAGTGTTCCACU (SEQ ID NO: 8), CCACTATCCTCCTTCAGCUC (SEQ ID NO: 9), CGTTGCAGTGTTCCACUAUC (SEQ ID NO: 10), CTATCCTCCTTCAGCUCCUG (SEQ ID NO: 11), GCAGTGTTCCACTATCCUCC (SEQ ID NO: 12), GTGTTCCACTATCCTCCUUC (SEQ ID NO: 13), GTTCCACTATCCTCCUUCAG (SEQ ID NO: 14), GUGUUCCACTATCCTCCTTC (SEQ ID NO: 15), TATCCTCCTTCAGCTCCUGC (SEQ ID NO: 16), TCCACTATCCTCCTTCAGCU (SEQ ID NO: 17), TGCAGTGTTCCACTAUCCUC (SEQ ID NO: 18), TGTTCCACTATCCTCCUUCA (SEQ ID NO: 19), TTCCACTATCCTCCUUCAGC (SEQ ID NO: 20), or TTGCAGTGTTCCACTAUCCU (SEQ ID NO: 21), wherein each T may be independently replaced with U and vice versa. In some embodiments, a base sequence of an oligonucleotide is or comprises such a sequence, wherein each T may be independently replaced with U and vice versa. In some embodiments, a base sequence of an oligonucleotide is such a sequence, wherein each T may be independently replaced with U and vice versa. In some embodiments, a base sequence of an oligonucleotide is, comprises, or comprises 10-20, e.g., 10, 11, 12, 13, 14, 15, 16, 17, 18, 19 or 20 contiguous bases of ACGTTGCAGTGTTCCACUAU (SEQ ID NO: 1), ACTATCCTCCTTCAGCUCCU (SEQ ID NO: 2), AGTGTTCCACTATCCUCCUU (SEQ ID NO: 3), ATCCTCCTTCAGCTCCUGCA (SEQ ID NO: 4), CACGTTGCAGTGTTCCACUA (SEQ ID NO: 5), CACTATCCTCCTTCAGCUCC (SEQ ID NO: 6), CAGTGTTCCACTATCCUCCU (SEQ ID NO: 7), CCACGTTGCAGTGTTCCACU (SEQ ID NO: 8), CCACTATCCTCCTTCAGCUC (SEQ ID NO: 9), CGTTGCAGTGTTCCACUAUC (SEQ ID NO: 10), CTATCCTCCTTCAGCUCCUG (SEQ ID NO: 11), GCAGTGTTCCACTATCCUCC (SEQ ID NO: 12), GTGTTCCACTATCCTCCUUC (SEQ ID NO: 13), GTTCCACTATCCTCCUUCAG (SEQ ID NO: 14), GUGUUCCACTATCCTCCTTC (SEQ ID NO: 15), TATCCTCCTTCAGCTCCUGC (SEQ ID NO: 16), TCCACTATCCTCCTTCAGCU (SEQ ID NO: 17), TGCAGTGTTCCACTAUCCUC (SEQ ID NO: 18), TGTTCCACTATCCTCCUUCA (SEQ ID NO: 19), TTCCACTATCCTCCTUCAGC (SEQ ID NO: 20), or TTGCAGTGTTCCACTAUCCU (SEQ ID NO: 21). In some embodiments, a base sequence of an oligonucleotide is or comprises such a sequence. In some embodiments, a base sequence of an oligonucleotide is such a sequence.

In some embodiments, a base sequence of an oligonucleotide is, comprises, or comprises 10-20, e.g., 10, 11, 12, 13, 14, 15, 16, 17, 18, 19 or 20 contiguous bases of GTGTTCCACTATCCTCCUUC (SEQ ID NO: 13), wherein each T may be independently replaced with U and vice versa. In some embodiments, a base sequence of an oligonucleotide is or comprises GTGTTCCACTATCCTCCUUC (SEQ ID NO: 13), wherein each T may be independently replaced with U and vice versa. In some embodiments, a base sequence of an oligonucleotide is GTGTTCCACTATCCTCCUUC (SEQ ID NO: 13), wherein each T may be independently replaced with U and vice versa. In some embodiments, a base sequence of an oligonucleotide is, comprises, or comprises 10-20, e.g., 10, 11, 12, 13, 14, 15, 16, 17, 18, 19 or 20 contiguous bases of GTGTTCCACTATCCTCCUUC (SEQ ID NO: 13). In some embodiments, a base sequence of an oligonucleotide is or comprises GTGTTCCACTATCCTCCUUC (SEQ ID NO: 13). In some embodiments, a base sequence of an oligonucleotide is GTGTTCCACTATCCTCCUUC (SEQ ID NO: 13).

In some embodiments, the present disclosure pertains to an oligonucleotide having a base sequence which comprises the base sequence of any oligonucleotide disclosed herein, wherein each T may be independently replaced with U and vice versa.

In some embodiments, the present disclosure pertains to an oligonucleotide having a base sequence which comprises at least 15 contiguous bases of the base sequence of any oligonucleotide disclosed herein, wherein each T may be independently replaced with U and vice versa.

In some embodiments, the present disclosure pertains to an oligonucleotide having a base sequence which is at least 90% identical to the base sequence of any oligonucleotide disclosed herein, wherein each T may be independently replaced with U and vice versa.

In some embodiments, the present disclosure pertains to an oligonucleotide having a base sequence which is at least 95% identical to the base sequence of any oligonucleotide disclosed herein, wherein each T may be independently replaced with U and vice versa.

In some embodiments, a base sequence of an oligonucleotide is, comprises, or comprises 10-20, e.g., 10, 11, 12, 13, 14, 15, 16, 17, 18, 19 or 20 contiguous bases of the base sequence of any oligonucleotide described herein, wherein each T may be independently replaced with U and vice versa.

In some embodiments, a MAPT oligonucleotide is selected from Table 1.

In some embodiments, the base sequence of a MAPT oligonucleotide is complementary to that of a MAPT transcript or a portion thereof.

In some embodiments, the base sequence of a MAPT oligonucleotide is complementary to a portion of a MAPT nucleic acid sequence, e.g., a MAPT gene sequence, a MAPT transcript, a MAPT mRNA sequence, etc. In some embodiments, a MAPT oligonucleotide is identical to a portion of a MAPT nucleic acid sequence, e.g., a MAPT gene sequence, a MAPT transcript, a MAPT mRNA sequence, etc. In some embodiments, a portion is or comprises 10 or more, e.g., 10, 11, 12, 13, 14, 15, 16, 17, 18, 19, 20 or more, contiguous nucleobases. In some embodiments, it is about 15 or more. In some embodiments, it is about 16 or more. In some embodiments, it is about 17 or more. In some embodiments, it is about 18 or more. In some embodiments, it is about 19 or more. In some embodiments, it is about 20 or more. In some embodiments, the base sequence of such a portion is characteristic of MAPT in that no other genomic or transcript sequences in a system contain the same sequence as the portion. In some embodiments, no other genomic or transcript sequences in a system contain a sequence that differs from such a portion at no more than 1 nucleobase. In some embodiments, no other genomic or transcript sequences in a system contain a sequence that differs from such a portion at no more than 2 nucleobases. In some embodiments, a portion of a gene that is complementary to an oligonucleotide is referred to as a target sequence of the oligonucleotide. In some embodiments, a system is or comprises a cell, sample, tissue, organ, or a species. For example, for oligonucleotides targeting human MAPT, a relevant species in many embodiments is human. In some embodiments, a system can be or comprises multiple species, e.g., when cross-species activities and/or properties are characterized and/or assessed. In some embodiments, such a portion is in an exon. In some embodiments, such a portion is in an intron. In some embodiments, such a portion is in intron 11. In some embodiments, such a portion spans an intron and an exon. In some embodiments, such a portion spans two exons. In some embodiments, such a portion is in a 5'-UTR region. In some embodiments, such a portion is in a 3'-UTR region.

In some embodiments, a MAPT oligonucleotide target two or more or all alleles (if multiple alleles exist in a relevant system) of MAPT. In some embodiments, an oligonucleotide reduces expressions, levels and/or activities of both wild-type MAPT and mutant MAPT, and/or transcripts and/or products thereof.

In some embodiments, base sequences of provided oligonucleotides are fully complementary to both human and a non-human primate (NHP) MAPT target sequences. In some embodiments, such sequences can be particularly useful as they can be readily assessed in both human and non-human primates.

In some embodiments, a MAPT oligonucleotide comprises a base sequence or portion thereof described in the Tables, wherein each T may be independently replaced with U and vice versa, and/or a sugar, nucleobase, and/or internucleotidic linkage modification and/or a pattern thereof described in the Tables, and/or an additional chemical moiety (in addition to an oligonucleotide chain, e.g., a target moiety, a lipid moiety, a carbohydrate moiety, etc.) described in the Tables.

In some embodiments, the terms "complementary," "fully complementary" and "substantially complementary" may be used with respect to the base matching between n oligonucleotide (e.g., a MAPT oligonucleotide) base sequence and a target sequence (e.g., a MAPT target sequence), as will be understood by those skilled in the art from the context of their use. As a non-limiting example, if a target sequence has, for example, a base sequence of 5'-GCAUAGCGAGCGAGGGAAAAC-3' (SEQ ID NO: 22), an oligonucleotide with a base sequence of 5'GUUUUCCCUCGCUCGCUAUGC-3' (SEQ ID NO: 23) is complementary (fully complementary) to such a target sequence. It is noted that substitution of T for U, or vice versa, generally does not alter the amount of complementarity. As used herein, an oligonucleotide that is "substantially complementary" to a target sequence is largely or mostly complementary but not 100% complementary. In some embodiments, a sequence (e.g., a MAPT oligonucleotide) which is substantially complementary has 1, 2, 3, 4 or 5 mismatches when aligned to its target sequence. In some embodiments, a MAPT oligonucleotide has a base sequence which is substantially complementary to a MAPT target sequence. In some embodiments, a MAPT oligonucleotide has a base sequence which is substantially complementary to the complement of the sequence of a MAPT oligonucleotide disclosed herein. As appreciated by those skilled in the art, in some embodiments, sequences of oligonucleotides need not be 100% complementary to their targets for the oligonucleotides to perform their functions (e.g., knockdown of target nucleic acids. Typically when determining complementarity, A and T (or U) are complementary nucleobases and C and G are complementary nucleobases.

In some embodiments, the present disclosure provides a MAPT oligonucleotide comprising a sequence found in an oligonucleotide described in a Table. In some embodiments, the present disclosure provides a MAPT oligonucleotide comprising a sequence found in an oligonucleotide described in a Table, wherein one or more U is independently and optionally replaced with T or vice versa. In some embodiments, a MAPT oligonucleotide can comprise at least one T and/or at least one U. In some embodiments, the present disclosure provides a MAPT oligonucleotide comprising a sequence found in an oligonucleotide described in a Table, wherein the said sequence has over 50% identity with the sequence of the oligonucleotide described in the Table. In some embodiments, the present disclosure provides a MAPT oligonucleotide comprising the sequence of an oligonucleotide disclosed in a Table. In some embodiments, the present disclosure provides a MAPT oligonucleotide whose base sequence is the sequence of an oligonucleotide disclosed in a Table, wherein each T may be independently replaced with U and vice versa. In some embodiments, the present disclosure provides a MAPT oligonucleotide comprising a sequence found in an oligonucleotide in a Table, wherein the oligonucleotides have a pattern of backbone linkages, pattern of backbone chiral centers, and/or pattern of backbone phosphorus modifications of the same oligonucleotide or another oligonucleotide in a Table herein.

Among other things, the present disclosure presents, in Table 1A and elsewhere, various oligonucleotides, each of which has a defined base sequence. In some embodiments, the present disclosure, the present disclosure provides an oligonucleotide whose base sequence which is, comprises, or comprises a portion of the base sequence of an oligonucleotide disclosed herein, e.g., in a Table, e.g., Table 1 herein, wherein each T may be independently replaced with U and vice versa. In some embodiments, the disclosure provides an oligonucleotide having a base sequence which is, comprises, or comprises a portion of the base sequence of an oligonucleotide disclosed herein, e.g., in a Table, wherein each T may be independently replaced with U and vice versa, wherein the oligonucleotide further comprises a chemical modification, stereochemistry, format, an additional chemical moiety described herein (e.g., a targeting moiety, lipid moiety, carbohydrate moiety, etc.), and/or another structural feature.

In some embodiments, a "portion" (e.g., of a base sequence or a pattern of modifications) is at least 5, 6, 7, 8, 9, 10, 11, 12, 13, 14, 15, 16, 17, 18, 19, or 20 monomeric units long (e.g., for a base sequence, at least 5, 6, 7, 8, 9, 10, 11, 12, 13, 14, 15, 16, 17, 18, 19, or 20 bases long). In some embodiments, a "portion" of a base sequence is at least 5 bases long. In some embodiments, a "portion" of a base sequence is at least 10 bases long. In some embodiments, a "portion" of a base sequence is at least 15 bases long. In some embodiments, a "portion" of a base sequence is at least 16, 17, 18, 19 or 20 bases long. In some embodiments, a "portion" of a base sequence is at least 20 bases long. In some embodiments, a portion of a base sequence is 10, 11, 12, 13, 14, 15, 16, 17, 18, 19 or more contiguous (consecutive) bases. In some embodiments, a portion of a base sequence is 15 or more contiguous (consecutive) bases. In some embodiments, a portion of a base sequence is 16, 17, 18, 19 or 20 or more contiguous (consecutive) bases. In some embodiments, a portion of a base sequence is 20 or more contiguous (consecutive) bases.

In some embodiments, the present disclosure provides an oligonucleotide (e.g., a MAPT oligonucleotide) whose base sequence is a base sequence of an oligonucleotide in a Table or a portion thereof, wherein each T may be independently replaced with U and vice versa. In some embodiments, the present disclosure provides a MAPT oligonucleotide of a sequence of an oligonucleotide in a Table, wherein the oligonucleotide is capable of directing a decrease in the expression, level and/or activity of a MAPT gene or a gene product thereof. As appreciated by those skilled in the art, in provided base sequence, each U may be optionally and independently replaced by T or vice versa, and a sequence can comprise a mixture of U and T. In some embodiments, C may be optionally and independently replaced with 5mC.

In some embodiments, a portion is a span of at least 15, 16, 17, 18, 19, 20, 21, 22, 23, 24, or 25 total nucleotides. In some embodiments, a portion is a span of at least 15, 16, 17, 18, 19, 20, 21, 22, 23, 24, or 25 total nucleotides with 0-3 mismatches. In some embodiments, a portion is a span of at least 15, 16, 17, 18, 19, 20, 21, 22, 23, 24, or 25 total nucleotides with 0-3 mismatches, wherein a span with 0 mismatches is complementary and a span with 1 or more mismatches is a non-limiting example of substantial complementarity. In some embodiments, a base comprises a portion characteristic of a nucleic acid (e.g., a gene) in that the portion is identical or complementary to a portion of the nucleic acid or a transcript thereof, and is not identical or complementary to a portion of any other nucleic acid (e.g., a gene) or a transcript thereof in the same genome. In some embodiments, a portion is characteristic of human MAPT.

In some embodiments, a provided oligonucleotide, e.g., a MAPT oligonucleotide, has a length of no more than about 49, 45, 40, 30, 35, 25, or 23 total nucleotides as described herein. In some embodiments, wherein the sequence recited herein starts with a U or T at the 5'-end, the U can be deleted and/or replaced by another base. In some embodiments, an oligonucleotide has abase sequence which is or comprises or comprises a portion of the base sequence of an oligonucleotide in a Table, wherein each T may be independently replaced with U and vice versa, which has a format or a portion of a format disclosed herein.

In some embodiments, oligonucleotides, e.g., MAPT oligonucleotides are stereorandom. In some embodiments, MAPT oligonucleotides are chirally controlled. In some embodiments, a MAPT oligonucleotide is chirally pure (or "stereopure", "stereochemically pure"), wherein the oligonucleotide exists as a single stereoisomeric form (in many cases a single diastereoisomeric (or "diastereomeric") form as multiple chiral centers may exist in an oligonucleotide, e.g., at linkage phosphorus, sugar carbon, etc.). As appreciated by those skilled in the art, a chirally pure oligonucleotide is separated from its other stereoisomeric forms (to the extent that some impurities may exist as chemical and biological processes, selectivities and/or purifications etc. rarely, if ever, go to absolute completeness). In a chirally pure oligonucleotide, each chiral center is independently defined with respect to its configuration (for a chirally pure oligonucleotide, each internucleotidic linkage is independently stereodefined or chirally controlled). In contrast to chirally controlled and chirally pure oligonucleotides which comprise stereodefined linkage phosphorus, racemic (or "stereorandom", "non-chirally controlled") oligonucleotides comprising chiral linkage phosphorus, e.g., from traditional phosphoramidite oligonucleotide synthesis without stereochemical control during coupling steps in combination with traditional sulfurization (creating stereorandom phosphorothioate internucleotidic linkages), refer to a random mixture of various stereoisomers (typically diastereoisomers (or "diastereomers") as there are multiple chiral centers in an oligonucleotide; e.g., from traditional oligonucleotide preparation using reagents containing no chiral elements other than those in nucleosides and linkage phosphorus). For example, for A*A*A wherein * is a phosphorothioate internucleotidic linkage (which comprises a chiral linkage phosphorus), a racemic oligonucleotide preparation includes four diastereomers [$2^2$=4, considering the two chiral linkage phosphorus, each of which can exist in either of two configurations (Sp or Rp)]: A *S A *S A, A *S A *R A, A *R A *S A, and A *R A *R A, wherein *S represents a Sp phosphorothioate internucleotidic linkage and *R represents a Rp phosphorothioate internucleotidic linkage. For a chirally pure oligonucleotide, e.g., A *S A *S A, it exists in a single stereoisomeric form and it is separated from the other stereoisomers (e.g., the diastereomers A *S A *R A, A *R A *S A, and A *R A *R A).

In some embodiments, MAPT oligonucleotides comprise 1, 2, 3, 4, 5, 6, 7, 8, 9, 10 or more stereorandom internucleotidic linkages (mixture of Rp and Sp linkage phosphorus at the internucleotidic linkage, e.g., from traditional non-chirally controlled oligonucleotide synthesis). In some embodiments, MAPT oligonucleotides comprise one or more (e.g., 1-50, 1-40, 1-30, 1-25, 1-20, 1, 2, 3, 4, 5, 6, 7, 8, 9, 10, 11, 12, 13, 14, 15, 16, 17, 18, 19, 20, 21, 22, 23, 24, 25 or more) chirally controlled internucleotidic linkages (Rp or Sp linkage phosphorus at the internucleotidic linkage, e.g., from chirally controlled oligonucleotide synthesis). In some embodiments, an internucleotidic linkage is a phosphorothioate internucleotidic linkage. In some embodiments, an internucleotidic linkage is a stereorandom phosphorothioate internucleotidic linkage. In some embodiments, an internucleotidic linkage is a chirally controlled phosphorothioate internucleotidic linkage.

Among other things, the present disclosure provides technologies for preparing chirally controlled (in some embodiments, stereochemically pure) oligonucleotides. In some embodiments, oligonucleotides are stereochemically pure. In some embodiments, oligonucleotides of the present disclosure are about 5%-100%, 10%-100%, 20%-100%, 30%-100%, 40%-100%, 50%-100%, 60%-100%, 70%-100%, 80-100%, 90-100%, 95-100%, 50%-90%, or about 5%0, 1%, 15%, 20%, 25%, 30%, 35%, 40%, 45%, 50%, 55%, 60%, 65%, 70%, 75%, 80%, 85%, 90%, 95%, or 100%, or at least about 5%, 10%, 15%, 20%, 25%, 30%, 35%, 40%, 45%, 50%, 55%, 60%, 65%, 70%, 75%, 80%, 85%, 90%, 95%, or 99%, pure. In some embodiments, internucleotidic linkages of oligonucleotides comprise or consist of one or more (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more) chiral internucleotidic linkages, each of which independently has a diastereopurity of at least 80%, 85%, 90%, 91%, 92%, 93%, 94%, 95%, 96%, 97%, 98%, 99% or 99.5%, typically at least 90%, 91%, 92%, 93%, 94%, 95%, 96%, 97%, 98%, 99% or 99.5%. In some embodiments, oligonucleotides of the present disclosure, e.g., MAPT oligonucleotides, have a diastereopurity of (DS)cIL, wherein DS is a diastereopurity as described in the present disclosure (e.g., 90%, 91%, 92%, 93%, 94%, 95%, 96%, 97%, 98%, 99% or 99.5% or more) and CIL is the number of chirally controlled internucleotidic linkages (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more). In some embodiments, DS is 95%-100%. In some embodiments, each internucleotidic linkage is independently chirally controlled, and CIL is the number of chirally controlled internucleotidic linkages.

As examples, certain MAPT oligonucleotides comprising certain example base sequences, nucleobase modifications and patterns thereof, sugar modifications and patterns thereof, internucleotidic linkages and patterns thereof, linkage phosphorus stereochemistry and patterns thereof, linkers, and/or additional chemical moieties are presented in Table 1A and Table 1B, below. Among other things, oligonucleotides, e.g., those in Table 1A, may be utilized to target a MAPT transcript, e.g., to reduce the level of a MAPT transcript and/or a product thereof.

TABLE 1A

Example MAPT Oligonucleotides/Compositions

| ID | Modified Sequence | Base Sequence | SEQ ID NO | Stereochemistry/ Linkages |
|---|---|---|---|---|
| WV-14104 | m5Ceo*m5CeoGeo*Teo*Teo*T*T*C*T*T*A*C*C*Aeo*m5Ceom5Ceo*m5Ceo*Teo | CCGTTTTCTTACCACCCT | 24 | XOXXXXXXXXXXXXXOXX |
| WV-26758 | Geo*STeoGeoTeoTeo*RC*SC*SA*SC*RT*SA*ST*SC*RC*ST*SmC*SmC*SmU*SmU*SmC | GTGTTCCACTATCCTCCUUC | 25 | SOOORSSSRSSSRSSSSSS |
| WV-26759 | Geo*STeoGeoTeoTeo*RC*SC*RA*SC*ST*SA*RT*SC*SC*ST*SmC*SmC*SmU*SmU*SmC | GTGTTCCACTATCCTCCUUC | 26 | SOOORSRSSSRSSSSSSSS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-29875 | Geo*STeoGeoTeoTeo*SC*SC*SA*SC*RT*SA*ST*SC*RC*ST*SmC*SmC*SmU*SmU*SmC | GTGTTCCACTATCCTCCUUC | 27 | SOOOSSSSRSSSRSSSSSS |
| WV-29876 | Geo*STeon001RGeon001RTeon001RTeo*SC*SC*SA*SC*RT*SA*ST*SC*RC*ST*SmC*SmC*SmU*SmU*SmC | GTGTTCCACTATCCTCCUUC | 28 | SnRnRnRSSSSRSSSRSSSSSS |
| WV-29877 | Geo*STeon001RGeoTeon001RTeo*SC*SC*SA*SC*RT*SA*ST*SC*RC*ST*SmC*SmC*SmU*SmU*SmC | GTGTTCCACTATCCTCCUUC | 29 | SnROnRSSSSRSSSRSSSSSS |
| WV-29878 | Geo*STeon001RGeoTeon001RTeo*SC*SC*SA*SC*RT*SA*ST*SC*RC*ST*SmCn001RmC*SmU*SmU*SmC | GTGTTCCACTATCCTCCUUC | 30 | SnROnRSSSSRSSSRSSnRSSS |
| WV-29879 | Geo*STeon001RGeoTeon001RTeo*SC*SC*SA*SC*RT*SA*ST*SC*RC*ST*SmC*SmCn001RmC*SmU*SmC | GTGTTCCACTATCCTCCUUC | 31 | SnROnRSSSSRSSSRSSSnRSS |
| WV-29880 | Geo*STeon001RGeoTeon001RTeo*SC*SC*SA*SC*RT*SA*ST*SC*RC*ST*SmC*SmC*SmUn001RmC*SmC | GTGTTCCACTATCCTCCUUC | 32 | SnROnRSSSSRSSSRSSSSnRS |
| WV-29881 | Geo*STeon001RGeoTeon001RTeo*SC*SC*SA*SC*RT*SA*ST*SC*RC*ST*SmC*SmC*SmU*SmUn001RmC | GTGTTCCACTATCCTCCUUC | 33 | SnROnRSSSSRSSSRSSSSSnR |
| WV-29882 | Geo*STeoGeoTeoTeo*SC*SC*RA*SC**ST*RA*ST*SC*RC*ST*SmC*SmC*SmU*SmU*SmC* | GTGTTCCACTATCCTCCUUC | 34 | SOOOSSRSSRSSRSSSSSS |
| WV-29883 | Geo*STeon001RGeon001RTeon001RTeo*SC*SC*RA*SC*ST*RA*ST*SC*RC*ST*SmC*SmC*SmU*SmU*SmC | GTGTTCCACTATCCTCCUUC | 35 | SnRnRnRSSRSSRSSRSSSSSS |
| WV-29884 | Geo*STeon001RGeoTeon001RTeo*SC*SC*RA*SC*ST*RA*ST*SC*RC*ST*SmC*SmC*SmU*SmU*SmC | GTGTTCCACTATCCTCCUUC | 36 | SnROnRSSRSSRSSRSSSSSS |
| WV-29885 | Geo*STeon001RGeoTeon001RTeo*SC*SC*RA*SC*ST*RA*ST*SC*RC*ST*SmCn001RmC*SmU*SmU*SmC | GTGTTCCACTATCCTCCUUC | 37 | SnROnRSSRSSRSSRSSnRSSS |
| WV-29886 | Geo*STeon001RGeoTeon001RTeo*SC*SC*RA*SC*ST*RA*ST*SC*RC*ST*SmC*SmCn001RmU*SmU*SmC | GTGTTCCACTATCCTCCUUC | 38 | SnROnRSSRSSRSSRSSSnRSS |
| WV-29887 | Geo*STeon001RGeoTeon001RTeo*SC*SC*RA*SC*ST*RA*ST*SC*RC*ST*SmC*SmC*SmUn001RmU*SmC | GTGTTCCACTATCCTCCUUC | 39 | SnROnRSSRSSRSSRSSSSnRS |
| WV-29888 | Geo*STeon001RGeoTeon001RTeo*SC*SC*RA*SC*ST*RA*ST*SC*RC*ST*SmC*SmC*SmUn001RmC | GTGTTCCACTATCCTCCUUC | 40 | SnROnRSSRSSRSSRSSSSSnR |
| WV-30672 | Geo*STeoGeoTeoTeo*RC*SC*RA*SC*RT*SA*ST*SC*RC*ST*SmC*SmC*SmU*SmU*SmC | GTGTTCCACTATCCTCCUUC | 41 | SOOORSRSRSSSRSSSSSS |
| WV-30673 | Geo*STeoGeoTeoTeo*RC*SC*RA*SC*ST*RA*ST*SC*RC*ST*SmC*SmC*SmU*SmU*SmC | GTGTTCCACTATCCTCCUUC | 42 | SOOORSRSSRSSRSSSSSS |
| WV-30674 | Geo*STeoGeoTeoTeo*SC*SC*RA*SC*RT*SA*ST*SC*RC*ST*SmC*SmC*SmU*SmU*SmC | GTGTTCCACTATCCTCCUUC | 43 | SOOOSSRSRSSSRSSSSSS |
| WV-30970 | Aeo*STeom5Ceom5CeoTeo*SC*SC*ST*ST*SC*RA*SG*SC*RT*SC*SmC*SmU*SmG*SmC*SmA* | ATCCTCCTTCAGCTCCUGCA | 44 | SOOOSSSSSRSSRSSSSSS |
| WV-30971 | Aeo*STeom5Ceom5CeoTeo*SC*SC*ST*ST*RC*SA*SG*SC*RT*SC*SmC*SmU*SmG*SmC*SmA* | ATCCTCCTTCAGCTCCUGCA | 45 | SOOOSSSSRSSSRSSSSSS |
| WV-30972 | Aeo*STeom5Ceom5CeoTeo*SC*SC*RT*ST*SC*RA*SG*SC*RT*SC*SmC*SmU*SmG*SmC*SmA* | ATCCTCCTTCAGCTCCUGCA | 46 | SOOOSSRSSRSSRSSSSSS |
| WV-30973 | Aeo*STeom5Ceom5CeoTeo*SC*SC*RT*ST*RC*SA*SG*SC*RT*SC*SmC*SmU*SmG*SmC*SmA* | ATCCTCCTTCAGCTCCUGCA | 47 | SOOOSSRSRSSSRSSSSSS |
| WV-30974 | Teo*SAeoTeom5Ceom5Ceo*ST*SC*SC*ST*ST*RC*SA*SG*RC*ST*SmC*SmC*SmU*SmG*SmC | TATCCTCCTTCAGCTCCUGC | 48 | SOOOSSSSSRSSRSSSSSS |
| WV-30975 | Teo*SAeoTeom5Ceom5Ceo*ST*SC*SC*RT*ST*SC*RA*SG*SC*ST*SmC*SmC*SmU*SmG*SmC | TATCCTCCTTCAGCTCCUGC | 49 | SOOOSSSRSSRSSSSSSS |
| WV-30976 | Teo*SAeoTeom5Ceom5Ceo*ST*SC*RC*ST*ST*RC*SA*SG*RC*ST*SmC*SmC*SmU*SmG*SmC | TATCCTCCTTCAGCTCCUGC | 50 | SOOOSSRSSRSSRSSSSSS |
| WV-30977 | Teo*SAeoTeom5Ceom5Ceo*ST*SC*RC*RT*ST*SC*RA*SG*SC*ST*SmC*SmC*SmU*SmG*SmC | TATCCTCCTTCAGCTCCUGC | 51 | SOOOSSRRSSRSSSSSSS |
| WV-30978 | m5Ceo*STeoAeoTeom5Ceo*SC*ST*SC*SC*RT*ST*SC*RA*SC*ST*SmU*SmC*SmC*SmU*SmG | CTATCCTCCTTCAGCUCCUG | 52 | SOOOSSSSRSSRSSSSSSS |
| WV-30979 | m5Ceo*STeoAeoTeom5Ceo*SC*ST*SC*RC*ST*ST*RC*SA*SG*SC*SmU*SmC*SmC*SmU*SmG | CTATCCTCCTTCAGCUCCUG | 53 | SOOOSSSRSSRSSSSSSS |
| WV-30980 | m5Ceo*STeoAeoTeom5Ceo*SC*ST*RC*SC*RT*ST*SC*RA*SG*SC*SmU*SmC*SmC*SmU*SmG | CTATCCTCCTTCAGCUCCUG | 54 | SOOOSSRSRSSRSSSSSS |
| WV-30981 | m5Ceo*STeoAeoTeom5Ceo*SC*ST*RC*RC*ST*ST*RC*SA*SG*SC*SmU*SmC*SmC*SmU*SmG | CTATCCTCCTTCAGCUCCUG | 55 | SOOOSSRRSSRSSSSSSS |
| WV-30982 | Aeo*Sm5CeoTeoAeoTeo*SC*SC*ST*SC*SC*RT*ST*SC*RA*SG*SmC*SmU*SmC*SmC*SmU* | ACTATCCTCCTTCAGCUCCU | 56 | SOOOSSSSSRSSRSSSSSS |
| WV-30983 | Aeo*Sm5CeoTeoAeoTeo*SC*SC*ST*SC*RC*ST*ST*RC*SA*SG*SmC*SmU*SmC*SmC*SmU* | ACTATCCTCCTTCAGCUCCU | 57 | SOOOSSSSRSSRSSSSSS |
| WV-30984 | Aeo*Sm5CeoTeoAeoTeo*SC*SC*RT*SC*SC*RT*ST*SC*RA*SG*SmC*SmU*SmC*SmC*SmU* | ACTATCCTCCTTCAGCUCCU | 58 | SOOOSSRSSRSSRSSSSSS |
| WV-30985 | Aeo*Sm5CeoTeoAeoTeo*SC*SC*RT*SC*RC*ST*ST*RC*SA*SG*SmC*SmU*SmC*SmC*SmU* | ACTATCCTCCTTCAGCUCCU | 59 | SOOOSSRSRSSRSSSSSS |
| WV-30986 | m5Ceo*SAeom5CeoTeoAeo*ST*SC*SC*ST*SC*RC*ST*ST*RC*SA*SmG*SmC*SmU*SmC*SmC | CACTATCCTCCTTCAGCUCC | 60 | SOOOSSSSSRSSRSSSSSS |
| WV-30987 | m5Ceo*SAeom5CeoTeoAeo*ST*SC*SC*RT*SC*SC*RT*ST*SC*SA*SmG*SmC*SmU*SmC*SmC | CACTATCCTCCTTCAGCUCC | 61 | SOOOSSSRSSRSSSSSSS |
| WV-30988 | m5Ceo*SAeom5CeoTeoAeo*ST*SC*RC*ST*SC*RC*ST*ST*RC*SA*SmG*SmC*SmU*SmC*SmC | CACTATCCTCCTTCAGCUCC | 62 | SOOOSSRSSRSSRSSSSSS |
| WV-30989 | m5Ceo*SAeom5CeoTeoAeo*ST*SC*RC*RT*SC*SC*RT*ST*SC*SA*SmG*SmC*SmU*SmC*SmC | CACTATCCTCCTTCAGCUCC | 63 | SOOOSSRRSSRSSSSSSS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-30990 | m5Ceo*Sm5CeoAeom5CeoTeo*SA*ST*SC*SC*RT*SC*SC*R T*ST*SC*SmA*SmG*SmC*SmU*SmC | CCACTATCCTCCTT CAGCUC | 64 | SOOOSSSSRSSRS SSSSSS |
| WV-30991 | m5Ceo*Sm5CeoAeom5CeoTeo*SA*ST*SC*RC*ST*SC*RC*S T*ST*SC*SmA*SmG*SmC*SmU*SmC | CCACTATCCTCCTT CAGCUC | 65 | SOOOSSSRSSRSS SSSSSS |
| WV-30992 | m5Ceo*Sm5CeoAeom5CeoTeo*SA*ST*RC*SC*RT*SC*SC*R T*ST*SC*SmA*SmG*SmC*SmU*SmC | CCACTATCCTCCTT CAGCUC | 66 | SOOOSSRSRSSRS SSSSSS |
| WV-30993 | m5Ceo*Sm5CeoAeom5CeoTeo*SA*ST*RC*RC*ST*SC*RC*S T*ST*SC*SmA*SmG*SmC*SmU*SmC | CCACTATCCTCCTT CAGCUC | 67 | SOOOSSRRSSRSS SSSSSS |
| WV-30994 | Teo*Sm5Ceom5CeoAoem5Ceo*ST*SA*ST*SC*SC*RT*SC*S C*RT*ST*SmC*SmA*SmG*SmC*SmU | TCCACTATCCTCCT TCAGCU | 68 | SOOOSSSSSRSSR SSSSSS |
| WV-30995 | Teo*Sm5Ceom5CeoAoem5Ceo*ST*SA*ST*SC*RC*ST*SC*R C*ST*ST*SmC*SmA*SmG*SmC*SmU | TCCACTATCCTCCT TCAGCU | 69 | SOOOSSSSRSSRS SSSSSS |
| WV-30996 | Teo*Sm5Ceom5CeoAoem5Ceo*ST*SA*RT*SC*SC*RT*SC*S C*RT*ST*SmC*SmA*SmG*SmC*SmU | TCCACTATCCTCCT TCAGCU | 70 | SOOOSSRSSRSSR SSSSSS |
| WV-30997 | Teo*Sm5Ceom5CeoAoem5Ceo*ST*SA*RT*SC*RC*ST*SC*R C*ST*ST*SmC*SmA*SmG*SmC*SmU | TCCACTATCCTCCT TCAGCU | 71 | SOOOSSRSRSSRS SSSSSS |
| WV-30998 | Teo*STeom5Ceom5CeoAeo*SC*ST*SA*ST*SC*RC*ST*SC* RC*ST*SmU*SmC*SmA*SmG*SmC | TTCCACTATCCTCC TUCAGC | 72 | SOOOSSSSSRSSR SSSSSS |
| WV-30999 | Teo*STeom5Ceom5CeoAeo*SC*ST*ST*SA*RT*SC*RT*SC* SC*ST*SmU*SmC*SmA*SmG*SmC | TTCCACTATCCTCC TUCAGC | 73 | SOOOSSSRSRSS SSSSSS |
| WV-31000 | Teo*STeom5Ceom5CeoAeo*SC*ST*RA*ST*SC*RT*ST*SC* SC*ST*SmU*SmC*SmA*SmG*SmC | TTCCACTATCCTCC TUCAGC | 74 | SOOOSSRSSRSSR SSSSSS |
| WV-31001 | Teo*STeom5Ceom5CeoAeo*SC*ST*RA*RT*SC*SC*RT*SC* SC*ST*SmU*SmC*SmA*SmG*SmC | TTCCACTATCCTCC TUCAGC | 75 | SOOOSSRRSSRSS SSSSSS |
| WV-31002 | Geo*STeoTeom5Ceom5Ceo*SA*SC*ST*SA*RT*SC*SC*RT* SC*SC*SmU*SmU*SmC*SmA*SmG | GTTCCACTATCCTC CUUCAG | 76 | SOOOSSSSRSSRS SSSSSS |
| WV-31003 | Geo*STeoTeom5Ceom5Ceo*SA*SC*ST*RA*ST*SC*RC*ST* SC*SC*SmU*SmU*SmC*SmA*SmG | GTTCCACTATCCTC CUUCAG | 77 | SOOOSSSRSSRSS SSSSSS |
| WV-31004 | Geo*STeoTeom5Ceom5Ceo*SA*SC*RT*SA*RT*SC*SC*RT* SC*SC*SmU*SmU*SmC*SmA*SmG | GTTCCACTATCCTC CUUCAG | 78 | SOOOSSRSRSSRS SSSSSS |
| WV-31005 | Geo*STeoTeom5Ceom5Ceo*SA*SC*RT*RA*ST*SC*RC*ST* SC*SC*SmU*SmU*SmC*SmA*SmG | GTTCCACTATCCTC CUUCAG | 79 | SOOOSSRRSSRSS SSSSSS |
| WV-31006 | Teo*SGeoTeoTeom5Ceo*SC*SA*SC*ST*SA*RT*SC*SC*RT* SC*SmU*SmU*SmC*SmC*SmA | TGTTCCACTATCCT CCUUCA | 80 | SOOOSSSSSRSSR SSSSSS |
| WV-31007 | Teo*SGeoTeoTeom5Ceo*SC*SA*SC*ST*RA*ST*SC*RC*ST* SC*SmU*SmU*SmC*SmC*SmA | TGTTCCACTATCCT CCUUCA | 81 | SOOOSSSSRSSRS SSSSSS |
| WV-31008 | Teo*SGeoTeoTeom5Ceo*SC*SA*RC*ST*SA*RT*SC*SC*RT *SC*SmU*SmU*SmC*SmC*SmA | TGTTCCACTATCCT CCUUCA | 82 | SOOOSSRSSRSSR SSSSSS |
| WV-31009 | Teo*SGeoTeoTeom5Ceo*SC*SA*RC*ST*RA*ST*SC*RC*ST *SC*SmU*SmU*SmC*SmC*SmA | TGTTCCACTATCCT CCUUCA | 83 | SOOOSSRSRSSRS SSSSSS |
| WV-31010 | Geo*STeoGeoTeoTeo*SC*SC*SA*SC*ST*RA*ST*SC*RC*ST *SmC*SmC*SmU*SmU*SmC* | GTGTTCCACTATCC TCCUUC | 84 | SOOOSSSSSRSSR SSSSSS |
| WV-31011 | Geo*STeoGeoTeoTeo*SC*SC*SA*RC*ST*SA*RT*SC*SC*ST *SmC*SmC*SmU*SmU*SmC* | GTGTTCCACTATCC TCCUUC | 85 | SOOOSSSRSRSS SSSSSS |
| WV-31012 | Geo*STeoGeoTeoTeo*SC*SC*RA*RC*ST*SA*RT*SC*SC*S T*SmC*SmC*SmU*SmU*SmC* | GTGTTCCACTATCC TCCUUC | 86 | SOOOSSRRSSRSS SSSSSS |
| WV-31013 | Aeo*SGeoTeoGeoTeo*ST*SC*SC*SA*RC*ST*SA*RT*SC*S C*SmU*SmC*SmC*SmU*SmU* | AGTGTTCCACTATC CUCCUU | 87 | SOOOSSSSRSSRS SSSSSS |
| WV-31014 | Aeo*SGeoTeoGeoTeo*ST*SC*SC*RA*SC*ST*SA*RT*SC*S C*SmU*SmC*SmC*SmU*SmU* | AGTGTTCCACTATC CUCCUU | 88 | SOOOSSSRSSSRS SSSSSS |
| WV-31015 | Aeo*SGeoTeoGeoTeo*ST*SC*RC*SA*RC*ST*SA*RT*SC*S C*SmU*SmC*SmC*SmU*SmU* | AGTGTTCCACTATC CUCCUU | 89 | SOOOSSRSRSSRS SSSSSS |
| WV-31016 | Aeo*SGeoTeoGeoTeo*ST*SC*RC*RA*SC*ST*SA*RT*SC*S C*SmU*SmC*SmC*SmU*SmU* | AGTGTTCCACTATC CUCCUU | 90 | SOOOSSRRSSSRS SSSSSS |
| WV-31017 | m5Ceo*SAeoGeoTeoGeo*ST*ST*SC*SC*RA*SC*ST*SA*RT *SC*SmC*SmU*SmC*SmC*SmU | CAGTGTTCCACTAT CCUCCU | 91 | SOOOSSSSRSSSR SSSSSS |
| WV-31018 | m5Ceo*SAeoGeoTeoGeo*ST*ST*SC*SC*RA*SC*ST*SA*RT *SC*SmC*SmU*SmC*SmC*SmU | CAGTGTTCCACTAT CCUCCU | 92 | SOOOSSSRSSSSR SSSSSS |
| WV-31019 | m5Ceo*SAeoGeoTeoGeo*ST*ST*RC*SC*RA*SC*ST*SA*RT *SC*SmC*SmU*SmC*SmC*SmU | CAGTGTTCCACTAT CCUCCU | 93 | SOOOSSRSRSSSR SSSSSS |
| WV-31020 | m5Ceo*SAeoGeoTeoGeo*ST*ST*RC*RC*SA*SC*ST*SA*RT *SC*SmC*SmU*SmC*SmC*SmU | CAGTGTTCCACTAT CCUCCU | 94 | SOOOSSRRSSSSR SSSSSS |
| WV-31021 | Geo*Sm5CeoAeoGeoTeo*SG*ST*ST*SC*SC*RA*SC*ST*RA *ST*SmC*SmC*SmU*SmC*SmC* | GCAGTGTTCCACTA TCCUCC | 95 | SOOOSSSSSRSSR SSSSSS |
| WV-31022 | Geo*Sm5CeoAeoGeoTeo*SG*ST*ST*SC*RC*SA*SC*ST*RA *ST*SmC*SmC*SmU*SmC*SmC* | GCAGTGTTCCACTA TCCUCC | 96 | SOOOSSSSRSSSR SSSSSS |
| WV-31023 | Geo*Sm5CeoAeoGeoTeo*SG*ST*ST*SC*SC*RA*SC*ST*RA *ST*SmC*SmC*SmU*SmC*SmC* | GCAGTGTTCCACTA TCCUCC | 97 | SOOOSSRSRSSR SSSSSS |
| WV-31024 | Geo*Sm5CeoAeoGeoTeo*SG*ST*RT*SC*RC*SA*SC*ST*RA *ST*SmC*SmC*SmU*SmC*SmC* | GCAGTGTTCCACTA TCCUCC | 98 | SOOOSSRSRSSSR SSSSSS |
| WV-31025 | Teo*SGeom5CeoAeoGeo*ST*SG*ST*ST*SC*RC*SA*SC*RT *SA*SmU*SmC*SmC*SmU*SmC | TGCAGTGTTCCACT AUCCUC | 99 | SOOOSSSSSRSSR SSSSSS |
| WV-31026 | Teo*SGeom5CeoAeoGeo*ST*SG*ST*RT*SC*SC*RA*SC*ST *SA*SmU*SmC*SmC*SmU*SmC | TGCAGTGTTCCACT AUCCUC | 100 | SOOOSSSRSRSS SSSSSS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-31027 | Teo*SGeom5CeoAeoGeo*ST*SG*RT*ST*SC*RC*SA*SC*RT *SA*SmU*SmC*SmC*SmU*SmC | TGCAGTGTTCCACT AUCCUC | 101 | SOOOSSRSSRSSR SSSSSS |
| WV-31028 | Teo*SGeom5CeoAeoGeo*ST*SG*RT*RT*SC*SC*RA*SC*ST *SA*SmU*SmC*SmC*SmU*SmC | TGCAGTGTTCCACT AUCCUC | 102 | SOOOSSRRSSRSS SSSSSS |
| WV-31029 | Teo*STeoGeom5CeoAeo*SG*ST*SG*ST*ST*RC*SC*SA*RC *ST*SmA*SmU*SmC*SmC*SmU | TTGCAGTGTTCCAC TAUCCU | 103 | SOOOSSSSSRSSR SSSSSS |
| WV-31030 | Teo*STeoGeom5CeoAeo*SG*ST*SG*RT*ST*SC*SC*RA*SC *ST*SmA*SmU*SmC*SmC*SmU | TTGCAGTGTTCCAC TAUCCU | 104 | SOOOSSSRSSSRS SSSSSS |
| WV-31031 | Teo*STeoGeom5CeoAeo*SG*ST*RG*ST*ST*RC*SC*SA*RC *ST*SmA*SmU*SmC*SmC*SmU | TTGCAGTGTTCCAC TAUCCU | 105 | SOOOSSRSSRSSR SSSSSS |
| WV-31032 | Teo*STeoGeom5CeoAeo*SG*ST*RG*RT*ST*SC*SC*RA*SC *ST*SmA*SmU*SmC*SmC*SmU | TTGCAGTGTTCCAC TAUCCU | 106 | SOOOSSRRSSSRS SSSSSS |
| WV-31033 | Geo*STeoTeoGeom5Ceo*SA*SG*ST*SG*RT*ST*SC*SC*RA *SC*SmU*SmA*SmU*SmC*SmC | GTTGCAGTGTTCCA CUAUCC | 107 | SOOOSSSSRSSSR SSSSSS |
| WV-31034 | Geo*STeoTeoGeom5Ceo*SA*SG*ST*SG*RT*ST*SC*RC*SA *SC*SmU*SmA*SmU*SmC*SmC | GTTGCAGTGTTCCA CUAUCC | 108 | SOOOSSSSRSSRS SSSSSS |
| WV-31035 | Geo*STeoTeoGeom5Ceo*SA*SG*RT*SG*RT*ST*SC*SC*RA *SC*SmU*SmA*SmU*SmC*SmC | GTTGCAGTGTTCCA CUAUCC | 109 | SOOOSSRSRSSSR SSSSSS |
| WV-31036 | Geo*STeoTeoGeom5Ceo*SA*SG*RT*SG*RT*ST*SC*RC*SA *SC*SmU*SmA*SmU*SmC*SmC | GTTGCAGTGTTCCA CUAUCC | 110 | SOOOSSRSRSSRS SSSSSS |
| WV-31037 | m5Ceo*SGeoTeoTeoGeo*SC*SA*SG*ST*SG*RT*ST*SC*RC *SA*SmC*SmU*SmA*SmU*SmC | CGTTGCAGTGTTCC ACUAUC | 111 | SOOOSSSSSRSSR SSSSSS |
| WV-31038 | m5Ceo*SGeoTeoTeoGeo*SC*SA*SG*ST*RG*ST*ST*RC*SC *SA*SmC*SmU*SmA*SmU*SmC | CGTTGCAGTGTTCC ACUAUC | 112 | SOOOSSSSRSSRS SSSSSS |
| WV-31039 | m5Ceo*SGeoTeoTeoGeo*SC*SA*RG*ST*SG*RT*ST*SC*RC *SA*SmC*SmU*SmA*SmU*SmC | CGTTGCAGTGTTCC ACUAUC | 113 | SOOOSSRSSRSSR SSSSSS |
| WV-31040 | m5Ceo*SGeoTeoTeoGeo*SC*SA*RG*ST*RG*ST*ST*RC*SC *SA*SmC*SmU*SmA*SmU*SmC | CGTTGCAGTGTTCC ACUAUC | 114 | SOOOSSRSRSSRS SSSSSS |
| WV-31041 | Aeo*Sm5CeoGeoTeoTeo*SG*SC*SA*SG*ST*RG*ST*ST*RC *SC*SmA*SmC*SmU*SmA*SmU | ACGTTGCAGTGTTC CACUAU | 115 | SOOOSSSSSRSSR SSSSSS |
| WV-31042 | Aeo*Sm5CeoGeoTeoTeo*SG*SC*SA*RG*ST*SG*RT*ST*SC *SC*SmA*SmC*SmU*SmA*SmU | ACGTTGCAGTGTTC CACUAU | 116 | SOOOSSSRSSRSS SSSSSS |
| WV-31043 | Aeo*Sm5CeoGeoTeoTeo*SG*SC*RA*SG*ST*RG*ST*ST*RC *SC*SmA*SmC*SmU*SmA*SmU | ACGTTGCAGTGTTC CACUAU | 117 | SOOOSSRSSRSSR SSSSSS |
| WV-31044 | Aeo*Sm5CeoGeoTeoTeo*SG*SC*RA*RG*ST*SG*RT*ST*SC *SC*SmA*SmC*SmU*SmA*SmU | ACGTTGCAGTGTTC CACUAU | 118 | SOOOSSRRSSRSS SSSSSS |
| WV-31045 | m5Ceo*SAeom5CeoGeoTeo*ST*SG*SC*SA*SG*RT*SG*ST* RT*SC*SmC*SmA*SmC*SmU*SmA | CACGTTGCAGTGTT CCACUA | 119 | SOOOSSSSSRSSR SSSSSS |
| WV-31046 | m5Ceo*SAeom5CeoGeoTeo*ST*SG*SC*SA*RG*ST*SG*RT* ST*SC*SmC*SmA*SmC*SmU*SmA | CACGTTGCAGTGTT CCACUA | 120 | SOOOSSSSRSSRS SSSSSS |
| WV-31048 | m5Ceo*SAeom5CeoGeoTeo*ST*SG*RC*SA*RG*ST*SG*RT* ST*SC*SmC*SmA*SmC*SmU*SmA | CACGTTGCAGTGTT CCACUA | 121 | SOOOSSRSRSSRS SSSSSS |
| WV-31049 | m5Ceo*Sm5CeoAeom5CeoGeo*ST*ST*SG*RC*SA*SG*ST*S G*RT*ST*SmC*SmC*SmA*SmC*SmU | CCACGTTGCAGTGT TCCACU | 122 | SOOOSSSRSSSSR SSSSSS |
| WV-31050 | m5Ceo*Sm5CeoAeom5CeoGeo*ST*ST*SG*SC*SA*RG*ST*S G*RT*ST*SmC*SmC*SmA*SmC*SmU | CCACGTTGCAGTGT TCCACU | 123 | SOOOSSSSSRSSR SSSSSS |
| WV-31051 | m5Ceo*Sm5CeoAeom5CeoGeo*ST*ST*RG*RC*SA*SG*ST*S G*RT*ST*SmC*SmC*SmA*SmC*SmU | CCACGTTGCAGTGT TCCACU | 124 | SOOOSSRRSSSSR SSSSSS |
| WV-31052 | m5Ceo*Sm5CeoAeom5CeoGeo*ST*ST*RG*SC*SA*RG*ST*S G*RT*ST*SmC*SmC*SmA*SmC*SmU | CCACGTTGCAGTGT TCCACU | 125 | SOOOSSRSSRSSR SSSSSS |
| WV-32808 | Geo*STeon001RGeoTeon001RTeo*RC*SC*SA*SC*RT*SA*S T*SC*RC*ST*SmC*SmC*SmU*SmU*SmC | GTGTTCCACTATCC TCCUUC | 126 | SnROnRRSSSRSS SRSSSSSS |
| WV-32809 | Geo*STeon001RGeoTeon001RTeo*RC*SC*SA*SC*RT*SA*S T*SC*RC*ST*SmCn001RmC*SmU*SmU*SmC | GTGTTCCACTATCC TCCUUC | 127 | SnROnRRSSSRSS SRSSSnRSSS |
| WV-32810 | Geo*STeon001RGeoTeon001RTeo*RC*SC*SA*SC*RT*SA*S T*SC*RC*ST*SmC*SmCn001RmU*SmU*SmC | GTGTTCCACTATCC TCCUUC | 128 | SnROnRRSSSRSS SRSSSnRSSS |
| WV-32811 | Geo*STeon001RGeoTeon001RTeo*RC*SC*SA*SC*RT*SA*S T*SC*RC*ST*SmC*SmC*SmUn001RmU*SmC | GTGTTCCACTATCC TCCUUC | 129 | SnROnRRSSSRSS SRSSSSnRS |
| WV-32812 | Geo*STeon001RGeoTeon001RTeo*RC*SC*SA*SC*RT*SA*S T*SC*RC*ST*SmC*SmC*SmU*SmUn001RmU | GTGTTCCACTATCC TCCUUC | 130 | SnROnRRSSSRSS SRSSSSSnR |
| WV-32813 | Geo*STeon001RGeoTeon001RTeo*RC*SC*RA*SC*RT*SA*S T*SC*RC*ST*SmC*SmC*SmU*SmU*SmC | GTGTTCCACTATCC TCCUUC | 131 | SnROnRRSRSRSS SRSSSSSS |
| WV-32814 | Geo*STeon001RGeoTeon001RTeo*RC*SC*RA*SC*RT*SA*S T*SC*RC*ST*SmCn001RmC*SmU*SmU*SmC | GTGTTCCACTATCC TCCUUC | 132 | SnROnRRSRSRSS SRSSnRSSS |
| WV-32815 | Geo*STeon001RGeoTeon001RTeo*RC*SC*RA*SC*RT*SA*S T*SC*RC*ST*SmC*SmCn001RmC*SmU*SmC | GTGTTCCACTATCC TCCUUC | 133 | SnROnRRSRSRSS SRSSSnRSS |
| WV-32816 | Geo*STeon001RGeoTeon001RTeo*RC*SC*RA*SC*RT*SA*S T*SC*RC*ST*SmC*SmC*SmUn001RmU*SmC | GTGTTCCACTATCC TCCUUC | 134 | SnROnRRSRSRSS SRSSSSnRS |
| WV-32817 | Geo*STeon001RGeoTeon001RTeo*RC*SC*RA*SC*RT*SA*S T*SC*RC*ST*SmC*SmC*SmU*SmUn001RmC | GTGTTCCACTATCC TCCUUC | 135 | SnROnRRSRSRSS SRSSSSSnR |
| WV-32818 | Geo*STeon001RGeoTeon001RTeo*RC*SC*RA*SC*RT*SA*S T*SC*RC*ST*SmC*SmC*SmU*SmU*SmC | GTGTTCCACTATCC TCCUUC | 136 | SnROnRRSRSSRS SRSSSSSS |
| WV-32819 | Geo*STeon001RGeoTeon001RTeo*RC*SC*RA*SC*RT*SA*S T*SC*RC*ST*SmCn001RmC*SmU*SmU*SmC | GTGTTCCACTATCC TCCUUC | 137 | SnROnRRSRSSRS SRSSnRSSS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-32820 | Geo*STeon001RGeoTeon001RTeo*RC*SC*RA*SC*ST*SA*S T*SC*RC*ST*SmC*SmCn001RmU*SmU*SmC | GTGTTCCACTATCC TCCUUC | 138 | SnROnRRSRSSRS SRSSSnRSS |
| WV-32821 | Geo*STeon001RGeoTeon001RTeo*RC*SC*RA*SC*ST*RA*S T*SC*RC*ST*SmC*SmC*SmUn001RmU*SmC | GTGTTCCACTATCC TCCUUC | 139 | SnROnRRSRSSRS SRSSSSnRS |
| WV-32822 | Geo*STeon001RGeoTeon001RTeo*RC*SC*RA*SC*ST*RA*S T*SC*RC*ST*SmC*SmC*SmU*SmUn001RmC | GTGTTCCACTATCC TCCUUC | 140 | SnROnRRSRSSRS SRSSSSSnR |
| WV-32823 | Geo*STeon001RGeoTeon001RTeo*SC*SC*RA*SC*RT*SA*S T*SC*RC*ST*SmC*SmC*SmU*SmU*SmC | GTGTTCCACTATCC TCCUUC | 141 | SnROnRSSRSRSS SRSSSSSS |
| WV-32824 | Geo*STeon001RGeoTeon001RTeo*SC*SC*RA*SC*RT*SA*S T*SC*RC*ST*SmCn001RmC*SmU*SmU*SmC | GTGTTCCACTATCC TCCUUC | 142 | SnROnRSSRSRSS SRSSnRSSS |
| WV-32825 | Geo*STeon001RGeoTeon001RTeo*SC*SC*RA*SC*RT*SA*S T*SC*RC*ST*SmC*SmCn001RmC*SmU*SmC | GTGTTCCACTATCC TCCUUC | 143 | SnROnRSSRSRSS SRSSSnRSS |
| WV-32826 | Geo*STeon001RGeoTeon001RTeo*SC*SC*RA*SC*RT*SA*S T*SC*RC*ST*SmC*SmC*SmUn001RmU*SmC | GTGTTCCACTATCC TCCUUC | 144 | SnROnRSSRSRSS SRSSSSnRS |
| WV-32827 | Geo*STeon001RGeoTeon001RTeo*SC*SC*RA*SC*RT*SA*S T*SC*RC*ST*SmC*SmC*SmU*SmUn001RmC | GTGTTCCACTATCC TCCUUC | 145 | SnROnRSSRSRSS SRSSSSSnR |
| WV-32008 | Aeo*STeon001Rm5Ceom5Ceon001RTeo*SC*SC*ST*ST*SC* RA*SG*SC*RT*SC*SmC*SmU*SmG*SmC*SmA | ATCCTCCTTCAGCT CCUGCA | 146 | SnROnRSSSSSRS SRSSSSSS |
| WV-32009 | Aeo*STeon001Rm5Ceom5Ceon001RTeo*SC*SC*ST*ST*SC* RA*SG*SC*RT*SC*SmC*SmU*SmG*SmC*SmA | ATCCTCCTTCAGCT CCUGCA | 147 | SnROnRSSSSRSS SRSSSSSS |
| WV-32010 | Aeo*STeon001Rm5Ceom5Ceon001RTeo*SC*SC*RT*ST*SC* RA*SG*SC*RT*SC*SmC*SmU*SmG*SmC*SmA | ATCCTCCTTCAGCT CCUGCA | 148 | SnROnRSSRSSRS SRSSSSSS |
| WV-32011 | Aeo*STeon001Rm5Ceom5Ceon001RTeo*SC*SC*RT*ST*RC* SA*SG*SC*RT*SC*SmC*SmU*SmG*SmC*SmA | ATCCTCCTTCAGCT CCUGCA | 149 | SnROnRSSRSRSS SRSSSSSS |
| WV-32012 | Teo*SAeon001RTeom5Ceon001Rm5Ceo*ST*SC*SC*ST*ST* RC*SA*SG*RC*ST*SmC*SmC*SmU*SmG*SmC | TATCCTCCTTCAGC TCCUGC | 150 | SnROnRSSSSSRS SRSSSSSS |
| WV-32013 | Teo*SAeon001RTeom5Ceon001Rm5Ceo*ST*SC*SC*RT*ST* SC*RA*SG*SC*ST*SmC*SmC*SmU*SmG*SmC | TATCCTCCTTCAGC TCCUGC | 151 | SnROnRSSSRSSR SSSSSSSS |
| WV-32014 | Teo*SAeon001RTeom5Ceon001Rm5Ceo*ST*SC*RC*ST*ST* RC*SA*SG*RC*ST*SmC*SmC*SmU*SmG*SmC | TATCCTCCTTCAGC TCCUGC | 152 | SnROnRSSRSSRS SRSSSSSS |
| WV-32015 | Teo*SAeon001RTeom5Ceon001Rm5Ceo*ST*SC*RC*RT*ST* SC*RA*SG*SC*ST*SmC*SmC*SmU*SmG*SmC | TATCCTCCTTCAGC TCCUGC | 153 | SnROnRSSRRSSR SSSSSSSS |
| WV-32016 | m5Ceo*STeon001RAeoTeon001Rm5Ceo*SC*ST*SC*SC*RT* ST*SC*RA*SG*SC*SmU*SmC*SmC*SmU*SmG | CTATCCTCCTTCAG CUCCUG | 154 | SnROnRSSSSRSS RSSSSSSS |
| WV-32017 | m5Ceo*STeon001RAeoTeon001Rm5Ceo*SC*ST*SC*SC*RT* ST*RC*SA*SG*SC*SmU*SmC*SmC*SmU*SmG | CTATCCTCCTTCAG CUCCUG | 155 | SnROnRSSSSRSSR SSSSSSSS |
| WV-32018 | m5Ceo*STeon001RAeoTeon001Rm5Ceo*SC*ST*RC*SC*RT* ST*SC*SA*SG*SC*SmU*SmC*SmC*SmU*SmG | CTATCCTCCTTCAG CUCCUG | 156 | SnROnRSSRSRSS RSSSSSSS |
| WV-32019 | m5Ceo*STeon001RAeoTeon001Rm5Ceo*SC*ST*RC*RC*RT* ST*RC*SA*SG*SC*SmU*SmC*SmC*SmU*SmG | CTATCCTCCTTCAG CUCCUG | 157 | SnROnRSSRRRSSR SSSSSSSS |
| WV-32020 | Aeo*Sm5Ceon001RTeoAeon001RTeo*SC*SC*ST*SC*SC*RT *ST*SC*RA*SG*SmC*SmU*SmC*SmC*SmU | ACTATCCTCCTTCA GCUCCU | 158 | SnROnRSSSSSRS SRSSSSSS |
| WV-32021 | Aeo*Sm5Ceon001RTeoAeon001RTeo*SC*SC*ST*SC*RC*ST *ST*RC*SA*SG*SmC*SmU*SmC*SmC*SmU | ACTATCCTCCTTCA GCUCCU | 159 | SnROnRSSSSRSS RSSSSSSS |
| WV-32022 | Aeo*Sm5Ceon001RTeoAeon001RTeo*SC*SC*RT*SC*SC*RT *ST*SC*RA*SG*SmC*SmU*SmC*SmC*SmU | ACTATCCTCCTTCA GCUCCU | 160 | SnROnRSSRSSRS SRSSSSSS |
| WV-32023 | Aeo*Sm5Ceon001RTeoAeon001RTeo*SC*SC*RT*SC*RC*ST *ST*RC*SA*SG*SmC*SmU*SmC*SmC*SmU | ACTATCCTCCTTCA GCUCCU | 161 | SnROnRSSRSRSS RSSSSSSS |
| WV-32024 | m5Ceo*SAeon001Rm5CeoTeon001RAeo*SC*SC*SC*ST*SC* RC*ST*ST*RC*SA*SmG*SmC*SmU*SmC*SmC | CACTATCCTCCTTC AGCUCC | 162 | SnROnRSSSSSRS SRSSSSSS |
| WV-32025 | m5Ceo*SAeon001Rm5CeoTeon001RAeo*ST*SC*SC*RT*SC* SC*RT*ST*SC*SA*SmG*SmC*SmU*SmC*SmC | CACTATCCTCCTTC AGCUCC | 163 | SnROnRSSSRSSR SSSSSSSS |
| WV-32026 | m5Ceo*SAeon001Rm5CeoTeon001RAeo*ST*SC*RC*ST*SC* RC*ST*ST*RC*SA*SmG*SmC*SmU*SmC*SmC | CACTATCCTCCTTC AGCUCC | 164 | SnROnRSSRSSRS SRSSSSSS |
| WV-32027 | m5Ceo*SAeon001Rm5CeoTeon001RAeo*ST*SC*RC*RT*SC* SC*RT*ST*SC*SA*SmG*SmC*SmU*SmC*SmC | CACTATCCTCCTTC AGCUCC | 165 | SnROnRSSRRSSR SSSSSSSS |
| WV-32028 | m5Ceo*Sm5Ceon001RAeom5Ceon001RTeo*SA*ST*SC*SC*R T*SC*SC*RT*ST*SC*SmA*SmG*SmC*SmU*SmC | CCACTATCCTCCTT CAGCUC | 166 | SnROnRSSSSRSS RSSSSSSS |
| WV-32029 | m5Ceo*Sm5Ceon001RAeom5Ceon001RTeo*SA*ST*SC*RC*S T*SC*RC*ST*ST*SC*SmA*SmG*SmC*SmU*SmC | CCACTATCCTCCTT CAGCUC | 167 | SnROnRSSSRSSR SSSSSSSS |
| WV-32030 | m5Ceo*Sm5Ceon001RAeom5Ceon001RTeo*SA*ST*SC*SC*R T*SC*RC*ST*ST*SC*SmA*SmG*SmC*SmU*SmC | CCACTATCCTCCTT CAGCUC | 168 | SnROnRSSRSRSS RSSSSSSS |
| WV-32031 | m5Ceo*Sm5Ceon001RAeom5Ceon001RTeo*SA*ST*RC*RC*S T*SC*RC*ST*ST*SC*SmA*SmG*SmC*SmU*SmC | CCACTATCCTCCTT CAGCUC | 169 | SnROnRSSRRSSR SSSSSSSS |
| WV-32032 | Teo*Sm5Ceon001Rm5CeoAeon001Rm5Ceo*ST*SA*ST*SC*R C*ST*SC*RC*ST*ST*SmC*SmA*SmG*SmC*SmU | TCCACTATCCTCCT TCAGCU | 170 | SnROnRSSSSSRS SRSSSSSS |
| WV-32033 | Teo*Sm5Ceon001Rm5CeoAeon001Rm5Ceo*ST*SA*ST*SC*R C*ST*SC*RC*ST*ST*SmC*SmA*SmG*SmC*SmU | TCCACTATCCTCCT TCAGCU | 171 | SnROnRSSSSRSS RSSSSSSS |
| WV-32034 | Teo*Sm5Ceon001Rm5CeoAeon001Rm5Ceo*ST*SA*RT*SC*S C*RT*SC*SC*RT*ST*SmC*SmA*SmG*SmC*SmU | TCCACTATCCTCCT TCAGCU | 172 | SnROnRSSRSSRS SRSSSSSS |
| WV-32035 | Teo*Sm5Ceon001Rm5CeoAeon001Rm5Ceo*ST*SA*RT*SC*R C*ST*SC*RC*ST*ST*SmC*SmA*SmG*SmC*SmU | TCCACTATCCTCCT TCAGCU | 173 | SnROnRSSRSRSS RSSSSSSS |
| WV-32036 | Teo*STeon001Rm5Ceom5Ceon001RAeo*SC*ST*SA*ST*SC* RC*ST*SC*RC*ST*SmU*SmC*SmA*SmG*SmC | TTCCACTATCCTCC TUCAGC | 174 | SnROnRSSSSSRS SRSSSSSS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-32037 | Teo*STeon001Rm5Ceom5Ceon001RAeo*SC*ST*SA*RT*SC*SC*RT*SC*SC*ST*SmU*SmC*SmA*SmG*SmC | TTCCACTATCCTCCTUCAGC | 175 | SnROnRSSSRSSRSSSSSSSS |
| WV-32038 | Teo*STeon001Rm5Ceom5Ceon001RAeo*SC*ST*SA*RT*SC*RC*ST*SC*RC*ST*SmU*SmC*SmA*SmG*SmC | TTCCACTATCCTCCTUCAGC | 176 | SnROnRSSRSSRSSRSSSSSSS |
| WV-32039 | Teo*STeon001Rm5Ceom5Ceon001RAeo*SC*ST*RA*RT*SC*SC*RT*SC*SC*ST*SmU*SmC*SmA*SmG*SmC | TTCCACTATCCTCCTUCAGC | 177 | SnROnRSSRRSSRSSSSSSSS |
| WV-32040 | Geo*STeon001RTeom5Ceon001Rm5Ceo*SA*SC*ST*SA*RT*SC*SC*RT*SC*SC*SmU*SmU*SmC*SmA*SmG | GTTCCACTATCCTCCUUCAG | 178 | SnROnRSSSSRSSRSSSSSSS |
| WV-32041 | Geo*STeon001RTeom5Ceon001Rm5Ceo*SA*SC*ST*RA*ST*SC*RC*ST*SC*SC*SmU*SmU*SmC*SmA*SmG | GTTCCACTATCCTCCUUCAG | 179 | SnROnRSSSRSSRSSSSSSSS |
| WV-32042 | Geo*STeon001RTeom5Ceon001Rm5Ceo*SA*SC*RT*SA*RT*SC*SC*RT*SC*SC*SmU*SmU*SmC*SmA*SmG | GTTCCACTATCCTCCUUCAG | 180 | SnROnRSSRSRSSRSSSSSSS |
| WV-32043 | Geo*STeon001RTeom5Ceon001Rm5Ceo*SA*SC*RT*RA*ST*SC*RC*ST*SC*SC*SmU*SmU*SmC*SmA*SmG | GTTCCACTATCCTCCUUCAG | 181 | SnROnRSSRRSSRSSSSSSSS |
| WV-32044 | Teo*SGeon001RTeoTeon001Rm5Ceo*SC*SA*SC*ST*SA*RT*SC*SC*RT*SC*SmC*SmU*SmU*SmC*SmA | TGTTCCACTATCCTCCUUCA | 182 | SnROnRSSSSSRSSRSSSSSSS |
| WV-32045 | Teo*SGeon001RTeoTeon001Rm5Ceo*SC*SA*SC*ST*RA*ST*SC*RC*ST*SC*SmC*SmU*SmU*SmC*SmA | TGTTCCACTATCCTCCUUCA | 183 | SnROnRSSSSRSSRSSSSSSS |
| WV-32046 | Teo*SGeon001RTeoTeon001Rm5Ceo*SC*SA*RC*ST*SA*ST*SC*RC*ST*SC*SmC*SmU*SmU*SmC*SmA | TGTTCCACTATCCTCCUUCA | 184 | SnROnRSSRSSRSSRSSSSSSS |
| WV-32047 | Teo*SGeon001RTeoTeon001Rm5Ceo*SC*SA*RC*ST*RA*ST*SC*RC*ST*SC*SmC*SmU*SmU*SmC*SmA | TGTTCCACTATCCTCCUUCA | 185 | SnROnRSSRSRSSRSSSSSSS |
| WV-32048 | Geo*STeon001RGeoTeon001RTeo*SC*SC*SA*SC*ST*RA*ST*SC*RC*ST*SmC*SmC*SmU*SmU*SmC | GTGTTCCACTATCCTCCUUC | 186 | SnROnRSSSSSRSSRSSSSSSS |
| WV-32049 | Geo*STeon001RGeoTeon001RTeo*SC*SC*SA*RC*ST*SA*RT*SC*SC*ST*SmC*SmC*SmU*SmU*SmC | GTGTTCCACTATCCTCCUUC | 187 | SnROnRSSSRSSRSSSSSSSS |
| WV-32050 | Geo*STeon001RGeoTeon001RTeo*SC*SC*RA*RC*ST*SA*RT*SC*SC*ST*SmC*SmC*SmU*SmU*SmC | GTGTTCCACTATCCTCCUUC | 188 | SnROnRSSRRSSRSSSSSSSS |
| WV-32051 | Aeo*SGeon001RTeoGeon001RTeo*ST*SC*SC*SA*RC*ST*SA*RT*SC*SC*SmU*SmC*SmC*SmU*SmU | AGTGTTCCACTATCCUCCUU | 189 | SnROnRSSSSRSSRSSSSSSS |
| WV-32052 | Aeo*SGeon001RTeoGeon001RTeo*ST*SC*SC*RA*SC*ST*SA*RT*SC*SC*SmU*SmC*SmC*SmU*SmU | AGTGTTCCACTATCCUCCUU | 190 | SnROnRSSSRSSSRSSSSSSS |
| WV-32053 | Aeo*SGeon001RTeoGeon001RTeo*ST*SC*RC*SA*RC*ST*SA*RT*SC*SC*SmU*SmC*SmC*SmU*SmU | AGTGTTCCACTATCCUCCUU | 191 | SnROnRSSRSRSSRSSSSSSS |
| WV-32054 | Aeo*SGeon001RTeoGeon001RTeo*ST*SC*RC*RA*SC*ST*SA*RT*SC*SC*SmU*SmC*SmC*SmU*SmU | AGTGTTCCACTATCCUCCUU | 192 | SnROnRSSRRSSSRSSSSSSS |
| WV-32055 | m5Ceo*SAeon001RGeoTeon001RGeo*ST*ST*SC*SC*RA*SC*ST*SA*RT*SC*SmU*SmU*SmC*SmC*SmU | CAGTGTTCCACTATCCUCCU | 193 | SnROnRSSSSRSSSRSSSSSSS |
| WV-32056 | m5Ceo*SAeon001RGeoTeon001RGeo*ST*ST*SC*SC*SA*SC*ST*SA*RT*SC*SmC*SmU*SmC*SmC*SmU | CAGTGTTCCACTATCCUCCU | 194 | SnROnRSSSSSSSRSSSSSSS |
| WV-32057 | m5Ceo*SAeon001RGeoTeon001RGeo*ST*ST*RC*SC*RA*SC*ST*SA*RT*SC*SmC*SmU*SmC*SmC*SmU | CAGTGTTCCACTATCCUCCU | 195 | SnROnRSSRSRSSSRSSSSSSS |
| WV-32058 | m5Ceo*SAeon001RGeoTeon001RGeo*ST*ST*RC*RC*SA*SC*ST*SA*RT*SC*SmC*SmU*SmC*SmC*SmU | CAGTGTTCCACTATCCUCCU | 196 | SnROnRSSRRSSSSRSSSSSSS |
| WV-32059 | Geo*Sm5Ceon001RAeoGeon001RTeo*SG*ST*ST*SC*SA*RA*SC*ST*RA*ST*SmC*SmC*SmU*SmC*SmC | GCAGTGTTCCACTATCCUCC | 197 | SnROnRSSSSSRSSRSSSSSSS |
| WV-32060 | Geo*Sm5Ceon001RAeoGeon001RTeo*SG*ST*ST*SC*RC*SA*SC*ST*RA*ST*SmC*SmC*SmU*SmC*SmC | GCAGTGTTCCACTATCCUCC | 198 | SnROnRSSSSRSSSRSSSSSSS |
| WV-32061 | Geo*Sm5Ceon001RAeoGeon001RTeo*SG*ST*RT*SC*SC*RA*SC*ST*RA*ST*SmC*SmC*SmU*SmC*SmC | GCAGTGTTCCACTATCCUCC | 199 | SnROnRSSRSSRSSRSSSSSSS |
| WV-32062 | Geo*Sm5Ceon001RAeoGeon001RTeo*SG*ST*RT*SC*RC*SA*SC*ST*RA*ST*SmC*SmC*SmU*SmC*SmC | GCAGTGTTCCACTATCCUCC | 200 | SnROnRSSRSRSSSRSSSSSSS |
| WV-32063 | Teo*SGeon001Rm5CeoAeon001RGeo*ST*SG*ST*ST*SC*RC*SA*SC*RT*SA*SmU*SmC*SmC*SmU*SmC | TGCAGTGTTCCACTAUCCUC | 201 | SnROnRSSSSSRSSRSSSSSSS |
| WV-32064 | Teo*SGeon001Rm5CeoAeon001RGeo*ST*SG*ST*ST*SC*SC*RA*SC*ST*SA*SmU*SmC*SmC*SmU*SmC | TGCAGTGTTCCACTAUCCUC | 202 | SnROnRSSSSRSSRSSSSSSSS |
| WV-32065 | Teo*SGeon001Rm5CeoAeon001RGeo*ST*SG*RT*ST*SC*RC*SA*SC*RT*SA*SmU*SmC*SmC*SmU*SmC | TGCAGTGTTCCACTAUCCUC | 203 | SnROnRSSRSSRSSRSSSSSSS |
| WV-32066 | Teo*SGeon001Rm5CeoAeon001RGeo*ST*SG*RT*RT*SC*SC*RA*SC*ST*SA*SmU*SmC*SmC*SmU*SmC | TGCAGTGTTCCACTAUCCUC | 204 | SnROnRSSRRSSRSSSSSSS |
| WV-32067 | Teo*STeon001RGeom5Ceon001RAeo*SG*ST*SG*ST*ST*RC*SA*SA*RC*ST*SmA*SmU*SmC*SmC*SmU | TTGCAGTGTTCCACTAUCCU | 205 | SnROnRSSSSSRSSRSSSSSSS |
| WV-32068 | Teo*STeon001RGeom5Ceon001RAeo*SG*ST*SG*RT*ST*SC*SC*RA*SC*ST*SmA*SmU*SmC*SmC*SmU | TTGCAGTGTTCCACTAUCCU | 206 | SnROnRSSSRSSSRSSSSSSS |
| WV-32069 | Teo*STeon001RGeom5Ceon001RAeo*SG*ST*RG*ST*ST*RC*SC*SA*RC*ST*SmA*SmU*SmC*SmC*SmU | TTGCAGTGTTCCACTAUCCU | 207 | SnROnRSSRSSRSSRSSSSSSS |
| WV-32070 | Teo*STeon001RGeom5Ceon001RAeo*SG*ST*RG*ST*ST*SC*SC*RA*SC*ST*SmA*SmU*SmC*SmC*SmU | TTGCAGTGTTCCACTAUCCU | 208 | SnROnRSSRRSSSRSSSSSSS |
| WV-32071 | Geo*STeon001RTeoGeon001Rm5Ceo*SA*SG*ST*SG*RT*ST*SC*SC*RA*SC*SmU*SmA*SmU*SmC*SmC | GTTGCAGTGTTCCACUAUCC | 209 | SnROnRSSSSRSSSRSSSSSSS |
| WV-32072 | Geo*STeon001RTeoGeon001Rm5Ceo*SA*SG*ST*SG*RT*ST*SC*RC*SA*SC*SmU*SmA*SmU*SmC*SmC | GTTGCAGTGTTCCACUAUCC | 210 | SnROnRSSSSRSSRSSSSSSS |
| WV-32073 | Geo*STeon001RTeoGeon001Rm5Ceo*SA*SG*RT*SG*RT*ST*SC*SC*RA*SC*SmU*SmA*SmU*SmC*SmC | GTTGCAGTGTTCCACUAUCC | 211 | SnROnRSSRSRSSSRSSSSSSS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-32074 | Geo*STeon001RTeoGeon001Rm5Ceo*SA*SG*RT*SG*RT*ST *SC*RC*SA*SC*SmU*SmA*SmU*SmC*SmC | GTTGCAGTGTTCCA CUAUCC | 212 | SnROnRSSRSRSS RSSSSSSS |
| WV-32075 | m5Ceo*SGeon001RTeoTeon001RGeo*SC*SA*SG*ST*SG*RT *ST*SC*RC*SA*SmC*SmU*SmA*SmU*SmC | CGTTGCAGTGTTCC ACUAUC | 213 | SnROnRSSSSSRS SRSSSSSS |
| WV-32076 | m5Ceo*SGeon001RTeoTeon001RGeo*SC*SA*SG*ST*RG*ST *ST*RC*SC*SA*SmC*SmU*SmA*SmU*SmC | CGTTGCAGTGTTCC ACUAUC | 214 | SnROnRSSSSRSS RSSSSSSS |
| WV-32077 | m5Ceo*SGeon001RTeoTeon001RGeo*SC*SA*RG*ST*SG*RT *ST*SC*RC*SA*SmC*SmU*SmA*SmU*SmC | CGTTGCAGTGTTCC ACUAUC | 215 | SnROnRSSRSSRS SRSSSSSS |
| WV-32078 | m5Ceo*SGeon001RTeoTeon001RGeo*SC*SA*RG*ST*RG*ST *ST*RC*SC*SA*SmC*SmU*SmA*SmU*SmC | CGTTGCAGTGTTCC ACUAUC | 216 | SnROnRSSRSRSS RSSSSSSS |
| WV-32079 | Aeo*Sm5Ceon001RGeoTeon001RTeo*SG*SC*SA*SG*ST*RG *ST*ST*RC*SC*SmA*SmC*SmA*SmA*SmU | ACGTTGCAGTGTTC CACUAU | 217 | SnROnRSSSSSRS SRSSSSSS |
| WV-32080 | Aeo*Sm5Ceon001RGeoTeon001RTeo*SG*SC*SA*RG*ST*SG *RT*ST*SC*SC*SmA*SmC*SmU*SmA*SmU | ACGTTGCAGTGTTC CACUAU | 218 | SnROnRSSSRSSR SSSSSSSS |
| WV-32081 | Aeo*Sm5Ceon001RGeoTeon001RTeo*SG*SC*RA*SG*ST*RG *ST*ST*RC*SC*SmA*SmC*SmU*SmA*SmU | ACGTTGCAGTGTTC CACUAU | 219 | SnROnRSSRSSRS SRSSSSSS |
| WV-32082 | Aeo*Sm5Ceon001RGeoTeon001RTeo*SG*SC*RA*SG*ST*SG *RT*ST*SC*SC*SmA*SmC*SmU*SmA*SmU | ACGTTGCAGTGTTC CACUAU | 220 | SnROnRSSRRSSR SSSSSSSS |
| WV-32083 | m5Ceo*SAeon001Rm5CeoGeon001RTeo*ST*SG*SC*SA*SG* RT*SG*ST*RT*SC*SmC*SmA*SmC*SmU*SmA | CACGTTGCAGTGTT CCACUA | 221 | SnROnRSSSSSRS SRSSSSSS |
| WV-32084 | m5Ceo*SAeon001Rm5CeoGeon001RTeo*ST*SG*SC*SA*RG* ST*SG*RT*ST*SC*SmC*SmA*SmC*SmU*SmA | CACGTTGCAGTGTT CCACUA | 222 | SnROnRSSSSRSS RSSSSSSS |
| WV-32085 | m5Ceo*SAeon001Rm5CeoGeon001RTeo*ST*SG*RC*SA*SG* RT*SG*ST*RT*SC*SmC*SmA*SmC*SmU*SmA | CACGTTGCAGTGTT CCACUA | 223 | SnROnRSSRSSRS SRSSSSSS |
| WV-32086 | m5Ceo*SAeon001Rm5CeoGeon001RTeo*ST*SG*RC*SA*RG* ST*SG*RT*ST*SC*SmC*SmA*SmC*SmU*SmA | CACGTTGCAGTGTT CCACUA | 224 | SnROnRSSRSRSS RSSSSSSS |
| WV-32087 | m5Ceo*Sm5Ceon001RAeom5Ceon001RGeo*ST*ST*SG*RC*S A*SG*ST*SG*RT*ST*SmC*SmC*SmA*SmC*SmU | CCACGTTGCAGTGT TCCACU | 225 | SnROnRSSSRSSS SRSSSSSS |
| WV-32088 | m5Ceo*Sm5Ceon001RAeom5Ceon001RGeo*ST*ST*SG*SC*S A*RG*ST*SG*RT*ST*SmC*SmC*SmA*SmC*SmU | CCACGTTGCAGTGT TCCACU | 226 | SnROnRSSSSSRS SRSSSSSS |
| WV-32089 | m5Ceo*Sm5Ceon001RAeom5Ceon001RGeo*ST*ST*RG*RC*S A*SG*ST*SG*RT*ST*SmC*SmC*SmA*SmC*SmU | CCACGTTGCAGTGT TCCACU | 227 | SnROnRSSRRSSS SRSSSSSS |
| WV-32090 | m5Ceo*Sm5Ceon001RAeom5Ceon001RGeo*ST*ST*RG*RC*S A*RG*ST*SG*RT*ST*SmC*SmC*SmA*SmC*SmU | CCACGTTGCAGTGT TCCACU | 228 | SnROnRSSRSRSS SRSSSSSS |
| WV-36875 | Geo*STeon001RGeoTeon001RTeo*SC*SC*SA*SC*RT*SA*S T*SC*RC*ST*SmCn001RmC*SmUn001RmU*SmC | GTGTTCCACTATCC TCCUUC | 229 | SnROnRSSSSRSS SRSSnRSnRS |
| WV-36876 | Geo*STeon001RGeoTeon001RTeo*SC*SC*SA*SC*RT*SA*S T*SC*RC*ST*SmCn001RmC*SmU*SmUn001RmU*SmC | GTGTTCCACTATCC TCCUUC | 230 | SnROnRSSSSRSS SRSSnRSSnR |
| WV-36877 | Geo*STeon001RGeoTeon001RTeo*SC*SC*SA*SC*RT*SA*S T*SC*RC*ST*SmCn001RmCmUn001RmU*SmC | GTGTTCCACTATCC TCCUUC | 231 | SnROnRSSSSRSS SRSSnROnRS |
| WV-37299 | mG*SmU*SmG*SmU*SmU*SC*SC*SA*SC*RT*SA*ST*SC* RC*ST*Sm5Ceom5CeoTeoTeo*Sm5Ceo | GUGUUCCACTATC CTCCTTC | 232 | SSSSSSSSRSSSR SSOOOS |
| WV-37300 | mG*SmU*SmG*SmU*SmU*SC*SC*SA*SC*RT*SA*ST*SC* RC*ST*Sm5Ceom001Rm5Ceon001RTeon001RTeo*Sm5Ceo | GUGUUCCACTATC CTCCTTC | 233 | SSSSSSSSRSSSR SSnRnRnRS |
| WV-37301 | mG*SmU*SmG*SmU*SmU*SC*SC*SA*SC*RT*SA*ST*SC* RC*ST*Sm5Ceon001Rm5CeoTeon001RTeo*Sm5Ceo | GUGUUCCACTATC CTCCTTC | 234 | SSSSSSSSRSSSR SSnROnRS |
| WV-37302 | mGn001RSmU*SmG*SmU*SmU*SC*SC*SA*SC*RT*SA*ST* SC*RC*ST*Sm5Ceon001Rm5CeoTeon001RTeo*Sm5Ceo | GUGUUCCACTATC CTCCTTC | 235 | nRSSSSSSSRSSS RSSnROnRS |
| WV-37303 | mG*SmUn001RmG*SmU*SmU*SC*SC*SA*SC*RT*SA*ST* SC*RC*ST*Sm5Ceon001Rm5CeoTeon001RTeo*Sm5Ceo | GUGUUCCACTATC CTCCTTC | 236 | SnRSSSSSSRSSS RSSnROnRS |
| WV-37304 | mG*SmU*SmGn001RmU*SmU*SC*SC*SA*SC*RT*SA*ST* SC*RC*ST*Sm5Ceon001Rm5CeoTeon001RTeo*Sm5Ceo | GUGUUCCACTATC CTCCTTC | 237 | SSnRSSSSSRSSS RSSnROnRS |
| WV-37305 | mG*SmU*SmG*SmUn001RmU*SC*SC*SA*SC*RT*SA*ST* SC*RC*ST*Sm5Ceon001Rm5CeoTeon001RTeo*Sm5Ceo | GUGUUCCACTATC CTCCTTC | 238 | SSSnRSSSSRSSS RSSnROnRS |
| WV-37497 | Geo*STeom5Ceom5CeoAeo*SC*ST*ST*ST*RC*ST*SG*RA* SC*SA*SmG*SmC*SmU*SmC*SmC | GTCCACTTTCTGAC AGCUCC | 239 | SOOOSSSSRSSR SSSSSSS |
| WV-37498 | Geo*STeon001Rm5Ceon001Rm5Ceon001RAeo*SC*ST*ST*ST *RC*ST*SG*RA*SC*SA*SmG*SmC*SmU*SmC*SmC | GTCCACTTTCTGAC AGCUCC | 240 | SnRnRnRSSSSRS SRSSSSSSS |
| WV-37499 | Geo*STeon001Rm5Ceom5Ceon001RAeo*SC*ST*ST*ST*RC* ST*SG*RA*SC*SA*SmG*SmC*SmU*SmC*SmC | GTCCACTTTCTGAC AGCUCC | 241 | SnROnRSSSSRSS RSSSSSSS |
| WV-37500 | Geo*STeon001Rm5Ceom5Ceon001RAeo*SC*ST*ST*ST*RC* ST*SG*RA*SC*SA*SmGn001RmC*SmU*SmC*SmC | GTCCACTTTCTGAC AGCUCC | 242 | SnROnRSSSSRSS RSSSnRSSS |
| WV-37501 | Geo*STeon001Rm5Ceom5Ceon001RAeo*SC*ST*ST*ST*RC* ST*SG*RA*SC*SA*SmG*SmCn001RmU*SmC*SmC | GTCCACTTTCTGAC AGCUCC | 243 | SnROnRSSSSRSS RSSSSnnRSS |
| WV-37502 | Geo*STeon001Rm5Ceom5Ceon001RAeo*SC*ST*ST*ST*RC* ST*SG*RA*SC*SA*SmG*SmUn001RmC*SmC*SmC | GTCCACTTTCTGAC AGCUCC | 244 | SnROnRSSSSRSS RSSSSSnRS |
| WV-37503 | Geo*STeon001Rm5Ceom5Ceon001RAeo*SC*ST*ST*ST*RC* ST*SG*RA*SC*SA*SmG*SmC*SmU*SmCn001RmC | GTCCACTTTCTGAC AGCUCC | 245 | SnROnRSSSSRSS RSSSSSSnR |
| WV-37504 | mG*SmU*SmC*SmC*SmA*SC*ST*ST*ST*RC*ST*SG*RA* SC*SA*SGeom5CeoTeom5Ceo*Sm5Ceo | GUCCACTTTCTGAC AGCTCC | 246 | SSSSSSSSRSSRS SSOOOS |
| WV-37505 | mG*SmU*SmC*SmC*SmA*SC*ST*ST*ST*RC*ST*SG*RA* SC*SA*SGeon001Rm5Ceon001RTeon001Rm5Ceo*Sm5Ceo | GUCCACTTTCTGAC AGCTCC | 247 | SSSSSSSSRSSRS SSnRnRnRS |
| WV-37506 | mG*SmU*SmC*SmC*SmA*SC*ST*ST*ST*RC*ST*SG*RA* SC*SA*SGeon001Rm5CeoTeon001Rm5Ceo*Sm5Ceo | GUCCACTTTCTGAC AGCTCC | 248 | SSSSSSSSRSSRS SSnROnRS |

TABLE 1A-continued

Example MAPT Oligonucleotides/Compositions

| ID | Modified Sequence | Base Sequence | SEQ ID NO | Stereochemistry/ Linkages |
|---|---|---|---|---|
| WV-37507 | mGn001RmU*SmC*SmC*SmA*SC*ST*ST*ST*RC*ST*SG*RA*SC*SA*SGeon001Rm5CeoTeon001Rm5Ceo*Sm5Ceo | GUCCACTTTCTGACAGCTCC | 249 | nRSSSSSSSRSSRSSSnROnRS |
| WV-37508 | mG*SmUn001RmC*SmC*SmA*SC*ST*ST*ST*RC*ST*SG*RA*SC*SA*SGeon001Rm5CeoTeon001Rm5Ceo*Sm5Ceo | GUCCACTTTCTGACAGCTCC | 250 | SnRSSSSSSRSSRSSSnROnRS |
| WV-37509 | mG*SmU*SmCn001RmC*SmA*SC*ST*ST*ST*RC*ST*SG*RA*SC*SA*SGeon001Rm5CeoTeon001Rm5Ceo*Sm5Ceo | GUCCACTTTCTGACAGCTCC | 251 | SSnRSSSSSRSSRSSSnROnRS |
| WV-37510 | mG*SmU*SmC*SmCn001RmA*SC*ST*ST*ST*RC*ST*SG*RA*SC*SA*SGeon001Rm5CeoTeon001Rm5Ceo*Sm5Ceo | GUCCACTTTCTGACAGCTCC | 252 | SSSnRSSSSRSSRSSSnROnRS |
| WV-37511 | Geo*STeom5Ceom5CeoAeo*SC*ST*ST*RT*SC*ST*SG*RA*SC*SA*SmG*SmC*SmU*SmC*SmC | GTCCACTTTCTGACAGCUCC | 253 | SOOOSSSRSSSRSSSSSSS |
| WV-37512 | Geo*STeon001Rm5Ceon001Rm5Ceon001RAeo*SC*ST*ST*RT*SC*ST*SG*RA*SC*SA*SmG*SmC*SmU*SmC*SmC | GTCCACTTTCTGACAGCUCC | 254 | SnRnRnRSSSRSSSRSSSSSSS |
| WV-37513 | Geo*STeon001Rm5Ceom5Ceon001RAeo*SC*ST*ST*RT*SC*ST*SG*RA*SC*SA*SmG*SmC*SmU*SmC*SmC | GTCCACTTTCTGACAGCUCC | 255 | SnROnRSSSRSSSRSSSSSSS |
| WV-37514 | Geo*STeon001Rm5Ceom5Ceon001RAeo*SC*ST*ST*RT*SC*ST*SG*RA*SC*SA*SmGn001RmC*SmU*SmC*SmC | GTCCACTTTCTGACAGCUCC | 256 | SnROnRSSSRSSSRSSSnRSSS |
| WV-37515 | Geo*STeon001Rm5Ceom5Ceon001RAeo*SC*ST*ST*RT*SC*ST*SG*RA*SC*SA*SmG*SmCn001RmU*SmC*SmC | GTCCACTTTCTGACAGCUCC | 257 | SnROnRSSSRSSSRSSSSnRSS |
| WV-37516 | Geo*STeon001Rm5Ceom5Ceon001RAeo*SC*ST*ST*RT*SC*ST*SG*RA*SC*SA*SmG*SmC*SmUn001RmC*SmC | GTCCACTTTCTGACAGCUCC | 258 | SnROnRSSSRSSSRSSSSSnRS |
| WV-37517 | Geo*STeon001Rm5Ceom5Ceon001RAeo*SC*ST*ST*RT*SC*ST*SG*RA*SC*SA*SmG*SmC*SmU*SmCn001RmC* | GTCCACTTTCTGACAGCUCC | 259 | SnROnRSSSRSSSRSSSSSSnR |
| WV-37518 | mG*SmU*SmC*SmC*SmA*SC*ST*ST*RT*SC*ST*SG*RA*SC*SA*SGeom5CeoTeom5Ceo*Sm5Ceo | GUCCACTTTCTGACAGCTCC | 260 | SSSSSSSRSSSRSSSOOOS |
| WV-37519 | mG*SmU*SmC*SmC*SmA*SC*ST*ST*RT*SC*ST*SG*RA*SC*SA*SGeon001Rm5Ceon001RTeon001Rm5Ceo*Sm5Ceo | GUCCACTTTCTGACAGCTCC | 261 | SSSSSSSRSSSRSSSnRnRnRS |
| WV-37520 | mG*SmU*SmC*SmC*SmA*SC*ST*ST*RT*SC*ST*SG*RA*SC*SA*SGeon001Rm5CeoTeon001Rm5Ceo*Sm5Ceo | GUCCACTTTCTGACAGCTCC | 262 | SSSSSSSSSSSRSSSnROnRS |
| WV-37521 | mGn001RmU*SmC*SmC*SmA*SC*ST*ST*RT*SC*ST*SG*RA*SC*SA*SGeon001Rm5CeoTeon001Rm5Ceo*Sm5Ceo | GUCCACTTTCTGACAGCTCC | 263 | nRSSSSSSRSSSRSSSnROnRS |
| WV-37522 | mG*SmUn001RmC*SmC*SmA*SC*ST*ST*RT*SC*ST*SG*RA*SC*SA*SGeon001Rm5CeoTeon001Rm5Ceo*Sm5Ceo | GUCCACTTTCTGACAGCTCC | 264 | SnRSSSSSRSSSRSSSnROnRS |
| WV-37523 | mG*SmU*SmCn001RmC*SmA*SC*ST*ST*RT*SC*ST*SG*RA*SC*SA*SGeon001Rm5CeoTeon001Rm5Ceo*Sm5Ceo | GUCCACTTTCTGACAGCTCC | 265 | SSnRSSSSRSSSRSSSnROnRS |
| WV-37534 | mG*SmU*SmC*SmCn001RmA*SC*ST*ST*RT*SC*ST*SG*RA*SC*SA*SGeon001Rm5CeoTeon001Rm5Ceo*Sm5Ceo | GUCCACTTTCTGACAGCTCC | 266 | SSSnRSSSRSSSRSSSnROnRS |
| WV-38925 | Geo*STeon001Rm5Ceom5Ceon001RAeo*SC*ST*ST*ST*RC*ST*SG*RA*SC*SA*SmG*SmCn001RmU*SmCn001RmC* | GTCCACTTTCTGACAGCUCC | 267 | SnROnRSSSSRSSRSSSSnRSnR |
| WV-38926 | mGn001RmU*SmCn001RmC*SmA*SC*ST*ST*ST*RC*ST*SG*RA*SC*SA*SGeon001Rm5CeoTeon001Rm5Ceo*Sm5Ceo | GUCCACTTTCTGACAGCTCC | 268 | nRSnRSSSSSRSSRSSSnROnRS |
| WV-38927 | mG*SmUn001RmC*SmCn001RmA*SC*ST*ST*ST*RC*ST*SG*RA*SC*SA*SGeon001Rm5CeoTeon001Rm5Ceo*Sm5Ceo | GUCCACTTTCTGACAGCTCC | 269 | SnRSnRSSSSRSSRSSSnROnRS |
| WV-38928 | Geo*STeon001Rm5Ceom5Ceon001RAeo*SC*ST*ST*RT*SC*ST*SG*RA*SC*SA*SmGn001RmC*SmUn001RmC*SmC | GTCCACTTTCTGACAGCUCC | 270 | SnROnRSSSRSSSRSSSnRSnRS |
| WV-38929 | Geo*STeon001Rm5Ceom5Ceon001RAeo*SC*ST*ST*RT*SC*ST*SG*RA*SC*SA*SmG*SmCn001RmU*SmCn001RmC | GTCCACTTTCTGACAGCUCC | 271 | SnROnRSSSRSSSRSSSSnRSnR |
| WV-38930 | mGn001RmU*SmCn001RmC*SmA*SC*ST*ST*RT*SC*ST*SG*RA*SC*SA*SGeon001Rm5CeoTeon001Rm5Ceo*Sm5Ceo | GUCCACTTTCTGACAGCTCC | 272 | nRSnRSSSSRSSSRSSSnROnRS |
| WV-38931 | mG*SmUn001RmC*SmCn001RmA*SC*ST*ST*RT*SC*ST*SG*RA*SC*SA*SGeon001Rm5CeoTeon001Rm5Ceo*Sm5Ceo | GUCCACTTTCTGACAGCTCC | 273 | SnRSnRSSSRSSSRSSSnROnRS |
| WV-40376 | Geo*STeon001RGeo*STeon001RTeo*SC*SC*SA*SC*RT*SA*ST*SA*RC*ST*SmGn001RmC*SmU*SmU*SmC | GTGTTCCACTATCCTCCUUC | 274 | SnRSnRSSSSRSSSRSSnRSSS |
| WV-40377 | Geo*STeon001Rm5Ceo*Sm5Ceon001RAeo*SC*ST*ST*ST*RC*ST*SG*RA*SC*SA*SmGn001RmC*SmU*SmU*SmC | GTCCACTTTCTGACAGCUCC | 275 | SnRSDRSSSSRSSRSSSoRSSS |
| WV-40378 | Geo*STeon001Rm5Ceo*Sm5Ceon001RAeo*SC*ST*ST*RT*SC*ST*SG*RA*SC*SA*SmGn001RmC*SmU*SmU*SmC | GTCCACTTTCTGACAGCUCC | 276 | SnRSnRSSSRSSSRSSSnRSSS |
| WV-40379 | Geo*STeon001RGeo*STeon001RTeo*SC*SC*SA*SC*RT*SA*ST*SC*RC*ST*SmCn001RmC*SmUn001RmU*SmC | GTGTTCCACTATCCTCCUUC | 277 | SnRSnRSSSSRSSSRSSnRSnRS |
| WV-40380 | Geo*STeon001Rm5Ceo*Sm5Ceon001RAeo*SC*ST*ST*ST*RC*ST*SG*RA*SC*SA*SmGn001RmC*SmUn001RmC*SmC | GTCCACTTTCTGACAGCUCC | 278 | SnRSnRSSSSRSSRSSSnRSnRS |
| WV-40381 | Geo*STeon001Rm5Ceo*Sm5Ceon001RAeo*SC*ST*ST*ST*SC*ST*SG*RA*SC*SA*SmGn001RmC*SmUn001RmC*SmC | GTCCACTTTCTGACAGCUCC | 279 | SnRSnRSSSRSSSRSSSnRSnRS |

TABLE 1B

| WV-12891. | | | | | |
|---|---|---|---|---|---|
| ID | Gene | Modified Sequence | Base Sequence | SEQ ID NO | Stereochemistry/ Linkages |
| WV-12891 | LUC | m5Ceo*M5CeoTeoTeomCeo* C*C*T*G*A*A*G*G*T*T*m C*mC*mU*mC*Me | CCTTCCCTGAAGG TTCCUCC | 280 | XOOOXXXXXXX XXXXXXXX |

Notes:

Description, Base Sequence and Stereochemistry/Linkage, due to their length, may be divided into multiple lines in Tables 1A and 1B. Unless otherwise specified, all oligonucleotides in Tables 1A and 1B are single-stranded. As appreciated by those skilled in the art, nucleoside units are unmodified and contain unmodified nucleobases and 2'-deoxy sugars unless otherwise indicated (e.g., with r, m, m5, eo, etc.); linkages, unless otherwise indicated, are natural phosphate linkages; and acidic/basic groups may independently exist in their salt forms. Moieties and modifications in oligonucleotides (or other compounds, e.g., those useful for preparing provided oligonucleotides comprising these moieties or modifications):

m: 2'-OMe;

m5: methyl at 5-position of C (nucleobase is 5-methylcytosine);

m5Ceo: 5-methyl 2'-O-methoxyethyl C;

eo: 2'-MOE (2'-O-methoxyethyl, 2'-$OCH_2CH_2OCH_3$);

O, PO: phosphodiester (phosphate). It can be an end group (or a component thereof), or a linkage, e.g., a linkage between a linker and an oligonucleotide chain, an internucleotidic linkage (a natural phosphate linkage), etc. Phosphodiesters are typically indicated with "O" in the Stereochemistry/Linkage column and are typically not marked in the Description column (if it is an end group, e.g., a 5'-end group, it is indicated in the Description and typically not in Stereochemistry/Linkage); if no linkage is indicated in the Description column, it is typically a phosphodiester unless otherwise indicated. Note that a phosphate linkage between a linker (e.g., L001) and an oligonucleotide chain may not be marked in the Description column, and may not be indicated with "O" in the Stereochemistry/Linkage column;

*, PS: Phosphorothioate. It can be an end group (if it is an end group, e.g., a 5'-end group, it is indicated in the Description and typically not in Stereochemistry/Linkage), or a linkage, e.g., a linkage between linker (e.g., L001) and an oligonucleotide chain, an internucleotidic linkage (a phosphorothioate internucleotidic linkage), etc.;

R, Rp: Phosphorothioate in the Rp configuration. Note that * R (or *R) indicates a single phosphorothioate linkage in the Rp configuration;

S, Sp: Phosphorothioate in the Sp configuration. Note that * S (or *S) indicates a single phosphorothioate linkage in the Sp configuration;

X: stereorandom phosphorothioate;

n001:

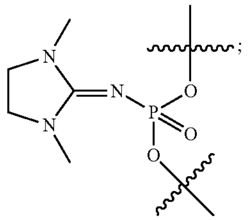 [SMILES: *OP(=O)(N=C1N(C)CCN1C)O*]

nX stereorandom n001;

n001R, nR: n001 in the Rp configuration;

n001S, nS: n001 in the Sp configuration.

Lengths

As appreciated by those skilled in the art, oligonucleotides can be of various lengths to provide desired properties and/or activities for various uses. Many technologies for assessing, selecting and/or optimizing oligonucleotide length are available in the art and can be utilized in accordance with the present disclosure. As demonstrated herein, in many embodiments, MAPT oligonucleotides are of suitable lengths to hybridize with their targets and reduce levels of their targets and/or an encoded product thereof. In some embodiments, an oligonucleotide is long enough to recognize a target nucleic acid (e.g., a MAPT mRNA). In some embodiments, an oligonucleotide is sufficiently long to distinguish between a target nucleic acid and other nucleic acids (e.g., a nucleic acid having a base sequence which is not MAPT) to reduce off-target effects. In some embodiments, a MAPT oligonucleotide is sufficiently short to reduce complexity of manufacture or production and to reduce cost of products.

In some embodiments, the base sequence of an oligonucleotide is about 10-500 nucleobases in length. In some embodiments, a base sequence is about 10-500 nucleobases in length. In some embodiments, a base sequence is about 10-50 nucleobases in length. In some embodiments, a base sequence is about 15-50 nucleobases in length. In some embodiments, a base sequence is from about 15 to about 30 nucleobases in length. In some embodiments, a base sequence is from about 10 to about 25 nucleobases in length. In some embodiments, a base sequence is from about 15 to about 22 nucleobases in length. In some embodiments, a base sequence is about 10, 11, 12, 13, 14, 15, 16, 17, 18, 19, 20, 21, 22, 23, 24, or 25 nucleobases in length. In some embodiments, abase sequence is about 18 nucleobases in length. In some embodiments, abase sequence is about 19 nucleobases in length. In some embodiments, a base sequence is about 20 nucleobases in length. In some embodiments, a base sequence is about 21 nucleobases in length. In some embodiments, a base sequence is about 22 nucleobases in length. In some embodiments, a base sequence is about 23 nucleobases in length. In some embodiments, a base sequence is about 24 nucleobases in length. In some embodiments, a base sequence is about 25 nucleobases in length. In some embodiments, each nucleobase is optionally substituted A, T, C, G, U, or an optionally substituted tautomer of A, T, C, G, or U.

Regions, Wings and Cores

In some embodiments, an oligonucleotide, e.g., a MAPT oligonucleotide, comprises several regions, each of which independently comprises one or more consecutive nucleosides and optionally one or more intemucleotidic linkages. In some embodiments, a region differs from its neighboring region(s) in that it contains one or more structural feature that are different from those corresponding structural features of its neighboring region(s). Example structural features include nucleobase modifications and patterns thereof, sugar modifications and patterns thereof, internucleotidic linkages and patterns thereof (which can be internucleotidic linkage types (e.g., phosphate, phosphorothioate, phosphorothioate triester, neutral internucleotidic linkage, etc.) and patterns thereof, linkage phosphorus modifications (backbone phosphorus modifications) and patterns thereof, backbone chiral center (linkage phosphorus) stereochemistry and patterns thereof [e.g., combination of Rp and/or Sp of chirally controlled internucleotidic linkages (sequentially from 5' to 3'), optionally with non-chirally controlled internucleotidic linkages and/or natural phosphate linkages, if any (e.g., OSOOO RSSRS SSSRS SOOOS)]. In some embodiments, a region comprises a chemical modification (e.g., a sugar modification, base modification, internucleotidic linkage, or stereochemistry of internucleotidic linkage) not present in its neighboring region(s). In some embodiments, a region lacks a chemical modification present in its neighboring regions(s).

In some embodiments, an oligonucleotide comprises or consists of two or more regions. In some embodiments, an oligonucleotide comprises or consists of three or more regions. In some embodiments, an oligonucleotide comprises or consists of two neighboring regions, wherein one region is designated as a wing region and the other a core region. The structure of such an oligonucleotide comprises or consists of a wing-core or core-wing structure. In some embodiments, an oligonucleotide comprises or consists of three neighboring regions, wherein one region is flanked by two neighboring regions. In some embodiments, the middle region is designated as the core region, and each of the flanking region a wing region (a 5'-wing if connected to the 5'-end of the core, a 3'-wing if connected to the 3'-end of the core). The structure of such an oligonucleotide comprises or consists of a wing-core-wing structure.

In some embodiments, a first region (e.g., a wing) differs from a second region (e.g., a core) in that the first region contains sugar modification(s) or a pattern thereof absent from the second region. In some embodiments, a first (e.g., wing) region comprises a sugar modification(s) or a pattern thereof absent from a second (e.g., core) region. In some embodiments, a sugar modification is a 2'-modification. In some embodiments, a 2'-modification is 2'-OR, wherein R is optionally substituted $C_{1-6}$ aliphatic. In some embodiments, a 2'-modification is 2'-OR, wherein R is optionally substituted $C_{1-6}$ alkyl. In some embodiments, a 2'-modification is 2'-MOE. In some embodiments, a 2'-modification is 2'-OMe. In some embodiments, a modified sugar is a bicyclic sugar, e.g., a LNA sugar. In some embodiments, each sugar in a region is independently modified. In some embodiments, each sugar of a region (e.g., a wing) independently comprises a modification, which can be the same or different from each other. In some embodiments, each sugar of a region (e.g., a wing) comprises the same modification, e.g., 2'-modification as described in the present disclosure. In some embodiments, sugars of a region (e.g., a core) are not modified. In some embodiments, each sugar of a region (e.g., a core) is a non-modified DNA sugar (with two —H at the 2'-position). In some embodiments, the structure of a provided oligonucleotide comprises or consists of a wing-core, core-wing, or wing-core-wing structure, wherein each wing independently comprises one or more sugar modifications, and each sugar in the core is a natural DNA sugar (with two —H at the 2'-position).

Additionally or alternatively, a first region (e.g., a wing) can contain internucleotidic linkage(s) or pattern thereof that differs from another region (e.g., a core or another wing). In some embodiments, a region (e.g., a wing) comprises two or more consecutive natural phosphate linkages. In some embodiments, a region (e.g., a core) comprises no consecutive natural phosphate linkages. In some embodiments, the structure of a provided oligonucleotide comprises or consists of awing-core, core-wing, or wing-core-wing structure, wherein at least one wing independently comprises two or more consecutive natural phosphate linkages, and the core comprises no consecutive natural phosphate linkages. In some embodiments, in a wing-core-wing structure, each wing independently comprises two or more consecutive internucleotidic linkages. Unless otherwise noted, for the purpose of stereochemistry of wing-core-wing structures, internucleotidic linkages connecting a core with a wing are included in the core (e.g., see above).

In some embodiments, a region is a 5'-wing, a 3'-wing, or a core. In some embodiments, the 5'-wing is to the 5' end of the oligonucleotide, the 3'-wing is to the 3'-end of the oligonucleotide and the core is between the 5'-wing and the 3'-wing, and the oligonucleotide comprises or consists of a wing-core-wing structure or format. In some embodiments, a core comprises a span of contiguous natural DNA sugars (2'-deoxyribose). In some embodiments, a core comprises a span of at least 5 contiguous natural DNA sugars (2'-deoxyribose). In some embodiments, a core comprises a span of at least 10 contiguous natural DNA sugars (2'-deoxyribose). In some embodiments, a core is referenced as a gap. In some embodiments, an oligonucleotide which comprises or consists of a wing-core-wing structure is described as a gapmer. In some embodiments, the structure of a provided oligonucleotide comprises or consists of a wing-core structure. In some embodiments, the structure of a provided oligonucleotide comprises or consists of a core-wing structure. In some embodiments, the structure of an oligonucleotide comprises or consists of an oligonucleotide chain which comprises or consists of wing-core-wing, wing-core, or wing-core, wherein the oligonucleotide chain is conjugated to an additional chemical moiety optionally through a linker as described in the present disclosure. In some embodiments, the present disclosure provides oligonucleotides that target MAPT and have a structure that comprises one or two wings and a core, and comprise or consist of a wing-core-wing, core-wing, or wing-core structure.

Ribonuclease H (RNase H, e.g., RNase H1, RNase H2, etc.) reportedly recognizes a structure comprising a hybrid of RNA and DNA (e.g., a heteroduplex), and cleaves the RNA. In some embodiments, an oligonucleotide comprising a span of contiguous natural DNA sugars (2'-deoxyribose, e.g., in a core region) is capable of annealing to a RNA such as a mRNA to form a heteroduplex; and this heteroduplex structure is capable of being recognized by RNase H and the RNA cleaved by RNase H. In some embodiments, a core of a provided oligonucleotide comprises 1, 2, 3, 4, 5, 6, 7, 8, 9, 10 or more contiguous natural DNA sugars, and the core is capable of annealing specifically to a target transcript [e.g., a MAPT transcript (e.g., pre-mRNA, mature mRNA, etc.)]; and the formed structure is capable of being recognized by RNase H and the transcript cleaved by RNase H. In some embodiments, a core of a provided oligonucleotide comprises 5 or more contiguous DNA sugars.

Regions, e.g., wings, cores, etc., can be of various suitable lengths. In some embodiments, a region (e.g., a wing, a core, etc.) comprises 1-30, e.g., 1, 2, 3, 4, 5, 6, 7, 8, 9, 10, 11, 12, 13, 14, 15, 16, 17, 18, 19, 20, 21, 22, 23, 24, 25 or more nucleobases. As described in the present disclosure, in some embodiments, each nucleobase independently comprises an optionally substituted monocyclic, bicyclic or polycyclic ring, which ring has at least one nitrogen ring atom; in some embodiments, each nucleobase is independently optionally substituted A, T, C, G or U, or a substituted tautomer of A, T, C, G or U. In some embodiments, a wing, e.g., a first wing, a second wing, a 5'-wing, a 3'-wing, etc. is about 1-10, e.g., about 1, 2, 3, 4, 5, 6, 7, 8, 9, 10, nucleobases in length. In some embodiments, a wing is 1 nucleobase in length. In some embodiments, a wing is about 2 nucleobases in length. In some embodiments, a wing is about 3 nucleobases in length. In some embodiments, a wing is about 4 nucleobases in length. In some embodiments, a wing is about 5 nucleobases in length. In some embodiments, a wing is about 6 nucleobases in length. In some embodiments, a wing is about 7 nucleobases in length. In some embodiments, each wing of a wing-core-wing structure independently has a length as described in the present disclosure. In some embodiments, the two wings are of the same length. In some embodiments, the two wings are of different length. In some embodiments, a core is about 5-25, e.g., about 5, 6, 7, 8, 9, 10, 11, 12, 13, 14, 15, 16, 17, 18, 19, 20, 21, 22, 23, 24, or 25 nucleobases in length. In some embodiments, a core is about 1, 2, 3, 4, 5, 6, 7, 8, 9, 10, 11, 12, 13, 14, 15 or more in length. In some embodiments, a core is about 5 nucleobases in length. In some embodiments, a core is about 6 nucleobases in length. In some embodiments, a core is about 7 nucleobases in length. In some embodiments, a core is about 8 nucleobases in length. In some embodiments, a core is about 9 nucleobases in length. In some embodiments, a core is about 10 nucleobases in length. In some embodiments, a core is about 11 nucleobases in length. In some embodiments, a core is about 12 nucleobases in length. In some embodiments, a core is about 13 nucleobases in length. In some embodiments, a core is about 14 nucleobases in length. In some embodiments, a core is about 15 nucleobases in length. For example, in some embodiments, wing-core-wing are of 2-9-6, 3-9-3, 3-9-4, 3-9-5, 4-7-4, 4-9-4, 4-9-5, 4-10-5, 4-11-4, 4-11-5, 5-7-5, 5-8-6, 5-9-3, 5- 9-5, 5-10-4, 5-10-5, 6-7-6, 6-8-5, or 6-9-2. In some embodiments, it is 5-10-5.

In some embodiments, a wing comprises one or more sugar modifications. In some embodiments, the two wings of a wing-core-wing structure comprise different patterns of sugar modifications or different sugar modifications (and the oligonucleotide has or comprises an "asymmetric" format). In some embodiments, sugar modifications provide improved stability and/or annealing properties compared to absence of sugar modifications.

In some embodiments, a first wing (e.g., a 5'-wing) comprises one or more 2'-OR modifications, wherein R is optionally substituted $C_{1-4}$ aliphatic. In some embodiments, each sugar of a first wing comprises a 2'-OR modification. In some embodiments, 2'-OR is 2'-MOE. In some embodiments, each sugar of a first wing comprises 2'-MOE.

In some embodiments, a second wing (e.g., a 3'-wing) comprises one or more 2'-OR modifications, wherein R is optionally substituted $C_{1-4}$ aliphatic. In some embodiments, each sugar of a second wing comprises a 2'-OR modification. In some embodiments, 2'-OR is 2'-OMe. In some embodiments, each sugar of a second wing comprises 2'-OMe. In some embodiments, a second wing, e.g., a 3'-wing, does not share the same pattern of sugar modifications of a first wing, e.g., a 5'-wing. In some embodiments, a second wing, e.g., a 3'-wing, does not contain a sugar modification of a first wing, e.g., a 5'-wing. As appreciated by those skilled in the art, in some embodiments, a first wing can be a 3'-wing, and a second wing can be a 5'-wing.

In some embodiments, a core comprises 1-25, e.g., 1, 2, 3, 4, 5, 6, 7, 8, 9, 10, 11, 12, 13, 14, 15, 16, 17, 18, 19, 20, 21, 22, 23, 24, 25 or sugars that comprises no 2'—OR groups or are not bicyclic or polycyclic sugars. In some embodiments, a core comprises 1-25, e.g., 1, 2, 3, 4, 5, 6, 7, 8, 9, 10, 11, 12, 13, 14, 15, 16, 17, 18, 19, 20, 21, 22, 23, 24, 25 or sugars that comprises no 2'—OR groups. In some embodiments, a core comprises 1-25, e.g., 1, 2, 3, 4, 5, 6, 7, 8, 9, 10, 11, 12, 13, 14, 15, 16, 17, 18, 19, 20, 21, 22, 23, 24, 25 or sugars that comprises two 2'-H. In many embodiments, a core comprises no 2'—OR groups. In many embodiments, sugars in core regions have two 2'-H.

In some embodiments, certain sugar modifications, e.g., 2'-MOE, provide more stability under certain conditions than other sugar modifications, e.g., 2'-OMe. In some embodiments, a wing comprises 2'-MOE modifications. In some embodiments, each nucleoside unit of a wing comprising a pyrimidine base (e.g., C, U, T, etc.) comprises a 2'-MOE modification. In some embodiments, each sugar unit of a wing comprises a 2'-MOE modification. In some embodiments, each nucleoside unit of a wing comprising a purine base (e.g., A, G, etc.) comprises no 2'-MOE modification (e.g., each such nucleoside unit comprises 2'-OMe, or no 2'-modification, etc.). In some embodiments, each nucleoside unit of a wing comprising a purine base comprises a 2'-OMe modification. In some embodiments, each internucleotidic linkage at the 3'-position of a sugar unit comprising a 2'-MOE modification is a natural phosphate linkage.

In some embodiments, a wing comprises no 2'-MOE modifications. In some embodiments, a wing comprises 2'-OMe modifications. In some embodiments, each nucleoside unit of a wing independently comprises a 2'-OMe modification.

In some embodiments, a wing comprises a bicyclic sugar. In some embodiments, each wing independently comprises one or more bicyclic sugars.

In some embodiments, a bicyclic sugar is a LNA, a cEt or a BNA sugar.

In some embodiments, a MAPT oligonucleotide has a wing-core-wing structure. In some embodiments, a core comprises 1 or more natural DNA sugars. In some embodiments, a core comprises 5 or more consecutive natural DNA sugars. In some embodiments, the core comprises 5-10, 5-15, 5-20, 5-25, 5-30, or 5, 6, 7, 8, 9, 10, 11, 12, 13, 14, 15 or more natural DNA sugars which are optionally consecutive. In some embodiments, the core comprises 5, 6, 7, 8, 9, 10, 11, 12, 13, 14, 15 or more consecutive natural DNA sugars. In some embodiments, core comprises 10 or more consecutive natural DNA sugars. In some embodiments, the core is able to hybridize to a target mRNA, forming a duplex structure recognizable by RNase H, such that RNase H is able to cleave the mRNA.

In some embodiments, a MAPT oligonucleotide has a wing-core-wing structure and has an asymmetrical format.

In some embodiments, in an oligonucleotide having an asymmetrical format, one wing differs from another in the sugar modifications or pattern thereof, or the backbone internucleotidic linkages or pattern thereof, or the backbone chiral centers or pattern thereof. In some embodiments, a MAPT oligonucleotide has an asymmetrical format in that one wing comprises a different sugar modification than the other wing. In some embodiments, a MAPT oligonucleotide has an asymmetrical format in that one wing comprises a different pattern of sugar modifications than the other wing.

In some embodiments, a MAPT oligonucleotide (or a wing, core, region, block or any portion thereof) can be or comprise a modification, a pattern of modifications, an internucleotidic linkage, a pattern of internucleotidic linkages, a pattern of chiral centers, a wing, a core, a block, a region, and/or a format (including but not limited to an asymmetrical format) described U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the modifications, patterns of modifications, internucleotidic linkages, patterns of internucleotidic linkages, patterns of chiral centers, wings, cores, blocks, regions, and formats of each of which are independently incorporated herein by reference.

In some embodiments, the structure of a MAPT oligonucleotide is or comprise a wing-core structure.

In some embodiments, the structure of a MAPT oligonucleotide is or comprises a wing-core-wing structure, wherein the first and second wings each independently comprise at least one 2'-MOE.

In some embodiments, the structure of a MAPT oligonucleotide is or comprises a wing-core-wing structure, wherein the first and second wings each independently comprise at least one 2'-OMe.

In some embodiments, the structure of a MAPT oligonucleotide comprises or consists of an asymmetrical format. In some embodiments, the structure of a MAPT oligonucleotide comprises or consists of a symmetrical format.

In some embodiments, the structure of a MAPT oligonucleotide is or comprises an asymmetrical format, wherein the structure of the oligonucleotide is a wing-core-wing structure, wherein the format of the first wing is different from that of the second wing. In some embodiments, the structure of a MAPT oligonucleotide is or comprises an asymmetrical format, wherein the structure of the oligonucleotide is a wing-core-wing structure, wherein the first and second wings differ in sugar modification (or combinations or patterns thereof) and/or in internucleotidic linkages (or combinations or patterns thereof). In some embodiments, the structure of a MAPT oligonucleotide is or comprises an asymmetrical format, wherein the structure of the oligonucleotide is a wing-core-wing structure, wherein the first and second wings differ in sugar modification (or combinations or patterns thereof).

In some embodiments, the structure of a MAPT oligonucleotide is or comprises a wing-core-wing structure, wherein one wing comprises one type of sugar, and the other comprises that type and a second type.

In some embodiments, the structure of a MAPT oligonucleotide comprises a core and at least one wing, the core comprises 2, 3, 4, 5, 6, 7, 8, 9, 10, 11, 12, 13, 14, 15, 16, 17, 18, 19, 20, or more consecutive 2'-deoxyribose sugars.

In some embodiments, the structure of a MAPT oligonucleotide comprises a core and at least one wing, the core comprises at least 5 consecutive 2'-deoxyribose sugars.

In some embodiments, the structure of a MAPT oligonucleotide comprises a core and at least one wing, the core comprises at least 6 consecutive 2'-deoxyribose sugars.

In some embodiments, the structure of a MAPT oligonucleotide comprises a core and at least one wing, the core comprises at least 7 consecutive 2'-deoxyribose sugars.

In some embodiments, the structure of a MAPT oligonucleotide comprises a core and at least one wing, wherein the core comprises at least 8 consecutive 2'-deoxyribose sugars.

In some embodiments, the structure of a MAPT oligonucleotide comprises a core and at least one wing, wherein the core comprises at least 9 consecutive 2'-deoxyribose sugars.

In some embodiments, the structure of a MAPT oligonucleotide comprises a core and at least one wing, wherein the core comprises at least 10 consecutive 2'-deoxyribose sugars.

In some embodiments, a MAPT oligonucleotide comprises at least three different types of internucleotidic linkages.

In some embodiments, a MAPT oligonucleotide comprises: at least one natural phosphate internucleotidic linkage; at least one phosphorothioate; and at least one neutral or non-negatively charged internucleotidic linkage.

In some embodiments, a MAPT oligonucleotide comprises: at least one natural phosphate internucleotidic linkage; at least one phosphorothioate which is chirally controlled; and at least one neutral or non-negatively charged internucleotidic linkage.

In some embodiments, a MAPT oligonucleotide comprises: at least one natural phosphate internucleotidic linkage; at least one phosphorothioate; and at least one neutral or non-negatively charged internucleotidic linkage which is chirally controlled.

In some embodiments, a MAPT oligonucleotide comprises: at least one natural phosphate internucleotidic linkage; at least one phosphorothioate which is chirally controlled; and at least one neutral or non-negatively charged internucleotidic linkage which is chirally controlled.

In some embodiments, the structure of a MAPT oligonucleotide comprises a core and at least one wing, wherein the core comprises at least 12 consecutive 2'-deoxyribose sugars.

In some embodiments, the structure of a MAPT oligonucleotide comprises a core and at least one wing, wherein the core comprises at least 14 consecutive 2'-deoxyribose sugars.

In some embodiments, the structure of a MAPT oligonucleotide is or comprises a wing-core-wing structure, wherein the first and second wing each comprise at least 2 different types of sugars.

In some embodiments, the structure of a MAPT oligonucleotide is or comprises a wing-core-wing structure, wherein the first and second wing each comprise 2'-DNA sugar (a natural 2'-deoxyribose) and a sugar comprising 2'-modification.

In some embodiments, the structure of a MAPT oligonucleotide is or comprises a wing-core-wing structure, wherein the first and second wing each comprise 2'-DNA sugar (a natural 2'-deoxyribose) and a 2'-OMe sugar.

In some embodiments, a MAPT oligonucleotide comprises at least one natural 2'-deoxyribose sugar (unmodified DNA sugar), at least one LNA sugar and at least one 2'-MOE sugar.

In some embodiments, the structure of a MAPT oligonucleotide is or comprises a wing-core-wing structure, wherein the first and second wing each comprise a natural 2'-deoxyribose (unmodified DNA sugar), a LNA sugar and 2'-MOE sugar.

In some embodiments, a MAPT oligonucleotide comprises at least one natural 2'-deoxyribose (unmodified DNA sugar), at least one LNA sugar and at least one 2'-OMe sugar.

In some embodiments, the structure of a MAPT oligonucleotide is or comprises a wing-core-wing structure, wherein the first and second wing each comprise a natural 2'-deoxyribose (unmodified DNA sugar), a LNA sugar and 2'-OMe sugar.

In some embodiments, the structure of a MAPT oligonucleotide is or comprises a wing-core-wing structure, wherein the first and second wing each comprise at least 3 different types of sugars (e.g., selected from unmodified sugars and modified sugars with various modifications).

In some embodiments, the structure of a MAPT oligonucleotide is or comprises a wing-core-wing structure, wherein at least one wing comprises one or more (1, 2, 3, 4, 5, 6, 7, 8, 9, or 10) LNA sugars.

In some embodiments, the structure of a MAPT oligonucleotide is or comprises a wing-core-wing structure, wherein the first and second wing each comprise one or more 2'-MOE sugars and one or more LNA sugars.

In some embodiments, the structure of a MAPT oligonucleotide is or comprises a wing-core-wing structure, wherein the first and second wing each comprise one or more LNA sugars.

In some embodiments, the structure of a MAPT oligonucleotide is or comprises a wing-core-wing structure, wherein one wing comprises one or more LNA sugars and one or more 2'-MOE sugars and the other wing comprises one or more LNA sugars and one or more 2'-OMe sugars.

In some embodiments, the structure of a MAPT oligonucleotide is or comprises a wing-core-wing structure, wherein one wing comprises a natural 2'-deoxyribose (unmodified DNA sugar), a LNA sugar, and a 2'-MOE sugar.

In some embodiments, the structure of a MAPT oligonucleotide is or comprises a wing-core-wing structure, wherein one wing comprises at least 3 different types of sugars.

In some embodiments, the structure of a MAPT oligonucleotide is or comprises a wing-core-wing structure, wherein the first and second wing each comprise a natural 2'-deoxyribose (unmodified DNA sugar) and at least 1 modified sugar (compared to 2'-deoxyribose (unmodified DNA sugar)).

In some embodiments, the structure of a MAPT oligonucleotide is or comprises a wing-core-wing structure, wherein the first and second wing each comprise a natural 2'-deoxyribose (unmodified DNA sugar) and at least 2 sugar modifications.

In some embodiments, the structure of a MAPT oligonucleotide is or comprises a wing, wherein the wing comprises at least 3 different types of sugars.

In some embodiments, the structure of a MAPT oligonucleotide comprises a wing, wherein the wing comprises at least 1 base(s).

In some embodiments, the structure of a MAPT oligonucleotide comprises a wing, wherein the wing comprises at least 2 base(s).

In some embodiments, the structure of a MAPT oligonucleotide comprises a wing, wherein the wing comprises at least 3 base(s).

In some embodiments, the structure of a MAPT oligonucleotide comprises a wing, wherein the wing comprises at least 4 base(s).

In some embodiments, the structure of a MAPT oligonucleotide comprises a wing, wherein the wing is 5 base(s).

In some embodiments, the structure of a MAPT oligonucleotide comprises a wing, wherein the wing comprises at least 6 base(s).

In some embodiments, the structure of a MAPT oligonucleotide comprises a wing, wherein the wing comprises at least 7 base(s).

In some embodiments, the structure of a MAPT oligonucleotide comprises a wing, wherein the wing is an 8 base(s).

In some embodiments, the structure of a MAPT oligonucleotide is or comprises a wing-core-wing structure, wherein the first and second wing each comprise two different types of sugars.

In some embodiments, the structure of a MAPT oligonucleotide is or comprises a wing-core-wing structure, wherein one wing comprises at least one 2'-MOE sugar and the other wing comprises at least one 2'-OMe sugar.

In some embodiments, the structure of a MAPT oligonucleotide is or comprises a wing-core-wing structure, wherein one wing comprises a natural 2'-deoxyribose (unmodified DNA sugar) and at least one modified sugar.

In some embodiments, the structure of a MAPT oligonucleotide is or comprises a wing-core-wing structure, wherein one wing comprises a natural 2'-deoxyribose (unmodified DNA sugar) and at least two modified sugars.

In some embodiments, a MAPT oligonucleotide may comprise any first wing, core and/or second wing, as described herein or known in the art.

In some embodiments, an oligonucleotide which has a base sequence which is, comprises or comprises a span of a MAPT oligonucleotide sequence disclosed herein can comprise a first wing, core and/or second wing, as described herein or known in the art.

Internucleotidic Linkages

In some embodiments, oligonucleotides comprise base modifications, sugar modifications, and/or internucleotidic linkage modifications. Various internucleotidic linkages can be utilized in accordance with the present disclosure to link units comprising nucleobases, e.g., nucleosides. In some embodiments, MAPT oligonucleotides comprise both one or more modified internucleotidic linkages and one or more natural phosphate linkages. As widely known by those skilled in the art, natural phosphate linkages are widely found in natural DNA and RNA molecules; they have the structure of —OP(O)(OH)O—, connect sugars in the nucleosides in DNA and RNA, and may be in various salt forms, for example, at physiological pH (about 7.4), natural phosphate linkages are predominantly exist in salt forms with the anion being —OP(O)($O^-$)O—. A modified internucleotidic linkage, or a non-natural phosphate linkage, is an internucleotidic linkage that is not natural phosphate linkage or a salt form thereof. Modified internucleotidic linkages, depending on their structures, may also be in their salt forms. For example, as appreciated by those skilled in the art, phosphorothioate internucleotidic linkages which have the structure of —OP(O)(SH)O— may be in various salt forms, e.g., at physiological pH (about 7.4) with the anion being —OP(O)($S^-$)O—.

In some embodiments, an oligonucleotide comprises an internucleotidic linkage which is a modified internucleotidic linkage, e.g., phosphorothioate, phosphorodithioate, methylphosphonate, phosphoroamidate, thiophosphate, 3'-thiophosphate, or 5'-thiophosphate.

In some embodiments, a modified internucleotidic linkage is a chiral internucleotidic linkage which comprises a chiral linkage phosphorus. In some embodiments, a chiral internucleotidic linkage is a phosphorothioate linkage. In some embodiments, a chiral internucleotidic linkage is a non-negatively charged internucleotidic linkage. In some embodiments, a chiral internucleotidic linkage is a neutral internucleotidic linkage. In some embodiments, a chiral internucleotidic linkage is chirally controlled with respect to its chiral linkage phosphorus. In some embodiments, a chiral internucleotidic linkage is stereochemically pure with respect to its chiral linkage phosphorus. In some embodiments, a chiral internucleotidic linkage is not chirally controlled. In some embodiments, a pattern of backbone chiral centers comprises or consists of positions and linkage phosphorus configurations of chirally controlled internucleotidic linkages (Rp or Sp) and positions of achiral internucleotidic linkages (e.g., natural phosphate linkages).

In some embodiments, an oligonucleotide comprises a modified internucleotidic linkage (e.g., a modified internucleotidic linkage having the structure of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc., or a salt form thereof) as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252 the internucleotidic linkages (e.g., those of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc.,) of each of which are independently incorporated herein by reference. In some embodiments, a modified internucleotidic linkage is a non-negatively charged internucleotidic linkage. In some embodiments, provided oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, the present disclosure provides oligonucleotides comprising one or more neutral internucleotidic linkages. In some embodiments, a non-negatively charged internucleotidic linkage or a neutral internucleotidic linkage (e.g., one of Formula I-n-1, I-n-2, I-n-3, I-n-4, II, II-a-1, II-a-2, II-b-1, II-b-2, II-c-1, II-c-2, II-d-1, II-d-2, etc.) is as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252. In some embodiments, a non-negatively charged internucleotidic linkage or neutral internucleotidic linkage is one of Formula I-n-1, I-n-2, I-n-3, I-n-4, II, II-a-1, II-a-2, II-b-1, II-b-2, II-c-1, II-c-2, II-d-1, II-d-2, etc. as described in WO 2018/223056, WO 2019/032607, WO 2019/075357, WO 2019/032607, WO 2019/075357, WO 2019/200185, WO 2019/217784, WO 2019/032612, and/or WO 2020/191252, such internucleotidic linkages of each of which are independently incorporated herein by reference.

In some embodiments, a non-negatively charged internucleotidic linkage can improve the delivery and/or activity (e.g., ability to decrease the level, activity and/or expression of a target gene or a gene product thereof) of an oligonucleotide.

In some embodiments, a modified internucleotidic linkage (e.g., a non-negatively charged internucleotidic linkage) comprises optionally substituted triazolyl. In some embodiments, a modified internucleotidic linkage (e.g., a non-negatively charged internucleotidic linkage) comprises optionally substituted alkynyl. In some embodiments, a modified internucleotidic linkage comprises a triazole or alkyne moiety. In some embodiments, a triazole moiety, e.g., a triazolyl group, is optionally substituted. In some embodiments, a triazole moiety, e.g., a triazolyl group) is substituted. In some embodiments, a triazole moiety is unsubstituted. In some embodiments, a modified internucleotidic linkage comprises an optionally substituted cyclic guanidine moiety. In some embodiments, a modified internucleotidic linkage comprises an optionally substituted cyclic guanidine moiety and has the structure of:

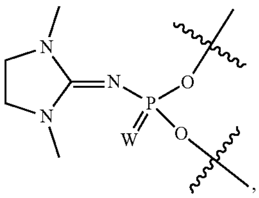
,
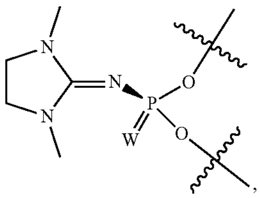
, or
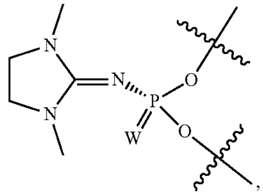
, wherein W is O or S. In some embodiments, W is O. In some embodiments, W is S. In some embodiments, a non-negatively charged internucleotidic linkage is stereochemically controlled.

In some embodiments, a non-negatively charged internucleotidic linkage or a neutral internucleotidic linkage is an internucleotidic linkage comprising a triazole moiety. In some embodiments, a non-negatively charged internucleotidic linkage or a non-negatively charged internucleotidic linkage comprises an optionally substituted triazolyl group. In some embodiments, an internucleotidic linkage comprising a triazole moiety (e.g., an optionally substituted triazolyl group) has the structure of

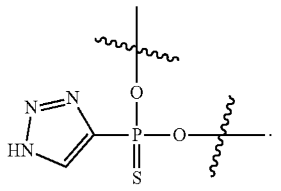 [SMILES: *OP(=S)(O*)c1c[nH]nn1]

In some embodiments, an internucleotidic linkage comprising a triazole moiety has the structure of

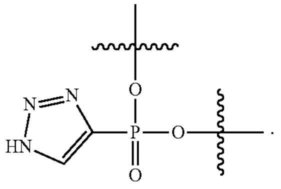 [SMILES: *OP(=O)(O*)c1c[nH]nn1]

In some embodiments, an internucleotidic linkage, e.g., a non-negatively charged internucleotidic linkage, a neutral internucleotidic linkage, comprises a cyclic guanidine moiety. In some embodiments, an internucleotidic linkage comprising a cyclic guanidine moiety has the structure of

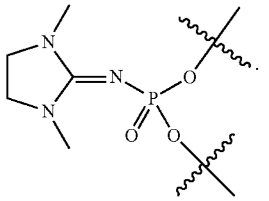 [SMILES: *OP(=O)(N=C1N(C)CCN1C)O*]

In some embodiments, a non-negatively charged internucleotidic linkage, or a neutral internucleotidic linkage, is or comprising a structure selected from

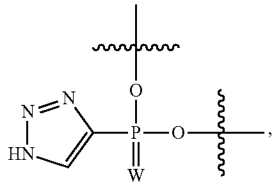

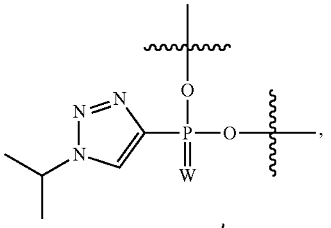

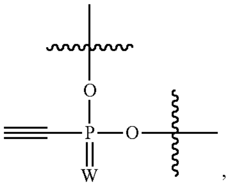

, or

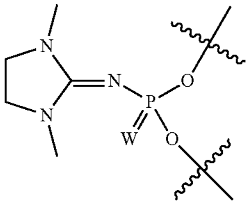

wherein W is O or S.

In some embodiments, an internucleotidic linkage comprises a Tmg group (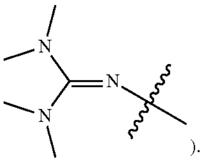).

In some embodiments, an internucleotidic linkage comprises a Tmg group and has the structure of

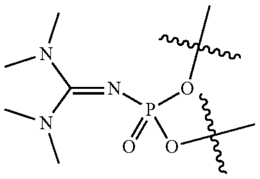 [SMILES: *OP(=O)(N=C(N(C)C)N(C)C)O*]

(the "Tmg internucleotidic linkage"). In some embodiments, neutral internucleotidic linkages include internucleotidic linkages of PNA and PMO, and an Tmg internucleotidic linkage.

In some embodiments, a non-negatively charged internucleotidic linkage comprises an optionally substituted 3-20 membered heterocyclyl or heteroaryl group having 1-10 heteroatoms. In some embodiments, a non-negatively charged internucleotidic linkage comprises an optionally substituted 3-20 membered heterocyclyl or heteroaryl group having 1-10 heteroatoms, wherein at least one heteroatom is nitrogen. In some embodiments, such a heterocyclyl or heteroaryl group is of a 5-membered ring. In some embodiments, such a heterocyclyl or heteroaryl group is of a 6-membered ring.

In some embodiments, a non-negatively charged internucleotidic linkage comprises an optionally substituted 5-20 membered heteroaryl group having 1-10 heteroatoms. In some embodiments, a non-negatively charged internucleotidic linkage comprises an optionally substituted 5-20 membered heteroaryl group having 1-10 heteroatoms, wherein at least one heteroatom is nitrogen. In some embodiments, a non-negatively charged internucleotidic linkage comprises an optionally substituted 5-6 membered heteroaryl group having 1-4 heteroatoms, wherein at least one heteroatom is nitrogen. In some embodiments, a non-negatively charged internucleotidic linkage comprises an optionally substituted 5-membered heteroaryl group having 1-4 heteroatoms, wherein at least one heteroatom is nitrogen. In some embodiments, a heteroaryl group is directly bonded to a linkage phosphorus. In some embodiments, a non-negatively charged internucleotidic linkage comprises an optionally substituted triazolyl group. In some embodiments, a non-negatively charged internucleotidic linkage comprises an unsubstituted triazolyl group, e.g.,

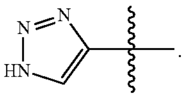

In some embodiments, a non-negatively charged internucleotidic linkage comprises a substituted triazolyl group, e.g.,

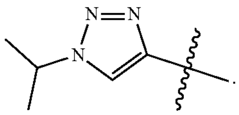 [SMILES: *c1cn(C(C)C)nn1]

In some embodiments, a non-negatively charged internucleotidic linkage comprises an optionally substituted 5-20 membered heterocyclyl group having 1-10 heteroatoms. In some embodiments, a non-negatively charged internucleotidic linkage comprises an optionally substituted 5-20 membered heterocyclyl group having 1-10 heteroatoms, wherein at least one heteroatom is nitrogen. In some embodiments, a non-negatively charged internucleotidic linkage comprises an optionally substituted 5-6 membered heterocyclyl group having 1-4 heteroatoms, wherein at least one heteroatom is nitrogen. In some embodiments, a non-negatively charged internucleotidic linkage comprises an optionally substituted 5-membered heterocyclyl group having 1-4 heteroatoms, wherein at least one heteroatom is nitrogen. In some embodiments, at least two heteroatoms are nitrogen. In some embodiments, a heterocyclyl group is directly bonded to a linkage phosphorus. In some embodiments, a heterocyclyl group is bonded to a linkage phosphorus through a linker, e.g., =N— when the heterocyclyl group is part of a guanidine moiety who directed bonded to a linkage phosphorus through its =N—. In some embodiments, a non-negatively charged internucleotidic linkage comprises an optionally substituted

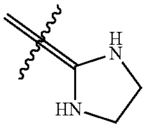 [SMILES: *=C1NCCN1]

group. In some embodiments, a non-negatively charged internucleotidic linkage comprises an substituted

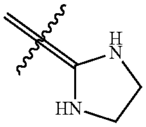 [SMILES: *=C1NCCN1]

group. In some embodiments, a non-negatively charged internucleotidic linkage comprises a

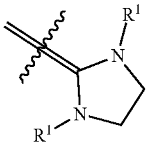

group. In some embodiments, each $R^1$ is independently optionally substituted $C_{1-6}$ alkyl. In some embodiments, each $R^1$ is independently methyl.

In some embodiments, a modified internucleotidic linkage, e.g., a non-negatively charged internucleotidic linkage, comprises a triazole or alkyne moiety, each of which is optionally substituted. In some embodiments, a modified internucleotidic linkage comprises a triazole moiety. In some embodiments, a modified internucleotidic linkage comprises a unsubstituted triazole moiety. In some embodiments, a modified internucleotidic linkage comprises a substituted triazole moiety. In some embodiments, a modified internucleotidic linkage comprises an alkyl moiety. In some embodiments, a modified internucleotidic linkage comprises an optionally substituted alkynyl group. In some embodiments, a modified internucleotidic linkage comprises an unsubstituted alkynyl group. In some embodiments, a modified internucleotidic linkage comprises a substituted alkynyl group. In some embodiments, an alkynyl group is directly bonded to a linkage phosphorus.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage.

Without wishing to be bound by any particular theory, the present disclosure notes that a neutral internucleotidic linkage can be more hydrophobic than a phosphorothioate internucleotidic linkage (PS), which can be more hydrophobic than a natural phosphate linkage (PO). Typically, unlike a PS or PO, a neutral internucleotidic linkage bears less charge. Without wishing to be bound by any particular theory, the present disclosure notes that incorporation of one or more neutral internucleotidic linkages into an oligonucleotide may increase oligonucleotides' ability to be taken up by a cell and/or to escape from endosomes. Without wishing to be bound by any particular theory, the present disclosure notes that incorporation of one or more neutral internucleotidic linkages can be utilized to modulate melting temperature of duplexes formed between an oligonucleotide and its target nucleic acid.

Without wishing to be bound by any particular theory, the present disclosure notes that incorporation of one or more non-negatively charged internucleotidic linkages, e.g., neutral internucleotidic linkages, into an oligonucleotide may be able to increase the oligonucleotide's ability to mediate a function such as gene knockdown. In some embodiments, an oligonucleotide, e.g., a MAPT oligonucleotide capable of mediating knockdown of level of a nucleic acid or a product encoded thereby comprises one or more non-negatively charged internucleotidic linkages. In some embodiments, an oligonucleotide, e.g., a MAPT oligonucleotide capable of mediating knockdown of expression of a target gene comprises one or more non-negatively charged internucleotidic linkages.

In many embodiments, as demonstrated extensively, oligonucleotides of the present disclosure comprise two or more different internucleotidic linkages. In some embodiments, an oligonucleotide comprises a phosphorothioate internucleotidic linkage and a non-negatively charged internucleotidic linkage. In some embodiments, an oligonucleotide comprises a phosphorothioate internucleotidic linkage, a non-negatively charged internucleotidic linkage, and a natural phosphate linkage. In some embodiments, a non-negatively charged internucleotidic linkage is a neutral internucleotidic linkage. In some embodiments, a non-negatively charged internucleotidic linkage is n001. In some embodiments, each phosphorothioate internucleotidic linkage is independently chirally controlled. In some embodiments, each chiral modified internucleotidic linkage is independently chirally controlled.

A typical connection, as in natural DNA and RNA, is that an internucleotidic linkage forms bonds with two sugars (which can be either unmodified or modified as described herein). In many embodiments, as exemplified herein an internucleotidic linkage forms bonds through its oxygen atoms or heteroatoms with one optionally modified ribose or deoxyribose at its 5' carbon, and the other optionally modified ribose or deoxyribose at its 3' carbon. In some embodiments, each nucleoside units connected by an internucleotidic linkage independently comprises a nucleobase which is independently an optionally substituted A, T, C, G, or U, or an optionally substituted tautomer of A, T, C, G or U.

In some embodiments, a MAPT oligonucleotide comprises an internucleotidic linkage wherein a negatively charged non-bridging oxygen of the canonical phosphodiester linkage is replaced by an uncharged alkyl substituent, such as a methyl (Met) or ethyl (Et) group, as in a P-alkyl phosphonate nucleic acid (phNA), such as a P-methyl or P-ethyl phNA. See, for example: Micklefield et al. 2001 Curr. Med. Chem. 8, 1157-1179; and Arangundy-Franklin et al. 2019 Nat. Chem. 11, 533-542.

In some embodiments, a MAPT oligonucleotide is a phosphonomethyl-threosyl nucleic acid (tPhoNA) and/or comprises a phosphonomethyl-threosyl internucleotidic linkage. Liu et al. 2018 J. Am. Chem. Soc. 140, 6690-6699.

As appreciated by those skilled in the art, many other types of internucleotidic linkages may be utilized in accordance with the present disclosure, for example, those described in U.S. Pat. Nos. 3,687,808; 4,469,863; 4,476,301; 5,177,195; 5,023,243; 5,034,506; 5,166,315; 5,185,444; 5,188,897; 5,214,134; 5,216,141; 5,235,033; 5,264,423; 5,264,564; 5,276,019; 5,278,302; 5,286,717; 5,321,131; 5,399,676; 5,405,938; 5,405,939; 5,434,257; 5,453,496; 5,455,233; 5,466,677; 5,466,677; 5,470,967; 5,476,925; 5,489,677; 5,519,126; 5,536,821; 5,541,307; 5,541,316; 5,550,111; 5,561,225; 5,563,253; 5,571,799; 5,587,361; 5,596,086; 5,602,240; 5,608,046; 5,610,289; 5,618,704; 5,623,070; 5,625,050; 5,633,360; 5,64,562; 5,663,312; 5,677,437; 5,677,439; 6,160,109; 6,239,265; 6,028,188; 6,124,445; 6,169,170; 6,172,209; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; or RE39464. In some embodiments, a modified internucleotidic linkage is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the nucleobases, sugars, internucleotidic linkages, chiral auxiliaries/reagents, and technologies for oligonucleotide synthesis (reagents, conditions, cycles, etc.) of each of which is independently incorporated herein by reference.

In some embodiments, an oligonucleotide comprises one or more nucleotides that independently comprise a phosphorus modification prone to "autorelease" under certain conditions. That is, under certain conditions, a particular phosphorus modification is designed such that it self-cleaves from the oligonucleotide to provide, e.g., a natural phosphate linkage. Certain examples of such phosphorus modification groups can be found in U.S. Pat. No. 9,982,257. In some embodiments, an autorelease group comprises a morpholino group. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a natural phosphate linkage.

In some embodiments, an oligonucleotide comprises one or more internucleotidic linkages that improve one or more pharmaceutical properties and/or activities of the oligonucleotide. It is well documented in the art that certain oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1):196-208; Bologna et al., (2002), Antisense & Nucleic Acid Drug Development 12:33-41). Vives et al., (Nucleic Acids Research (1999), 27(20):4071-76) reported that tert-butyl SATE pro-oligonucleotides displayed markedly increased cellular penetration compared to the parent oligonucleotide under certain conditions.

Various types of internucleotidic linkages may be utilized in combination of other structural elements, e.g., sugars, to achieve desired oligonucleotide properties and/or activities. For example, the present disclosure routinely utilizes modified internucleotidic linkages and modified sugars, optionally with natural phosphate linkages and natural sugars, in designing oligonucleotides. In some embodiments, the present disclosure provides an oligonucleotide comprising one or more modified sugars. In some embodiments, the present disclosure provides an oligonucleotide comprising one or more modified sugars and one or more modified internucleotidic linkages, one or more of which are natural phosphate linkages.

Oligonucleotide Compositions

Among other things, the present disclosure provides various oligonucleotide compositions. In some embodiments, the present disclosure provides oligonucleotide compositions of oligonucleotides described herein. In some embodiments, an oligonucleotide composition, e.g., a MAPT oligonucleotide composition, comprises a plurality of an oligonucleotide described in the present disclosure. In some embodiments, an oligonucleotide composition, e.g., a MAPT oligonucleotide composition, is chirally controlled. In some embodiments, an oligonucleotide composition, e.g., a MAPT oligonucleotide composition, is not chirally controlled (stereorandom).

Linkage phosphorus of natural phosphate linkages is achiral. Linkage phosphorus of many modified internucleotidic linkages, e.g., phosphorothioate internucleotidic linkages, are chiral. In some embodiments, during preparation of oligonucleotide compositions (e.g., in traditional phosphoramidite oligonucleotide synthesis), configurations of chiral linkage phosphorus are not purposefully designed or controlled, creating non-chirally controlled (stereorandom) oligonucleotide compositions (substantially racemic preparations) which are complex, random mixtures of various stereoisomers (diastereoisomers)—for oligonucleotides with n chiral internucleotidic linkages (linkage phosphorus being chiral), typically $2^n$ stereoisomers (e.g., when n is 10, $2^{10}$=1,032; when n is 20, $2^{20}$=1,048,576). These stereoisomers have the same constitution, but differ with respect to the pattern of stereochemistry of their linkage phosphorus.

In some embodiments, stereorandom oligonucleotide compositions have sufficient properties and/or activities for certain purposes and/or applications. In some embodiments, stereorandom oligonucleotide compositions can be cheaper, easier and/or simpler to produce than chirally controlled oligonucleotide compositions. However, stereoisomers within stereorandom compositions may have different properties, activities, and/or toxicities, resulting in inconsistent therapeutic effects and/or unintended side effects by stereorandom compositions, particularly compared to certain chirally controlled oligonucleotide compositions of oligonucleotides of the same constitution.

Chirally Controlled Oligonucleotide Compositions

In some embodiments, the present disclosure encompasses technologies for designing and preparing chirally controlled oligonucleotide compositions. In some embodiments, a chirally controlled oligonucleotide composition comprises a controlled/pre-determined (not random as in stereorandom compositions) level of a plurality of oligonucleotides, wherein the oligonucleotides share the same linkage phosphorus stereochemistry at one or more chiral internucleotidic linkages (chirally controlled internucleotidic linkages). In some embodiments, oligonucleotides of a plurality share the same pattern of backbone chiral centers (stereochemistry of linkage phosphorus). In some embodiments, a pattern of backbone chiral centers is as described in the present disclosure. In some embodiments, oligonucleotides of a plurality share a common constitution. In some embodiments, they are structurally identical.

For example, in some embodiments, the present disclosure provides an oligonucleotide composition comprising a plurality of oligonucleotides, wherein oligonucleotides of the plurality share:

1) a common base sequence, and
2) the same linkage phosphorus stereochemistry independently at one or more (e.g., about 1-50, 1-40, 1-30, 1-25, 1-20, 1-15, 1-10, 5-50, 5-40, 5-30, 5-25, 5-20, 5-15, 5-10, 1,2,3,4,5, 6, 7, 8, 9, 10, 11, 12, 13, 14, 15, 16, 17, 18, 19, 20, 21, 22, 23, 24, or 25 or more) chiral internucleotidic linkages ("chirally controlled internucleotidic linkages");

wherein level of oligonucleotides of the plurality in the composition is non-random (e.g., controlled/pre-determined as described herein).

In some embodiments, the present disclosure provides an oligonucleotide composition comprising a plurality of oligonucleotides, wherein oligonucleotides of the plurality share:

1) a common base sequence, and
2) the same linkage phosphorus stereochemistry independently at one or more (e.g., about 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more) chiral internucleotidic linkages ("chirally controlled internucleotidic linkages");

wherein the composition is enriched relative to a substantially racemic preparation of oligonucleotides sharing the common base sequence for oligonucleotides of the plurality.

In some embodiments, the present disclosure provides an oligonucleotide composition comprising a plurality of oligonucleotides, wherein oligonucleotides of the plurality share:

1) a common base sequence, and
2) the same linkage phosphorus stereochemistry independently at one or more (e.g., about 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more) chiral internucleotidic linkages ("chirally controlled internucleotidic linkages");

wherein about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in the composition that share the common base sequence are oligonucleotides of the plurality.

In some embodiments, the percentage/level of the oligonucleotides of a plurality is or is at least $(DS)^{nc}$, wherein DS is 90%-100%, and nc is the number of chirally controlled internucleotidic linkages. In some embodiments, nc is 5, 6, 7, 8, 9, 10 or more. In some embodiments, a percentage/level is at least 10%. In some embodiments, a percentage/level is at least 20%. In some embodiments, a percentage/level is at least 30%. In some embodiments, a percentage/level is at least 40%. In some embodiments, a percentage/level is at least 50%. In some embodiments, a percentage/level is at least 60%. In some embodiments, a percentage/level is at least 65%. In some embodiments, a percentage/level is at least 70%. In some embodiments, a percentage/level is at least 75%. In some embodiments, a percentage/level is at least 80%. In some embodiments, a percentage/level is at least 85%. In some embodiments, a percentage/level is at least 90%. In some embodiments, a percentage/level is at least 95%.

In some embodiments, oligonucleotides of a plurality share a common pattern of backbone linkages. In some embodiments, each oligonucleotide of a plurality independently has an internucleotidic linkage of a particular constitution (e.g., —O—P(O)(SH)—O—) or a salt form thereof (e.g., —O—P(O)(SNa)—O—) independently at each internucleotidic linkage site. In some embodiments, internucleotidic linkages at each internucleotidic linkage site are of the same form. In some embodiments, internucleotidic linkages at each internucleotidic linkage site are of different forms.

In some embodiments, oligonucleotides of a plurality share a common constitution. In some embodiments, oligonucleotides of a plurality are of the same form of a common constitution. In some embodiments, oligonucleotides of a plurality are of two or more forms of a common constitution. In some embodiments, oligonucleotides of a plurality are each independently of a particularly oligonucleotide or a pharmaceutically acceptable salt thereof, or of an oligonucleotide having the same constitution as the particularly oligonucleotide or a pharmaceutically acceptable salt thereof. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in the composition that share a common constitution are oligonucleotides of the plurality. In some embodiments, a percentage of a level is or is at least $(DS)^{nc}$, wherein DS is 90%-100%, and nc is the number of chirally controlled internucleotidic linkages. In some embodiments, nc is 5, 6, 7, 8, 9, 10 or more. In some embodiments, a level is at least 10%. In some embodiments, a level is at least 20%. In some embodiments, a level is at least 30%. In some embodiments, a level is at least 40%. In some embodiments, a level is at least 50%. In some embodiments, a level is at least 60%. In some embodiments, a level is at least 65%. In some embodiments, a level is at least 70%. In some embodiments, a level is at least 75%. In some embodiments, a level is at least 80%. In some embodiments, a level is at least 85%. In some embodiments, a level is at least 90%. In some embodiments, a level is at least 95%.

In some embodiments, each phosphorothioate internucleotidic linkage is independently a chirally controlled internucleotidic linkage.

In some embodiments, the present disclosure provides a chirally controlled oligonucleotide composition comprising a plurality of oligonucleotides of a particular oligonucleotide type characterized by:

a) a common base sequence;

b) a common pattern of backbone linkages;

c) a common pattern of backbone chiral centers;

wherein the composition is enriched, relative to a substantially racemic preparation of oligonucleotides having the same common base sequence, for oligonucleotides of the particular oligonucleotide type.

In some embodiments, the present disclosure provides a chirally controlled oligonucleotide composition comprising a plurality of oligonucleotides of a particular oligonucleotide type characterized by:

a) a common base sequence;

b) a common pattern of backbone linkages;

c) a common pattern of backbone chiral centers;

wherein oligonucleotides of the plurality comprise at least one internucleotidic linkage comprising a common linkage phosphorus in the Sp configuration;

wherein the composition is enriched, relative to a substantially racemic preparation of oligonucleotides having the same common base sequence, for oligonucleotides of the particular oligonucleotide type.

Common patterns of backbone chiral centers, as appreciated by those skilled in the art, comprise at least one Rp or at least one Sp. Certain patterns of backbone chiral centers are illustrated in, e.g., Table 1A.

In some embodiments, a chirally controlled oligonucleotide composition is enriched, relative to a substantially racemic preparation of oligonucleotides share the same common base sequence and a common pattern of backbone linkages, for oligonucleotides of the particular oligonucleotide type.

In some embodiments, oligonucleotides of a plurality, e.g., a particular oligonucleotide type, have a common pattern of backbone phosphorus modifications and a common pattern of nucleoside modifications. In some embodiments, oligonucleotides of a plurality have a common pattern of sugar modifications. In some embodiments, oligonucleotides of a plurality have a common pattern of base modifications. In some embodiments, oligonucleotides of a plurality have a common pattern of nucleoside modifications. In some embodiments, oligonucleotides of a plurality have the same constitution. In many embodiments, oligonucleotides of a plurality are identical. In some embodiments, oligonucleotides of a plurality are of the same oligonucleotide (as those skilled in the art will appreciate, such oligonucleotides may each independently exist in one of the various forms of the oligonucleotide, and may be the same, or different forms of the oligonucleotide). In some embodiments, oligonucleotides of a plurality are each independently of the same oligonucleotide or a pharmaceutically acceptable salt thereof.

In some embodiments, the present disclosure provides chirally controlled oligonucleotide compositions, e.g., of many oligonucleotides in Table 1 whose "stereochemistry/linkage" contain S and/or R. In some embodiments, oligonucleotides of a plurality are each independently a particularly oligonucleotide in Table 1 whose "stereochemistry/linkage" contains S and/or R, optionally in various forms. In some embodiments, oligonucleotides of a plurality are each independently a particularly oligonucleotide in Table 1 whose "stereochemistry/linkage" contains S and/or R, or a pharmaceutically acceptable salt thereof.

In some embodiments, level of a plurality of oligonucleotides in a composition can be determined as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions.

In some embodiments, all chiral internucleotidic linkages are independently chiral controlled, and the composition is a completely chirally controlled oligonucleotide composition. In some embodiments, not all chiral internucleotidic linkages are chiral controlled internucleotidic linkages, and the composition is a partially chirally controlled oligonucleotide composition.

Oligonucleotides may comprise or consist of various patterns of backbone chiral centers (patterns of stereochemistry of chiral linkage phosphorus). Certain useful patterns of backbone chiral centers are described in the present disclosure. In some embodiments, a plurality of oligonucleotides share a common pattern of backbone chiral centers, which is or comprises a pattern described in the present disclosure (e.g., as in "Stereochemistry and Patterns of Backbone Chiral Centers", a pattern of backbone chiral centers of a chirally controlled oligonucleotide in Table 1, etc.).

In some embodiments, a chirally controlled oligonucleotide composition is chirally pure (or stereopure, stereochemically pure) oligonucleotide composition, wherein the oligonucleotide composition comprises a plurality of oligonucleotides, wherein the oligonucleotides are independently of the same stereoisomer [including that each chiral element of the oligonucleotides, including each chiral linkage phosphorus, is independently defined (stereodefined)]. A chirally pure (or stereopure, stereochemically pure) oligonucleotide composition of an oligonucleotide stereoisomer does not contain other stereoisomers (as appreciated by those skilled in the art, one or more unintended stereoisomers may exist as impurities from, e.g., preparation, storage, etc.).

Chirally controlled oligonucleotide compositions can demonstrate a number of advantages over stereorandom oligonucleotide compositions. Among other things, chirally controlled oligonucleotide compositions are more uniform than corresponding stereorandom oligonucleotide compositions with respect to oligonucleotide structures. By controlling stereochemistry, compositions of individual stereoisomers can be prepared and assessed, so that chirally controlled oligonucleotide composition of stereoisomers with desired properties and/or activities can be developed. In some embodiments, chirally controlled oligonucleotide compositions provides better delivery, stability, clearance, activity, selectivity, and/or toxicity profiles compared to, e.g., corresponding stereorandom oligonucleotide compositions. In some embodiments, chirally controlled oligonucleotide compositions provide better efficacy, fewer side effects, and/or more convenient and effective dosage regimens. Among other things, patterns of backbone chiral centers as described herein can be utilized to provide controlled cleavage of oligonucleotide targets (e.g., transcripts such as pre-mRNA, mature mRNA, etc.; including control of cleavage sites, rate and/or extent of cleavage at cleavage sites, and/or overall rate and extent of cleavage, etc.).

In some embodiments, oligonucleotides in provided compositions, e.g., chirally controlled oligonucleotide compositions, are MAPT oligonucleotides as described herein.

In some embodiments, the present disclosure provides a stereorandom oligonucleotide composition, e.g., a stereorandom MAPT oligonucleotide composition. In some embodiments, the present disclosure provides a stereorandom MAPT oligonucleotide composition which is capable of decreasing the level, activity or expression of a MAPT gene or a gene product thereof. In some embodiments, the present disclosure provides a stereorandom MAPT oligonucleotide composition which is capable of decreasing the level, activity or expression of a MAPT gene or a gene product thereof, and wherein the base sequence of the MAPT oligonucleotides is, comprises, or comprises a span (e.g., at least 10 or 15 contiguous bases) of a base sequence disclosed herein (e.g., a base sequence in Table 1, wherein each T may be independently replaced with U and vice versa).

In some embodiments, an oligonucleotide composition comprises one or more internucleotidic linkages which are stereocontrolled (chirally controlled; in some embodiments, stereopure) and one or more internucleotidic linkages which are stereorandom. In some embodiments, a MAPT oligonucleotide composition comprises one or more internucleotidic linkages which are stereocontrolled (chirally controlled; in some embodiments, stereopure) and one or more internucleotidic linkages which are stereorandom.

In some embodiments, an oligonucleotide composition comprises one or more internucleotidic linkages which are stereocontrolled (e.g., chirally controlled or stereopure) and one or more internucleotidic linkages which are stereorandom. Such oligonucleotides may target various targets and may have various base sequences, and may be capable of operating via one or more of various modalities (e.g., RNase H mechanism, steric hindrance, double- or single-stranded RNA interference, exon skipping modulation, CRISPR, aptamer, etc.).

In some embodiments, the present disclosure provides a chirally controlled oligonucleotide composition, e.g., chirally controlled MAPT oligonucleotide composition. In some embodiments, provided chirally controlled oligonucleotide compositions comprise a plurality of oligonucleotides, e.g., MAPT oligonucleotides, of the same constitution, and have one or more internucleotidic linkages. In some embodiments, a plurality of oligonucleotides, e.g., in a chirally controlled oligonucleotide composition, is a plurality of an oligonucleotide selected from Table 1, wherein the oligonucleotide comprises at least one Rp or Sp linkage phosphorus in a chirally controlled internucleotidic linkage. In some embodiments, a plurality of oligonucleotides, e.g., in a chirally controlled oligonucleotide composition, is a plurality of an oligonucleotide selected from Table 1, wherein each phosphorothioate internucleotidic linkage in the oligonucleotide is independently chirally controlled (each phosphorothioate internucleotidic linkage is independently Rp or Sp). In some embodiments, an oligonucleotide composition, e.g., a MAPT oligonucleotide composition is a substantially pure preparation of a single oligonucleotide in that oligonucleotides in the composition that are not the single oligonucleotide are impurities from the preparation process of the single oligonucleotide, in some case, after certain purification procedures. In some embodiments, a single oligonucleotide is an oligonucleotide of Table 1, wherein each chiral internucleotidic linkage of the oligonucleotide is chirally controlled (e.g., indicated as S or R but not X in "Stereochemistry/Linkage").

In some embodiments, a chirally controlled oligonucleotide composition can have, relative to a corresponding stereorandom oligonucleotide composition, increased activity and/or stability, increased delivery, and/or decreased ability to elicit adverse effects such as complement, TLR9 activation, etc. In some embodiments, a stereorandom (non-chirally controlled) oligonucleotide composition differs from a chirally controlled oligonucleotide composition in that its corresponding plurality of oligonucleotides do not contain any chirally controlled internucleotidic linkages but the stereorandom oligonucleotide composition is otherwise identical to the chirally controlled oligonucleotide composition.

In some embodiments, the present disclosure pertains to a chirally controlled MAPT oligonucleotide composition which is capable of decreasing the level, activity or expression of a MAPT gene or a gene product thereof.

In some embodiments, the present disclosure provides a chirally controlled MAPT oligonucleotide composition which is capable of decreasing the level, activity or expression of a MAPT gene or a gene product thereof, and comprises a plurality of oligonucleotides which share a common base sequence that is or comprises a base sequence disclosed herein (e.g., in Table 1, wherein each T may be independently replaced with U and vice versa).

In some embodiments, a provided chirally controlled oligonucleotide composition is a chirally controlled MAPT oligonucleotide composition comprising a plurality of MAPT oligonucleotides. In some embodiments, a chirally controlled oligonucleotide composition is a chirally pure (or "stereochemically pure") oligonucleotide composition. In some embodiments, the present disclosure provides a chirally pure oligonucleotide composition of an oligonucleotide in Table 1 (e.g., 1A), wherein each chiral internucleotidic linkage of the oligonucleotide is independently chirally controlled (Rp or Sp, e.g., R or S but not X in "Stereochemistry/Linkage"). As one of ordinary skill in the art will understand, chemical selectivity rarely, if ever, achieves completeness (absolute 100%). In some embodiments, a chirally pure oligonucleotide composition comprises a plurality of oligonucleotides, wherein oligonucleotides of the plurality are structurally identical and all have the same structure (the same stereoisomeric form; in the context of oligonucleotide, typically the same diastereomeric form as typically multiple chiral centers exist in an oligonucleotide), and the chirally pure oligonucleotide composition does not contain any other stereoisomers (in the context of oligonucleotide, typically diastereomers as typically multiple chiral centers exist in an oligonucleotide; to the extent, e.g., achievable by stereoselective preparation). As appreciated by those skilled in the art, stereorandom (or "racemic", "non-chirally controlled") oligonucleotide compositions are random mixtures of many stereoisomers (e.g., $2^n$ diastereoisomers wherein n is the number of chiral linkage phosphorus for oligonucleotides in which other chiral centers (e.g., carbon chiral centers in sugars) are chirally controlled each independently existing in one configuration and only chiral linkage phosphorus centers are not chirally controlled).

Certain data showing properties and/or activities of chirally controlled oligonucleotide composition, e.g., chirally controlled MAPT oligonucleotide compositions in decreasing the level, activity and/or expression of a MAPT target gene or a gene product thereof, are shown in, for example, the Examples section of this document.

In some embodiments, the present disclosure provides an oligonucleotide composition comprising oligonucleotides that comprise at least one chiral linkage phosphorus. In some embodiments, the present disclosure provides a MAPT oligonucleotide composition comprising MAPT oligonucleotides that comprise at least one chiral linkage phosphorus. In some embodiments, the present disclosure provides a MAPT oligonucleotide composition in which the MAPT oligonucleotides comprise a chirally controlled phosphorothioate internucleotidic linkage, wherein the linkage phosphorus has a Rp configuration. In some embodiments, the present disclosure provides a MAPT oligonucleotide composition in which the MAPT oligonucleotides comprise a chirally controlled phosphorothioate internucleotidic linkage, wherein the linkage phosphorus has a Sp configuration.

In some embodiments, compared to reference oligonucleotide compositions, provided chirally controlled oligonucleotide compositions (e.g., chirally controlled MAPT oligonucleotide compositions) are surprisingly effective. In some embodiments, desired biological effects (e.g., as measured by decreased levels of mRNA, proteins, etc. whose levels are targeted for reduction) can be enhanced by more than 5, 10, 15, 20, 25, 30, 40, 50, or 100 fold (e.g., as measured by remaining levels of mRNA, proteins, etc.). In some embodiments, a change is measured by decrease of an undesired mRNA level compared to a reference condition. In some embodiments, a change is measured by increase of a desired mRNA level compared to a reference condition. In some embodiments, a change is measured by decrease of an undesired mRNA level compared to a reference condition. In some embodiments, a reference condition is absence of treatment, e.g., by a chirally controlled oligonucleotide composition. In some embodiments, a reference condition is a corresponding stereorandom composition of oligonucleotides having the same constitution.

In some embodiments, the present disclosure provides a chirally controlled oligonucleotide composition, e.g., a chirally controlled MAPT oligonucleotide composition, wherein the linkage phosphorus of at least one chirally controlled internucleotidic linkage is Sp. In some embodiments, the present disclosure provides a chirally controlled oligonucleotide composition, e.g., a chirally controlled MAPT oligonucleotide composition, wherein the majority of linkage phosphorus of chirally controlled internucleotidic linkages are Sp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all chirally controlled phosphorothioate internucleotidic linkages are Sp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all phosphorothioate internucleotidic linkages are chirally controlled and are Sp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all chirally controlled internucleotidic linkages (or of all chiral internucleotidic linkages, or of all internucleotidic linkages) are Sp. In some embodiments, the present disclosure provides a chirally controlled oligonucleotide composition, e.g., a chirally controlled MAPT oligonucleotide composition, wherein the majority of chiral internucleotidic linkages are chirally controlled and are Sp at their linkage phosphorus. In some embodiments, the present disclosure provides a chirally controlled oligonucleotide composition, e.g., a chirally controlled MAPT oligonucleotide composition, wherein each chiral internucleotidic linkage is chirally controlled and each chiral linkage phosphorus is Sp. In some embodiments, the present disclosure provides a chirally controlled oligonucleotide composition, e.g., chirally controlled MAPT oligonucleotide composition, wherein at least one chirally controlled internucleotidic linkage has a Rp linkage phosphorus. In some embodiments, the present disclosure provides a chirally controlled oligonucleotide composition, e.g., a chirally controlled MAPT oligonucleotide composition, wherein at least one chirally controlled internucleotidic linkage comprises a Rp linkage phosphorus and at least one chirally controlled internucleotidic linkage comprises a Sp linkage phosphorus. In some embodiments, at least one phosphorothioate internucleotidic linkage is chirally controlled and Rp. In some embodiments, about 1-5, e.g., about 1, 2, 3, 4, or 5 phosphorothioate internucleotidic linkage is chirally controlled and Rp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all chirally controlled non-negatively charged internucleotidic linkages (e.g., n001) are Rp. In some embodiments, each chirally controlled n001 is Rp.

Stereochemistry and Patterns of Backbone Chiral Centers

In contrast to natural phosphate linkages, linkage phosphorus of chiral modified internucleotidic linkages, e.g., phosphorothioate internucleotidic linkages, are chiral. Among other things, the present disclosure provides technologies (e.g., oligonucleotides, compositions, methods, etc.) comprising control of stereochemistry of chiral linkage phosphorus in chiral internucleotidic linkages. In some embodiments, as demonstrated herein, control of stereochemistry can provide improved properties and/or activities, including desired stability, reduced toxicity, improved reduction of target nucleic acids, etc. In some embodiments, the present disclosure provides useful patterns of backbone chiral centers for oligonucleotides and/or regions thereof, which pattern is a combination of stereochemistry of each chiral linkage phosphorus (Rp or Sp) of chiral linkage phosphorus, indication of each achiral linkage phosphorus (Op, if any), etc. from 5' to 3'. In some embodiments, patterns of backbone chiral centers can control cleavage patterns of target nucleic acids when they are contacted with provided oligonucleotides or compositions thereof in a cleavage system (e.g., in vitro assay, cells, tissues, organs, organisms, subjects, etc.). In some embodiments, patterns of backbone chiral centers improve cleavage efficiency and/or selectivity of target nucleic acids when they are contacted with provided oligonucleotides or compositions thereof in a cleavage system.

In some embodiments, a pattern of backbone chiral centers of an oligonucleotide or a region thereof comprises or is any (Np)n(Op)m, wherein Np is Rp or Sp, Op represents a linkage phosphorus being achiral (e.g., as for the linkage phosphorus of natural phosphate linkages), and each of n and m is independently as defined and described in the present disclosure. In some embodiments, a pattern of backbone chiral centers of an oligonucleotide or a region thereof comprises or is (Sp)n(Op)m, wherein each variable is independently as defined and described in the present disclosure. In some embodiments, a pattern of backbone chiral centers of an oligonucleotide or a region thereof comprises or is (Rp)n(Op)m, wherein each variable is independently as defined and described in the present disclosure. In some embodiments, n is 1. In some embodiments, a pattern of backbone chiral centers of an oligonucleotide or a region thereof comprises or is (Sp)(Op)m, wherein m is 1, 2, 3, 4, 5, 6, 7, 8, 9, or 10. In some embodiments, a pattern of backbone chiral centers of an oligonucleotide or a region thereof comprises or is (Rp)(Op)m, wherein m is 1, 2, 3, 4, 5, 6, 7, 8, 9, or 10. In some embodiments, the pattern of backbone chiral centers of a 5'-wing is or comprises (Np)n (Op)m. In some embodiments, the pattern of backbone chiral centers of a 5'-wing is or comprises (Sp)n(Op)m. In some embodiments, the pattern of backbone chiral centers of a 5'-wing is or comprises (Rp)n(Op)m. In some embodiments, the pattern of backbone chiral centers of a 5'-wing is or comprises (Sp)(Op)m. In some embodiments, the pattern of backbone chiral centers of a 5'-wing is or comprises (Rp)(Op)m. In some embodiments, the pattern of backbone chiral centers of a 5'-wing is (Sp)(Op)m. In some embodiments, the pattern of backbone chiral centers of a 5'-wing is (Rp)(Op)m. In some embodiments, the pattern of backbone chiral centers of a 5'-wing is (Sp)(Op)m, wherein Sp is the linkage phosphorus configuration of the first internucleotidic linkage of the oligonucleotide from the 5'-end. In some embodiments, the pattern of backbone chiral centers of a 5'-wing is (Rp)(Op)m, wherein Rp is the linkage phosphorus configuration of the first internucleotidic linkage of the oligonucleotide from the 5'-end. In some embodiments, as described in the present disclosure, m is 2; in some embodiments, m is 3; in some embodiments, m is 4; in some embodiments, m is 5; in some embodiments, m is 6.

In some embodiments, a pattern of backbone chiral centers of an oligonucleotide or a region thereof comprises or is (Op)m(Np)n, wherein Np is Rp or Sp, Op represents a linkage phosphorus being achiral (e.g., as for the linkage phosphorus of natural phosphate linkages), and each of n and m is independently as defined and described in the present disclosure. In some embodiments, a pattern of backbone chiral centers of an oligonucleotide or a region thereof comprises or is (Op)m(Sp)n, wherein each variable is independently as defined and described in the present disclosure. In some embodiments, a pattern of backbone chiral centers of an oligonucleotide or a region thereof comprises or is (Op)m(Rp)n, wherein each variable is independently as defined and described in the present disclosure. In some embodiments, n is 1. In some embodiments, a pattern of backbone chiral centers of an oligonucleotide or a region thereof comprises or is (Op)m(Sp), wherein m is 1, 2, 3, 4, 5, 6, 7, 8, 9, or 10. In some embodiments, a pattern of backbone chiral centers of an oligonucleotide or a region thereof comprises or is (Op)m(Rp), wherein m is 1, 2, 3, 4, 5, 6, 7, 8, 9, or 10. In some embodiments, the pattern of backbone chiral centers of a 3'-wing is or comprises (Op) m(Np)n. In some embodiments, the pattern of backbone chiral centers of a 3'-wing is or comprises (Op)m(Sp)n. In some embodiments, the pattern of backbone chiral centers of a 3'-wing is or comprises (Op)m(Rp)n. In some embodiments, the pattern of backbone chiral centers of a 3'-wing is or comprises (Op)m(Sp). In some embodiments, the pattern of backbone chiral centers of a 3'-wing is or comprises (Op)m(Rp). In some embodiments, the pattern of backbone chiral centers of a 3'-wing is (Op)m(Sp). In some embodiments, the pattern of backbone chiral centers of a 3'-wing is (Op)m(Rp). In some embodiments, the pattern of backbone chiral centers of a 3'-wing is (Op)m(Sp), wherein Sp is the linkage phosphorus configuration of the last internucleotidic linkage of the oligonucleotide from the 5'-end. In some embodiments, the pattern of backbone chiral centers of a 3'-wing is (Op)m(Rp), wherein Rp is the linkage phosphorus configuration of the last internucleotidic linkage of the oligonucleotide from the 5'-end. In some embodiments, as described in the present disclosure, m is 2; in some embodiments, m is 3; in some embodiments, m is 4; in some embodiments, m is 5; in some embodiments, m is 6.

In some embodiments, a pattern of backbone chiral centers of an oligonucleotide or a region thereof (e.g., a core) comprises or is (Sp)m(Rp/Op)n or (Rp/Op)n(Sp)m, wherein each variable is independently as described in the present disclosure. In some embodiments, a pattern of backbone chiral centers of an oligonucleotide or a region thereof (e.g., a core) comprises or is (Sp)m(Rp)n or (Rp)n(Sp)m, wherein each variable is independently as described in the present disclosure. In some embodiments, a pattern of backbone chiral centers of an oligonucleotide or a region thereof (e.g., a core) comprises or is (Sp)m(Op)n or (Op)n(Sp)m, wherein each variable is independently as described in the present disclosure. In some embodiments, a pattern of backbone chiral centers of an oligonucleotide or a region thereof (e.g., a core) comprises or is (Np)t[(Rp/Op)n(Sp)m]y or [(Rp/Op) n(Sp)m]y(Np)t, wherein y is 1-50, and each other variable is independently as described in the present disclosure. In some embodiments, a pattern of backbone chiral centers of an oligonucleotide or a region thereof (e.g., a core) comprises or is (Np)t[(Rp)n(Sp)m]y or [(Rp)n(Sp)m]y(Np)t, wherein each variable is independently as described in the present disclosure. In some embodiments, a pattern of backbone chiral centers of an oligonucleotide or a region thereof (e.g., a core) comprises or is [(Rp/Op)n(Sp)m]y(Rp) k, [(Rp/Op)n(Sp)m]y, (Sp)t[(Rp/Op)n(Sp)m]y, (Sp)t[(Rp/Op)n(Sp)m]y(Rp)k, wherein k is 1-50, and each other variable is independently as described in the present disclosure. In some embodiments, a pattern of backbone chiral centers of an oligonucleotide or a region thereof (e.g., a core) comprises or is [(Op)n(Sp)m]y(Rp)k, [(Op)n(Sp)m]y, (Sp)t [(Op)n(Sp)m]y, (Sp)t[(Op)n(Sp)m]y(Rp)k, wherein each variable is independently as described in the present disclosure. In some embodiments, a pattern of backbone chiral centers of an oligonucleotide or a region thereof (e.g., a core) comprises or is [(Rp)n(Sp)m]y(Rp)k, [(Rp)n(Sp)m]y, (Sp)t[(Rp)n(Sp)m]y, (Sp)t[(Rp)n(Sp)m]y(Rp)k, wherein each variable is independently as described in the present disclosure. In some embodiments, an oligonucleotide comprises a core region. In some embodiments, an oligonucleotide comprises a core region, wherein each sugar in the core region does not contain a 2'-OR$^1$, wherein $R^1$ is as described in the present disclosure. In some embodiments, an oligonucleotide comprises a core region, wherein each sugar in the core region is independently a natural DNA sugar. In some embodiments, the pattern of backbone chiral centers of the core comprises or is (Rp)(Sp)m. In some embodiments, the pattern of backbone chiral centers of the core comprises or is (Op)(Sp)m. In some embodiments, the pattern of backbone chiral centers of the core comprises or is (Np)t[(Rp/Op)n(Sp)m]y or [(Rp/Op)n(Sp)m]y(Np)t. In some embodiments, the pattern of backbone chiral centers of the core comprises or is (Np)t[(Rp/Op)n(Sp)m]y or [(Rp/Op)n(Sp)m]y(Np)t. In some embodiments, the pattern of backbone chiral centers of the core comprises or is (Np)t[(Rp)n(Sp)m]y or [(Rp)n(Sp)m]y(Np)t. In some embodiments, the pattern of backbone chiral centers of a core comprises or is [(Rp/Op)n(Sp)m]y(Rp)k, [(Rp/Op)n(Sp)m]y, (Sp)t[(Rp/Op)n(Sp)m]y, (Sp)t[(Rp/Op)n(Sp)m]y(Rp)k. In some embodiments, a pattern of backbone chiral centers of a core comprises or is [(Op)n(Sp)m]y(Rp)k, [(Op)n(Sp)m]y, (Sp)t[(Op)n(Sp)m]y, (Sp)t[(Op)n(Sp)m]y(Rp)k. In some embodiments, a pattern of backbone chiral centers of a core comprises or is [(Rp)n(Sp)m]y(Rp)k, [(Rp)n(Sp)m]y, (Sp)t[(Rp)n(Sp)m]y, or (Sp)t[(Rp)n(Sp)m]y(Rp)k. In some embodiments, a pattern of backbone chiral centers of a core comprises [(Rp)n(Sp)m]y(Rp)k. In some embodiments, a pattern of backbone chiral centers of a core comprises [(Rp)n(Sp)m]y(Rp). In some embodiments, a pattern of backbone chiral centers of a core comprises [(Rp)n(Sp)m]y. In some embodiments, a pattern of backbone chiral centers of a core comprises (Sp)t[(Rp)n(Sp)m]y. In some embodiments, a pattern of backbone chiral centers of a core comprises (Sp)t[(Rp)n(Sp)m]y(Rp)k. In some embodiments, a pattern of backbone chiral centers of a core comprises (Sp)t[(Rp)n(Sp)m]y(Rp). In some embodiments, a pattern of backbone chiral centers of a core is [(Rp)n(Sp)m]y(Rp)k. In some embodiments, a pattern of backbone chiral centers of a core is [(Rp)n(Sp)m]y(Rp). In some embodiments, a pattern of backbone chiral centers of a core is [(Rp)n(Sp)m]y. In some embodiments, a pattern of backbone chiral centers of a core is (Sp)t[(Rp)n(Sp)m]y. In some embodiments, a pattern of backbone chiral centers of a core is (Sp)t[(Rp)n(Sp)m]y(Rp)k. In some embodiments, a pattern of backbone chiral centers of a core is (Sp)t[(Rp)n(Sp)m]y(Rp). In some embodiments, each n is 1. In some embodiments, each t is 1. In some embodiments, t is 2, 3, 4, 5, 6, 7, 8, 9, or 10. In some embodiments, each of t and n is 1. In some embodiments, each m is 2 or more. In some embodiments, k is 1. In some embodiments, k is 2-10.

In some embodiments, a pattern of backbone chiral centers comprises or is (Sp)m(Rp)n, (Rp)n(Sp)m, (Np)t(Rp)n(Sp)m, (Sp)t(Rp)n(Sp)m, (Np)t[(Rp)n(Sp)m]2, (Sp)t[(Rp)n(Sp)m]2, (Np)t(Op)n(Sp)m, (Sp)t(Op)n(Sp)m, (Np)t[(Op)n(Sp)m]2, or (Sp)t[(Op)n(Sp)m]2. In some embodiments, a pattern is (Np)t(Op/Rp)n(Sp)m(Op/Rp)n(Sp)m. In some embodiments, a pattern is (Np)t(Op/Rp)n(Sp)1-5(Op/Rp)n(Sp)m. In some embodiments, a pattern is (Np)t(Op/Rp)n(Sp)2-5(Op/Rp)n(Sp)m. In some embodiments, a pattern is (Np)t(Op/Rp)n(Sp)2(Op/Rp)n(Sp)m. In some embodiments, a pattern is (Np)t(Op/Rp)n(Sp)3(Op/Rp)n(Sp)m. In some embodiments, a pattern is (Np)t(Op/Rp)n(Sp)4(Op/Rp)n(Sp)m. In some embodiments, a pattern is (Np)t(Op/Rp)n(Sp)5(Op/Rp)n(Sp)m.

In some embodiments, Np is Sp. In some embodiments, (Op/Rp) is Op. In some embodiments, (Op/Rp) is Rp. In some embodiments, Np is Sp and (Op/Rp) is Rp. In some embodiments, Np is Sp and (Op/Rp) is Op. In some embodiments, Np is Sp and at least one (Op/Rp) is Rp, and at least one (Op/Rp) is Op. In some embodiments, a pattern of backbone chiral centers comprises or is (Rp)n(Sp)m, (Np)t(Rp)n(Sp)m, or (Sp)t(Rp)n(Sp)m, wherein m>2. In some embodiments, a pattern of backbone chiral centers comprises or is (Rp)n(Sp)m, (Np)t(Rp)n(Sp)m, or (Sp)t(Rp)n(Sp)m, wherein n is 1, at least one t>1, and at least one m>2.

In some embodiments, oligonucleotides comprising core regions whose patterns of backbone chiral centers starting with Rp can provide high activities and/or improved properties. In some embodiments, oligonucleotides comprising core regions whose patterns of backbone chiral centers ending with Rp can provide high activities and/or improved properties. In some embodiments, oligonucleotides comprising core regions whose patterns of backbone chiral centers starting with Rp provide high activities (e.g., target cleavage) without significantly impacting its properties, e.g., stability. In some embodiments, oligonucleotides comprising core regions whose patterns of backbone chiral centers ending with Rp provide high activities (e.g., target cleavage) without significantly impacting its properties, e.g., stability. In some embodiments, patterns of backbone chiral centers start with Rp and end with Sp. In some embodiments, patterns of backbone chiral centers start with Rp and end with Rp. In some embodiments, patterns of backbone chiral centers start with Sp and end with Rp. Typically, for patterns of backbone chiral centers internucleotidic linkages connecting core nucleosides and wing nucleosides are included in the patterns of the core regions. In many embodiments as described in the present disclosure (e.g., various oligonucleotides in Table 1), the wing sugar connected by such a connecting internucleotidic linkage has a different structure than the core sugar connected by the same connecting internucleotidic linkage (e.g., in some embodiments, the wing sugar comprises a 2'-modification while the core sugar does not contain the same 2'-modification or have two —H at the 2' position). In some embodiments, the wing sugar comprises a sugar modification that the core sugar does not contain. In some embodiments, the wing sugar is a modified sugar while the core sugar is a natural DNA sugar. In some embodiments, the wing sugar comprises a sugar modification at the 2' position (less than two —H at the 2' position), and the core sugar has no modification at the 2'-position (two —H at the 2' position).

In some embodiments, as demonstrated herein, an additional Rp internucleotidic linkage links a sugar containing no 2'-substituent (e.g., a core sugar) and a sugar comprising a 2'-modification (e.g., 2'-OR', wherein R' is optionally substituted $C_{1-6}$ aliphatic (e.g., 2'-OMe, 2'-MOE, etc.), which can be a wing sugar). In some embodiments, an internucleotidic linkage linking a sugar containing no 2'-substituent to the 5'-end (e.g., to the 3'-carbon of the sugar) and a sugar comprising a 2'-modification to the 3'-end (e.g., to the 5'-carbon of the sugar) is a Rp internucleotidic linkage. In some embodiments, an internucleotidic linkage linking a sugar containing no 2'-substituent to the 3'-end (e.g., to the 5'-carbon of the sugar) and a sugar comprising a 2'-modification to the 5'-end (e.g., to the 3'-carbon of the sugar) is a Rp internucleotidic linkage. In some embodiments, each internucleotidic linkage linking a sugar containing no 2'-substituent and a sugar comprising a 2'-modification is independently a Rp internucleotidic linkage. In some embodiments, a Rp internucleotidic linkage is a Rp phosphorothioate internucleotidic linkage.

In some embodiments, a pattern of backbone chiral centers of a MAPT oligonucleotide or a region thereof (e.g., a core) comprises or is (Op)[(Rp/Op)n(Sp)m]y(Rp)k(Op), (Op)[(Rp/Op)n(Sp)m]y(Op), (Op)(Sp)t[(Rp/Op)n(Sp)m]y(Op), or (Op)(Sp)t[(Rp/Op)n(Sp)m]y(Rp)k(Op), wherein k is 1-50, and each other variable is independently as described in the present disclosure. In some embodiments, a pattern of backbone chiral centers of a MAPT oligonucleotide comprises or is (Op)[(Rp/Op)n(Sp)m]y(Rp)k(Op), (Op)[(Rp/Op)n(Sp)m]y(Op), (Op)(Sp)t[(Rp/Op)n(Sp)m]y (Op), or (Op)(Sp)t[(Rp/Op)n(Sp)m]y(Rp)k(Op), wherein each of f, g, h and j is independently 1-50, and each other variable is independently as described in the present disclosure, and the oligonucleotide comprises a core region whose pattern of backbone chiral centers comprises or is [(Rp/Op) n(Sp)m]y(Rp)k, [(Rp/Op)n(Sp)m]y, (Sp)t[(Rp/Op)n(Sp)m] y, or (Sp)t[(Rp/Op)n(Sp)m]y(Rp)k as described in the present disclosure. In some embodiments, a pattern of backbone chiral centers is or comprises (Op)[(Rp/Op)n(Sp)m]y(Rp)k (Op). In some embodiments, a pattern of backbone chiral centers is or comprises (Op)[(Rp/Op)n(Sp)m]y(Rp)(Op). In some embodiments, a pattern of backbone chiral centers is or comprises (Op)[(Rp/Op)n(Sp)m]y(Op). In some embodiments, a pattern of backbone chiral centers is or comprises (Op)(Sp)t[(Rp/Op)n(Sp)m]y(Op). In some embodiments, a pattern of backbone chiral centers is or comprises (Op)(Sp) t[(Rp/Op)n(Sp)m]y(Rp)k(Op). In some embodiments, a pattern of backbone chiral centers is or comprises (Op)(Sp)t [(Rp/Op)n(Sp)m]y(Rp)(Op). In some embodiments, a pattern of backbone chiral centers is or comprises (Op)[(Rp) n(Sp)m]y(Rp)k(Op). In some embodiments, a pattern of backbone chiral centers is or comprises (Op)[(Rp)n(Sp)m] y(Rp)(Op). In some embodiments, a pattern of backbone chiral centers is or comprises (Op)[(Rp)n(Sp)m]y(Op). In some embodiments, a pattern of backbone chiral centers is or comprises (Op)(Sp)t[(Rp)n(Sp)m]y(Op). In some embodiments, a pattern of backbone chiral centers is or comprises (Op)(Sp)t[(Rp)n(Sp)m]y(Rp)k(Op). In some embodiments, a pattern of backbone chiral centers is or comprises (Op)(Sp)t[(Rp)n(Sp)m]y(Rp)(Op). In some embodiments, each n is 1. In some embodiments, k is 1. In some embodiments, k is 2-10.

In some embodiments, a pattern of backbone chiral centers of a MAPT oligonucleotide or a region thereof (e.g., a core) comprises or is (Np)f(Op)g[(Rp/Op)n(Sp)m]y(Rp)k (Op)h(Np)j, (Np)f(Op)g[(Rp/Op)n(Sp)m]y(Op)h(Np)j, (Np) f(Op)g(Sp)t[(Rp/Op)n(Sp)m]y(Op)h(Np)j, or (Np)f(Op)g (Sp)t[(Rp/Op)n(Sp)m]y(Rp)k(Op)h(Np)j, wherein each of f, g, h and j is independently 1-50, and each other variable is independently as described in the present disclosure. In some embodiments, a pattern of backbone chiral centers of a MAPT oligonucleotide comprises or is (Np)f(Op)g[(Rp/ Op)n(Sp)m]y(Rp)k(Op)h(Np)j, (Np)f(Op)g[(Rp/Op)n(Sp) m]y(Op)h(Np)j, (Np)f(Op)g(Sp)t[(Rp/Op)n(Sp)m]y(Op)h (Np)j, or (Np)f(Op)g(Sp)t[(Rp/Op)n(Sp)m]y(Rp)k(Op)h (Np)j, and the oligonucleotide comprises a core region whose pattern of backbone chiral centers comprises or is [(Rp/Op)n(Sp)m]y(Rp)k, [(Rp/Op)n(Sp)m]y, (Sp)t[(Rp/Op) n(Sp)m]y, or (Sp)t[(Rp/Op)n(Sp)m]y(Rp)k as described in the present disclosure. In some embodiments, a pattern of backbone chiral centers of a MAPT oligonucleotide is (Np)f(Op)g[(Rp/Op)n(Sp)m]y(Rp)k(Op)h(Np)j, (Np)f(Op) g[(Rp/Op)n(Sp)m]y(Op)h(Np)j, (Np)f(Op)g(Sp)t[(Rp/Op)n (Sp)m]y(Op)h(Np)j, or (Np)f(Op)g(Sp)t[(Rp/Op)n(Sp)m]y (Rp)k(Op)h(Np)j, and the oligonucleotide comprises a core region whose pattern of backbone chiral centers comprises or is [(Rp/Op)n(Sp)m]y(Rp)k, [(Rp/Op)n(Sp)m]y, (Sp)t [(Rp/Op)n(Sp)m]y, or (Sp)t[(Rp/Op)n(Sp)m]y(Rp)k as described in the present disclosure. In some embodiments, a pattern of backbone chiral centers is or comprises (Np)f(Op) g[(Rp/Op)n(Sp)m]y(Rp)k(Op)h(Np)j. In some embodiments, a pattern of backbone chiral centers is or comprises (Np)f(Op)g[(Rp/Op)n(Sp)m]y(Rp)(Op)h(Np)j. In some embodiments, a pattern of backbone chiral centers is or comprises (Np)f(Op)g[(Rp/Op)n(Sp)m]y(Op)h(Np)j. In some embodiments, a pattern of backbone chiral centers is or comprises (Np)f(Op)g(Sp)t[(Rp/Op)n(Sp)m]y(Op)h(Np) j. In some embodiments, a pattern of backbone chiral centers is or comprises (Np)f(Op)g(Sp)t[(Rp/Op)n(Sp)m]y(Rp)k (Op)h(Np)j. In some embodiments, a pattern of backbone chiral centers is or comprises (Np)f(Op)g(Sp)t[(Rp/Op)n (Sp)m]y(Rp)(Op)h(Np)j. In some embodiments, a pattern of backbone chiral centers is or comprises (Np)f(Op)g[(Rp)n (Sp)m]y(Rp)k(Op)h(Np)j. In some embodiments, a pattern of backbone chiral centers is or comprises (Np)f(Op)g[(Rp) n(Sp)m]y(Rp)(Op)h(Np)j. In some embodiments, a pattern of backbone chiral centers is or comprises (Np)f(Op)g[(Rp) n(Sp)m]y(Op)h(Np)j. In some embodiments, a pattern of backbone chiral centers is or comprises (Np)f(Op)g(Sp)t [(Rp)n(Sp)m]y(Op)h(Np)j. In some embodiments, a pattern of backbone chiral centers is or comprises (Np)f(Op)g(Sp) t[(Rp)n(Sp)m]y(Rp)k(Op)h(Np)j. In some embodiments, a pattern of backbone chiral centers is or comprises (Np)f(Op) g(Sp)t[(Rp)n(Sp)m]y(Rp)(Op)h(Np)j. In some embodiments, at least one Np is Sp. In some embodiments, at least one Np is Rp. In some embodiments, the 5' most Np is Sp. In some embodiments, the 3' most Np is Sp. In some embodiments, each Np is Sp. In some embodiments, (Np)f (Op)g[(Rp/Op)n(Sp)m]y(Rp)k(Op)h(Np)j is (Sp)(Op)g [(Rp)n(Sp)m]y(Rp)k(Op)h(Sp). In some embodiments, (Np) f(Op)g[(Rp/Op)n(Sp)m]y(Rp)k(Op)h(Np)j is (Sp)(Op)g [(Rp)n(Sp)m]y(Rp)(Op)h(Sp). In some embodiments, a pattern of backbone chiral center of an oligonucleotide is or comprises (Sp)(Op)g[(Rp)n(Sp)m]y(Rp)(Op)h(Sp). In some embodiments, a pattern of backbone chiral center of an oligonucleotide is (Sp)(Op)g[(Rp)n(Sp)m]y(Rp)(Op)h(Sp). In some embodiments, (Np)f(Op)g[(Rp/Op)n(Sp)m]y(Op)h (Np)j is (Sp)(Op)g[(Rp)n(Sp)m]y(Op)h(Sp). In some embodiments, a pattern of backbone chiral center of an oligonucleotide is or comprises (Sp)(Op)g[(Rp)n(Sp)m]y (Op)h(Sp). In some embodiments, a pattern of backbone chiral center of an oligonucleotide is (Sp)(Op)g[(Rp)n(Sp) m]y(Op)h(Sp). In some embodiments, (Np)f(Op)g(Sp)t [(Rp/Op)n(Sp)m]y(Op)h(Np)j is (Sp)(Op)g(Sp)t[(Rp)n(Sp) m]y(Op)h(Sp). In some embodiments, a pattern of backbone chiral center of an oligonucleotide is or comprises (Sp)(Op) g(Sp)t[(Rp)n(Sp)m]y(Op)h(Sp). In some embodiments, a pattern of backbone chiral center of an oligonucleotide is (Sp)(Op)g(Sp)t[(Rp)n(Sp)m]y(Op)h(Sp). In some embodiments, (Np)f(Op)g(Sp)t[(Rp/Op)n(Sp)m]y(Rp)k(Op)h(Np)j is (Sp)(Op)g(Sp)t[(Rp)n(Sp)m]y(Rp)k(Op)h(Sp). In some embodiments, (Np)f(Op)g(Sp)t[(Rp/Op)n(Sp)m]y(Rp)k (Op)h(Np)j is (Sp)(Op)g(Sp)t[(Rp)n(Sp)m]y(Rp)(Op)h(Sp). In some embodiments, a pattern of backbone chiral center of an oligonucleotide is or comprises (Sp)(Op)g(Sp)t[(Rp)n (Sp)m]y(Rp)(Op)h(Sp). In some embodiments, a pattern of backbone chiral center of an oligonucleotide is (Sp)(Op)g (Sp)t[(Rp)n(Sp)m]y(Rp)(Op)h(Sp). In some embodiments, each n is 1. In some embodiments, f is 1. In some embodiments, g is 1. In some embodiments, g is greater than 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In some embodiments, h is 1. In some embodiments, h is greater than 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10. In some embodiments, j is 1. In some embodiments, k is 1. In some embodiments, k is 2-10.

In some embodiments, a pattern of backbone chiral centers of a MAPT oligonucleotide or a region thereof (e.g., a core) comprises or is [(Rp/Op)n(Sp)m]y, (Sp)t[(Rp/Op)n(Sp)m]y, (Sp)t[(Rp/Op)n(Sp)m]yRp, [(Rp/Op)n(Sp)m]y(Rp)k, (Sp)t[(Rp/Op)n(Sp)m]y(Rp)k, (Sp)t[(Rp/Op)n(Sp)m]y(Rp)k(Op)h, (Sp)t[(Rp/Op)n(Sp)m]y(Rp)k(Op)h(Np)j, wherein each variable is independently as described in the present disclosure.

In some embodiments, in a provided pattern of backbone chiral centers, at least one (Rp/Op) is Rp. In some embodiments, at least one (Rp/Op) is Op. In some embodiments, each (Rp/Op) is Rp. In some embodiments, each (Rp/Op) is Op. In some embodiments, at least one of [(Rp)n(Sp)m]y or [(Rp/Op)n(Sp)m]y of a pattern is RpSp. In some embodiments, at least one of [(Rp)n(Sp)m]y or [(Rp/Op)n(Sp)m]y of a pattern is or comprises RpSpSp. In some embodiments, at least one of [(Rp)n(Sp)m]y or [(Rp/Op)n(Sp)m]y in a pattern is RpSp, and at least one of [(Rp)n(Sp)m]y or [(Rp/Op)n(Sp)m]y in a pattern is or comprises RpSpSp. For example, in some embodiments, [(Rp)n(Sp)m]y in a pattern is (RpSp)[(Rp)n(Sp)m]$_{(y-1)}$; in some embodiments, [(Rp)n(Sp)m]y in a pattern is (RpSp)[RpSpSp(Sp)$_{(m-2)}$][(Rp)n(Sp)m]$_{(y-2)}$. In some embodiments, (Sp)t[(Rp)n(Sp)m]y(Rp) is (Sp)t(RpSp)[(Rp)n(Sp)m]$_{(y-1)}$(Rp). In some embodiments, (Sp)t[(Rp)n(Sp)m]y(Rp) is (Sp)t(RpSp)[RpSpSp(Sp)$_{(m-2)}$][(Rp)n(Sp)m]$_{(y-2)}$(Rp). In some embodiments, each [(Rp/Op)n(Sp)m] is independently [Rp(Sp)m]. In some embodiments, the first Sp of (Sp)t represents linkage phosphorus stereochemistry of the first internucleotidic linkage of an oligonucleotide from 5' to 3'. In some embodiments, the first Sp of (Sp)t represents linkage phosphorus stereochemistry of the first internucleotidic linkage of a region from 5' to 3', e.g., a core. In some embodiments, the last Np of (Np)j represents linkage phosphorus stereochemistry of the last internucleotidic linkage of the oligonucleotide from 5' to 3'. In some embodiments, the last Np is Sp.

In some embodiments, a pattern of backbone chiral centers of an oligonucleotide or a region (e.g., of a 5'-wing) is or comprises Sp(Op)$_3$. In some embodiments, a pattern of backbone chiral centers of an oligonucleotide or a region (e.g., of a 5'-wing) is or comprises Rp(Op)$_3$. In some embodiments, a pattern of backbone chiral centers of an oligonucleotide or a region (e.g., of a 3'-wing) is or comprises (Op)$_3$Sp. In some embodiments, a pattern of backbone chiral centers of an oligonucleotide or a region (e.g., of a 3'-wing) is or comprises (Op)$_3$Rp. In some embodiments, a pattern of backbone chiral centers of an oligonucleotide or a region (e.g., of a core) is or comprises Rp(Sp)$_4$Rp(Sp)$_4$Rp. In some embodiments, a pattern of backbone chiral centers of an oligonucleotide or a region (e.g., of a core) is or comprises (Sp)$_5$Rp(Sp)$_4$Rp. In some embodiments, a pattern of backbone chiral centers of an oligonucleotide or a region (e.g., of a core) is or comprises (Sp)$_5$Rp(Sp)$_5$. In some embodiments, a pattern of backbone chiral centers of an oligonucleotide or a region (e.g., of a core) is or comprises Rp(Sp)$_4$Rp(Sp)$_5$. In some embodiments, a pattern of backbone chiral centers of an oligonucleotide is or comprises Np(Op)$_3$Rp(Sp)$_4$Rp(Sp)$_4$Rp(Op)$_3$Np. In some embodiments, a pattern of backbone chiral centers of an oligonucleotide is or comprises Np(Op)$_3$(Sp)$_5$Rp(Sp)$_4$Rp(Op)$_3$Np. In some embodiments, a pattern of backbone chiral centers of an oligonucleotide is or comprises Np(Op)$_3$(Sp)$_5$Rp(Sp)$_5$(Op)$_3$Np. In some embodiments, a pattern of backbone chiral centers of an oligonucleotide is or comprises Np(Op)$_3$Rp(Sp)$_4$Rp(Sp)$_5$(Op)$_3$Np. In some embodiments, a pattern of backbone chiral centers of an oligonucleotide is or comprises Sp(Op)$_3$Rp(Sp)$_4$Rp(Sp)$_4$Rp(Op)$_3$Sp. In some embodiments, a pattern of backbone chiral centers of an oligonucleotide is or comprises Sp(Op)$_3$(Sp)$_5$Rp(Sp)$_4$Rp(Op)$_3$Sp. In some embodiments, a pattern of backbone chiral centers of an oligonucleotide is or comprises Sp(Op)$_3$(Sp)$_5$Rp(Sp)$_5$(Op)$_3$Sp. In some embodiments, a pattern of backbone chiral centers of an oligonucleotide is or comprises Sp(Op)$_3$Rp(Sp)$_4$Rp(Sp)$_5$(Op)$_3$Sp. In some embodiments, a pattern of backbone chiral centers of an oligonucleotide is or comprises Rp(Op)$_3$Rp(Sp)$_4$Rp(Sp)$_4$Rp(Op)$_3$Rp. In some embodiments, a pattern of backbone chiral centers of an oligonucleotide is or comprises Rp(Op)$_3$(Sp)$_5$Rp(Sp)$_4$Rp(Op)$_3$Rp. In some embodiments, a pattern of backbone chiral centers of an oligonucleotide is or comprises Rp(Op)$_3$(Sp)$_5$Rp(Sp)$_5$(Op)$_3$Rp. In some embodiments, a pattern of backbone chiral centers of an oligonucleotide is or comprises Rp(Op)$_3$Rp(Sp)$_4$Rp(Sp)$_5$(Op)$_3$Rp.

In some embodiments, each of m, y, t, n, k, f, g, h, and j is independently 1-25.

In some embodiments, m is 1-25. In some embodiments, m is 1-20. In some embodiments, m is 1-15. In some embodiments, m is 1-10. In some embodiments, m is 1-5. In some embodiments, m is 2-20. In some embodiments, m is 2-15. In some embodiments, m is 2-10. In some embodiments, m is 2-5. In some embodiments, m is 1, 2, 3, 4, 5, 6, 7, 8, 9, 10, 11, 12, 13, 14, 15, 16, 17, 18, 19, 20, 21, 22, 23, 24, or 25. In some embodiments, in a pattern of backbone chiral centers each m is independently 2 or more. In some embodiments, each m is independently 2, 3, 4, 5, 6, 7, 8, 9, or 10. In some embodiments, each m is independently 2-3, 2-5, 2-6, or 2-10. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, where there are two or more occurrences of m, they can be the same or different, and each of them is independently as described in the present disclosure.

In some embodiments, y is 1-25. In some embodiments, y is 1-20. In some embodiments, y is 1-15. In some embodiments, y is 1-10. In some embodiments, y is 1-5. In some embodiments, y is 2-20. In some embodiments, y is 2-15. In some embodiments, y is 2-10. In some embodiments, y is 2-5. In some embodiments, y is 1, 2, 3, 4, 5, 6, 7, 8, 9, 10, 11, 12, 13, 14, 15, 16, 17, 18, 19, 20, 21, 22, 23, 24, or 25. In some embodiments, y is 1, 2, 3, 4, 5, 6, 7, 8, 9, or 10. In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10.

In some embodiments, t is 1-25. In some embodiments, t is 1-20. In some embodiments, t is 1-15. In some embodiments, t is 1-10. In some embodiments, t is 1-5. In some embodiments, t is 2-20. In some embodiments, t is 2-15. In some embodiments, t is 2-10. In some embodiments, t is 2-5. In some embodiments, t is 1, 2, 3, 4, 5, 6, 7, 8, 9, 10, 11, 12, 13, 14, 15, 16, 17, 18, 19, 20, 21, 22, 23, 24, or 25. In some embodiments, each t is independently 1, 2, 3, 4, 5, 6, 7, 8, 9, or 10. In some embodiments, t is 2 or more. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, where there are two or more occurrences of t, they can be the same or different, and each of them is independently as described in the present disclosure.

In some embodiments, n is 1-25. In some embodiments, n is 1, 2, 3, 4, 5, 6, 7, 8, 9, 10, 11, 12, 13, 14, 15, 16, 17, 18, 19, 20, 21, 22, 23, 24, or 25. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, where there are two or more occurrences of n, they can be the same or different, and each of them is independently as described in the present disclosure. In many embodiments, in a pattern of backbone chiral centers, at least one occurrence of n is 1; in some cases, each n is 1.

In some embodiments, k is 1-25. In some embodiments, k is 1, 2, 3, 4, 5, 6, 7, 8, 9, 10, 11, 12, 13, 14, 15, 16, 17, 18, 19, 20, 21, 22, 23, 24, or 25. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10.

In some embodiments, f is 1-25. In some embodiments, f is 1-20. In some embodiments, f is 1-10. In some embodiments, f is 1-5. In some embodiments, f is 1, 2, 3, 4, 5, 6, 7, 8, 9, 10, 11, 12, 13, 14, 15, 16, 17, 18, 19, 20, 21, 22, 23, 24, or 25. In some embodiments, f is 1. In some embodiments, f is 2. In some embodiments, f is 3. In some embodiments, f is 4. In some embodiments, f is 5. In some embodiments, f is 6. In some embodiments, f is 7. In some embodiments, f is 8. In some embodiments, f is 9. In some embodiments, f is 10.

In some embodiments, g is 1-25. In some embodiments, g is 1-20. In some embodiments, g is 1-10. In some embodiments, g is 1-5. In some embodiments, g is 2-10. In some embodiments, g is 2-5. In some embodiments, g is 1, 2, 3, 4, 5, 6, 7, 8, 9, 10, 11, 12, 13, 14, 15, 16, 17, 18, 19, 20, 21, 22, 23, 24, or 25. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10.

In some embodiments, h is 1-25. In some embodiments, h is 1-10. In some embodiments, h is 1-5. In some embodiments, h is 2-10. In some embodiments, h is 2-5. In some embodiments, h is 1, 2, 3, 4, 5, 6, 7, 8, 9, 10, 11, 12, 13, 14, 15, 16, 17, 18, 19, 20, 21, 22, 23, 24, or 25. In some embodiments, h is 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10.

In some embodiments, j is 1-25. In some embodiments, j is 1-10. In some embodiments, j is 1-5. In some embodiments, j is 1, 2, 3, 4, 5, 6, 7, 8, 9, 10, 11, 12, 13, 14, 15, 16, 17, 18, 19, 20, 21, 22, 23, 24, or 25. In some embodiments, j is 1. In some embodiments, j is 2. In some embodiments, j is 3. In some embodiments, j is 4. In some embodiments, j is 5. In some embodiments, j is 6. In some embodiments, j is 7. In some embodiments, j is 8. In some embodiments, j is 9. In some embodiments, j is 10.

In some embodiments, at least one n is 1, and at least one m is no less than 2. In some embodiments, at least one n is 1, at least one t is no less than 2, and at least one m is no less than 3. In some embodiments, each n is 1. In some embodiments, t is 1. In some embodiments, at least one t>1. In some embodiments, at least one t>2. In some embodiments, at least one t>3. In some embodiments, at least one t>4. In some embodiments, at least one m>1. In some embodiments, at least one m>2. In some embodiments, at least one m>3. In some embodiments, at least one m>4. In some embodiments, a pattern of backbone chiral centers comprises one or more achiral natural phosphate linkages. In some embodiments, the sum of m, t, and n (or m and n if no t in a pattern) is no less than 5, 6, 7, 8, 9, 10, 11, 12, 13, 14, 15, 16, 17, 18, 19 or 20. In some embodiments, the sum is 5. In some embodiments, the sum is 6. In some embodiments, the sum is 7. In some embodiments, the sum is 8. In some embodiments, the sum is 9. In some embodiments, the sum is 10. In some embodiments, the sum is 11. In some embodiments, the sum is 12. In some embodiments, the sum is 13. In some embodiments, the sum is 14. In some embodiments, the sum is 15.

In some embodiments, a number of linkage phosphorus in chirally controlled internucleotidic linkages are Sp. In some embodiments, at least 10%, 20%, 25%, 30%, 35%, 40%, 45%, 50%, 55%, 60%, 65%, 70%, 75%, 80%, 85%, 90% or 95% of chirally controlled internucleotidic linkages have Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all chiral internucleotidic linkages are chirally controlled internucleotidic linkages having Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all internucleotidic linkages are chirally controlled internucleotidic linkages having Sp linkage phosphorus. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 65%. In some embodiments, the percentage is at least 70%. In some embodiments, the percentage is at least 75%. In some embodiments, the percentage is at least 80%. In some embodiments, the percentage is at least 90%. In some embodiments, the percentage is at least 95%. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Sp linkage phosphorus. In some embodiments, at least 5 internucleotidic linkages are chirally controlled internucleotidic linkages having Sp linkage phosphorus. In some embodiments, at least 6 internucleotidic linkages are chirally controlled internucleotidic linkages having Sp linkage phosphorus. In some embodiments, at least 7 internucleotidic linkages are chirally controlled internucleotidic linkages having Sp linkage phosphorus. In some embodiments, at least 8 internucleotidic linkages are chirally controlled internucleotidic linkages having Sp linkage phosphorus. In some embodiments, at least 9 internucleotidic linkages are chirally controlled internucleotidic linkages having Sp linkage phosphorus. In some embodiments, at least 10 internucleotidic linkages are chirally controlled internucleotidic linkages having Sp linkage phosphorus. In some embodiments, at least 11 internucleotidic linkages are chirally controlled internucleotidic linkages having Sp linkage phosphorus. In some embodiments, at least 12 internucleotidic linkages are chirally controlled internucleotidic linkages having Sp linkage phosphorus. In some embodiments, at least 13 internucleotidic linkages are chirally controlled internucleotidic linkages having Sp linkage phosphorus. In some embodiments, at least 14 internucleotidic linkages are chirally controlled internucleotidic linkages having Sp linkage phosphorus. In some embodiments, at least 15 internucleotidic linkages are chirally controlled internucleotidic linkages having Sp linkage phosphorus. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Rp linkage phosphorus. In some embodiments, no more than 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Rp linkage phosphorus. In some embodiments, one and no more than one internucleotidic linkage in an oligonucleotide is a chirally controlled internucleotidic linkage having Rp linkage phosphorus. In some embodiments, 2 and no more than 2 internucleotidic linkages in an oligonucleotide are chirally controlled internucleotidic linkages having Rp linkage phosphorus. In some embodiments, 3 and no more than 3 internucleotidic linkages in an oligonucleotide are chirally controlled internucleotidic linkages having Rp linkage phosphorus. In some embodiments, 4 and no more than 4 internucleotidic linkages in an oligonucleotide are chirally controlled internucleotidic linkages having Rp linkage phosphorus. In some embodiments, 5 and no more than 5 internucleotidic linkages in an oligonucleotide are chirally controlled internucleotidic linkages having Rp linkage phosphorus.

In some embodiments, all, essentially all or most of the internucleotidic linkages in an oligonucleotide are in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages in the oligonucleotide) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages in the oligonucleotide) being in the Rp configuration. In some embodiments, all, essentially all or most of the internucleotidic linkages in a core are in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) being in the Rp configuration. In some embodiments, all, essentially all or most of the internucleotidic linkages in the core are a phosphorothioate in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) being a phosphorothioate in the Rp configuration. In some embodiments, each internucleotidic linkage in the core is a phosphorothioate in the Sp configuration except for one phosphorothioate in the Rp configuration. In some embodiments, each internucleotidic linkage in the core is a phosphorothioate in the Sp configuration except for one phosphorothioate in the Rp configuration.

In some embodiments, an oligonucleotide comprises one or more Rp internucleotidic linkages. In some embodiments, an oligonucleotide comprises one and no more than one Rp internucleotidic linkages. In some embodiments, an oligonucleotide comprises two or more Rp internucleotidic linkages. In some embodiments, an oligonucleotide comprises three or more Rp internucleotidic linkages. In some embodiments, an oligonucleotide comprises four or more Rp internucleotidic linkages. In some embodiments, an oligonucleotide comprises five or more Rp internucleotidic linkages. In some embodiments, about 5%-50% of all chirally controlled internucleotidic linkages in an oligonucleotide are Rp. In some embodiments, about 5%-40% of all chirally controlled internucleotidic linkages in an oligonucleotide are Rp. In some embodiments, about 10%-40% of all chirally controlled internucleotidic linkages in an oligonucleotide are Rp. In some embodiments, about 15%-40% of all chirally controlled internucleotidic linkages in an oligonucleotide are Rp. In some embodiments, about 20%-40% of all chirally controlled internucleotidic linkages in an oligonucleotide are Rp. In some embodiments, about 25%-40% of all chirally controlled internucleotidic linkages in an oligonucleotide are Rp. In some embodiments, about 30%-40% of all chirally controlled internucleotidic linkages in an oligonucleotide are Rp. In some embodiments, about 35%-40% of all chirally controlled internucleotidic linkages in an oligonucleotide are Rp.

In some embodiments, instead of an Rp internucleotidic linkage, a natural phosphate linkage may be similarly utilized, optionally with a modification, e.g., a sugar modification (e.g., a 5'-modification such as $R^{5s}$ as described herein). In some embodiments, a modification improves stability of a natural phosphate linkage.

In some embodiments, the present disclosure provides an oligonucleotide having a pattern of backbone chiral centers as described herein. In some embodiments, oligonucleotides in a chirally controlled oligonucleotide composition share a common pattern of backbone chiral centers as described herein.

In some embodiments, at least about 25% of the internucleotidic linkages of a MAPT oligonucleotide are chirally controlled and have Sp linkage phosphorus. In some embodiments, at least about 30% of the internucleotidic linkages of an oligonucleotide are chirally controlled and have Sp linkage phosphorus. In some embodiments, at least about 40% of the internucleotidic linkages of a provided oligonucleotide are chirally controlled and have Sp linkage phosphorus. In some embodiments, at least about 50% of the internucleotidic linkages of a provided oligonucleotide are chirally controlled and have Sp linkage phosphorus. In some embodiments, at least about 60% of the internucleotidic linkages of a provided oligonucleotide are chirally controlled and have Sp linkage phosphorus. In some embodiments, at least about 65% of the internucleotidic linkages of a provided oligonucleotide are chirally controlled and have Sp linkage phosphorus. In some embodiments, at least about 70% of the internucleotidic linkages of a provided oligonucleotide are chirally controlled and have Sp linkage phosphorus. In some embodiments, at least about 75% of the internucleotidic linkages of a provided oligonucleotide are chirally controlled and have Sp linkage phosphorus. In some embodiments, at least about 80% of the internucleotidic linkages of a provided oligonucleotide are chirally controlled and have Sp linkage phosphorus. In some embodiments, at least about 85% of the internucleotidic linkages of a provided oligonucleotide are chirally controlled and have Sp linkage phosphorus. In some embodiments, at least about 90% of the internucleotidic linkages of a provided oligonucleotide are chirally controlled and have Sp linkage phosphorus. In some embodiments, at least about 95% of the internucleotidic linkages of a provided oligonucleotide are chirally controlled and have Sp linkage phosphorus.

In some embodiments, the present disclosure provides chirally controlled oligonucleotide compositions, e.g., chirally controlled MAPT oligonucleotide compositions, wherein the composition comprises a non-random or controlled level of a plurality of oligonucleotides, wherein oligonucleotides of the plurality share a common base sequence, and share the same configuration of linkage phosphorus independently at 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more chiral internucleotidic linkages.

In some embodiments, MAPT oligonucleotides comprise 2-30 chirally controlled internucleotidic linkages. In some embodiments, provided oligonucleotide compositions comprise 5-30 chirally controlled internucleotidic linkages. In some embodiments, provided oligonucleotide compositions comprise 10-30 chirally controlled internucleotidic linkages.

In some embodiments, a percentage is about 5%-100%. In some embodiments, a percentage is at least 50%, 55%, 60%, 65%, 70%, 75%, 80%, 85%, 90%, 95%, 965, 96%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 965, 96%, 98%, or 99%.

In some embodiments, a pattern of backbone chiral centers in a MAPT oligonucleotide comprises a pattern of $i^o$-$i^s$-$i^o$-$i^s$-$i^o$, $i^o$-$i^s$-$i^s$-$i^s$-$i^o$, $i^o$-$i^s$-$i^s$-$i^s$-$i^o$-$i^s$, $i^s$-$i^o$-$i^s$-$i^o$, $i^s$- $i^o$-$i^s$-$i^o$, $i^s$-$i^o$-$i^s$-$i^o$-$i^s$, $i^s$-$i^o$-$i^s$-$i^o$-$i^s$-$i^o$, $i^s$-$i^o$-$i^s$-$i^o$-$i^s$-$i^o$-$i^s$-$i^o$, $i^s$-$i^o$-$i^s$-$i^s$-$i^s$-$i^o$, $i^s$-$i^s$-$i^o$-$i^s$-$i^s$-$i^s$-$i^o$-$i^s$-$i^s$, $i^s$-$i^s$-$i^s$-$i^o$-$i^s$-$i^o$-$i^s$-$i^s$-$i^s$, $i^s$-$i^s$-$i^s$-$i^s$-$i^o$-$i^s$-$i^o$-$i^s$-$i^s$-$i^s$-$i^s$, $i^s$-$i^s$-$i^s$-$i^s$-$i^s$, $i^s$-$i^s$-$i^s$-$i^s$-$i^s$- $i^s$, $i^s$-$i^s$-$i^s$-$i^s$-$i^s$-$i^s$-$i^s$, $i^s$-$i^s$-$i^s$-$i^s$-$i^s$-$i^s$-$i^s$-$i^s$, $i^s$-$i^s$-$i^s$-$i^s$-$i^s$-$i^s$-$i^s$-$i^s$-$i^s$, or $i^r$- $i^r$-$i^r$ wherein $i^s$ represents an internucleotidic linkage in the Sp configuration; $i^o$ represents an achiral internucleotidic linkage; and $i^r$ represents an internucleotidic linkage in the Rp configuration.

In some embodiments, an internucleotidic linkage in the Sp configuration (having a Sp linkage phosphorus) is a phosphorothioate internucleotidic linkage. In some embodiments, an achiral internucleotidic linkage is a natural phosphate linkage. In some embodiments, an internucleotidic linkage in the Rp configuration (having a Rp linkage phosphorus) is a phosphorothioate internucleotidic linkage. In some embodiments, each internucleotidic linkage in the Sp configuration is a phosphorothioate internucleotidic linkage. In some embodiments, each achiral internucleotidic linkage is a natural phosphate linkage. In some embodiments, each internucleotidic linkage in the Rp configuration is a phosphorothioate internucleotidic linkage. In some embodiments, each internucleotidic linkage in the Sp configuration is a phosphorothioate internucleotidic linkage, each achiral internucleotidic linkage is a natural phosphate linkage, and each internucleotidic linkage in the Rp configuration is a phosphorothioate internucleotidic linkage.

In some embodiments, a pattern of backbone chiral centers (e.g., a pattern of backbone chiral centers in an oligonucleotide, e.g., a MAPT oligonucleotide or in a core or a wing or in two wings of an oligonucleotide, e.g., a MAPT oligonucleotide) comprises a pattern of OpSpOpSpOp, OpSpSpSpOp, OpSpSpSpOpSp, SpOpSpOp, SpOpSpOp, SpOpSpOpSp, SpOpSpOpSpOp, SpOpSpOpSpOpSpOp, SpOpSpSpSpOp, SpSpOpSpSpSpOpSpSp, SpSpSpOpSpOpSpSpSp, SpSpSpSpOpSpOpSpSpSpSp, SpSpSpSpSp, SpSpSpSpSpSp, SpSpSpSpSpSpSp, SpSpSpSpSpSpSpSp, SpSpSpSpSpSpSpSpSp, or RpRpRp, wherein each Rp and Sp is independently the linkage phosphorus configuration of a chirally controlled internucleotidic linkage (in some embodiments, each Rp and Sp is independently the linkage phosphorus configuration of a chirally controlled phosphorothioate internucleotidic linkage), and each Op independently represents linkage phosphorus being achiral in a natural phosphate linkage.

In some embodiments, a pattern of backbone chiral centers (e.g., of an oligonucleotide, e.g., a MAPT oligonucleotide, or a portion thereof) is or comprises a pattern of backbone chiral centers described in Table 1A.

In some embodiments, an internucleotidic linkage bonded to a wing nucleoside and a core nucleoside is considered one of the core internucleotidic linkages, for example, when describing types, modifications, numbers, and/or patterns of core internucleotidic linkages. In some embodiments, each internucleotidic linkage bonded to a wing nucleoside and a core nucleoside is considered one of the core internucleotidic linkages, for example, when describing types, modifications, numbers, and/or patterns of core internucleotidic linkages. In some embodiments, a core internucleotidic linkage is bonded to two core nucleosides. In some embodiments, a core internucleotidic linkage is bonded to a core nucleoside and a wing nucleoside. In some embodiments, each core internucleotidic linkage is independently bonded to two core nucleosides, or a core nucleoside and a wing nucleoside. In some embodiments, each wing internucleotidic linkage is independently bonded to two wing nucleosides.

In some embodiments, MAPT oligonucleotides in chirally controlled oligonucleotide compositions each comprise different types of internucleotidic linkages. In some embodiments, MAPT oligonucleotides comprise at least one natural phosphate linkage and at least one modified internucleotidic linkage. In some embodiments, MAPT oligonucleotides comprise at least one natural phosphate linkage and at least two modified internucleotidic linkages. In some embodiments, MAPT oligonucleotides comprise at least one natural phosphate linkage and at least three modified internucleotidic linkages. In some embodiments, MAPT oligonucleotides comprise at least one natural phosphate linkage and at least four modified internucleotidic linkages. In some embodiments, MAPT oligonucleotides comprise at least one natural phosphate linkage and at least five modified internucleotidic linkages. In some embodiments, MAPT oligonucleotides comprise at least one natural phosphate linkage and 1, 2, 3, 4, 5, 6, 7, 8, 9, 10, 11, 12, 13, 14, 15, 16, 17, 18, 19, 20, 21, 22, 23, 24, or 25 modified internucleotidic linkages. In some embodiments, a modified internucleotidic linkage is a phosphorothioate internucleotidic linkage. In some embodiments, each modified internucleotidic linkage is a phosphorothioate internucleotidic linkage. In some embodiments, a modified internucleotidic linkage is a phosphorothioate triester internucleotidic linkage. In some embodiments, each modified internucleotidic linkage is a phosphorothioate triester internucleotidic linkage. In some embodiments, MAPT oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive modified internucleotidic linkages. In some embodiments, MAPT oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive phosphorothioate internucleotidic linkages. In some embodiments, MAPT oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive phosphorothioate triester internucleotidic linkages.

In some embodiments, oligonucleotides in a chirally controlled oligonucleotide composition each comprise at least two internucleotidic linkages that have different stereochemistry and/or different P-modifications relative to one another. In some embodiments, at least two internucleotidic linkages have different stereochemistry relative to one another, and the oligonucleotides each comprise a pattern of backbone chiral centers comprising alternating linkage phosphorus stereochemistry.

In some embodiments, a linkage comprises a chiral auxiliary, which, for example, is used to control the stereoselectivity of a reaction, e.g., a coupling reaction in an oligonucleotide synthesis cycle. In some embodiments, a phosphorothioate triester linkage does not comprise a chiral auxiliary. In some embodiments, a phosphorothioate triester linkage is intentionally maintained until and/or during the administration of the oligonucleotide composition to a subject.

In some embodiments, purity, particularly stereochemical purity, and particularly diastereomeric purity of many oligonucleotides and compositions thereof wherein all other chiral centers in the oligonucleotides but the chiral linkage phosphorus centers have been stereodefined (e.g., carbon chiral centers in the sugars, which are defined in, e.g., phosphoramidites for oligonucleotide synthesis), can be controlled by stereoselectivity (as appreciated by those skilled in this art, diastereoselectivity in many cases of oligonucleotide synthesis wherein the oligonucleotide comprise more than one chiral centers) at chiral linkage phosphorus in coupling steps when forming chiral internucleotidic linkages. In some embodiments, a coupling step has a stereoselectivity (diastereoselectivity when there are other chiral centers) of 60% at the linkage phosphorus. After such a coupling step, the new internucleotidic linkage formed may be referred to have a 60% stereochemical purity (for oligonucleotides, typically diastereomeric purity in view of the existence of other chiral centers). In some embodiments, each coupling step independently has a stereoselectivity of at least 60%. In some embodiments, each coupling step independently has a stereoselectivity of at least 70%. In some embodiments, each coupling step independently has a stereoselectivity of at least 80%. In some embodiments, each coupling step independently has a stereoselectivity of at least 85%. In some embodiments, each coupling step independently has a stereoselectivity of at least 90%. In some embodiments, each coupling step independently has a stereoselectivity of at least 91%. In some embodiments, each coupling step independently has a stereoselectivity of at least 92%. In some embodiments, each coupling step independently has a stereoselectivity of at least 93%. In some embodiments, each coupling step independently has a stereoselectivity of at least 94%. In some embodiments, each coupling step independently has a stereoselectivity of at least 95%. In some embodiments, each coupling step independently has a stereoselectivity of at least 96%. In some embodiments, each coupling step independently has a stereoselectivity of at least 97%. In some embodiments, each coupling step independently has a stereoselectivity of at least 98%. In some embodiments, each coupling step independently has a stereoselectivity of at least 99%. In some embodiments, each coupling step independently has a stereoselectivity of at least 99.5%. In some embodiments, each coupling step independently has a stereoselectivity of virtually 100%. In some embodiments, a coupling step has a stereoselectivity of virtually 100% in that each detectable product from the coupling step analyzed by an analytical method (e.g., NMR, HPLC, etc.) has the intended stereoselectivity. In some embodiments, a chirally controlled internucleotidic linkage is typically formed with a stereoselectivity of at least 90%, 91%, 92%, 93%, 94%, 95%, 96%, 97%, 98%, 99.5% or virtually 100% (in some embodiments, at least 90%; in some embodiments, at least 95%; in some embodiments, at least 96%; in some embodiments, at least 97%; in some embodiments, at least 98%; in some embodiments, at least 99%). In some embodiments, a chirally controlled internucleotidic linkage has a stereochemical purity (typically diastereomeric purity for oligonucleotides with multiple chiral centers) of at least 90%, 91%, 92%, 93%, 94%, 95%, 96%, 97%, 98%, 99.5% or virtually 100% (in some embodiments, at least 90%; in some embodiments, at least 95%; in some embodiments, at least 96%; in some embodiments, at least 97%; in some embodiments, at least 98%; in some embodiments, at least 99%) at its chiral linkage phosphorus. In some embodiments, each chirally controlled internucleotidic linkage independently has a stereochemical purity (typically diastereomeric purity for oligonucleotides with multiple chiral centers) of at least 90%, 91%, 92%, 93%, 94%, 95%, 96%, 97%, 98%, 99.5% or virtually 100% (in some embodiments, at least 90%; in some embodiments, at least 95%; in some embodiments, at least 96%; in some embodiments, at least 97%; in some embodiments, at least 98%; in some embodiments, at least 99%) at its chiral linkage phosphorus. In some embodiments, a non-chirally controlled internucleotidic linkage is typically formed with a stereoselectivity of less than 60%, 70%, 80%, 85%, or 90% (in some embodiments, less than 60%; in some embodiments, less than 70%; in some embodiments, less than 80%; in some embodiments, less than 85%; in some embodiments, less than 90%). In some embodiments, each non-chirally controlled internucleotidic linkage is independently formed with a stereoselectivity of less than 60%, 70%, 80%, 85%, or 90% (in some embodiments, less than 60%; in some embodiments, less than 70%; in some embodiments, less than 80%; in some embodiments, less than 85%; in some embodiments, less than 90%). In some embodiments, a non-chirally controlled internucleotidic linkage has a stereochemical purity (typically diastereomeric purity for oligonucleotides with multiple chiral centers) of less than 60%, 70%, 80%, 85%, or 90% (in some embodiments, less than 60%; in some embodiments, less than 70%; in some embodiments, less than 80%; in some embodiments, less than 85%; in some embodiments, less than 90%) at its chiral linkage phosphorus. In some embodiments, each non-chirally controlled internucleotidic linkage independently has a stereochemical purity (typically diastereomeric purity for oligonucleotides with multiple chiral centers) of less than 60%, 70%, 80%, 85%, or 90% (in some embodiments, less than 60%; in some embodiments, less than 70%; in some embodiments, less than 80%; in some embodiments, less than 85%; in some embodiments, less than 90%) at its chiral linkage phosphorus.

In some embodiments, at least 1, 2, 3, 4, 5, 6, 7, 8, 9, or 10 couplings of a monomer (as appreciated by those skilled in the art in many embodiments a phosphoramidite for oligonucleotide synthesis) independently have a stereoselectivity less than about 60%, 70%, 80%, 85%, or 90% [for oligonucleotide synthesis, typically diastereoselectivity with respect to formed linkage phosphorus chiral center(s)]. In some embodiments, at least one coupling has a stereoselectivity less than about 60%, 70%, 80%, 85%, or 90%. In some embodiments, at least two couplings independently have a stereoselectivity less than about 60%, 70%, 80%, 85%, or 90%. In some embodiments, at least three couplings independently have a stereoselectivity less than about 60%, 70%, 80%, 85%, or 90%. In some embodiments, at least four couplings independently have a stereoselectivity less than about 60%, 70%, 80%, 85%, or 90%. In some embodiments, at least five couplings independently have a stereoselectivity less than about 60%, 70%, 80%, 85%, or 90%. In some embodiments, each coupling independently has a stereoselectivity less than about 60%, 70%, 80%, 85%, or 90%. In some embodiments, each non-chirally controlled internucleotidic linkage is independently formed with a stereoselectivity less than about 60%, 70%, 80%, 85%, or 90%. In some embodiments, a stereoselectivity is less than about 60%. In some embodiments, a stereoselectivity is less than about 70%. In some embodiments, a stereoselectivity is less than about 80%. In some embodiments, a stereoselectivity is less than about 90%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 90%. In some embodiments, at least one coupling has a stereoselectivity less than about 90%. In some embodiments, at least two couplings have a stereoselectivity less than about 90%. In some embodiments, at least three couplings have a stereoselectivity less than about 90%. In some embodiments, at least four couplings have a stereoselectivity less than about 90%. In some embodiments, at least five couplings have a stereoselectivity less than about 90%. In some embodiments, each coupling independently has a stereoselectivity less than about 90%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 85%. In some embodiments, each coupling independently has a stereoselectivity less than about 85%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 80%. In some embodiments, each coupling independently has a stereoselectivity less than about 80%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 70%. In some embodiments, each coupling independently has a stereoselectivity less than about 70%.

In some embodiments, oligonucleotides and compositions of the present disclosure have high purity. In some embodiments, oligonucleotides and compositions of the present disclosure have high stereochemical purity. In some embodiments, a stereochemical purity, e.g., diastereomeric purity, is about 60%-100%. In some embodiments, a diastereomeric purity, is about 60%-100%. In some embodiments, the percentage is at least 60%, 65%, 70%, 75%, 80%, 85%, 90%, 91%, 92%, 93%, 93%, 95%, 96%, 97%, 98%, or 99%. In some embodiments, the percentage is at least 80%, 85%, 90%, 91%, 92%, 93%, 93%, 95%, 96%, 97%, 98%, or 99%. In some embodiments, the percentage is at least 90%, 91%, 92%, 93%, 93%, 95%, 96%, 97%, 98%, or 99%. In some embodiments, a diastereomeric purity is at least 60%. In some embodiments, a diastereomeric purity is at least 70%. In some embodiments, a diastereomeric purity is at least 80%. In some embodiments, a diastereomeric purity is at least 85%. In some embodiments, a diastereomeric purity is at least 90%. In some embodiments, a diastereomeric purity is at least 91%. In some embodiments, a diastereomeric purity is at least 92%. In some embodiments, a diastereomeric purity is at least 93%. In some embodiments, a diastereomeric purity is at least 94%. In some embodiments, a diastereomeric purity is at least 95%. In some embodiments, a diastereomeric purity is at least 96%. In some embodiments, a diastereomeric purity is at least 97%. In some embodiments, a diastereomeric purity is at least 98%. In some embodiments, a diastereomeric purity is at least 99%. In some embodiments, a diastereomeric purity is at least 99.5%.

In some embodiments, compounds of the present disclosure (e.g., oligonucleotides, chiral auxiliaries, etc.) comprise multiple chiral elements (e.g., multiple carbon and/or phosphorus (e.g., linkage phosphorus of chiral internucleotidic linkages) chiral centers). In some embodiments, at least 1, 2, 3, 4, 5, 6, 7, 8, 9 or more chiral elements of a provided compound (e.g., an oligonucleotide) each independently have a diastereomeric purity as described herein. In some embodiments, at least 1, 2, 3, 4, 5, 6, 7, 8, 9 or more chiral carbon centers of a provided compound each independently have a diastereomeric purity as described herein. In some embodiments, at least 1, 2, 3, 4, 5, 6, 7, 8, 9 or more chiral phosphorus centers of a provided compound each independently have a diastereomeric purity as described herein. In some embodiments, each chiral element independently has a diastereomeric purity as described herein. In some embodiments, each chiral center independently has a diastereomeric purity as described herein. In some embodiments, each chiral carbon center independently has a diastereomeric purity as described herein. In some embodiments, each chiral phosphorus center independently has a diastereomeric purity as described herein. In some embodiments, each chiral phosphorus center independently has a diastereomeric purity of at least 90%, 91%, 92%, 93%, 93%, 95%, 96%, 97%, 98%, or 99% or more.

As understood by a person having ordinary skill in the art, in some embodiments, diastereoselectivity of a coupling or diastereomeric purity of a chiral linkage phosphorus center can be assessed through the diastereoselectivity of a dimer formation or diastereomeric purity of a dimer prepared under the same or comparable conditions, wherein the dimer has the same 5'- and 3'-nucleosides and internucleotidic linkage.

Various technologies can be utilized for identifying or confirming stereochemistry of chiral elements (e.g., configuration of chiral linkage phosphorus) and/or patterns of backbone chiral centers, and/or for assessing stereoselectivity (e.g., diastereoselectivity of couple steps in oligonucleotide synthesis) and/or stereochemical purity (e.g., diastereomeric purity of internucleotidic linkages, compounds (e.g., oligonucleotides), etc.). Example technologies include NMR [e.g., 1D (one-dimensional) and/or 2D (two-dimensional) $^{1}H$-$^{31}P$ HETCOR (heteronuclear correlation spectroscopy)], HPLC, RP-HPLC, mass spectrometry, LC-MS, and cleavage of internucleotidic linkages by stereospecific nucleases, etc., which may be utilized individually or in combination. Example useful nucleases include benzonase, micrococcal nuclease, and svPDE (snake venom phosphodiesterase), which are specific for certain internucleotidic linkages with Rp linkage phosphorus (e.g., a Rp phosphorothioate linkage); and nuclease P1, mung bean nuclease, and nuclease S1, which are specific for internucleotidic linkages with Sp linkage phosphorus (e.g., a Sp phosphorothioate linkage). Without wishing to be bound by any particular theory, the present disclosure notes that, in at least some cases, cleavage of oligonucleotides by a particular nuclease may be impacted by structural elements, e.g., chemical modifications (e.g., 2'-modifications of a sugars), base sequences, or stereochemical contexts. For example, it is observed that in some cases, benzonase and micrococcal nuclease, which are specific for internucleotidic linkages with Rp linkage phosphorus, were unable to cleave an isolated Rp phosphorothioate internucleotidic linkage flanked by Sp phosphorothioate internucleotidic linkages.

In some embodiments, oligonucleotides sharing a common base sequence, a common pattern of backbone linkages, and a common pattern of backbone chiral centers share a common pattern of backbone phosphorus modifications and a common pattern of base modifications. In some embodiments, oligonucleotide compositions sharing a common base sequence, a common pattern of backbone linkages, and a common pattern of backbone chiral centers share a common pattern of backbone phosphorus modifications and a common pattern of nucleoside modifications. In some embodiments, oligonucleotides share a common base sequence, a common pattern of backbone linkages, and a common pattern of backbone chiral centers have identical structures.

In some embodiments, the present disclosure provides an oligonucleotide composition comprising a plurality of oligonucleotides capable of directing MAPT knockdown, wherein oligonucleotides of the plurality are of a particular oligonucleotide type, which composition is chirally controlled in that it is enriched, relative to a substantially racemic preparation of oligonucleotides having the same base sequence, for oligonucleotides of the particular oligonucleotide type.

In some embodiments, oligonucleotides having a common base sequence, a common pattern of backbone linkages, and a common pattern of backbone chiral centers have a common pattern of backbone phosphorus modifications and a common pattern of base modifications. In some embodiments, oligonucleotides having a common base sequence, a common pattern of backbone linkages, and a common pattern of backbone chiral centers have a common pattern of backbone phosphorus modifications and a common pattern of nucleoside modifications. In some embodiments, oligonucleotides having a common base sequence, a common pattern of backbone linkages, and a common pattern of backbone chiral centers have identical structures.

In some embodiments, the present disclosure provides MAPT oligonucleotide compositions comprising a plurality of oligonucleotides. In some embodiments, the present disclosure provides chirally controlled oligonucleotide compositions of MAPT oligonucleotides. In some embodiments, the present disclosure provides a MAPT oligonucleotide whose base sequence is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide whose base sequence comprises a base sequence that is or is complementary to a MAPT sequence disclosed herein or a portion thereof (e.g., various bases sequences in Table 1). In some embodiments, the present disclosure provides a MAPT oligonucleotide whose base sequence comprises 15 contiguous bases of a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide which has a base sequence comprising 15 contiguous bases with 0-3 mismatches of a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide composition wherein the MAPT oligonucleotides comprise at least one chiral internucleotidic linkage which is not chirally controlled. In some embodiments, the present disclosure provides a MAPT oligonucleotide comprising a non-chirally controlled chiral internucleotidic linkage, wherein the base sequence of the MAPT oligonucleotide comprises a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide composition comprising a non-chirally controlled chiral internucleotidic linkage, wherein the base sequence of the MAPT oligonucleotide is a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide comprising a non-chirally controlled chiral internucleotidic linkage, wherein the base sequence of the MAPT oligonucleotide comprises 15 contiguous bases of a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide comprising a non-chirally controlled chiral internucleotidic linkage, wherein the base sequence of the MAPT oligonucleotides comprises 15 contiguous bases with 0-3 mismatches of a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide comprising a chirally controlled chiral internucleotidic linkage, wherein the base sequence of the MAPT oligonucleotide comprises a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide composition comprising a chirally controlled chiral internucleotidic linkage, wherein the base sequence of the MAPT oligonucleotide is a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide comprising a chirally controlled chiral internucleotidic linkage, wherein the base sequence of the MAPT oligonucleotide comprises 15 contiguous bases of a base sequence that is or is complementary to a MAPT sequence disclosed herein or a portion thereof (e.g., various bases sequences in Table 1, wherein each T may be independently replaced with U and vice versa). In some embodiments, the present disclosure provides a MAPT oligonucleotide comprising a chirally controlled chiral internucleotidic linkage, wherein the base sequence of the MAPT oligonucleotides comprises 15 contiguous bases with 0-3 mismatches of a base sequence that is or is complementary to a MAPT sequence disclosed herein or a portion thereof (e.g., various bases sequences in Table 1, wherein each T may be independently replaced with U and vice versa).

In some embodiments, oligonucleotides of the same oligonucleotide type have a common pattern of backbone phosphorus modifications and a common pattern of nucleoside modifications. In some embodiments, oligonucleotides of the same oligonucleotide type have a common pattern of sugar modifications. In some embodiments, oligonucleotides of the same oligonucleotide type have a common pattern of base modifications. In some embodiments, oligonucleotides of the same oligonucleotide type have a common pattern of nucleoside modifications. In some embodiments, oligonucleotides of the same oligonucleotide type have the same constitution. In many embodiments, oligonucleotides of the same oligonucleotide type are identical. In some embodiments, oligonucleotides of the same oligonucleotide type are of the same oligonucleotide (as those skilled in the art will appreciate, such oligonucleotides may each independently exist in one of the various forms of the oligonucleotide, and may be the same, or different forms of the oligonucleotide). In some embodiments, oligonucleotides of the same oligonucleotide type are each independently of the same oligonucleotide or a pharmaceutically acceptable salt thereof.

In some embodiments, a plurality of oligonucleotides or oligonucleotides of a particular oligonucleotide type in a provided oligonucleotide composition are MAPT oligonucleotides. In some embodiments, the present disclosure provides a chirally controlled MAPT oligonucleotide composition comprising a plurality of MAPT oligonucleotides, wherein the oligonucleotides share:

1) a common base sequence;
2) a common pattern of backbone linkages; and
3) the same linkage phosphorus stereochemistry at one or more chiral internucleotidic linkages (chirally controlled internucleotidic linkages), wherein the composition is enriched, relative to a substantially racemic preparation of oligonucleotides sharing the common base sequence and pattern of backbone linkages, for oligonucleotides of the plurality.

In some embodiments, as used herein, "one or more" or "at least one" is 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more.

In some embodiments, an oligonucleotide type is further defined by: 4) additional chemical moiety, if any.

In some embodiments, the percentage is at least about 10%. In some embodiments, the percentage is at least about 20%. In some embodiments, the percentage is at least about 30%. In some embodiments, the percentage is at least about 40%. In some embodiments, the percentage is at least about 50%. In some embodiments, the percentage is at least about 60%. In some embodiments, the percentage is at least about 70%. In some embodiments, the percentage is at least about 75%. In some embodiments, the percentage is at least about 80%. In some embodiments, the percentage is at least about 85%. In some embodiments, the percentage is at least about 90%. In some embodiments, the percentage is at least about 91%. In some embodiments, the percentage is at least about 92%. In some embodiments, the percentage is at least about 93%. In some embodiments, the percentage is at least about 94%. In some embodiments, the percentage is at least about 95%. In some embodiments, the percentage is at least about 96%. In some embodiments, the percentage is at least about 97%. In some embodiments, the percentage is at least about 98%. In some embodiments, the percentage is at least about 99%. In some embodiments, the percentage is or is greater than $(DS)^{nc}$, wherein DS and nc are each independently as described in the present disclosure.

In some embodiments, a plurality of oligonucleotides, e.g., MAPT oligonucleotides, share the same constitution. In some embodiments, a plurality of oligonucleotides, e.g., MAPT oligonucleotides, are identical (the same stereoisomer). In some embodiments, a chirally controlled oligonucleotide composition, e.g., a chirally controlled MAPT oligonucleotide composition, is a stereopure oligonucleotide composition wherein oligonucleotides of the plurality are identical (the same stereoisomer), and the composition does not contain any other stereoisomers. Those skilled in the art will appreciate that one or more other stereoisomers may exist as impurities as processes, selectivities, purifications, etc. may not achieve completeness.

In some embodiments, a provided composition is characterized in that when it is contacted with a target nucleic acid [e.g., a MAPT transcript (e.g., pre-mRNA, mature mRNA, other types of RNA, etc. that hybridizes with oligonucleotides of the composition)], levels of the target nucleic acid and/or a product encoded thereby is reduced compared to that observed under a reference condition. In some embodiments, a reference condition is selected from the group consisting of absence of the composition, presence of a reference composition, and combinations thereof. In some embodiments, a reference condition is absence of the composition. In some embodiments, a reference condition is presence of a reference composition. In some embodiments, a reference composition is a composition whose oligonucleotides do not hybridize with the target nucleic acid. In some embodiments, a reference composition is a composition whose oligonucleotides do not comprise a sequence that is sufficiently complementary to the target nucleic acid. In some embodiments, a provided composition is a chirally controlled oligonucleotide composition and a reference composition is a non-chirally controlled oligonucleotide composition which is otherwise identical but is not chirally controlled (e.g., a racemic preparation of oligonucleotides of the same constitution as oligonucleotides of a plurality in the chirally controlled oligonucleotide composition).

In some embodiments, the present disclosure provides a chirally controlled MAPT oligonucleotide composition comprising a plurality of MAPT oligonucleotides capable of directing MAPT knockdown, wherein the oligonucleotides share:

1) a common base sequence,
2) a common pattern of backbone linkages, and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the composition is enriched, relative to a substantially racemic preparation of oligonucleotides sharing the common base sequence and pattern of backbone linkages, for oligonucleotides of the plurality, the oligonucleotide composition being characterized in that, when it is contacted with a MAPT transcript in a MAPT knockdown system, knockdown of the transcript is improved relative to that observed under reference conditions selected from the group consisting of absence of the composition, presence of a reference composition, and combinations thereof.

As noted above and understood in the art, in some embodiments, the base sequence of an oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

As demonstrated herein, oligonucleotide structural elements (e.g., patterns of sugar modifications, backbone linkages, backbone chiral centers, backbone phosphorus modifications, etc.) and combinations thereof can provide surprisingly improved properties and/or bioactivities.

In some embodiments, oligonucleotide compositions are capable of reducing the expression, level and/or activity of a target gene or a gene product thereof. In some embodiments, oligonucleotide compositions are capable of reducing in the expression, level and/or activity of a target gene or a gene product thereof by sterically blocking translation after annealing to a target gene mRNA, by cleaving mRNA (pre-mRNA or mature mRNA), and/or by altering or interfering with mRNA splicing. In some embodiments, provided MAPT oligonucleotide compositions are capable of reducing the expression, level and/or activity of a MAPT target gene or a gene product thereof. In some embodiments, provided MAPT oligonucleotide compositions are capable of reducing in the expression, level and/or activity of a MAPT target gene or a gene product thereof by sterically blocking translation after annealing to a MAPT target gene mRNA, by cleaving MAPT mRNA (pre-mRNA or mature mRNA), and/or by altering or interfering with mRNA splicing.

In some embodiments, an oligonucleotide composition, e.g., a MAPT oligonucleotide composition, is a substantially pure preparation of a single oligonucleotide stereoisomer, e.g., a MAPT oligonucleotide stereoisomer, in that oligonucleotides in the composition that are not of the oligonucleotide stereoisomer are impurities from the preparation process of said oligonucleotide stereoisomer, in some case, after certain purification procedures.

In some embodiments, the present disclosure provides oligonucleotides and oligonucleotide compositions that are chirally controlled, and in some embodiments, stereopure. For instance, in some embodiments, a provided composition contains non-random or controlled levels of one or more individual oligonucleotide types as described herein. In some embodiments, oligonucleotides of the same oligonucleotide type are identical.

Sugars

Various sugars, including modified sugars, can be utilized in accordance with the present disclosure. In some embodiments, the present disclosure provides sugar modifications and patterns thereof optionally in combination with other structural elements (e.g., internucleotidic linkage modifications and patterns thereof, pattern of backbone chiral centers thereof, etc.) that when incorporated into oligonucleotides can provide improved properties and/or activities.

The most common naturally occurring nucleosides comprise ribose sugars (e.g., in RNA) or deoxyribose sugars (e.g., in DNA) linked to the nucleobases adenosine (A), cytosine (C), guanine (G), thymine (T) or uracil (U). In some embodiments, a sugar, e.g., various sugars in many oligonucleotides in Table 1 (unless otherwise notes), is a natural DNA sugar (in DNA nucleic acids or oligonucleotides, having the structure of

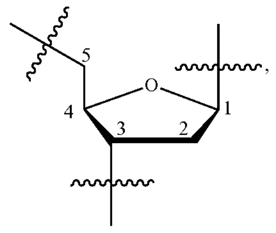 [SMILES: *C[C@H]1O[C@@H](*)C[C@H]1*]

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3'-end group (e.g., —OH). In some embodiments, a sugar is a natural RNA sugar (in RNA nucleic acids or oligonucleotides, having the structure of

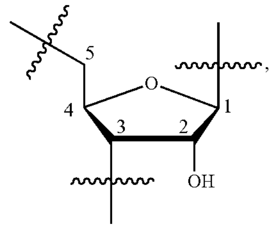

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3'-end group (e.g., —OH). In some embodiments, a sugar is a modified sugar in that it is not a natural DNA sugar or a natural RNA sugar. Among other things, modified sugars may provide improved stability. In some embodiments, modified sugars can be utilized to alter and/or optimize one or more hybridization characteristics. In some embodiments, modified sugars can be utilized to alter and/or optimize target recognition. In some embodiments, modified sugars can be utilized to optimize Tm. In some embodiments, modified sugars can be utilized to improve oligonucleotide activities.

Sugars can be bonded to internucleotidic linkages at various positions. As non-limiting examples, internucleotidic linkages can be bonded to the 2', 3', 4' or 5' positions of sugars. In some embodiments, as most commonly in natural nucleic acids, an internucleotidic linkage connects with one sugar at the 5' position and another sugar at the 3' position unless otherwise indicated.

In some embodiments, a sugar is an optionally substituted natural DNA or RNA sugar. In some embodiments, a sugar is optionally substituted

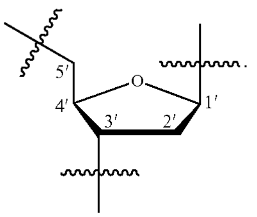 [SMILES: *C[C@H]1O[C@@H](*)C[C@H]1*]

In some embodiments, the 2' position is optionally substituted. In some embodiments, a sugar is

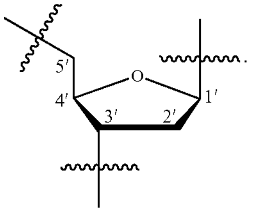 [SMILES: *C[C@H]1O[C@@H](*)C[C@H]1*]

In some embodiments, a sugar has the structure of

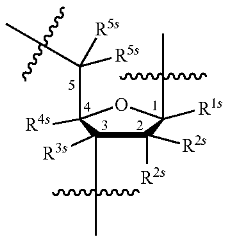

or

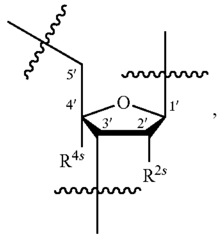

, wherein each of $R^{1s}$, $R^{2s}$, $R^{3s}$, $R^{4s}$, and $R^{5s}$ is independently —H, a suitable substituent or suitable sugar modification (e.g., those described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/022473, WO 2018/223056, WO 2018/223073, WO 2018/223081, WO 2018/237194, WO 2019/032607, WO 2019/055951, WO 2019/075357, WO 2019/032612, and/or WO 2020/191252, the substituents, sugar modifications, descriptions of $R^{1s}$, $R^{2s}$, $R^{3s}$, $R^{4s}$, and $R^{5s}$, and modified sugars of each of which are independently incorporated herein by reference). In some embodiments, a sugar has the structure of

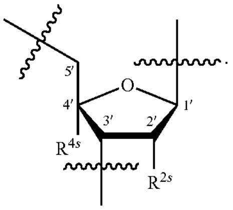

In some embodiments, $R^{4s}$ is —H. In some embodiments, a sugar has the structure of

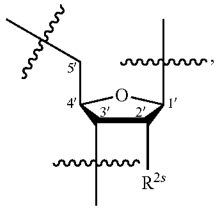

wherein $R^{2s}$ is —H, halogen, or —OR, wherein R is optionally substituted $C_{1-6}$ aliphatic. In some embodiments, $R^{2s}$ is —H. In some embodiments, $R^{2s}$ is —F. In some embodiments, $R^{2s}$ is —OMe. In some embodiments, $R^{2s}$ is —$OCH_2CH_2OMe$.

In some embodiments, a sugar has the structure of

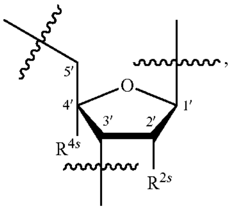

wherein $R^{2s}$ and $R^{4s}$ are taken together to form -$L^s$-, wherein $L^s$ is a covalent bond or optionally substituted bivalent $C_{1-6}$ aliphatic or heteroaliphatic having 1-4 heteroatoms. In some embodiments, each heteroatom is independently selected from nitrogen, oxygen or sulfur). In some embodiments, $L^s$ is optionally substituted $C_2$—O—$CH_2$—C4. In some embodiments, $L^s$ is C2-O—$CH_2$—C4. In some embodiments, $L^s$ is C2-O—(R)—$CH(CH_2CH_3)$—C4. In some embodiments, $L^s$ is C2-O—(S)—$CH(CH_2CH_3)$—C4.

In some embodiments, a sugar is a bicyclic sugar, e.g., sugars wherein $R^{2s}$ and $R^{4s}$ are taken together to form a link as described in the present disclosure. In some embodiments, a sugar is selected from LNA sugars, BNA sugars, cEt sugars, etc. In some embodiments, a bridge is between the 2' and 4'-carbon atoms (corresponding to $R^{2s}$ and $R^{4s}$ taken together with their intervening atoms to form an optionally substituted ring as described herein). In some embodiments, examples of bicyclic sugars include alpha-L-methyleneoxy (4'-$CH_2$—O-2') LNA, beta-D-methyleneoxy (4'-$CH_2$—O-2') LNA, ethyleneoxy (4'-$(CH_2)$2-O-2') LNA, aminooxy (4'-$CH_2$—O—N(R)-2') LNA, and oxyamino (4'-$CH_2$—N(R)—O-2') LNA. In some embodiments, a bicyclic sugar, e.g., a LNA or BNA sugar, is sugar having at least one bridge between two sugar carbons. In some embodiments, a bicyclic sugar in a nucleoside may have the stereochemical configurations of alpha-L-ribofuranose or beta-D-ribofuranose. In some embodiments, a sugar is a sugar described in WO 1999014226. In some embodiments, a 4'-2' bicyclic sugar or 4' to 2' bicyclic sugar is a bicyclic sugar comprising a furanose ring which comprises a bridge connecting the 2' carbon atom and the 4' carbon atom of the sugar ring. In some embodiments, a bicyclic sugar, e.g., a LNA or BNA sugar, comprises at least one bridge between two pentofuranosyl sugar carbons. In some embodiments, a LNA or BNA sugar, comprises at least one bridge between the 4' and the 2' pentofuranosyl sugar carbons.

In some embodiments, a bicyclic sugar is a sugar of alpha-L-methyleneoxy (4'-$CH_2$—O-2') BNA, beta-D-methyleneoxy (4'-$CH_2$—O-2') BNA, ethyleneoxy (4'-$(CH_2)$2-O-

2') BNA, aminooxy (4'-$CH_2$—O—N(R)-2') BNA, oxyamino (4'-$CH_2$—N(R)—O-2') BNA, methyl(methyleneoxy) (4'-$CH(CH_3)$—O-2') BNA (also referred to as constrained ethyl or cEt), methylene-thio (4'-$CH_2$—S-2') BNA, methylene-amino (4'-$CH_2$—N(R)-2') BNA, methyl carbocyclic (4'-$CH_2$—$CH(CH_3)$-2') BNA, propylene carbocyclic (4'-$(CH_2)$3-2') BNA, or vinyl BNA.

In some embodiments, a sugar modification is 2'-OMe, 2'-MOE, 2'-LNA, 2'-F, 5'-vinyl, or S-cEt. In some embodiments, a modified sugar is a sugar of FRNA, FANA, or morpholino. In some embodiments, an oligonucleotide comprises a nucleic acid analog, e.g., GNA, LNA, PNA, TNA, F-HNA (F-THP or 3'-fluoro tetrahydropyran), MNA (mannitol nucleic acid, e.g., Leumann 2002 Bioorg. Med. Chem. 10: 841-854), ANA (anitol nucleic acid), or morpholino, or a portion thereof. In some embodiments, a sugar modification replaces a natural sugar with another cyclic or acyclic moiety. Examples of such moieties are widely known in the art, e.g., those used in morpholino, glycol nucleic acids, etc. and may be utilized in accordance with the present disclosure. As appreciated by those skilled in the art, when utilized with modified sugars, in some embodiments intemucleotidic linkages may be modified, e.g., as in morpholino, PNA, etc.

In some embodiments, a sugar is a 6'-modified bicyclic sugar that have either (R) or (S)-chirality at the 6-position, e.g., those described in U.S. Pat. No. 7,399,845. In some embodiments, a sugar is a 5'-modified bicyclic sugar that has either (R) or (S)-chirality at the 5-position, e.g., those described in US 20070287831.

In some embodiments, a modified sugar contains one or more substituents at the 2' position (typically one substituent, and often at the axial position) independently selected from —F; —$CF_3$, —CN, —$N_3$, —NO, —$NO_2$, —OR', —SR', or —$N(R')_2$, wherein each R' is independently optionally substituted $C_{1-10}$ aliphatic; —O—($C_1$-$C_{10}$ alkyl), —S—($C_1$-$C_{10}$ alkyl), —NH—($C_1$-$C_{10}$ alkyl), or —N($C_1$-$C_{10}$ $alkyl)_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)2; —O—($C_2$-$C_{10}$ alkynyl), —S—($C_2$-$C_{10}$ alkynyl), —NH—($C_2$-$C_{10}$ alkynyl), or —N($C_2$-$C_{10}$ $alkynyl)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ $alkyl)_2$, —NH—($C_1$-$C_{10}$ alkylene)-O—($C_1$—$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, a substituent is —$O(CH_2)_nOCH_3$, —$O(CH_2)_nNH_2$, MOE, DMAOE, or DMAEOE, wherein wherein n is from 1 to about 10. In some embodiments, a modified sugar is one described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the 2', 3', 4', or 5' positions, including the 3' position of the sugar on the 3'-terminal nucleoside or in the 5' position of the 5'-terminal nucleoside.

In some embodiments, the 2'-OH of a ribose is replaced with a group selected from —H, —F; —$CF_3$, —CN, —$N_3$, —NO, —$NO_2$, —OR', —SR', or —$N(R')_2$, wherein each R' is independently described in the present disclosure; —O—($C_1$-$C_{10}$ alkyl), —S—($C_1$-$C_{10}$ alkyl), —NH—($C_1$-$C_{10}$ alkyl), or —N($C_1$-$C_{10}$ $alkyl)_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ $alkenyl)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ $alkynyl)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ $alkyl)_2$, —NH—($C_1$-$C_{10}$ alkylene)-O—($C_i$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —$OCH_2CH_2OMe$.

In some embodiments, a sugar modification is a 2'-modification. Commonly used 2'-modifications include but are not limited to 2'-OR, wherein R is optionally substituted $C_{1-6}$ aliphatic. In some embodiments, a modification is 2'-OR, wherein R is optionally substituted $C_{1-6}$ alkyl. In some embodiments, a modification is 2'-OMe. In some embodiments, a modification is 2'-MOE. In some embodiments, a 2'-modification is S-cEt. In some embodiments, a modified sugar is an LNA sugar. In some embodiments, a 2'-modification is —F. In some embodiments, a 2'-modification is FANA. In some embodiments, a 2'-modification is FRNA. In some embodiments, a sugar modification is a 5'-modification, e.g., 5'-Me. In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, one or more of the sugars of a MAPT oligonucleotide are modified. In some embodiments, each sugar of an oligonucleotide is independently modified. In some embodiments, a modified sugar comprises a 2'-modification. In some embodiments, each modified sugar independently comprises a 2'-modification. In some embodiments, a 2'-modification is 2'-OR, wherein R is optionally substituted $C_{1-6}$ aliphatic. In some embodiments, a 2'-modification is a 2'-OMe. In some embodiments, a 2'-modification is a 2'-MOE. In some embodiments, a 2'-modification is an LNA sugar modification. In some embodiments, a 2'-modification is 2'-F. In some embodiments, each sugar modification is independently a 2'-modification. In some embodiments, each sugar modification is independently 2'-OR. In some embodiments, each sugar modification is independently 2'-OR, wherein R is optionally substituted $C_{1-6}$ alkyl. In some embodiments, each sugar modification is 2'-OMe. In some embodiments, each sugar modification is 2'-MOE. In some embodiments, each sugar modification is independently 2'-OMe or 2'-MOE. In some embodiments, each sugar modification is independently 2'-OMe, 2'-MOE, or a LNA sugar.

In some embodiments, a modified sugar is an optionally substituted ENA sugar. In some embodiments, a sugar is one described in, e.g., Seth et al., J Am Chem Soc. 2010 Oct. 27; 132(42): 14942-14950. In some embodiments, a modified sugar is a sugar in XNA (xenonucleic acid), for instance, arabinose, anhydrohexitol, threose, 2'fluoroarabinose, or cyclohexene.

Modified sugars include cyclobutyl or cyclopentyl moieties in place of a pentofuranosyl sugar. Representative examples of such modified sugars include those described in U.S. Pat. Nos. 4,981,957, 5,118,800, 5,319,080, or U.S. Pat. No. 5,359,044. In some embodiments, the oxygen atom within the ribose ring is replaced by nitrogen, sulfur, selenium, or carbon. In some embodiments, —O— is replaced with —N(R')—, —S—, —Se— or —C(R')$_2$—. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

In some embodiments, sugars are connected by internucleotidic linkages, in some embodiments, modified internucleotidic linkage. In some embodiments, an internucleotidic linkage does not contain a linkage phosphorus. In some embodiments, an internucleotidic linkage is -L-. In some embodiments, an internucleotidic linkage is —OP(O)(—C≡CH)O—, —OP(O)(R)O—(e.g., R is —$CH_3$), 3'-NHP(O)(OH)O—5', 3' —OP(O)($CH_3$)$OCH_2$—5', 3'—$CH_2$C(O)$NHCH_2$-5', 3'—$SCH_2OCH_2$-5', 3'—$OCH_2OCH_2$-5', 3'—$CH_2$NR'$CH_2$-5', 3'—$CH_2$N(Me)$OCH_2$-5', 3'—NHC(O)$CH_2CH_2$-5', 3'—NR'C(O)$CH_2CH_2$-5', 3'—$CH_2CH_2$NR'-5', 3'—$CH_2CH_2$NH-5', or 3'-$OCH_2CH_2$N(R')-5'. In some embodiments, a 5' carbon may be optionally substituted with =O.

In some embodiments, a modified sugar is an optionally substituted pentose or hexose. In some embodiments, a modified sugar is an optionally substituted pentose. In some embodiments, a modified sugar is an optionally substituted hexose. In some embodiments, a modified sugar is an optionally substituted ribose or hexitol. In some embodiments, a modified sugar is an optionally substituted ribose. In some embodiments, a modified sugar is an optionally substituted hexitol.

In some embodiments, a sugar modification is 5'-vinyl (R or S), 5'-methyl (R or S), 2'-SH, 2'-F, 2'-$OCH_3$, 2'-$OCH_2CH_3$, 2'—$OCH_2CH_2$F or 2'-O$(CH_2)_{20}CH_3$. In some embodiments, a substituent at the 2' position, e.g., a 2'-modification, is allyl, amino, azido, thio, O-allyl, O—$C_1$-$C_{10}$ alkyl, $OCF_3$, $OCH_2F$, O$(CH_2)_2SCH_3$, O$(CH_2)_2$—O—N($R_m$)($R_n$), O—$CH_2$—C(=O)—N($R_m$)($R_n$), and O—$CH_2$—C(=O)—N($R_l$)—$(CH_2)_2$—N($R_m$)($R_n$), wherein each allyl, amino and alkyl is optionally substituted, and each of $R_l$, $R_m$ and $R_n$ is independently R' as described in the present disclosure. In some embodiments, each of $R_l$, $R_m$ and $R_n$ is independently —H or optionally substituted $C_1$-$C_{10}$ alkyl.

In some embodiments, a sugar is a tetrahydropyran or THP sugar. In some embodiments, a modified nucleoside is tetrahydropyran nucleoside or THP nucleoside which is a nucleoside having a six-membered tetrahydropyran sugar substituted for a pentofuranosyl residue in typical natural nucleosides. THP sugars and/or nucleosides include those used in hexitol nucleic acid (HNA), anitol nucleic acid (ANA), mannitol nucleic acid (MNA) (e.g., Leumann, Bioorg. Med. Chem., 2002, 10, 841-854) or fluoro HNA (F-HNA).

In some embodiments, sugars comprise rings having more than 5 atoms and/or more than one heteroatom, e.g., morpholino sugars.

As those skilled in the art will appreciate, modifications of sugars, nucleobases, intemucleotidic linkages, etc. can and are often utilized in combination in oligonucleotides, e.g., see various oligonucleotides in Table 1. For example, a combination of sugar modification and nucleobase modification is 2'-F (sugar) 5-methyl (nucleobase) modified nucleosides. In some embodiments, a combination is replacement of a ribosyl ring oxygen atom with S and substitution at the 2'-position.

In some embodiments, a 2'-modified sugar is a furanosyl sugar modified at the 2' position. In some embodiments, a 2'-modification is halogen, —R' (wherein R' is not —H), —OR' (wherein R' is not —H), —SR', —N(R')$_2$, optionally substituted —$CH_2$—CH=$CH_2$, optionally substituted alkenyl, or optionally substituted alkynyl. In some embodiments, a 2'-modifications is selected from —O[$(CH_2)_n$O]$_m$ $CH_3$, —O$(CH_2)_n$$NH_2$, —O$(CH_2)_n$$CH_3$, —O$(CH_2)_n$F, —O$(CH_2)_n$$ONH_2$, —$OCH_2$C(=O)N(H)$CH_3$, and —O$(CH_2)_n$ON[$(CH_2)_n$$CH_3$]$_2$, wherein each n and m is independently from 1 to about 10. In some embodiments, a 2'-modification is optionally substituted $C_1$-$C_{12}$ alkyl, optionally substituted alkenyl, optionally substituted alkynyl, optionally substituted alkaryl, optionally substituted aralkyl, optionally substituted —O-alkaryl, optionally substituted —O-aralkyl, —SH, —$SCH_3$, —OCN, —Cl, —Br, —CN, —F, —$CF_3$, —$OCF_3$, —$SOCH_3$, —$SO_2CH_3$, —$ONO_2$, —$NO_2$, —$N_3$, —$NH_2$, optionally substituted heterocycloalkyl, optionally substituted heterocycloalkaryl, optionally substituted aminoalkylamino, optionally substituted polyalkylamino, substituted silyl, a reporter group, an intercalator, a group for improving pharmacokinetic properties, a group for improving the pharmacodynamic properties, and other substituents. In some embodiments, a 2'-modification is a 2'-MOE modification.

In some embodiments, a 2'-modified or 2'-substituted sugar or nucleoside is a sugar or nucleoside comprising a substituent at the 2' position of the sugar which is other than —H (typically not considered a substituent) or —OH. In some embodiments, a 2'-modified sugar is a bicyclic sugar comprising a bridge connecting two carbon atoms of the sugar ring one of which is the 2' carbon. In some embodiments, a 2'-modification is non-bridging, e.g., allyl, amino, azido, thio, optionally substituted —O-allyl, optionally substituted —O—$C_1$-$C_{10}$ alkyl, —$OCF_3$, —O$(CH_2)_2OCH_3$, 2'—O$(CH_2)_2SCH_3$, —O$(CH_2)_2$ON($R_m$)($R_n$), or —$OCH_2$C(=O)N($R_m$)($R_n$), where each $R_m$ and $R_n$ is independently —H or optionally substituted $C_1$-$C_{10}$ alkyl.

In some embodiments, a sugar is the sugar of N-methanocarba, LNA, cMOE BNA, cEt BNA, a-L-LNA or related analogs, HNA, Me-ANA, MOE-ANA, Ara-FHNA, FHNA, R-6'-Me-FHNA, S-6'-Me-FHNA, ENA, or c-ANA. In some embodiments, a modified internucleotidic linkage is C3-amide (e.g., sugar that has the amide modification attached to the C3', Mutisya et al. 2014 Nucleic Acids Res. 2014 Jun. 1; 42(10): 6542-6551), formacetal, thioformacetal, MMI [e.g., methylene(methylimino), Peoc'h et al. 2006 Nucleosides and Nucleotides 16 (7-9)], a PMO (phosphorodiamidate linked morpholino) linkage (which connects two sugars), or a PNA (peptide nucleic acid) linkage.

In some embodiments, a sugar is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the sugars of each of which is incorporated herein by reference.

Various additional sugars useful for preparing oligonucleotides or analogs thereof are known in the art and may be utilized in accordance with the present disclosure.

Nucleobases

Various nucleobases may be utilized in provided oligonucleotides in accordance with the present disclosure. In some embodiments, a nucleobase is a natural nucleobase, the most commonly occurring ones being A, T, C, G and U. In some embodiments, a nucleobase is a modified nucleobase in that it is not A, T, C, G or U. In some embodiments, a nucleobase is optionally substituted A, T, C, G or U, or a substituted tautomer of A T, C, G or U. In some embodiments, a nucleobase is optionally substituted A, T, C, G or U, e.g., 5mC, 5-hydroxymethyl C, etc. In some embodiments, a nucleobase is alkyl-substituted A, T, C, G or U. In some embodiments, a nucleobase is A. In some embodiments, a nucleobase is T. In some embodiments, a nucleobase is C. In some embodiments, a nucleobase is G. In some embodiments, a nucleobase is U. In some embodiments, a nucleobase is 5mC. In some embodiments, a nucleobase is substituted A, T, C, G or U. In some embodiments, a nucleobase is a substituted tautomer of A, T, C, G or U. In some embodiments, substitution protects certain functional groups in nucleobases to minimize undesired reactions during oligonucleotide synthesis. Suitable technologies for nucleobase protection in oligonucleotide synthesis are widely known in the art and may be utilized in accordance with the present disclosure. In some embodiments, modified nucleobases improves properties and/or activities of oligonucleotides. For example, in many cases, 5mC may be utilized in place of C to modulate certain undesired biological effects, e.g., immune responses. In some embodiments, when determining sequence identity, a substituted nucleobase having the same hydrogen-bonding pattern is treated as the same as the unsubstituted nucleobase, e.g., 5mC may be treated the same as C [e.g., an oligonucleotide having 5mC in place of C (e.g., AT5mCG) is considered to have the same base sequence as an oligonucleotide having C at the corresponding location(s) (e.g., ATCG)].

In some embodiments, an oligonucleotide comprises one or more A, T, C, G or U. In some embodiments, an oligonucleotide comprises one or more optionally substituted A, T, C, G or U. In some embodiments, an oligonucleotide comprises one or more 5-methylcytidine, 5-hydroxymethylcytidine, 5-formylcytosine, or 5-carboxylcytosine. In some embodiments, an oligonucleotide comprises one or more 5-methylcytidine. In some embodiments, each nucleobase in an oligonucleotide is selected from the group consisting of optionally substituted A, T, C, G and U, and optionally substituted tautomers of A, T, C, G and U. In some embodiments, each nucleobase in an oligonucleotide is optionally protected A, T, C, G and U. In some embodiments, each nucleobase in an oligonucleotide is optionally substituted A, T, C, G or U. In some embodiments, each nucleobase in an oligonucleotide is selected from the group consisting of A, T, C, G, U, and 5mC.

In some embodiments, a nucleobase is optionally substituted 2AP or DAP. In some embodiments, a nucleobase is optionally substituted 2AP. In some embodiments, a nucleobase is optionally substituted DAP. In some embodiments, a nucleobase is 2AP. In some embodiments, a nucleobase is DAP.

In some embodiments, a nucleobase is a natural nucleobase or a modified nucleobase derived from a natural nucleobase. Examples include uracil, thymine, adenine, cytosine, and guanine optionally having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Certain examples of modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a provided oligonucleotide comprises one or more 5-methylcytosine. In some embodiments, the present disclosure provides an oligonucleotide whose base sequence is disclosed herein, e.g., in Table 1, wherein each T may be independently replaced with U and vice versa, and each cytosine is optionally and independently replaced with 5-methylcytosine or vice versa. As appreciated by those skilled in the art, in some embodiments, 5mC may be treated as C with respect to base sequence of an oligonucleotide—such oligonucleotide comprises a nucleobase modification at the C position (e.g., see various oligonucleotides in Table 1). In description of oligonucleotides, typically unless otherwise noted, nucleobases, sugars and intemucleotidic linkages are non-modified.

In some embodiments, a modified base is optionally substituted adenine, cytosine, guanine, thymine, or uracil, or a tautomer thereof. In some embodiments, a modified nucleobase is a modified adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof, (2) one or more atoms of a nucleobase are independently replaced with a different atom selected from carbon, nitrogen and sulfur;

(3) one or more double bonds in a nucleobase are independently hydrogenated; or (4) one or more aryl or heteroaryl rings are independently inserted into a nucleobase.

In some embodiments, a modified nucleobase is a modified nucleobase known in the art, e.g., WO2017/210647. In some embodiments, modified nucleobases are expanded-size nucleobases in which one or more aryl and/or heteroaryl rings, such as phenyl rings, have been added.

In some embodiments, a modified nucleobase is selected from 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from 2-aminopropyladenine, 5-hydroxymethyl cytosine, xanthine, hypoxanthine, 2-aminoadenine, 6-N-methylguanine, 6-N—methyladenine, 2-propyladenine, 2-thiouracil, 2-thiothymine and 2-thiocytosine, 5-propynyl (—C—C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N—benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. In some embodiments, modified nucleobases are tricyclic pyrimidines, such as 1,3-diazaphenoxazine-2-one, 1,3-diazaphenothiazine-2-one or 9-(2-aminoethoxy)-1,3-diazaphenoxazine-2-one (G-clamp). In some embodiments, modified nucleobases are those in which the purine or pyrimidine base is replaced with other heterocycles, for example, 7-deaza-adenine, 7-deazaguanosine, 2-aminopyridine or 2-pyridone.

In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One example of a universal base is 3-nitropyrrole.

In some embodiments, nucleosides that can be utilized in provided technologies comprise modified nucleobases and/or modified sugars, e.g., 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, a nucleobase, e.g., a modified nucleobase comprises one or more biomolecule binding moieties such as e.g., antibodies, antibody fragments, biotin, avidin, streptavidin, receptor ligands, or chelating moieties. In other embodiments, a nucleobase is 5-bromouracil, 5-iodouracil, or 2,6-diaminopurine. In some embodiments, a nucleobase comprises substitution with a fluorescent or biomolecule binding moiety. In some embodiments, a substituent is a fluorescent moiety. In some embodiments, a substituent is biotin or avidin.

In some embodiments, a nucleobase is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the nucleobases of each of which is incorporated herein by reference.

Additional Chemical Moieties

In some embodiments, a MAPT oligonucleotide comprises one or more additional chemical moieties. Various additional chemical moieties, e.g., targeting moieties, carbohydrate moieties, lipid moieties, etc. are known in the art and can be utilized in accordance with the present disclosure to modulate properties and/or activities of MAPT oligonucleotides, e.g., stability, half life, activities, delivery, pharmacodynamics properties, pharmacokinetic properties, etc. In some embodiments, certain additional chemical moieties facilitate delivery of oligonucleotides to desired cells, tissues and/or organs, including but not limited the cells of the central nervous system. In some embodiments, certain additional chemical moieties facilitate internalization of oligonucleotides. In some embodiments, certain additional chemical moieties increase oligonucleotide stability. In some embodiments, the present disclosure provides technologies for incorporating various additional chemical moieties into oligonucleotides.

In some embodiments, an additional chemical moiety is capable of improving the stability and/or delivery of a MAPT oligonucleotide, e.g., throughout a particular tissue, organ or body part, or throughout the entire patient's body.

In some embodiments, additional chemical moieties are carbohydrate moieties, targeting moieties, etc., which, when incorporated into oligonucleotides, can improve one or more properties. In some embodiments, an additional chemical moiety is selected from glucose, GluNAc (N-acetyl amine glucosamine) and anisamide moieties.

In some embodiments, an additional chemical moiety is a targeting moiety. In some embodiments, an additional chemical moiety is or comprises a carbohydrate moiety. In some embodiments, an additional chemical moiety is or comprises a lipid moiety. In some embodiments, an additional chemical moiety is or comprises a ligand moiety for, e.g., cell receptors such as a sigma receptor, an asialoglycoprotein receptor, etc. In some embodiments, a ligand moiety is or comprises an anisamide moiety, which may be a ligand moiety for a sigma receptor. In some embodiments, an additional chemical moiety is or comprises a ligand moiety for an asialoglycoprotein receptor.

In some embodiments, an additional chemical moiety is or comprises a GalNAc moiety.

Certain useful additional chemical moieties are described in U.S. Ser. No. 10/479,995, US 2020/0056173, US 2018/0216107, US 2019/0127733, U.S. Ser. No. 10/450,568, US 2019/0249173, WO 2018/223056, WO 2018/223073, WO 2018/223081, WO 2019/032607, WO 2019/075357, WO 2019/200185, WO 2019/217784, WO 2019/032612, and/or WO 2020/191252.

Production of Oligonucleotides and Compositions

Various methods can be utilized for production of oligonucleotides and compositions and can be utilized in accordance with the present disclosure. For example, traditional phosphoramidite chemistry can be utilized to prepare stereorandom oligonucleotides and compositions, and certain reagents and chirally controlled technologies can be utilized to prepare chirally controlled oligonucleotide compositions, e.g., as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the reagents and methods of each of which is incorporated herein by reference.

In some embodiments, chirally controlled/stereoselective preparation of oligonucleotides and compositions thereof comprise utilization of a chiral auxiliary, e.g., as part of monomeric phosphoramidites. Examples of such chiral auxiliary reagents and phosphoramidites are described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the chiral auxiliary reagents and phosphoramidites of each of which are independently incorporated herein by reference. In some embodiments, a chiral auxiliary is

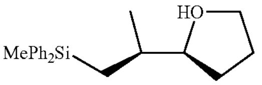
or
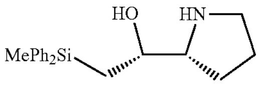

(DPSE chiral auxiliaries). In some embodiments, a chiral auxiliary is

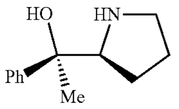
or
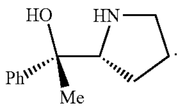

In some embodiments, a chiral auxiliary is

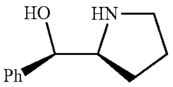
or
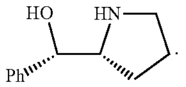

In some embodiments, a chiral auxiliary comprises —$SO_2R^{AU}$, wherein $R^{AU}$ is an optionally substituted group selected from $C_{1-20}$ aliphatic, $C_{1-20}$ heteroaliphatic having 1-10 heteroatoms, $C_{6-20}$ aryl, $C_{6-20}$ arylaliphatic, $C_{6-20}$ arylheteroaliphatic having 1-10 heteroatoms, 5-20 membered heteroaryl having 1-10 heteroatoms, and 3-20 membered heterocyclyl having 1-10 heteroatoms. In some embodiments, a chiral auxiliary is

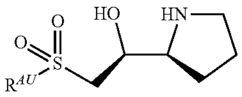
or
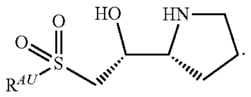

In some embodiments, $R^{AU}$ is optionally substituted aryl. In some embodiments, $R^{AU}$ is optionally substituted phenyl. In some embodiments, $R^{AU}$ is optionally substituted $C_{1-6}$ aliphatic. In some embodiments, a chiral auxiliary is

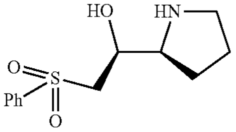
or
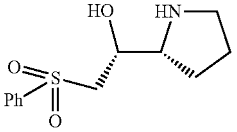

(PSM chiral auxiliaries). In some embodiments, utilization of such chiral auxiliaries, e.g., preparation, phosphoramidites comprising such chiral auxiliaries, intermediate oligonucleotides comprising such auxiliaries (which auxiliaries are typically bonded to linkage phosphorus through —O— of —OH, and —NH— are optionally capped, e.g., by —C(O)R), protection, removal, etc., is described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252 and incorporated herein by reference.

In some embodiments, chirally controlled preparation technologies, including oligonucleotide synthesis cycles, reagents and conditions are described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the oligonucleotide synthesis methods, cycles, reagents and conditions of each of which are independently incorporated herein by reference.

Once synthesized, MAPT oligonucleotides and compositions are typically further purified. Suitable purification technologies are widely known and practiced by those skilled in the art, including but not limited to those described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the purification technologies of each of which are independently incorporated herein by reference.

In some embodiments, a cycle comprises or consists of coupling, capping, modification and deblocking. In some embodiments, a cycle comprises or consists of coupling, capping, modification, capping and deblocking. These steps are typically performed in the order they are listed, but in some embodiments, as appreciated by those skilled in the art, the order of certain steps, e.g., capping and modification, may be altered. If desired, one or more steps may be repeated to improve conversion, yield and/or purity as those skilled in the art often perform in syntheses. For example, in some embodiments, coupling may be repeated; in some embodiments, modification (e.g., oxidation to install =O, sulfurization to install =S, etc.) may be repeated; in some embodiments, coupling is repeated after modification which can convert a P(III) linkage to a P(V) linkage which can be more stable under certain circumstances, and coupling is routinely followed by modification to convert newly formed P(III) linkages to P(V) linkages. In some embodiments, when steps are repeated, different conditions may be employed (e.g., concentration, temperature, reagent, time, etc.).

In some embodiments, oligonucleotides are linked to a solid support. In some embodiments, a solid support is a support for oligonucleotide synthesis. In some embodiments, a solid support comprises glass. In some embodiments, a solid support is CPG (controlled pore glass). In some embodiments, a solid support is polymer. In some embodiments, a solid support is polystyrene. In some embodiments, the solid support is Highly Crosslinked Polystyrene (HCP). In some embodiments, the solid support is hybrid support of Controlled Pore Glass (CPG) and Highly Cross-linked Polystyrene (HCP). In some embodiments, a solid support is a metal foam. In some embodiments, a solid support is a resin. In some embodiments, oligonucleotides are cleaved from a solid support.

Technologies for formulating provided oligonucleotides and/or preparing pharmaceutical compositions, e.g., for administration to subjects via various routes, are readily available in the art and can be utilized in accordance with the present disclosure, e.g., those described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252.

Metabolites and Shortened Versions of Oligonucleotides

In some embodiments, a MAPT oligonucleotide corresponds to a metabolite produced by cleavage (e.g., enzymatic cleavage by a nuclease) of a longer oligonucleotide, e.g., a longer MAPT oligonucleotide. In some embodiments, the present disclosure pertains to a MAPT oligonucleotide which corresponds to a portion, or fragment of a MAPT oligonucleotide disclosed herein.

In some embodiments, the present disclosure pertains to an oligonucleotide which corresponds to a metabolite of a MAPT oligonucleotide disclosed herein. In some embodiments, the present disclosure pertains to an oligonucleotide which is 1, 2, 3, 4, 5, 6, 7, 8, 9, 10, 11, 12, 13, or more bases shorter than an oligonucleotide disclosed herein. In some embodiments, the present disclosure pertains to an oligonucleotide which has a base sequence which is 1, 2, 3, 4, 5, 6, 7, 8, 9, 10, 11, 12, 13, or more bases shorter than that of an oligonucleotide disclosed herein.

In some embodiments, a metabolite is designated as 3'-N—#, or 5'-N—#, wherein the # indicates the number of bases removed, and the 3' or 5' indicates which end of the molecule from which the bases were deleted. For example, 3'-N-1 indicates a fragment or metabolite wherein 1 base was removed from the 3' end.

In some embodiments, the present disclosure perhaps to an oligonucleotide which corresponds to a fragment or metabolite of an oligonucleotide disclosed herein, wherein the fragment or metabolite can be described as corresponding to 3'-N-1, 3'—N-2, 3'—N-3, 3'—N-4, 3'—N-5, 3'—N-6, 3'—N-7, 3'—N-8, 3'—N-9, 3'—N-10, 3'—N-11, 3'—N-12, 5'—N-1, 5'—N-2, 5'—N-3, 5'—N-4, 5'—N-5, 5'—N-6, 5'—N-7, 5'—N-8, 5'—N-9, 5'—N-10, 5'—N-11, or 5'-N-12 of an oligonucleotide described herein, wherein each T may be independently replaced with U and vice versa.

In some embodiments, the present disclosure pertains to an oligonucleotide which corresponds to a metabolite of an oligonucleotide, wherein the metabolite is truncated on the 5' and/or 3' end relative to the oligonucleotide disclosed herein, wherein each T may be independently replaced with U and vice versa. In some embodiments, the present disclosure pertains to an which corresponds to a metabolite of an oligonucleotide, wherein the metabolite is truncated on both the 5' and 3' end relative to the oligonucleotide disclosed herein, wherein each T may be independently replaced with U and vice versa. In some embodiments, the present disclosure pertains to an oligonucleotide which is 1, 2, 3, 4, 5, 6, 7, 8, 9, 10, 11, 12, 13, or more total bases shorter on the 5' and/or 3' end than an oligonucleotide disclosed herein. In some embodiments, the present disclosure pertains to an oligonucleotide which has a base sequence which is 1, 2, 3, 4, 5, 6, 7, 8, 9, 10, 11, 12, 13, or more bases total shorter on the 5' and/or 3' end than that of an oligonucleotide disclosed herein, wherein each T may be independently replaced with U and vice versa.

In some embodiments, the present disclosure pertains to an oligonucleotide which is a product of a cleavage of an oligonucleotide disclosed herein cleaved at a natural phosphate linkage. In some embodiments, the present disclosure pertains to an oligonucleotide which is a product of a cleavage of an oligonucleotide disclosed herein cleaved at a Rp phosphorothioate internucleotidic linkage.

Various technologies can be utilized to identify, characterize and/or assess metabolites and/or shortened MAPT oligonucleotides in accordance with the present disclosure, for example, those described in U.S. Ser. No. 10/479,995, US 2020/0056173, US 2018/0216107, US 2019/0127733, U.S. Ser. No. 10/450,568, US 2019/0249173, WO 2018/223056, WO 2018/223073, WO 2018/223081, WO 2019/032607, WO 2019/075357, WO 2019/200185, WO 2019/217784, WO 2019/032612, and/or WO 2020/191252.

Characterization and Assessment

In some embodiments, properties and/or activities of MAPT oligonucleotides and compositions thereof can be characterized and/or assessed using various technologies available to those skilled in the art, e.g., biochemical assays (e.g., RNase H assays), cell based assays, animal models, clinical trials, etc.

In some embodiments, a method of identifying and/or characterizing an oligonucleotide composition, e.g., a MAPT oligonucleotide composition, comprises steps of:

providing at least one composition comprising a plurality of oligonucleotides; and assessing delivery relative to a reference composition.

In some embodiments, the present disclosure provides a method of identifying and/or characterizing an oligonucleotide composition, e.g., a MAPT oligonucleotide composition, comprises steps of:

providing at least one composition comprising a plurality of oligonucleotides; and assessing cellular uptake relative to a reference composition.

In some embodiments, the present disclosure provides a method of identifying and/or characterizing an oligonucleotide composition, e.g., a MAPT oligonucleotide composition, comprises steps of:

providing at least one composition comprising a plurality of oligonucleotides; and assessing reduction of transcripts of a target gene and/or a product encoded thereby relative to a reference composition.

In some embodiments, the present disclosure provides a method of identifying and/or characterizing an oligonucleotide composition, e.g., a MAPT oligonucleotide composition, comprises steps of:

providing at least one composition comprising a plurality of oligonucleotides; and assessing reduction of tau levels, its aggregation and/or spreading relative to a reference composition.

In some embodiments, properties and/or activities of oligonucleotides, e.g., MAPT oligonucleotides, and compositions thereof are compared to reference oligonucleotides and compositions thereof, respectively.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages. In some embodiments, a reference oligonucleotide composition is otherwise identical to a provided chirally controlled oligonucleotide composition except that it is not chirally controlled. In some embodiments, a reference oligonucleotide composition is otherwise identical to a provided chirally controlled oligonucleotide composition except that it has a different pattern of stereochemistry. In some embodiments, a reference oligonucleotide composition is similar to a provided oligonucleotide composition except that it has a different modification of one or more sugar, base, and/or internucleotidic linkage, or pattern of modifications. In some embodiments, an oligonucleotide composition is stereorandom and a reference oligonucleotide composition is also stereorandom, but they differ in regards to sugar and/or base modification(s) or patterns thereof.

In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a non-chirally controlled (or stereorandom) composition of oligonucleotides having the same base sequence and chemical modifications. In some embodiments, a reference composition is a non-chirally controlled (or stereorandom) composition of oligonucleotides of the same constitution but is otherwise identical to a provided chirally controlled oligonucleotide composition.

In some embodiments, a reference oligonucleotide composition is of oligonucleotides having a different base sequence. In some embodiments, a reference oligonucleotide composition is of oligonucleotides that do not target MAPT (e.g., as negative control for certain assays).

In some embodiments, a reference composition is a composition of oligonucleotides having the same base sequence but different chemical modifications, including but not limited to chemical modifications described herein. In some embodiments, a reference composition is a composition of oligonucleotides having the same base sequence but different patterns of internucleotidic linkages and/or stereochemistry of internucleotidic linkages and/or chemical modifications.

Various methods are known in the art for detection of gene products, the expression, level and/or activity of which may be altered after introduction or administration of a provided oligonucleotide. For example, transcripts and their knockdown can be detected and quantified with qPCR, and protein levels can be determined via Western blot.

In some embodiments, assessment of efficacy of oligonucleotides can be performed in biochemical assays or in vitro in cells. In some embodiments, MAPT oligonucleotides can be introduced to cells via various methods available to those skilled in the art, e.g., gymnotic delivery, transfection, lipofection, etc.

In some embodiments, the efficacy of a putative MAPT oligonucleotide can be tested in vitro.

In some embodiments, the efficacy of a putative MAPT oligonucleotide can be tested in vitro using any known method of testing the expression, level and/or activity of a MAPT gene or gene product thereof.

In some embodiments, MAPT levels in neuronal nuclei of ventral pons can be assessed by immunofluorescence.

In some embodiments, MAPT soluble aggregates can be observed by immunoblotting.

In some embodiments, a MAPT oligonucleotide is tested in a cell or animal model of Alzheimer's Disease (AD) and/or Frontotemporal Dementia (FTD).

In some embodiments, an animal model administered a MAPT oligonucleotide can be evaluated for safety and/or efficacy.

In some embodiments, the effect(s) of administration of an oligonucleotide to an animal can be evaluated, including any effects on behavior, inflammation, and toxicity. In some embodiments, following dosing, animals can be observed for signs of toxicity including trouble grooming, lack of food consumption, and any other signs of lethargy. In some embodiments, in a mouse model of Alzheimer's Disease (AD) or Frontotemporal Dementia (FTD), following administration of a MAPT oligonucleotide, the animals can be monitored for timing of onset of a rear paw clasping phenotype.

In some embodiments, following administration of a MAPT oligonucleotide to an animal, the animal can be sacrificed and analysis of tissues or cells can be performed to determine changes in MAPT, or other biochemical or other changes. In some embodiments, following necropsy, liver, heart, lung, kidney, and spleen can be collected, fixed, and processed for histopathological evaluation (standard light microscopic examination of hematoxylin and eosin-stained tissue slides).

In some embodiments, following administration of a MAPT oligonucleotide to an animal, behavioral changes can be monitored or assessed. In some embodiments, such an assessment can be performed using a technique described in the scientific literature.

Various effects of testing in animals described herein can also be monitored in human subjects or patients following administration of a MAPT oligonucleotide.

In addition, the efficacy of a MAPT oligonucleotide in a human subject can be measured by evaluating, after administration of the oligonucleotide, any of various parameters known in the art, including but not limited to a reduction in a symptom of Alzheimer's Disease (AD) and/or Frontotemporal Dementia (FTD), or a decrease in the rate of worsening or onset of a symptom of Alzheimer's Disease (AD) and/or Frontotemporal Dementia (FTD).

In some embodiments, following human treatment with an oligonucleotide, or contacting a cell or tissue in vitro with an oligonucleotide, cells and/or tissues are collected for analysis.

In some embodiments, in various cells and/or tissues, target nucleic acid levels can be quantitated by methods available in the art, many of which can be accomplished with commercially available kits and materials. Such methods include, e.g., Northern blot analysis, competitive polymerase chain reaction (PCR), quantitative real-time PCR, etc. RNA analysis can be performed on total cellular RNA or poly(A)+mRNA. Probes and primers are designed to hybridize to a nucleic acid to be detected. Methods for designing real-time PCR probes and primers are well known and widely practiced in the art. For example, to detect and quantify MAPT RNA, an example method comprises isolation of total RNA (e.g., including mRNA) from a cell or animal treated with an oligonucleotide or a composition and subjecting the RNA to reverse transcription and/or quantitative real-time PCR, for example, as described herein, or in: Moon et al. 2012 Cell Metab. 15: 240-246.

In some embodiments, protein levels can be evaluated or quantitated in various methods known in the art, e.g., enzyme-linked immunosorbent assay (ELISA), Western blot analysis (immunoblotting), immunocytochemistry, fluorescence-activated cell sorting (FACS), immunohistochemistry, immunoprecipitation, protein activity assays (for example, caspase activity assays), and quantitative protein assays. Antibodies useful for the detection of mouse, rat, monkey, and human proteins are commercially available or can be generated if needed. For example, various MAPT antibodies have been reported.

Various technologies are available and/or known in the art for detecting levels of oligonucleotides or other nucleic acids. Such technologies are useful for detecting MAPT oligonucleotides when administered to assess, e.g., delivery, cell uptake, stability, distribution, etc.

In some embodiments, selection criteria are used to evaluate the data resulting from various assays and to select particularly desirable oligonucleotides, e.g., desirable MAPT oligonucleotides, with certain properties and activities. In some embodiments, selection criteria include an $IC_{50}$ of less than about 10 nM, less than about 5 nM or less than about 1 nM. In some embodiments, selection criteria for a stability assay include at least 50% stability [at least 50% of an oligonucleotide is still remaining and/or detectable] at Day 1. In some embodiments, selection criteria for a stability assay include at least 50% stability at Day 2. In some embodiments, selection criteria for a stability assay include at least 50% stability at Day 3. In some embodiments, selection criteria for a stability assay include at least 50% stability at Day 4. In some embodiments, selection criteria for a stability assay include at least 50% stability at Day 5. In some embodiments, selection criteria for a stability assay include at least 80% [at least 80% of the oligonucleotide remains] at Day 5.

In some embodiments, efficacy of a MAPT oligonucleotide is assessed directly or indirectly by monitoring, measuring or detecting a change in a condition, disorder or disease or a biological pathway associated with MAPT.

In some embodiments, efficacy of a MAPT oligonucleotide is assessed directly or indirectly by monitoring, measuring or detecting a change in a response to be affected by MAPT knockdown.

In some embodiments, a provided oligonucleotide (e.g., a MAPT oligonucleotide) can by analyzed by a sequence analysis to determine what other genes [e.g., genes which are not a target gene (e.g., MAPT)] have a sequence which is complementary to the base sequence of the provided oligonucleotide (e.g., the MAPT oligonucleotide) or which have 0, 1, 2 or more mismatches from the base sequence of the provided oligonucleotide (e.g., the MAPT oligonucleotide). Knockdown, if any, by the oligonucleotide of these potential off-targets can be determined to evaluate potential off-target effects of an oligonucleotide (e.g., a MAPT oligonucleotide). In some embodiments, an off-target effect is also termed an unintended effect and/or related to hybridization to a bystander (non-target) sequence or gene.

Oligonucleotides which have been evaluated and tested for efficacy in knocking down MAPT have various uses, e.g., in treatment or prevention of a MAPT-associated condition, disorder or disease or a symptom thereof.

In some embodiments, a MAPT oligonucleotide which has been evaluated and tested for its ability to provide a particular biological effect (e.g., reduction of level, expression and/or activity of a MAPT target gene or a gene product thereof) can be used to treat, ameliorate and/or prevent a MAPT-associated condition, disorder or disease.

Treatment of MAPT-Associated Conditions, Disorders or Diseases

In some embodiments, the present disclosure provides a MAPT oligonucleotide which targets MAPT and directs target-specific knockdown of MAPT. In some embodiments, the present disclosure provides methods for preventing and/or treating MAPT-associated conditions, disorders or diseases using provided MAPT oligonucleotides and compositions thereof. In some embodiments, the present disclosure provides oligonucleotides and compositions thereof for use as medicaments, e.g., for MAPT-associated conditions, disorders or diseases. In some embodiments, the present disclosure provides oligonucleotides and compositions thereof for use in the treatment of MAPT-associated conditions, disorders or diseases. In some embodiments, the present disclosure provides oligonucleotides and compositions thereof for the manufacture of medicaments for the treatment of MAPT-associated conditions, disorders or diseases.

In some embodiments, the present disclosure provides a method for treating and/or ameliorating one or more symptoms associated with a MAPT-associated condition, disorder or disease in a mammal in need thereof, the method comprising administering to the mammal a therapeutically effective amount of a MAPT oligonucleotide or a composition thereof. In some embodiments, the present disclosure provides a method for reducing susceptibility to a MAPT-associated condition, disorder or disease in a mammal in need thereof, the method comprising: administering to the mammal a therapeutically effective amount of a MAPT oligonucleotide or a composition thereof. In some embodiments, the present disclosure provides a method for preventing or delaying the onset of a MAPT-associated condition, disorder or disease in a mammal in need thereof, the method comprising: administering to the mammal a therapeutically effective amount of a MAPT oligonucleotide or a composition thereof. In some embodiments, the present disclosure provides a method for treating and/or ameliorating one or more symptoms associated with a MAPT-associated condition, disorder or disease in a mammal in need thereof, the method comprising: administering to the mammal a therapeutically effective amount of a nucleic acid-lipid particle comprising a MAPT oligonucleotide. In some embodiments, the present disclosure provides a method for reducing susceptibility to a MAPT-associated condition, disorder or disease in a mammal in need thereof, the method comprising: administering to the mammal a therapeutically effective amount of a nucleic acid-lipid particle comprising a MAPT oligonucleotide. In some embodiments, the present disclosure provides a method for preventing or delaying the onset of a MAPT-associated condition, disorder or disease in a mammal in need thereof, the method comprising: administering to the mammal a therapeutically effective amount of a nucleic acid-lipid particle comprising a MAPT oligonucleotide. In some embodiments, a mammal is a human. In some embodiments, a mammal is susceptible to, afflicted with and/or suffering from a MAPT-associated condition, disorder or disease. In some embodiments, a MAPT-associated condition, disorder or disease is Alzheimer's Disease (AD). In some embodiments, a MAPT-associated condition, disorder or disease is Frontotemporal Dementia (FTD). In some embodiments, a MAPT-associated condition, disorder or disease is behavioral variant FTD (bvFTD). In some embodiments, a MAPT-associated condition, disorder or disease is non-fluent variant primary progressive aphasia (nfvPPA). In some embodiments, a MAPT-associated condition, disorder or disease is Corticobasal Degeneration (CBD). In some embodiments, a MAPT-associated condition, disorder or disease is Progressive Supranulcear Palsy (PSP). In some embodiments, a MAPT-associated condition, disorder or disease is epilepsy. In some embodiments, a MAPT-associated condition, disorder or disease is Dravet syndrome. In some embodiments, a MAPT-associated condition, disorder or disease is Chronic Traumatic Encephalopthy (CTE).

In some embodiments, provided methods reduce express, level and/or activities of tau. In some embodiments, provided methods reduce aggregation of tau in neurons. In some embodiments, provided methods reduce spreading of tau among neurons.

In some embodiments, provided oligonucleotides and compositions are useful for preventing and/or treating neurodegenerative diseases, e.g., Alzheimer's Disease (AD), Frontotemporal Dementia (FTD), behavioral variant FTD (bvFTD), non-fluent variant primary progressive aphasia (nfvPPA), Corticobasal Degeneration (CBD), Progressive Supranulcear Palsy (PSP), epilepsy, Dravet syndrome, Chronic Traumatic Encephalopthy (CTE), etc. In some embodiments, the present disclosure provides methods for preventing and/or treating a neurodegenerative disease, e.g., Alzheimer's Disease (AD), Frontotemporal Dementia (FTD), behavioral variant FTD (bvFTD), non-fluent variant primary progressive aphasia (nfvPPA), Corticobasal Degeneration (CBD), Progressive Supranulcear Palsy (PSP), epilepsy, Dravet syndrome, Chronic Traumatic Encephalopthy (CTE), etc., comprising administering to a subject susceptible to or suffering therefrom a therapeutically effective amount of a MAPT oligonucleotide or a composition as described herein. In some embodiments, the present disclosure provides methods for treating a neurodegenerative disease comprising administering to a subject suffering therefrom a therapeutically effective amount of a MAPT oligonucleotide or a composition as described herein. In some embodiments, the present disclosure provides methods for preventing and/or treating a tauopathy comprising administering to a subject susceptible to or suffering therefrom a therapeutically effective amount of a MAPT oligonucleotide or a composition as described herein. In some embodiments, the present disclosure provides methods for treating a tauopathy comprising administering to a subject suffering therefrom a therapeutically effective amount of a MAPT oligonucleotide or a composition as described herein. In some embodiments, the present disclosure provides methods for preventing and/or treating Alzheimer's Disease (AD), Frontotemporal Dementia (FTD), behavioral variant FTD (bvFTD), non-fluent variant primary progressive aphasia (nfvPPA), Corticobasal Degeneration (CBD), Progressive Supranulcear Palsy (PSP), epilepsy, Dravet syndrome, or Chronic Traumatic Encephalopthy (CTE) comprising administering to a subject susceptible to or suffering therefrom a therapeutically effective amount of a MAPT oligonucleotide or a composition as described herein. In some embodiments, the present disclosure provides methods for treating Alzheimer's Disease (AD), Frontotemporal Dementia (FTD), behavioral variant FTD (bvFTD), non-fluent variant primary progressive aphasia (nfvPPA), Corticobasal Degeneration (CBD), Progressive Supranulcear Palsy (PSP), epilepsy, Dravet syndrome, Chronic Traumatic Encephalopthy (CTE) comprising administering to a subject suffering therefrom a therapeutically effective amount of a MAPT oligonucleotide or a composition as described herein. In some embodiments, a method is for preventing and/or treating AD. In some embodiments, a method is for preventing and/or treating FTD. In some embodiments, a method is for preventing and/or treating bvFTD. In some embodiments, a method is for preventing and/or treating nfvPPA. In some embodiments, a method is for preventing and/or treating CBD. In some embodiments, a method is for preventing and/or treating PSP. In some embodiments, a method is for preventing and/or treating epilepsy. In some embodiments, a method is for preventing and/or treating Dravet syndrome. In some embodiments, a method is for preventing and/or treating CTE. In some embodiments, a subject is a human. In some embodiments, a subject has increased MAPT expression, and/or increased levels of one or more MAPT products (e.g., transcripts, proteins (e.g., tau protein), etc.) compared to, e.g., a health subject (or a population thereof), a subject that is not susceptible to and/or not suffering from such a neurodegenerative disease (or a population thereof), etc.

In some embodiments, provided oligonucleotides and compositions may be optionally utilized in combination with one or more other therapeutic agents.

Administration of Oligonucleotides and Compositions

Many delivery methods, regimen, etc. can be utilized in accordance with the present disclosure for administering provided oligonucleotides and compositions thereof (typically pharmaceutical compositions for therapeutic purposes), including various technologies known in the art.

In some embodiments, an oligonucleotide composition, e.g., a MAPT oligonucleotide composition, is administered at a dose and/or frequency lower than that of an otherwise comparable reference oligonucleotide composition and has comparable or improved effects. In some embodiments, a chirally controlled oligonucleotide composition is administered at a dose and/or frequency lower than that of a comparable, otherwise identical stereorandom reference oligonucleotide composition and with comparable or improved effects, e.g., in improving the knockdown of the target transcript.

In some embodiments, the present disclosure recognizes that properties and activities, e.g., knockdown activity, stability, toxicity, etc. of oligonucleotides and compositions thereof can be modulated and optimized by chemical modifications and/or stereochemistry. In some embodiments, the present disclosure provides methods for optimizing oligonucleotide properties and/or activities through chemical modifications and/or stereochemistry. In some embodiments, the present disclosure provides oligonucleotides and compositions thereof with improved properties and/or activities. Without wishing to be bound by any theory, due to, e.g., their better activity, stability, delivery, distribution, toxicity, pharmacokinetic, pharmacodynamics and/or efficacy profiles, Applicant notes that provided oligonucleotides and compositions thereof in some embodiments can be administered at lower dosage and/or reduced frequency to achieve comparable or better efficacy, and in some embodiments can be administered at higher dosage and/or increased frequency to provide enhanced effects.

In some embodiments, the present disclosure provides, in a method of administering an oligonucleotide composition comprising a plurality of oligonucleotides sharing a common base sequence, the improvement comprising administering an oligonucleotide comprising a plurality of oligonucleotides that is characterized by improved delivery relative to a reference oligonucleotide composition of the same common base sequence.

In some embodiments, provided oligonucleotides, compositions and methods provide improved delivery. In some embodiments, provided oligonucleotides, compositions and methods provide improved cytoplasmatic delivery. In some embodiments, improved delivery is to a population of cells. In some embodiments, improved delivery is to a tissue. In some embodiments, improved delivery is to an organ. In some embodiments, improved delivery is to an organism, e.g., a patient or subject. Example structural elements (e.g., chemical modifications, stereochemistry, combinations thereof, etc.), oligonucleotides, compositions and methods that provide improved delivery are extensively described in the present disclosure.

Various dosing regimens can be utilized to administer oligonucleotides and compositions of the present disclosure. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is the same as or different from the first dose (or another prior dose) amount. In some embodiments, a chirally controlled oligonucleotide composition is administered according to a dosing regimen that differs from that utilized for a non-chirally controlled (e.g., stereorandom) oligonucleotide composition of the same sequence, and/or of a different chirally controlled oligonucleotide composition of the same sequence. In some embodiments, a chirally controlled oligonucleotide composition is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, a chirally uncontrolled oligonucleotide is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, with their improved delivery (and other properties), provided compositions can be administered in lower dosages and/or with lower frequency to achieve biological effects, for example, clinical efficacy.

Pharmaceutical Compositions

When used as therapeutics, a provided oligonucleotide, e.g., a MAPT oligonucleotide, or oligonucleotide composition thereof is typically administered as a pharmaceutical composition. In some embodiments, the present disclosure provides pharmaceutical compositions comprising a provided compound, e.g., an oligonucleotide, or a pharmaceutically acceptable salt thereof, and a pharmaceutical carrier. In some embodiments, for therapeutic and clinical purposes, oligonucleotides of the present disclosure are provided as pharmaceutical compositions. As appreciated by those skilled in the art, oligonucleotides of the present disclosure can be provided in their acid, base or salt forms. In some embodiments, oligonucleotides can be in acid forms, e.g., for natural phosphate linkages, in the form of —OP(O)(OH)O—; for phosphorothioate internucleotidic linkages, in the form of —OP(O)(SH)O—; etc. In some embodiments, MAPT oligonucleotides can be in salt forms, e.g., for natural phosphate linkages, in the form of —OP(O)(ONa)O—in sodium salts; for phosphorothioate internucleotidic linkages, in the form of —OP(O)(SNa)O—in sodium salts; etc. Unless otherwise noted, oligonucleotides of the present disclosure can exist in acid, base and/or salt forms.

In some embodiments, a pharmaceutical composition is a liquid composition. In some embodiments, a pharmaceutical composition is provided by dissolving a solid oligonucleotide composition, or diluting a concentrated oligonucleotide composition, using a suitable solvent, e.g., water or a pharmaceutically acceptable buffer. In some embodiments, liquid compositions comprise anionic forms of provided oligonucleotides and one or more cations. In some embodiments, liquid compositions have pH values in the weak acidic, about neutral, or basic range. In some embodiments, pH of a liquid composition is about a physiological pH, e.g., about 7.4.

In some embodiments, a provided oligonucleotide is formulated for administration to and/or contact with a body cell and/or tissue expressing its target. For example, in some embodiments, a provided MAPT oligonucleotide is formulated for administration to a body cell and/or tissue expressing MAPT. In some embodiments, such a body cell and/or tissue are a neuron or a cell and/or tissue of the central nervous system. In some embodiments, broad distribution of oligonucleotides and compositions may be achieved with intraparenchymal administration, intrathecal administration, or intracerebroventricular administration.

In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide or composition thereof, in admixture with a pharmaceutically acceptable inactive ingredient (e.g., a pharmaceutically acceptable excipient, a pharmaceutically acceptable carrier, etc.). In some embodiments, the present disclosure provides a pharmaceutical composition delivering chirally controlled oligonucleotide or composition thereof, in admixture with a pharmaceutically acceptable inactive ingredient (e.g., a pharmaceutically acceptable excipient, a pharmaceutically acceptable carrier, etc.). One of skill in the art will recognize that the pharmaceutical compositions include pharmaceutically acceptable salts of provided oligonucleotide or compositions. In some embodiments, a pharmaceutical composition is a chirally controlled oligonucleotide composition. In some embodiments, a pharmaceutical composition is a stereopure oligonucleotide composition.

In some embodiments, the present disclosure provides salts of oligonucleotides and pharmaceutical compositions thereof. In some embodiments, a salt is a pharmaceutically acceptable salt. In some embodiments, a pharmaceutical composition comprises an oligonucleotide, optionally in its salt form, and a sodium salt. In some embodiments, a pharmaceutical composition comprises an oligonucleotide, optionally in its salt form, and sodium chloride. In some embodiments, each hydrogen ion of an oligonucleotide that may be donated to a base (e.g., under conditions of an aqueous solution, a pharmaceutical composition, etc.) is replaced by a non-$H^+$ cation. For example, in some embodiments, a pharmaceutically acceptable salt of an oligonucleotide is an all-metal ion salt, wherein each hydrogen ion (for example, of —OH, —SH, etc.) of each internucleotidic linkage (e.g., a natural phosphate linkage, a phosphorothioate internucleotidic linkage, etc.) is replaced by a metal ion. Various suitable metal salts for pharmaceutical compositions are widely known in the art and can be utilized in accordance with the present disclosure. In some embodiments, a pharmaceutically acceptable salt is a sodium salt. In some embodiments, a pharmaceutically acceptable salt is magnesium salt. In some embodiments, a pharmaceutically acceptable salt is a calcium salt. In some embodiments, a pharmaceutically acceptable salt is a potassium salt. In some embodiments, a pharmaceutically acceptable salt is an ammonium salt (cation $N(R)_4^+$). In some embodiments, a pharmaceutically acceptable salt comprises one and no more than one types of cation. In some embodiments, a pharmaceutically acceptable salt comprises two or more types of cation. In some embodiments, a cation is $Li^+$, $Na^+$, $K^+$, $Mg^{2+}$ or $Ca^{2+}$. In some embodiments, a pharmaceutically acceptable salt is an all-sodium salt. In some embodiments, a pharmaceutically acceptable salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate internucleotidic linkage (acid form —O—P(O)(SH)—O—), if any, exists as its sodium salt form (—O—P(O)(SNa)—O—).

Various technologies for delivering nucleic acids and/or oligonucleotides are known in the art can be utilized in accordance with the present disclosure. For example, a variety of supramolecular nanocarriers can be used to deliver nucleic acids. Example nanocarriers include, but are not limited to liposomes, cationic polymer complexes and various polymeric compounds. Complexation of nucleic acids with various polycations is another approach for intracellular delivery; this includes use of PEGylated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly (lactic acid), liquid depot, polymer micelles, quantum dots and lipoplexes. In some embodiments, an oligonucleotide is conjugated to another molecule.

In therapeutic and/or diagnostic applications, compounds, e.g., oligonucleotides, of the disclosure can be formulated for a variety of modes of administration, including systemic and topical or localized administration. Techniques and formulations generally may be found in Remington, The Science and Practice of Pharmacy (20th ed. 2000).

Pharmaceutically acceptable salts for basic moieties are generally well known to those of ordinary skill in the art, and may include, e.g., acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In some embodiments, MAPT oligonucleotides are formulated in pharmaceutical compositions described in WO 2005/060697, WO 2011/076807 or WO 2014/136086.

Depending on the specific conditions, disorders or diseases being treated, provided agents, e.g., oligonucleotides, may be formulated into liquid or solid dosage forms and administered systemically or locally. Provided oligonucleotides may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-stemal, intra-synovial, intra-hepatic, intralesional, intracranial, intraperitoneal, intranasal, or intraocular injections or another mode of delivery.

For injection, provided agents, e.g., oligonucleotides may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulations. Such penetrants are generally known in the art and can be utilized in accordance with the present disclosure.

Use of pharmaceutically acceptable carriers to formulate compounds, e.g., provided oligonucleotides, for the practice of the disclosure into dosages suitable for various mods of administration is well known in the art. With proper choice of carrier and suitable manufacturing practice, compositions of the present disclosure, e.g., those formulated as solutions, may be administered via various routes, e.g., parenterally, such as by intravenous injection.

In some embodiments, a composition comprising a MAPT oligonucleotide further comprises any or all of: calcium chloride dihydrate, magnesium chloride hexahydrate, potassium chloride, sodium chloride, sodium phosphate dibasic anhydrous, sodium phosphate, monobasic dihydrate, and/or water for Injection. In some embodiments, a composition further comprises any or all of: calcium chloride dihydrate (0.21 mg) USP, magnesium chloride hexahydrate (0.16 mg) USP, potassium chloride (0.22 mg) USP, sodium chloride (8.77 mg) USP, sodium phosphate dibasic anhydrous (0.10 mg) USP, sodium phosphate monobasic dihydrate (0.05 m g) USP, and Water for Injection USP.

In some embodiments, a composition comprising an oligonucleotide further comprises any or all of: cholesterol, (6Z,9Z,28Z,31Z)-heptatriaconta-6,9,28,31-tetraen-19-yl-4-(dimethylamino) butanoate(DLin-MC3-DMA), 1,2-distearoyl-sn-glycero-3-phosphocholine (DSPC), alpha-(3'-{[1,2-di(myristyloxy)propanoxy]carbonylamino}propyl)-omega-methoxy, polyoxyethylene(PEG2000-C-DMG), potassium phosphate monobasic anhydrous NF, sodium chloride, sodium phosphate dibasic heptahydrate, and Water for Injection. In some embodiments, the pH of a composition comprising a MAPT oligonucleotide is ~7.0. In some embodiments, a composition comprising an oligonucleotide further comprises any or all of: 6.2 mg cholesterol USP, 13.0 mg (6Z,9Z,28Z,31Z)-heptatriaconta-6,9,28,31-tetraen-19-yl-4-(dimethylamino) butanoate(DLin-MC3-DMA), 3.3 mg 1,2-distearoyl-sn-glycero-3-phosphocholine (DSPC), 1.6 mg a-(3'-{[1,2-di(myristyloxy)propanoxy]carbonylamino} propyl)-o-methoxy, polyoxyethylene(PEG2000-C-DMG), 0.2 mg potassium phosphate monobasic anhydrous NF, 8.8 mg sodium chloride USP, 2.3 mg sodium phosphate dibasic heptahydrate USP, and Water for Injection USP, in an approximately 1 mL total volume.

Provided compounds, e.g., oligonucleotides, can be formulated readily using pharmaceutically acceptable carriers well known in the art into dosages suitable for oral administration. In some embodiments, such carriers enable provided oligonucleotides to be formulated as tablets, pills, capsules, liquids, gels, syrups, slurries, suspensions and the like, for, e.g., oral ingestion by a subject (e.g., patient) to be treated.

For nasal or inhalation delivery, provided compounds, e.g., oligonucleotides, may be formulated by methods known to those of skill in the art, and may include, e.g., examples of solubilizing, diluting, or dispersing substances such as saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions may be achieved with methods of administration described herein and/or known in the art.

In certain embodiments, parenteral administration is by injection, by, e.g., a syringe, a pump, etc. In certain embodiments, an injection is a bolus injection. In certain embodiments, an injection is administered directly to a tissue or location, such as striatum, caudate, cortex, hippocampus and/or cerebellum.

In certain embodiments, methods of specifically localizing provided compounds, e.g., oligonucleotides, such as by bolus injection, may decrease median effective concentration (EC50) by a factor of 20, 25, 30, 35, 40, 45 or 50. In certain embodiments, a targeted tissue is brain tissue. In certain embodiments, a targeted tissue is striatal tissue. In certain embodiments, decreasing EC50 is desirable because it reduces the dose required to achieve a pharmacological result in a patient in need thereof.

In certain embodiments, a provided oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients, e.g., oligonucleotides, are contained in effective amounts to achieve their intended purposes. Determination of the effective amounts is well within the capability of those skilled in the art, especially in light of the detailed disclosure provided herein.

In addition to active ingredients, pharmaceutical compositions may contain suitable pharmaceutically acceptable carriers comprising excipients and auxiliaries which facilitate processing of an active compound into preparations which can be used pharmaceutically. Preparations formulated for oral administration may be in the form of tablets, dragees, capsules, or solutions.

In some embodiments, pharmaceutical compositions for oral use can be obtained by combining an active compound with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

In some embodiments, dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. Push-fit capsules can contain active ingredients, e.g., oligonucleotides, in admixture with fillers such as lactose, binders such as starches, and/or lubricants such as talc or magnesium stearate and, optionally, stabilizers. In soft capsules, active compounds, e.g., oligonucleotides, may be dissolved or suspended in suitable liquids, such as fatty oils, liquid paraffin, or liquid polyethylene glycols (PEGs). In addition, stabilizers may be added.

In some embodiments, a provided composition comprises a lipid. In some embodiments, a lipid is conjugated to an active compound, e.g., an oligonucleotide. In some embodiments, a lipid is not conjugated to an active compound. In some embodiments, a lipid comprises a $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, the lipid is selected from the group consisting of lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl alcohol. In some embodiments, an active compound is a provided oligonucleotide. In some embodiments, a composition comprises a lipid and an an active compound, and further comprises another component which is another lipid or a targeting compound or moiety. In some embodiments, a lipid is an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; a targeting lipid; or another lipid described herein or reported in the art suitable for pharmaceutical uses. In some embodiments, a composition comprises a lipid and a portion of another lipid capable of mediating at least one function of another lipid. In some embodiments, a targeting compound or moiety is capable of targeting a compound (e.g., an oligonucleotide) to a particular cell or tissue or subset of cells or tissues. In some embodiments, a targeting moiety is designed to take advantage of cell- or tissue-specific expression of particular targets, receptors, proteins, or another subcellular component. In some embodiments, a targeting moiety is a ligand (e.g., a small molecule, antibody, peptide, protein, carbohydrate, aptamer, etc.) that targets a composition to a cell or tissue, and/or binds to a target, receptor, protein, or another subcellular component.

Certain example lipids for delivery of an active compound, e.g., an oligonucleotide, allow (e.g., do not prevent or interfere with) the function of an active compound. In some embodiments, a lipid is lauric acid, myristic acid, palmitic acid, stearic acid, oleic acid, linoleic acid, alpha-linolenic acid, gamma-linolenic acid, docosahexaenoic acid (cis-DHA), turbinaric acid or dilinoleyl alcohol.

As described in the present disclosure, lipid conjugation, such as conjugation with fatty acids, may improve one or more properties of oligonucleotides.

In some embodiments, a composition for delivery of an active compound, e.g., an oligonucleotide, is capable of targeting an active compound to particular cells or tissues as desired. In some embodiments, a composition for delivery of an active compound is capable of targeting an active compound to a muscle cell or tissue. In some embodiments, the present disclosure provides compositions and methods related to delivery of active compounds, wherein the compositions comprise an active compound and a lipid. In various embodiments to a muscle cell or tissue, a lipid is selected from lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl alcohol.

In some embodiments, a MAPT oligonucleotide is delivered to the central nervous system, or a cell or tissue or portion thereof, via a delivery method or composition designed for delivery of nucleic acids to the central nervous system, or a cell or tissue or portion thereof.

In some embodiments, a MAPT oligonucleotide is delivered via a composition comprising any one or more of, or a method of delivery involving the use of any one or more of: transferrin receptor-targeted nanoparticle; cationic liposome-based delivery strategy; cationic liposome; polymeric nanoparticle; viral carrier; retrovirus; adeno-associated virus; stable nucleic acid lipid particle; polymer; cell-penetrating peptide; lipid; dendrimer; neutral lipid; cholesterol; lipid-like molecule; fusogenic lipid; hydrophilic molecule; polyethylene glycol (PEG) or a derivative thereof; shielding lipid; PEGylated lipid; PEG-C-DMSO; PEG-C-DMSA; DSPC; ionizable lipid; a guanidinium-based cholesterol derivative; ion-coated nanoparticle; metal-ion coated nanoparticle; manganese ion-coated nanoparticle; angubindin-1; nanogel; incorporation of the MAPT into a branched nucleic acid structure; and/or incorporation of the MAPT into a branched nucleic acid structure comprising 2, 3, 4 or more oligonucleotides.

In some embodiments, a composition comprising an oligonucleotide is lyophilized. In some embodiments, a composition comprising an oligonucleotide is lyophilized, and the lyophilized oligonucleotide is in a vial. In some embodiments, the vial is back filled with nitrogen. In some embodiments, the lyophilized oligonucleotide composition is reconstituted prior to administration. In some embodiments, the lyophilized oligonucleotide composition is reconstituted with a sodium chloride solution prior to administration. In some embodiments, the lyophilized oligonucleotide composition is reconstituted with a 0.9% sodium chloride solution prior to administration. In some embodiments, reconstitution occurs at the clinical site for administration. In some embodiments, in a lyophilized composition, an oligonucleotide composition is chirally controlled or comprises at least one chirally controlled internucleotidic linkage and/or the oligonucleotide targets MAPT.

Among other things, the present disclosure provides the following embodiments:

1. An oligonucleotide, wherein the base sequence of the oligonucleotide comprises at least 15, 16, 17, 18, 19, 20, 21, 22, 23, 24, or 25 contiguous bases of a base sequence that is identical with or complementary to a base sequence of a MAPT gene or a transcript thereof, wherein the oligonucleotide comprises one or more modified sugars, one or more modified nucleobases, and/or one or more modified internucleotidic linkages.
2. The oligonucleotide of Embodiment 1, wherein the base sequence of the oligonucleotide comprises at least 15, 16, 17, 18, 19, 20, 21, 22, 23, 24, or 25 contiguous bases of a base sequence that is complementary to a MAPT transcript.
3. The oligonucleotide of Embodiment 1, wherein the base sequence of the oligonucleotide comprises at least 15, 16, 17, 18, 19, 20, 21, 22, 23, 24, or 25 contiguous bases of a base sequence that is complementary to a MAPT mRNA.
4. The oligonucleotide of Embodiment 1, wherein the base sequence of the oligonucleotide comprises at least 15, 16, 17, 18, 19, 20, 21, 22, 23, 24, or 25 contiguous bases of a base sequence that is complementary to intron 11 of a MAPT RNA.
5. The oligonucleotide of any one of the preceding Embodiments, wherein the base sequence of the oligonucleotide comprises at least 10, 11, 12, 13, 14, 15, 16, 17, 18, 19, or 20 contiguous bases of ACGTTGCAGTGTTCCACUAU (SEQ ID NO: 1), ACTATCCTCCTTCAGCUCCU (SEQ ID NO: 2), AGTGTTCCACTATCCUCCUU (SEQ ID NO: 3), ATCCTCCTTCAGCTCCUGCA (SEQ ID NO: 4), CACGTTGCAGTGTTCCACUA (SEQ ID NO: 5), CACTATCCTCCTTCAGCUCC (SEQ ID NO: 6), CAGTGTTCCACTATCCUCCU (SEQ ID NO: 7), CCACGTTGCAGTGTTCCACU (SEQ ID NO: 8), CCACTATCCTCCTTCAGCUC (SEQ ID NO: 9), CGTTGCAGTGTTCCACUAUC (SEQ ID NO: 10), CTATCCTCCTTCAGCUCCUG (SEQ ID NO: 11), GCAGTGTTCCACTATCCUCC (SEQ ID NO: 12), GTGTTCCACTATCCTCCUUC (SEQ ID NO: 13), GTTCCACTATCCTCCUUCAG (SEQ ID NO: 14), GUGUUCCACTATCCTCCTTC (SEQ ID NO: 15), TATCCTCCTTCAGCTCCUGC (SEQ ID NO: 16), TCCACTATCCTCCTTCAGCU (SEQ ID NO: 17), TGCAGTGTTCCACTAUCCUC (SEQ ID NO: 18), TGTTCCACTATCCTCCUUCA (SEQ ID NO: 19), TTCCACTATCCTCCTUCAGC (SEQ ID NO: 20), or TTGCAGTGTTCCACTAUCCU (SEQ ID NO: 21), wherein each T can be independently substituted with U and vice versa.

6. The oligonucleotide of any one of the preceding Embodiments, wherein the oligonucleotide comprises about 20 nucleobases each independently selected from optionally substituted A, T, C, G, U, and tautomers thereof.
7. The oligonucleotide of any one of the preceding Embodiments, wherein the oligonucleotide comprises a 5'-wing-core-wing-3' moiety, wherein the 5'-wing and the 3'-wing each independently comprises two or more modified sugars.
8. The oligonucleotide of Embodiment 7, wherein the 5'-wing comprises two or more sugars each independently comprising 2'-OR, wherein R is optionally substituted $C_{1-4}$ aliphatic.
9. The oligonucleotide of Embodiment 8, wherein the 5'-wing comprises one or more 2'-MOE modified sugars.
10. The oligonucleotide of any one of Embodiments 7-9, wherein each sugar in the 5'-wing comprises a 2'-modified sugar.
11. The oligonucleotide of any one of Embodiments 7-10, wherein each sugar in the 5'-wing comprises the same modification.
12. The oligonucleotide of any one of Embodiments 7-11, wherein the 5'-wing comprises 4, 5, or 7 nucleosides.
13. The oligonucleotide of any one of Embodiments 7-12, wherein the 5'-wing comprises one or more phosphorothioate internucleotidic linkages.
14. The oligonucleotide of any one of Embodiments 7-13, wherein the 5'-wing comprises one or more non-negatively charged internucleotidic linkages.
15. The oligonucleotide of any one of Embodiments 7-14, wherein the 5'-wing comprises one or more natural phosphate linkages.
16. The oligonucleotide of any one of Embodiments 7-15, wherein the 3'-wing comprises two or more sugars each independently comprising 2'-OR, wherein R is optionally substituted $C_{1-4}$ aliphatic.
17. The oligonucleotide of any one of Embodiments 7-16, wherein the sugar modification pattern of the 5'-wing is different from that of the 3'-wing.
18. The oligonucleotide of any one of Embodiments 7-17, wherein the 3'-wing comprises a sugar modification that is absent from the 5'-wing.
19. The oligonucleotide of any one of Embodiments 7-18, wherein the 3'-wing comprises one or more 2'-OMe modified sugars.
20. The oligonucleotide of any one of Embodiments 7-19, wherein each sugar in the 3'-wing comprises a 2'-modified sugar.
21. The oligonucleotide of any one of Embodiments 7-20, wherein each sugar in the 3'-wing comprises the same modification.
22. The oligonucleotide of any one of Embodiments 7-21, wherein the 3'-wing comprises 4, 5, or 7 nucleosides.
23. The oligonucleotide of any one of Embodiments 7-22, wherein the 3'-wing comprises one or more phosphorothioate internucleotidic linkages.
24. The oligonucleotide of any one of Embodiments 7-23, wherein the 3'-wing comprises one or more non-negatively charged internucleotidic linkages.
25. The oligonucleotide of any one of Embodiments 7-24, wherein the 3'-wing comprises one or more natural phosphate linkages.
26. The oligonucleotide of any one of Embodiments 7-25, wherein each phosphorothioate internucleotidic linkage in a 5'-wing is Sp.
27. The oligonucleotide of any one of Embodiments 7-26, wherein each phosphorothioate internucleotidic linkage in a 3'-wing is Sp.
28. The oligonucleotide of any one of Embodiments 7-27, wherein each non-negatively charged internucleotidic linkage in a 5'-wing is n001.
29. The oligonucleotide of any one of Embodiments 7-28, wherein each non-negatively charged internucleotidic linkage in a 3'-wing is n001.
30. The oligonucleotide of any one of Embodiments 28-29, wherein the n001 is Rp.
31. The oligonucleotide of any one of Embodiments 7-30, wherein the core comprises no 2'-OR sugar modifications, wherein R is optionally substituted $C_{1-4}$ aliphatic.
32. The oligonucleotide of any one of Embodiments 7-31, wherein each sugar in the core is a natural DNA sugar (comprising two 2'-H).
33. The oligonucleotide of any one of Embodiments 7-32, wherein the core comprises about 7, 8, 9, 10, or 11 nucleoside.
34. The oligonucleotide of any one of Embodiments 7-33, wherein each internucleotidic linkage bonded to a nucleoside in the core is independently a phosphorothioate internucleotidic linkage.
35. The oligonucleotide of any one of the preceding Embodiments, wherein the pattern of backbone chiral centers of the oligonucleotide is or comprises [(Rp)n(Sp)m]y, wherein each of n, m, and y is independently 1-25.
36. The oligonucleotide of any one of the preceding Embodiments, wherein the pattern of backbone chiral centers of the oligonucleotide is or comprises (Sp)t[(Rp)n(Sp)m]y, wherein each of t, n, m, and y is independently 1-25.
37. The oligonucleotide of any one of Embodiments 7-36, wherein the pattern of backbone chiral centers of the core is or comprises [(Rp)n(Sp)m]y, wherein each of n, m, and y is independently 1-25.
38. The oligonucleotide of any one of Embodiments 7-37, wherein the pattern of backbone chiral centers of the core is or comprises (Sp)t[(Rp)n(Sp)m]y, wherein each of t, n, m, and y is independently 1-25.

39. The oligonucleotide of any one of Embodiments 35-38, wherein at least one n is 1.

40. The oligonucleotide of any one of Embodiments 35-39, wherein each n is 1.

41. The oligonucleotide of any one of Embodiments 35-40, wherein each m is independently 2-25.

42. The oligonucleotide of any one of Embodiments 35-41, wherein y is 1.

43. The oligonucleotide of any one of Embodiments 35-42, wherein y is 2-5.

44. The oligonucleotide of any one of the preceding Embodiments, wherein the base sequence of the oligonucleotide is about 90%-100% complementary to a base sequence in a MAPT transcript.

45. The oligonucleotide of any one of the preceding Embodiments, wherein the base sequence of the oligonucleotide is ACGTTGCAGTGTTCCACUAU (SEQ ID NO: 1), ACTATCCTCCTTCAGCUCCU (SEQ ID NO: 2), AGTGTTCCACTATCCUCCUU (SEQ ID NO: 3), ATCCTCCTTCAGCTCCUGCA (SEQ ID NO: 4), CACGTTGCAGTGTTCCACUA (SEQ ID NO: 5), CACTATCCTCCTTCAGCUCC (SEQ ID NO: 6), CAGTGTTCCACTATCCUCCU (SEQ ID NO: 7), CCACGTTGCAGTGTTCCACU (SEQ ID NO: 8), CCACTATCCTCCTTCAGCUC (SEQ ID NO: 9), CGTTGCAGTGTTCCACUAUC (SEQ ID NO: 10), CTATCCTCCTTCAGCUCCUG (SEQ ID NO: 11), GCAGTGTTCCACTATCCUCC (SEQ ID NO: 12), GTGTTCCACTATCCTCCUUC (SEQ ID NO: 13), GTTCCACTATCCTCCUUCAG (SEQ ID NO: 14), GUGUUCCACTATCCTCCUUC (SEQ ID NO: 15), TATCCTCCTTCAGCTCCUGC (SEQ ID NO: 16), TCCACTATCCTCCTTCAGCU (SEQ ID NO: 17), TGCAGTGTTCCACTAUCCUC (SEQ ID NO: 18), TGTTCCACTATCCTCCUUCA (SEQ ID NO: 19), TTCCACTATCCTCCTUCAGC (SEQ ID NO: 20), or TTGCAGTGTTCCACTAUCCU (SEQ ID NO: 21), wherein each T can be independently substituted with U and vice versa.

46. The oligonucleotide of any one of the preceding Embodiments, wherein the base sequence of the oligonucleotide is GTGTTCCACTATCCTCCUUC (SEQ ID NO: 13), wherein each T can be independently substituted with U and vice versa.

47. The oligonucleotide of any one of the preceding Embodiments, wherein the base sequence of the oligonucleotide is GTGTTCCACTATCCTCCUUC (SEQ ID NO: 13).

48. An oligonucleotide, wherein the oligonucleotide is WV-26758, WV-26759, WV-29875, WV-29876, WV-29877, WV-29878, WV-29879, WV-29880, WV-29881, WV-29882, WV-29883, WV-29884, WV-29885, WV-29886, WV-29887, WV-29888, WV-30672, WV-30673, WV-30674, WV-30970, WV-30971, WV-30972, WV-30973, WV-30974, WV-30975, WV-30976, WV-30977, WV-30978, WV-30979, WV-30980, WV-30981, WV-30982, WV-30983, WV-30984, WV-30985, WV-30986, WV-30987, WV-30988, WV-30989, WV-30990, WV-30991, WV-30992, WV-30993, WV-30994, WV-30995, WV-30996, WV-30997, WV-30998, WV-30999, WV-31000, WV-31001, WV-31002, WV-31003, WV-31004, WV-31005, WV-31006, WV-31007, WV-31008, WV-31009, WV-31010, WV-31011, WV-31012, WV-31013, WV-31014, WV-31015, WV-31016, WV-31017, WV-31018, WV-31019, WV-31020, WV-31021, WV-31022, WV-31023, WV-31024, WV-31025, WV-31026, WV-31027, WV-31028, WV-31029, WV-31030, WV-31031, WV-31032, WV-31033, WV-31034, WV-31035, WV-31036, WV-31037, WV-31038, WV-31039, WV-31040, WV-31041, WV-31042, WV-31043, WV-31044, WV-31045, WV-31046, WV-31048, WV-31049, WV-31050, WV-31051, WV-31052, WV-32808, WV-32809, WV-32810, WV-32811, WV-32812, WV-32813, WV-32814, WV-32815, WV-32816, WV-32817, WV-32818, WV-32819, WV-32820, WV-32821, WV-32822, WV-32823, WV-32824, WV-32825, WV-32826, WV-32827, WV-33008, WV-33009, WV-33010, WV-33011, WV-33012, WV-33013, WV-33014, WV-33015, WV-33016, WV-33017, WV-33018, WV-33019, WV-33020, WV-33021, WV-33022, WV-33023, WV-33024, WV-33025, WV-33026, WV-33027, WV-33028, WV-33029, WV-33030, WV-33031, WV-33032, WV-33033, WV-33034, WV-33035, WV-33036, WV-33037, WV-33038, WV-33039, WV-33040, WV-33041, WV-33042, WV-33043, WV-33044, WV-33045, WV-33046, WV-33047, WV-33048, WV-33049, WV-33050, WV-33051, WV-33052, WV-33053, WV-33054, WV-33055, WV-33056, WV-33057, WV-33058, WV-33059, WV-33060, WV-33061, WV-33062, WV-33063, WV-33064, WV-33065, WV-33066, WV-33067, WV-33068, WV-33069, WV-33070, WV-33071, WV-33072, WV-33073, WV-33074, WV-33075, WV-33076, WV-33077, WV-33078, WV-33079, WV-33080, WV-33081, WV-33082, WV-33083, WV-33084, WV-33085, WV-33086, WV-33087, WV-33088, WV-33089, WV-33090, WV-36875, WV-36876, WV-36877, WV-37299, WV-37300, WV-37301, WV-37302, WV-37303, WV-37304, or WV-37305.

49. The oligonucleotide of Embodiment 48, wherein the oligonucleotide is WV-29883.

50. The oligonucleotide of Embodiment 48, wherein the oligonucleotide is WV-32823.

51. The oligonucleotide of Embodiment 48, wherein the oligonucleotide is WV-29876.

52. The oligonucleotide of Embodiment 48, wherein the oligonucleotide is WV-32824.

53. The oligonucleotide of Embodiment 48, wherein the oligonucleotide is WV-32826.

54. The oligonucleotide of Embodiment 48, wherein the oligonucleotide is WV-29884.

55. The oligonucleotide of Embodiment 48, wherein the oligonucleotide is WV-29886.

56. The oligonucleotide of Embodiment 48, wherein the oligonucleotide is WV-29877.

57. The oligonucleotide of Embodiment 48, wherein the oligonucleotide is WV-32816.

58. The oligonucleotide of Embodiment 48, wherein the oligonucleotide is WV-32817.

59. The oligonucleotide of Embodiment 48, wherein the oligonucleotide is WV-29878.

60. The oligonucleotide of Embodiment 48, wherein the oligonucleotide is WV-29887.

61. The oligonucleotide of Embodiment 48, wherein the oligonucleotide is WV-32827.

62. The oligonucleotide of Embodiment 48, wherein the oligonucleotide is WV-32825.

63. The oligonucleotide of Embodiment 48, wherein the oligonucleotide is WV-29885.
64. The oligonucleotide of Embodiment 48, wherein the oligonucleotide is WV-29882.
65. The oligonucleotide of any one of Embodiments 48-64, wherein the oligonucleotide is in a salt form.
66. The oligonucleotide of any one of Embodiments 48-64, wherein the oligonucleotide is in a pharmaceutically acceptable salt form.
67. The oligonucleotide of Embodiment 66, wherein the oligonucleotide is in sodium salt form.
68. The oligonucleotide of any one of the preceding Embodiments, wherein the oligonucleotides has a diastereomeric purity of about 60%-100%.
69. The oligonucleotide of any one of the preceding Embodiments, wherein the oligonucleotides has a diastereomeric purity of at least about 60%,
70. The oligonucleotide of any one of the preceding Embodiments, wherein the oligonucleotide is capable of reducing the level, expression and/or activity of a MAPT transcript when administered to a system comprising the MAPT transcript.
71. A pharmaceutical composition, which composition delivers or comprises an oligonucleotide of any one of the preceding Embodiments and a pharmaceutically acceptable carrier.
72. The composition of Embodiment 71, which composition delivers or comprises a pharmaceutically acceptable salt of the oligonucleotide.
73. The composition of any one of Embodiments 71-72, wherein the composition comprises two or more forms of the oligonucleotide.
74. The composition of any one of Embodiments 71-73, wherein the composition is an aqueous composition comprising one or more dissolved pharmaceutically acceptable salt forms of the oligonucleotide.
75. An oligonucleotide composition comprising a plurality of oligonucleotides, wherein oligonucleotides of the plurality share:
 1) a common base sequence, and
 2) the same linkage phosphorus stereochemistry independently at one or more (e.g., about 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more) chiral intemucleotidic linkages ("chirally controlled intemucleotidic linkages");

wherein oligonucleotides of the plurality each independently target MAPT.
76. An oligonucleotide composition comprising a plurality of oligonucleotides, wherein oligonucleotides of the plurality share:
 1) a common base sequence, and
 2) the same linkage phosphorus stereochemistry independently at one or more (e.g., about 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more) chiral intemucleotidic linkages ("chirally controlled intemucleotidic linkages");

wherein the composition is enriched relative to a substantially racemic preparation of oligonucleotides sharing the common base sequence for oligonucleotides of the plurality.
77. A composition comprising oligonucleotides of a particular oligonucleotide type characterized by:
 a) a common base sequence;
 b) a common pattern of backbone linkages;
 c) a common pattern of backbone chiral centers;

wherein oligonucleotides of the plurality comprise at least one internucleotidic linkage comprising a common linkage phosphorus in the Sp configuration;

wherein the composition is enriched, relative to a substantially racemic preparation of oligonucleotides having the same common base sequence, for oligonucleotides of the particular oligonucleotide type; and wherein oligonucleotides of the plurality each independently target MAPT.
78. The composition of any one of Embodiments 75-76, wherein the oligonucleotides are capable of reducing the level, expression and/or activity of a MAPT transcript when administered to a system comprising the MAPT transcript.
79. The composition of any one of Embodiments 75-78, wherein the oligonucleotide hybridizes with a site in a MAPT transcript.
80. The composition of any one of Embodiments 75-79, wherein the oligonucleotide comprises a first wing, a core, and a second wing.
81. The composition of any one of Embodiments 75-80, wherein the pattern of sugar modifications of the first wing differs from the pattern of sugar modifications of the second wing.
82. The composition of any one of Embodiments 75-81, wherein nucleoside units of the core comprise no sugar modifications.
83. The composition of any one of Embodiments 75-82, wherein the oligonucleotide targets MAPT intron 11.
84. The composition of any one of Embodiments 75-82, wherein the oligonucleotide targets MAPT intron 11 and the oligonucleotide has a base sequence comprising at least 10 contiguous bases of the base sequence of: ACGTTGCAGTGTTCCACUAU (SEQ ID NO: 1), ACTATCCTCCTTCAGCUCCU (SEQ ID NO: 2), AGTGTTCCACTATCCUCCUU(SEQ ID NO: 3), ATCCTCCTTCAGCTCCUGCA(SEQ ID NO: 4), CACGTTGCAGTGTTCCACUA (SEQ ID NO: 5), CACTATCCTCCTTCAGCUCC (SEQ ID NO: 6), CAGTGTTCCACTATCCUCCU (SEQ ID NO: 7), CCACGTTGCAGTGTTCCACU (SEQ ID NO: 8), CCACTATCCTCCTTCAGCUC (SEQ ID NO: 9), CGTTGCAGTGTTCCACUAUC (SEQ ID NO: 10), CTATCCTCCTTCAGCUCCUG (SEQ ID NO: 11), GCAGTGTTCCACTATCCUCC (SEQ ID NO: 12), GTGTTCCACTATCCTCCUUC (SEQ ID NO: 13), GTTCCACTATCCTCCUUCAG (SEQ ID NO: 14), GUGUUCCACTATCCTCCTTC (SEQ ID NO: 15), TATCCTCCTTCAGCTCCUGC (SEQ ID NO: 16), TCCACTATCCTCCTTCAGCU (SEQ ID NO: 17), TGCAGTGTTCCACTAUCCUC (SEQ ID NO: 18), TGTTCCACTATCCTCCUUCA (SEQ ID NO: 19), TTCCACTATCCTCCTUCAGC (SEQ ID NO: 20), or TTGCAGTGTTCCACTAUCCU (SEQ ID NO: 21), wherein each T can be independently substituted with U and vice versa.
85. An oligonucleotide composition comprising a plurality of oligonucleotides, wherein oligonucleotides of the plurality share:
 1) a common base sequence, and
 2) the same linkage phosphorus stereochemistry independently at one or more (e.g., about 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more) chiral internucleotidic linkages ("chirally controlled internucleotidic linkages");

wherein each oligonucleotide of the plurality is independently an oligonucleotide of any one of Embodiments 1-67.

86. A composition comprising oligonucleotides of a particular oligonucleotide type characterized by:

a) a common base sequence;

b) a common pattern of backbone linkages;

c) a common pattern of backbone chiral centers;

wherein oligonucleotides of the plurality comprise at least one internucleotidic linkage comprising a common linkage phosphorus in the Sp configuration;

wherein the composition is enriched, relative to a substantially racemic preparation of oligonucleotides having the same common base sequence, for oligonucleotides of the particular oligonucleotide type; and wherein each oligonucleotide of the plurality is independently an oligonucleotide of any one of Embodiments 1-67.

87. The composition of any one of Embodiments 75-86, wherein the oligonucleotides of the plurality share the same linkage phosphorus stereochemistry independently at 5, 6, 7, 8, 9, 10, 11, 12, 13, 14, 15, 16, 17, 18, 19, 20, 21, 22, 23, 24, or 25 or more internucleotidic linkages.

88. The composition of any one of Embodiments 75-76, wherein oligonucleotides of the plurality are oligonucleotides of the same constitution, optionally in one or more salt forms.

89. The composition of any one of Embodiments 75-88, wherein oligonucleotides of the plurality are each independently of the same oligonucleotide or a pharmaceutically acceptable salt thereof.

90. The composition of any one of Embodiments 75-89, wherein oligonucleotides of the plurality are each independently of the same oligonucleotide or a pharmaceutically acceptable salt thereof.

91. The composition of any one of Embodiments 75-90, wherein oligonucleotides of the plurality are one or more pharmaceutically acceptable salts of the same acid-form oligonucleotide.

92. The composition of any one of Embodiments 75-91, wherein oligonucleotides of the plurality are of the same structure.

93. The composition of any one of Embodiments 75-92, wherein oligonucleotides of the plurality are sodium salts.

94. The composition of any one of Embodiments 75-93, wherein oligonucleotides of the plurality share the same linkage phosphorus stereochemistry independently at each phosphorothioate internucleotidic linkage.

95. The composition of any one of Embodiments 75-93, wherein oligonucleotides of the plurality share the same linkage phosphorus stereochemistry independently at each chiral linkage phosphorus 96. The composition of any one of Embodiments 75-86, wherein oligonucleotides of the plurality are each independently an oligonucleotide of Embodiment 48, optionally in a pharmaceutically acceptable salt form.

97. The composition of any one of Embodiments 75-86, wherein oligonucleotides of the plurality are each independently an oligonucleotide of Embodiment 49, optionally in a pharmaceutically acceptable salt form.

98. The composition of any one of Embodiments 75-86, wherein oligonucleotides of the plurality are each independently an oligonucleotide of Embodiment 50, optionally in a pharmaceutically acceptable salt form.

99. The composition of any one of Embodiments 75-86, wherein oligonucleotides of the plurality are each independently an oligonucleotide of Embodiment 51, optionally in a pharmaceutically acceptable salt form.

100. The composition of any one of Embodiments 75-86, wherein oligonucleotides of the plurality are each independently an oligonucleotide of Embodiment 52, optionally in a pharmaceutically acceptable salt form.

101. The composition of any one of Embodiments 75-86, wherein oligonucleotides of the plurality are each independently an oligonucleotide of Embodiment 53, optionally in a pharmaceutically acceptable salt form.

102. The composition of any one of Embodiments 75-86, wherein oligonucleotides of the plurality are each independently an oligonucleotide of Embodiment 54, optionally in a pharmaceutically acceptable salt form.

103. The composition of any one of Embodiments 75-86, wherein oligonucleotides of the plurality are each independently an oligonucleotide of Embodiment 55, optionally in a pharmaceutically acceptable salt form.

104. The composition of any one of Embodiments 75-86, wherein oligonucleotides of the plurality are each independently an oligonucleotide of Embodiment 56, optionally in a pharmaceutically acceptable salt form.

105. The composition of any one of Embodiments 75-86, wherein oligonucleotides of the plurality are each independently an oligonucleotide of Embodiment 57, optionally in a pharmaceutically acceptable salt form.

106. The composition of any one of Embodiments 75-86, wherein oligonucleotides of the plurality are each independently an oligonucleotide of Embodiment 58, optionally in a pharmaceutically acceptable salt form.

107. The composition of any one of Embodiments 75-86, wherein oligonucleotides of the plurality are each independently an oligonucleotide of Embodiment 59, optionally in a pharmaceutically acceptable salt form.

108. The composition of any one of Embodiments 75-86, wherein oligonucleotides of the plurality are each independently an oligonucleotide of Embodiment 60, optionally in a pharmaceutically acceptable salt form.

109. The composition of any one of Embodiments 75-86, wherein oligonucleotides of the plurality are each independently an oligonucleotide of Embodiment 61, optionally in a pharmaceutically acceptable salt form.

110. The composition of any one of Embodiments 75-86, wherein oligonucleotides of the plurality are each independently an oligonucleotide of Embodiment 62, optionally in a pharmaceutically acceptable salt form.

111. The composition of any one of Embodiments 75-86, wherein oligonucleotides of the plurality are each independently an oligonucleotide of Embodiment 63, optionally in a pharmaceutically acceptable salt form.

112. The composition of any one of Embodiments 75-86, wherein oligonucleotides of the plurality are each independently an oligonucleotide of Embodiment 64, optionally in a pharmaceutically acceptable salt form.

113. The composition of any one of Embodiments 75-112, wherein a non-random level of all oligonucleotides in the composition that share the common base sequence are oligonucleotides of the plurality.

114. The composition of any one of Embodiments 75-113, wherein a non-random level of all oligonucleotides in the composition that share the same constitution are oligonucleotides of the plurality.

115. The composition of any one of Embodiments 113-114, wherein the non-random level is about 40%-100%, or about 40%, 50%, 60%, 65%, 70%, 75%, 80%, 85%, 90% or 95%.

116. A pharmaceutical composition comprising or delivering an oligonucleotide of present disclosure or a composition of any one of Embodiments 75-115, and a pharmaceutically acceptable carrier.

117. A method for preparing an oligonucleotide or composition of any one of the preceding Embodiments, comprising utilizing a chiral auxiliary.

118. The method of Embodiment 117, comprising utilizing a phosphoramidite that comprising a chiral auxiliary moiety.

119. The method of any one of Embodiments 117-118, wherein a chiral auxiliary is DPSE.

120. The method of any one of Embodiments 117-119, wherein a chiral auxiliary is PSM.

121. The method of any one of Embodiments 117-120, wherein each chirally controlled intemucleotidic linkage whose linkage phosphorus is bonded to nitrogen is independently prepared using PSM.

122. The method of any one of Embodiments 117-121, wherein each chirally controlled n001 is independently prepared using PSM.

123. The method of any one of Embodiments 117-122, wherein each chirally controlled phosphorothioate intemucleotidic linkage is independently prepared using DPSE.

124. The method of any one of Embodiments 117-118, wherein each chirally controlled intemucleotidic linkage is independently prepared using PSM.

125. A method for reducing a level, function and/or activity of a tau protein, comprising contacting the protein with an oligonucleotide or a composition of any one of the preceding Embodiments.

126. A method for reducing tau intracellular aggregation, comprising contacting the protein with an oligonucleotide or a composition of any one of the preceding Embodiments.

127. A method for reducing tau spreading, comprising contacting the protein with an oligonucleotide or a composition of any one of the preceding Embodiments.

128. A method for reducing tau intracellular aggregation and spreading, comprising contacting the protein with an oligonucleotide or a composition of any one of the preceding Embodiments.

129. A method for reducing a level, function and/or activity of a tau protein in a system, comprising administering to the system an effective amount of an oligonucleotide or composition of any one of the preceding Embodiments.

130. A method for reducing tau intracellular aggregation in a system, comprising administering to the system an effective amount of an oligonucleotide or composition of any one of the preceding Embodiments.

131. A method for reducing tau spreading in a system, comprising administering to the system an effective amount of an oligonucleotide or composition of any one of the preceding Embodiments.

132. A method for reducing tau intracellular aggregation and spreading in a system, comprising administering to the system an effective amount of an oligonucleotide or composition of any one of the preceding Embodiments.

133. The method of any one of Embodiments 129-132, wherein a system is a human.

134. A method for treating or preventing a MAPT-related condition, disorder or disease or a symptom thereof in a subject suffering therefrom or susceptible thereto, comprising administering to the subject a therapeutically effective amount of an oligonucleotide or composition of any one of the preceding Embodiments.

135. A method for treating or preventing a neurodegenerative disease in a subject suffering therefrom or susceptible thereto, comprising administering to the subject a therapeutically effective amount of an oligonucleotide or composition of any one of the preceding Embodiments.

136. A method for treating or preventing a tauopathy in a subject suffering therefrom or susceptible thereto, comprising administering to the subject a therapeutically effective amount of an oligonucleotide or composition of any one of the preceding Embodiments.

137. The method of any one of Embodiments 134-136, wherein the condition, disorder or disease is Alzheimer's Disease (AD).

138. The method of any one of Embodiments 134-136, wherein the condition, disorder or disease is Frontotemporal Dementia (FTD).

139. The method of any one of Embodiments 134-136, wherein the condition, disorder or disease is behavioral variant FTD (bvFTD).

140. The method of any one of Embodiments 134-136, wherein the condition, disorder or disease is non-fluent variant primary progressive aphasia (nfvPPA).

141. The method of any one of Embodiments 134-136, wherein the condition, disorder or disease is Corticobasal Degeneration (CBD).

142. The method of any one of Embodiments 134-136, wherein the condition, disorder or disease is Progressive Supranulcear Palsy (PSP).

143. The method of any one of Embodiments 134-136, wherein the condition, disorder or disease is epilepsy.

144. The method of any one of Embodiments 134-136, wherein the condition, disorder or disease is Dravet syndrome.

145. The method of any one of Embodiments 134-136, wherein the condition, disorder or disease is Chronic Traumatic Encephalopthy (CTE).

EXEMPLIFICATION

Certain examples of provided technologies (compounds (oligonucleotides, reagents, etc.), compositions, methods (methods of preparation, use, assessment, etc.), etc.) were described below.

Example 1. Oligonucleotide Synthesis

Various technologies for preparing oligonucleotides and oligonucleotide compositions (both stereorandom and chirally controlled) are known and can be utilized in accordance with the present disclosure, including, for example, those in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/

032612, and/or WO 2020/191252, the methods and reagents of each of which are incorporated herein by reference.

In some embodiments, oligonucleotides were prepared using suitable chiral auxiliaries, e.g., DPSE and PSM chiral auxiliaries. Various oligonucleotides, e.g., those in Table 1, and compositions thereof, were prepared in accordance with the present disclosure.

For example, in some embodiments, oligonucleotides were prepared utilizing DPSE and PSM chiral auxiliaries for chirally controlled internucleotidic linkages. In some embodiments, DPSE chiral auxiliaries were utilized to construct chirally controlled phosphorothioate internucleotidic linkages. In some embodiments, PSM chiral auxiliaries were utilized to construct chirally controlled non-negatively charged internucleotidic linkages, e.g., n001. In some embodiments, PSM chiral auxiliaries were utilized to prepare multiple or all types of chirally controlled internucleotidic linkages in oligonucleotides (e.g., both chirally controlled phosphorothioate and n001 internucleotidic linkages). Certain uses of DPSE and PSM chiral auxiliaries, including certain phosphoramidites comprising DPSE or PSM chiral auxiliaries useful for chirally controlled oligonucleotide preparations are described below as examples. In some embodiments, natural phosphate linkages (PO) were prepared utilizing standard phosphoramidites. Among other things, technologies of the present disclosure are highly effective for chirally controlled construction of chiral internucleotidic linkages of various types. As demonstrated and confirmed by the WV-29878 preparations as examples, provided technologies can deliver high stereoselectivity, high crude purity and high yield.

As appreciated by those skilled in the art, oligonucleotide preparations often comprise multiple cycles. In some embodiments, the present disclosure provides methods for preparing oligonucleotides and compositions thereof comprising multiple cycles described in. In some embodiments, each cycle, e.g., a cycle utilized for preparing chirally controlled internucleotidic linkages, independently comprises deblocking (e.g., which deblocks a capped hydroxyl group such as detritylation described herein), coupling (e.g., coupling a phosphoramidite comprising a chiral auxiliary with a hydroxyl group such as coupling-i as described herein), a first capping (e.g., utilizing conditions that can cap amino groups in chiral auxiliaries such as Cap-i as described herein), modification (e.g., thiolation, azide reaction, etc. as described herein), and a second capping group (e.g., utilizing conditions that can cap hydroxyl groups such as Cap-2 as described herein). Certain useful technologies, e.g., cycles, steps, conditions, reagents, etc. are as described below as examples.

In some embodiments, chirally controlled oligonucleotide compositions were prepared utilizing DPSE chiral auxiliaries for chirally controlled phosphorothioate (PS) linkages and PSM chiral auxiliaries for chirally controlled PN linkages (in which a nitrogen is bonded to linkage phosphorus, e.g., n001). An example preparation of WV-29878 is described below. In this example, preparation of WV-29878 was conducted on mC-CPG solid support using 2.7×7.0 cm stainless steel column at a scale of 746 mol.

| Abbreviations: | |
|---|---|
| mC-CPG | 2'-OMe-C via CNA linker CPG (600Å LBD) |
| dA-L-DPSE | 5'-O-DMT-dA (Bz)-(L)-DPSE Phosphoramidite |
| dC-L-DPSE | 5'-O-DMT-dC (Ac)-(L)-DPSE Phosphoramidite |
| dC-D-DPSE | 5'-O-DMT-dC (Ac)-(D)-DPSE Phosphoramidite |
| dT-L-DPSE | 5'-O-DMT-dT-(L)-DPSE Phosphoramidite |
| mC-L-DPSE | 5'-O-DMT-2'-OMe-C (Ac)-(L)-DPSE Phosphoramidite |
| mU-L-DPSE | 5'-O-DMT-2'-OMe-U-(L)-DPSE Phosphoramidite |
| Geo-L-DPSE | 5'-O-DMT-2'-O-MOE-G (iBu)-(L)-DPSE Phosphoramidite |
| Teo-L-DPSE | 5'-O-DMT-2'-O-MOE-5-Me-U-(L)-DPSE Phosphoramidite |
| mC-L-PSM | 5'-O-DMT-2'-OMe-C (Ac)-(L)-PSM Phosphoramidite |
| Teo-L-PSM | 5'-O-DMT-2'-O-MOE-5-Me-U-(L)-PSM Phosphoramidite |
| Geo-CE | 5'-O-DMT-2'-O-MOE-G (iBu)-β-Cyanoethyl Phosphoramidite |
| ADIH | 2-Azide-1,3-dimethylimidazolium Hexafluorophosphate |
| Cap A | N-Methylimidazole in Acetonitrile, 20/80, v/v |
| Cap B | Acetic Ahydride/2,6-Lutidine/Acetonitrile, 20/30/50, v/v/v |
| CE | β-Cyanoethyl |
| Conc. $NH_4OH$ | 28-30% Concentrated Ammonium Hydroxide |
| CT | Contact Time |
| CV | Column Volume |
| CMIMT | 1-(Cyanomethyl)-1H-imidazol-3-ium-1-yl Trifluoromethanesulfonate |
| DCA | Dichloroacetic Acid |
| DEA | Diethylamine |
| Deblock | 3% DCA in Toluene |
| DMSO | Dimethylsulfoxide |
| ETT | 5-Ethylthio-1H-tetrazole |
| Filter unit | Filter Device, 0.22 micron filter, CORNING |
| IBN | Isobutyronitrile |
| MeCN | Acetonitrile |
| MS3A | Molecular Sieves, 3Å |
| NLT | No less than |
| NMI | N-methylimidazole |
| Ox | 0.04-0.06M Iodine in pyridine/water, 90/10, v/v |
| TEA | Triethylamine |
| TEA•3HF | Triethylamine Trihydrofluoride |
| XH | Xanthane Hydride |
| WFI | Water for Injection (water) |

Example Synthesis Process Parameters.

| Process Step | Parameter | Set Points |
|---|---|---|
| Synthesis Cycle | DPSE Chiral Amidite | 1. Detritylation<br>2. Coupling-1<br>3. Cap-1<br>4. Modification - Thiolation<br>5. Cap-2 |
| | PSM Chiral Amidite | 1. Detritylation<br>2. Coupling-1<br>3. Cap-1<br>4. Modification - Azide reaction<br>5. Cap-2 |

-continued

| Example Synthesis Process Parameters. | | |
|---|---|---|
| Process Step | Parameter | Set Points |
| | Standard Amidite | 1. Detritylation<br>2. Coupling-2<br>3. Modification - Oxidation<br>4. Cap-2 |
| Column, Scale, Synthesizer | Column | Stainless Steel |
| | Column Diameter | 2.7 cm |
| | Column Bed Height | 7.0 cm |
| | Column Volume | 40.1 mL |
| | Scale | 746 μmol |
| | Synthesizer | AKTA OligoPilot 100 |
| CPG | Solid Support | mC-CPG |
| | Support Loading | 77 μmol/g |
| | Adjusted Support Density | 0.24 g/c.c. |
| Pre-Synthesis Wash | Pre-Synthesis Wash Solvent | MeCN |
| | Pre-Synthesis Wash Flow Rate | 424 cm/h |
| | Pre-Synthesis Wash Volume | 2.0 CV |
| De-blocking (Detritylation) | Reagent | Deblock |
| | Control Mode | UV watch command |
| | Detrit Wavelength | 436 nm |
| | Detrit UV Watch | On: 500 mAu with 1.2 CV delay<br>Off: 1000 mAu |
| | UV Autozero | Autozero on Deblock in bypass prior to the 1$^{st}$ detrit |
| | Detrit Flow Rate | 424 cm/h |
| | Post Detritylation MeCN Wash | 4.0 CV<br>424 cm/h |
| Coupling-1 | Amidite Eq./Support | 2.5 eq. |
| | Concentration and Diluent of Amidite | 0.2M of dA-L-DPSE, dT-L-DPSE, Geo-L-DPSE, Teo-L-DPSE, Teo-L-PSM in 100% MeCN, and 0.2M mC-L-DPSE, mC-L-PSM in IBN-MeCN (20:80), and dC-L-DPSE, dC-D-DPSE, mU-L-DPSE in 100% IBN |
| | Density of the Amidite Solution | Non-adjusted |
| | Drying of Amidite Solution | MS3A, 15-20% w.r.t. Amidite solution, v/v<br>Drying Time = NLT 4 h |
| | Activator | CMIMT |
| | Activator Concentration | 0.5M in MeCN |
| | Activator Eq./Support | 10.20 |
| | Density of Activator Solution | Non-adjusted |
| | Drying of Activator Solution | MS3A, 10%, w.r.t. Activator solution, v/v<br>Drying Time = NLT 4 h |
| | Activator/Amidite Molar Ratio | 4.079:1 |
| | Activator vol % | 62% |
| | Coupling Charge Flow Rate for all Amidites | 58.7 cm/h |
| | Coupling Charge Flow Rate for Activator | 95.7 cm/h |
| | Coupling Charge Volume (Amidite + Activator) | 24.5 mL |
| | Push Volume | 4.5 mL |
| | Recycle Flow Rate | 212 cm/h |
| | Recycle Times | 8 min |
| | MeCN Wash Flow Rate | 424 cm/h |
| | MeCN Wash Volume | 2.0 CV |
| Coupling-2 | Amidite Eq./Support | 2.5 eq. |
| | Concentration and Diluent of Amidite | 0.2M of Geo-CE in 100% |
| | Density of the Amidite Solution | Non-adjusted |
| | Drying of Amidite Solution | MS3A, 15-20% w.r.t. Amidite solution, v/v<br>Drying Time = NLT 4 h |
| | Activator | ETT |
| | Activator Concentration | 0.5M in MeCN |
| | Activator Eq./Support | 7.64 |
| | Density of Activator Solution | Non-adjusted |
| | Drying of Activator Solution | MS3A, 10%, w.r.t. Activator solution, v/v<br>Drying Time = NLT 4 h |
| | Activator/Amidite Molar Ratio | 3.056:1 |
| | Activator Vol % | 55% |
| | Coupling Charge Flow Rate for all Amidites | 58.7 cm/h |
| | Coupling Charge Flow Rate for Activator | 71.7 cm/h |
| | Coupling Charge Volume (Amidite + Activator) | 20.7 mL |
| | Push Volume | 4.5 mL |
| | Recycle Flow Rate | 212 cm/h |

-continued

| Example Synthesis Process Parameters. | | |
|---|---|---|
| Process Step | Parameter | Set Points |
| | Recycle Times | 8 min |
| | Coupling MeCN Wash Flow Rate | 424 cm/h |
| | Coupling MeCN Wash Volume | 2.0 CV |
| Cap 1 | Mode | Flow Through |
| | Reagent | Cap B |
| | Column Volumn (CV) | 2.0 CV |
| | Contact Time (CT) | 4 min |
| | Reagent Charge Flow Rate | 20.0 mL/min |
| | MeCN Push Volume | 1.3 CV |
| | MeCN Push Flow Rate | 20.0 mL/min |
| Modification (Thiolation) | Mode | Flow Through |
| | Reagent | 0.1M XH in pyridine |
| | Density of thiolation reagent | Non-adjusted |
| | Charge Volume | 1.2 CV |
| | Charge Flow Rate | 84.0 cm/h |
| | Contact Time | 6 min |
| | MeCN Push Flow Rate | 84.0 cm/h |
| | MeCN Push Volume | 1.3 CV |
| | Post-thio MeCN Wash Flow Rate (Flow AB) | 424 cm/h |
| | Post-thio MeCN Wash Volume | 1.0 CV |
| Modification (Azide reaction) | Mode | Flow Through |
| | Reagent | 0.3M ADIH in MeCN |
| | Density of Azide Reagent | Non-adjusted |
| | Charge Volume | 1.0 CV |
| | Contact Time | 15 min |
| | Charge Flow Rate | 28.0 cm/h |
| | MeCN Push Flow Rate | 28.0 cm/h |
| | MeCN Push Volume | 1.5 CV |
| Modification (Oxidation) | Mode | Flow Through |
| | Reagent | Ox |
| | Iodine Eq./Solid Support | 3.0 eq. |
| | Contact Time | 2.0 min |
| | Reagent Charge Flow Rate | 234.6 cm/h |
| | MeCN Push Flow Rate | 234.6 cm/h |
| | MeCN Push Volume | 1.3 CV |
| | MeCN Wash Flow rate | 424 cm/h |
| | MeCN Wash Volume | 1.0 CV |
| Cap 2 | Reagent | Cap A<br>Cap B |
| | Mode | Flow Through |
| | Charge Volume | 0.4 CV |
| | Contact Time | 0.8 min |
| | Charge Flow Rate | Cap A Pump A = 105.0 cm/h<br>Cap B Pump B = 105.0 cm/h |
| | MeCN Push Volume AB | 1.3 CV |
| | MeCN Push Flow Rate_AB | MeCN Pump A = 105.0 cm/h<br>MeCN Pump B = 105.0 cm/h |
| | Capping Wash Volume_AB | 1.0 CV |
| | Capping Wash Flow Rate_AB | 424 cm/h |
| Post Synthesis MeCN Wash | MeCN Wash Flow Rate | 424 cm/h |
| | MeCN Wash Flow Volume | 2.0 CV |
| Removal of PSM and CE groups | Reagent | 20% DEA in MeCN |
| | Delivery Mode | Flow Through |
| | Charge Volume | 5.0 CV |
| | Contact Time | 15 min |
| | Charge Flow Rate | 140 cm/h |
| | Charge MeCN Push Flow Rate | 140 cm/h |
| | Charge MeCN Push Volume | 1.3 CV |
| | MeCN Wash Flow Rate | 424 cm/h |
| | MeCN Wash Volume | 3.0 CV |

In some embodiments, chiral auxiliaries such as PSM (whose amino groups can be capped, e.g., by —C(O)R), and/or CE groups are removed by contacting oligonucleotides comprising such moieties with a base in an organic solvent (e.g., 20% o DEA in MeCN). In some embodiments, chiral auxiliaries such as PSM (whose amino groups can be capped, e.g., by —C(O)R) in internucleotidic linkages whose linkage phosphorus is bonded to nitrogen (e.g., a precursor of n001) are removed before such internucleotidic linkages are contacted with water.

In a preparation, cleavage and deprotection (C & D) was conducted at a scale of 746 µmol. Certain useful cleavage & deprotection process parameters are presented below (cleavage of PSM and CE phosphorous protecting group is described above):

| Example recipe for preparation of a DS1 solution (1 L) | |
|---|---|
| Solvent/Reagents | Volume (mL) |
| DMSO | 733 ± 36.7 |
| WFI | 147 ± 7.4 |
| TEA | 70 ± 3.5 |
| TEA•3HF | 50 ± 2.5 |

Example cleavage and deprotection parameters

| Process Step | Parameter | Set Points |
|---|---|---|
| Removal of DPSE group | Reaction Vessel | Appropriate for TEA-HF/ Ammonium Hydroxide solution |
| | Scale | 746 µmol |
| | Reagent | DS1 |
| | Volume | 100 ± 5 mL/mmol |
| | Reaction Temp | 28 ± 2.5° C. |
| | Incubator shaker rpm | 180 ± 10 rpm |
| | Reaction Time | 3 ± 0.5 hrs |
| Removal of Residual Protecting group | Reaction Vessel | Appropriate for TEA-HF/ Ammonium Hydroxide solution |
| | Reagent | Conc. $NH_4OH$ |
| | Reagent Volume | 200 ± 5 mL/mmol |
| | Reaction Time | 16 ± 1 hrs |
| | Reaction Temperature | 45 ± 2° C. |
| | Cooling to room temp prior to filtration | <25° C. |
| Filtration | Initial Crude Filtration Device | Filter unit |
| | Filtration Mode | Under vacuum |
| | Support Wash Solvent | WFI |
| | Support Wash Volume | 250-350 mL/mmol |

In a preparation, UPLC analysis of crude oligonucleotide composition showed a purity of full length product (SM FLP) of 69.1 in a crude sample before de-salting. Crude yield was estimated as 74 OD units/umol. Net FLP yield was 51 OD/umol (1.90 mg/umol). In some embodiments, crude storage condition was 2-8 PC; other suitable storage conditions may also be utilized. Molecular mass ofthe WV-29878 was confirmed by LC-MS (calculated 6988.8; observed 6987.0).

In some embodiments, chirally controlled oligonucleotide compositions were prepared utilizing PSM chiral auxiliaries for both chirally controlled PS and PN (e.g., n001) internucleotidic linkages. In some embodiments, such technologies can deliver high selectivity, high crude purity, high yield, and/or simplified/alternative manufacturing processes (e.g., no use of F sources to remove chiral auxiliaries such PSM), etc. In some embodiments, technologies of the present disclosure facilitate purification and/or formulation processes by delivering crude compositions with high purity, high stereoselectivity and/or low amount of salts.

An example preparation of WV-29878 utilizing PSM chiral auxiliaries is described below. In this example, preparation of WV-29878 was conducted on mC-CPG solid support using 2.7×7.0 cm stainless steel column at a scale of 743 µmol.

| Abbreviations: | |
|---|---|
| mC-CPG | 2'-OMe-C via CNA linker CPG (600Å LBD) |
| dA-L-PSM | 5'-O-DMT-dA (Bz)-(L)-PSM Phosphoramidite |
| dC-L-PSM | 5'-O-DMT-dC (Ac)-(L)-PSM Phosphoramidite |
| dC-D-PSM | 5'-O-DMT-dC (Ac)-(D)-PSM Phosphoramidite |
| dT-L-PSM | 5'-O-DMT-dT-(L)-PSM Phosphoramidite |
| mC-L-PSM | 5'-O-DMT-2'-OMe-C (Ac)-(L)-PSM Phosphoramidite |
| mU-L-PSM | 5'-O-DMT-2'-OMe-U-(L)-PSM Phosphoramidite |
| Geo-L-PSM | 5'-O-DMT-2'-O-MOE-G (iBu)-(L)-PSM Phosphoramidite |
| Teo-L-PSM | 5'-O-DMT-2'-O-MOE-5-Me-U-(L)-PSM Phosphoramidite |
| Geo-CE | 5'-O-DMT-2'-O-MOE-G (iBu)-β-Cyanoethyl Phosphoramidite |
| ADIH | 2-Azide-1,3-dimethylimidazolium Hexafluorophosphate |
| Cap A | N-Methylimidazole in Acetonitrile, 20/80, v/v |
| Cap B | Acetic Ahydride/2,6-Lutidine/Acetonitrile, 20/30/50, v/v/v |
| Conc. $NH_4OH$ | 28-30% Concentrated Ammonium Hydroxide |
| CT | Contact Time |
| CV | Column Volume |
| CMIMT | 1-(Cyanomethyl)-1H-imidazol-3-ium-1-yl Trifluoromethanesulfonate |
| DCA | Dichloroacetic Acid |
| DEA | Diethylamine |
| Deblock | 3% DCA in Toluene |
| Filter unit | Filter Device, 0.22 micron filter, CORNING |
| IBN | Isobutyronitrile |
| MeCN | Acetonitrile |
| MS3A | Molecular Sieves, 3Å |
| NLT | No less than |
| NMI | N-methylimidazole |
| Ox | 0.04-0.06M Iodine in pyridine/water, 90/10, v/v |
| TEA | Triethylamine |
| XH | Xanthane Hydride |
| WFI | Water for Injection (water) |

Certain cycles, steps, reactions, reagents, conditions, etc. are described below as examples.

Example Synthesis Process Parameters.

| Process Step | Parameter | Set Points |
|---|---|---|
| Synthesis Cycle | From $1^{st}$ to $6^{th}$ couplings | 1. Detritylation<br>2. Coupling-1<br>3. Cap-1<br>4. Coupling-1<br>5. Cap-1<br>6. Modification - Thiolation or Azide reaction<br>7. Cap-2 |
| | From $7^{th}$ to $19^{th}$, except for $17^{th}$ couplings | 1. Detritylation<br>2. Coupling-2<br>3. Cap-1<br>4. Modification - Thiolation or Azide reaction<br>5. Cap-2 |

-continued

| Example Synthesis Process Parameters. | | |
|---|---|---|
| Process Step | Parameter | Set Points |
| | $17^{th}$ coupling | 1. Detritylation<br>2. Coupling-2<br>3. Modification - Oxidation<br>4. Cap-2 |
| Column, Scale, Synthesizer | Column | Stainless Steel |
| | Column Diameter | 2.7 cm |
| | Column Bed Height | 7.0 cm |
| | Column Volume | 40.1 mL |
| | Scale | 743 μmol |
| | Synthesizer | AKTA OligoPilot 100 |
| CPG | Solid Support | mC-CPG |
| | Support Loading | 77 μmol/g |
| | Adjusted Support Density | 0.24 g/c.c. |
| Pre-Synthesis Wash | Pre-Synthesis Wash Solvent | MeCN |
| | Pre-Synthesis Wash Flow Rate | 424 cm/h |
| | Pre-Synthesis Wash Volume | 2.0 CV |
| De-blocking (Detritylation) | Reagent | Deblock |
| | Control Mode | UV watch command |
| | Detrit Wavelength | 436 nm |
| | Detrit UV Watch | On: 500 mAu with 1.2 CV delay<br>Off: 1000 mAu |
| | UV Autozero | Autozero on Deblock in bypass prior to the $1^{st}$ detrit |
| | Detrit Flow Rate | 424 cm/h |
| | Post Detritylation MeCN Wash | 4.0 CV<br>424 cm/h |
| Coupling-1 | Amidite Eq./Support | 2.5 eq. |
| | Concentration and Diluent of Amidite | 0.2M of dT-L-PSM in 100% MeCN, and 0.2M dC-L-PSM, dC-D-PSM, mC-L-PSM, mU-L-PSM in IBN-MeCN (20:80) |
| | Density of the Amidite Solution | Non-adjusted |
| | Drying of Amidite Solution | MS3A, 15-20% w.r.t. Amidite solution, v/v<br>Drying time = NLT 4 h |
| | Activator | CMIMT |
| | Activator Concentration | 0.5M in MeCN |
| | Activator Eq./Support | 10.20 |
| | Density of Activator Solution | Non-adjusted |
| | Drying of Activator Solution | MS3A, 10%, w.r.t. Activator solution, v/v<br>Drying time = NLT 4 h |
| | Activator/Amidite Molar Ratio | 4.079:1 |
| | Activator Vol % | 62% |
| | Coupling Charge Flow Rate for all Amidites | 58.4 cm/h |
| | Coupling Charge Flow Rate for Activator | 95.3 cm/h |
| | Coupling Charge Volume (Amidite + Activator) | 24.5 mL |
| | Push Volume | 4.5 mL |
| | Recycle Flow Rate | 212 cm/h |
| | Recycle Times | 16 min |
| | MeCN Wash Flow Rate | 424 cm/h |
| | MeCN Wash Volume | 2.0 CV |
| Coupling-2 | Amidite Eq./Support | 2.5 eq. |
| | Concentration and Diluent of Amidite | 0.2M of dA-L-PSM, dT-L-PSM, Geo-L-PSM, Teo-L-PSM, Geo-CE in 100% MeCN, and 0.2M dC-L-PSM, dC-D-PSM in IBN-MeCN (20:80) |
| | Density of the Amidite Solution | Non-adjusted |
| | Drying of Amidite Solution | MS3A, 15-20% w.r.t. Amidite solution, v/v<br>Drying time = NLT 4 h |
| | Activator | CMIMT |
| | Activator Concentration | 0.5M in MeCN |
| | Activator Eq./Support | 10.20 |
| | Density of Activator Solution | Non-adjusted |
| | Drying of Activator Solution | MS3A, 10%, w.r.t. Activator solution, v/v<br>Drying time = NLT 4 h |
| | Activator/Amidite Molar Ratio | 4.079:1 |
| | Activator Vol % | 62% |
| | Coupling Charge Flow Rate for all Amidites | 58.4 cm/h |
| | Coupling Charge Flow Rate for Activator | 95.3 cm/h |
| | Coupling Charge Volume (Amidite + Activator) | 24.5 mL |
| | Push Volume | 4.5 mL |
| | Recycle Flow Rate | 212 cm/h |
| | Recycle Times | 8 min |

-continued

| Example Synthesis Process Parameters. | | |
|---|---|---|
| Process Step | Parameter | Set Points |
| | MeCN Wash Flow Rate | 424 cm/h |
| | MeCN Wash Volume | 2.0 CV |
| Cap 1 | Mode | Flow Through |
| | Reagent | Cap B |
| | Column Volumn (CV) | 0.1 CV |
| | Contact Time (CT) | 0.5 min |
| | Reagent Charge Flow Rate | 4 mL/min |
| | MeCN Push Volume | 1.3 CV |
| | MeCN Push Flow Rate | 4 mL/min |
| Modification (Thiolation) | Mode | Flow Through |
| | Reagent | 0.1M XH in pyridine |
| | Density of thiolation reagent | Non-adjusted |
| | Charge Volume | 0.6 CV |
| | Charge Flow Rate | 84.0 cm/h |
| | Contact Time | 3 min |
| | MeCN Push Flow Rate | 84.0 cm/h |
| | MeCN Push Volume | 1.3 CV |
| | Post-thio MeCN Wash Flow Rate (Flow AB) | 424 cm/h |
| | Post-thio MeCN Wash Volume | 1.0 CV |
| Modification (Azide reaction) | Mode | Flow Through |
| | Reagent | 0.3M ADIH in MeCN |
| | Density of Azide Reagent | Non-adjusted |
| | Charge Volume | 1.0 CV |
| | Contact Time | 15 min |
| | Charge Flow Rate | 28.0 cm/h |
| | MeCN Push Flow Rate | 28.0 cm/h |
| | MeCN Push Volume | 1.5 CV |
| Modification (Oxidation) | Mode | Flow Through |
| | Reagent | Ox |
| | Iodine Eq./Solid Support | 3.0 eq. |
| | Contact Time | 2.0 min |
| | Reagent Charge Flow Rate | 233.6 cm/h |
| | MeCN Push Flow Rate | 233.6 cm/h |
| | MeCN Push Volume | 1.3 CV |
| | MeCN Wash Flow rate | 424 cm/h |
| | MeCN Wash Volume | 1.0 CV |
| Cap 2 | Reagent | Cap A<br>Cap B |
| | Mode | Flow Through |
| | Charge Volume | 0.4 CV |
| | Contact Time | 0.8 min |
| | Charge Flow Rate | Cap A Pump A = 105.0 cm/h<br>Cap B Pump B = 105.0 cm/h |
| | MeCN Push Volume_AB | 1.3 CV |
| | MeCN Push Flow Rate_AB | MeCN Pump A = 105.0 cm/h<br>MeCN Pump B = 105.0 cm/h |
| | Capping Wash Volume_AB | 1.0 CV |
| | Capping Wash Flow Rate_AB | 424 cm/h |
| Post Synthesis MeCN Wash | MeCN Wash Flow Rate | 424 cm/h |
| | MeCN Wash Flow Volume | 2.0 CV |
| Removal of Phosphorous protecting group | Reagent | 20% DEA in MeCN |
| | Delivery Mode | Flow Through |
| | Charge Volume | 5.0 CV |
| | Contact Time | 15 min |
| | Charge Flow Rate | 140 cm/h |
| | Charge MeCN Push Flow Rate | 140 cm/h |
| | Charge MeCN Push Volume | 1.3 CV |
| | MeCN Wash Flowrate | 424 cm/h |
| | MeCN Wash Volume | 3.0 CV |

Cleavage and deprotection (C & D) was conducted at a scale of 743 μmol. Certain useful cleavage & deprotection process parameters are presented below (cleavage of phosphorous protecting group, e.g., chiral auxiliaries such as PSM (e.g., capped at amino groups by —C(O)R such as acetyl), CE, etc., is described above):

| Process Step | Parameter | Set Points |
|---|---|---|
| Cleavage & Deprotection | Reaction Vessel | Pressure rated reactor |
| | Scale | 743 μmol |
| | Reagent | Cold conc. $NH_4OH$ |
| | Reagent Volume | 200 ± 10 mL/mmol |
| | Reaction Time | 16.0 ± 1.0 h |
| | Incubator shaker rpm | 180 ± 10 rpm |
| | Reaction Temperature | 45.0 ± 2.0° C. |
| | Cooling to room temp prior to filtration | <25° C. |
| | Initial Crude Filtration Device | Filter unit |
| | Filtration Mode | Under Vacuum |
| | Support Wash Solvent | WFI |
| | Support Wash Volume | 250-350 mL/mmol |

UPLC analysis of crude oligonucleotide showed the purity of full length product (% FLP) was 63.9% in the crude sample before de-salting. Crude yield was estimated as 85 OD units/umol. Net FLP yield was 54 OD/umol (2.01 mg/umol). Crude storage condition was 2-8° C.; other suitable storage conditions may also be utilized. Molecular mass of the WV-29878 was confirmed by LC-MS (calculated 6988.8; observed 6987.1).

Example 2. Provided Oligonucleotides and Compositions can Effectively Knockdown MAPT Various MAPT oligonucleotides and compositions were designed, constructed, characterized and assessed. As appreciated by those skilled in the art, various technologies can be utilized to assess properties and/or activities of provided oligonucleotides and compositions thereof. Some of such technologies are described in this Example. Those skilled in the art appreciate that many other technologies can be readily utilized in accordance with the present disclosure. As demonstrated herein, MAPT oligonucleotides and compositions, among other things, can be highly active, e.g., in reducing levels of their target nucleic acids and proteins encoded thereby.

In some embodiments, various MAPT oligonucleotides were assessed in an iCell Neuron model. In one set of assessment, for determination of MAPT oligonucleotide activity, different concentrations of oligonucleotides were delivered to iCell Neurons (FUJIFILM Cellular Dynamics) plated on Matrigel* (Corning, Corning, NY, USA) coated 384-well plates using the Agilent Bravo liquid handling platform (Agilent). 24 hours after plating, media was replaced with fresh media containing oligonucleotide at a fixed concentration and cells were allowed to incubate with oligonucleotide for 5 days under gymnotic (free uptake) conditions. On day 5 after treatment, cells were lysed and mRNA was quantified using a QuantiGene™ Singleplex branched DNA assay (Thermo Fisher). In some experiments, a control oligonucleotide which does not target MAPT was used (e.g., WV-12891, as shown in Table % A).

Human MAPT mRNA was quantified and levels were normalized using human tubulin. mRNA knockdown levels were calculated as mRNA remaining (at 1 uM oligonucleotide treatment) relative to non-targeting control (e.g., WV-12891 as shown in Table ) treatment and IC50 values can be determined by four parameter curve fitting of oligonucleotide concentration vs. 00 mRNA remaining.

Table 2A shows 00mRNA remaining relative to non-targeting control (e.g., WV-12891) treatment; Table 2B shows IC50 values (e.g., determined by four parameter curve fitting of oligonucleotide concentration vs. 0% mRNA remaining).

TABLE 2A

Activity of certain oligonucleotides/compositions. This Table shows % mRNA remaining (at 1 uM oligonucleotide treatment) relative to non-targeting control (e.g., WV-12891) treatment.

| ID | % MAPT remaining (1 uM) | SD | n |
|---|---|---|---|
| WV-30673 | 18.3 | 2.9 | 4 |
| WV-30970 | 90.85 | 6.96 | 4 |
| WV-30971 | 83.35 | 2.36 | 4 |
| WV-30972 | 71.83 | 4.87 | 4 |
| WV-30973 | 77.41 | 5.33 | 4 |
| WV-30974 | 109.55 | 2.46 | 4 |
| WV-30975 | 92.25 | 15.34 | 4 |
| WV-30976 | 93.11 | 14.2 | 4 |
| WV-30977 | 89.31 | 4.88 | 4 |
| WV-30978 | 95.91 | 1.7 | 3 |
| WV-30979 | 107.72 | 18.66 | 4 |
| WV-30980 | 86.12 | 11.36 | 4 |
| WV-30981 | 113.03 | 6.19 | 4 |
| WV-30982 | 82.32 | 9.17 | 4 |
| WV-30983 | 95.54 | 8.46 | 4 |
| WV-30984 | 90.35 | 7.23 | 4 |
| WV-30985 | 91.71 | 19.8 | 4 |
| WV-30986 | 109.4 | 11.11 | 4 |
| WV-30987 | 118.49 | 9.3 | 4 |
| WV-30988 | 105.79 | 11.46 | 4 |
| WV-30989 | 100.67 | 5.44 | 4 |
| WV-30990 | 81.49 | 3.99 | 4 |
| WV-30991 | 82.77 | 0.24 | 3 |
| WV-30992 | 81.88 | 5.17 | 3 |
| WV-30993 | 85.28 | 5.52 | 4 |
| WV-30994 | 75.57 | 3.01 | 3 |
| WV-30995 | 73.55 | 6.85 | 4 |
| WV-30996 | 60.96 | 3.68 | 4 |
| WV-30997 | 52.84 | 3.68 | 4 |
| WV-30998 | 66.44 | 0.4 | 3 |
| WV-30999 | 92.51 | 5.58 | 3 |
| WV-31000 | 54.77 | 2.07 | 3 |
| WV-31001 | 79.84 | 3.9 | 4 |
| WV-31002 | 61.37 | 1.41 | 3 |
| WV-31003 | 79.16 | 2.56 | 3 |
| WV-31004 | 41.93 | 1.06 | 3 |
| WV-31005 | 58.25 | 6.04 | 4 |
| WV-31006 | 48.35 | 3.23 | 4 |
| WV-31007 | 57.71 | 4.88 | 4 |
| WV-31008 | 33.63 | 2.05 | 4 |
| WV-31009 | 35.21 | 7.98 | 4 |
| WV-31010 | 27.09 | 5.21 | 4 |
| WV-31011 | 60.96 | 9.46 | 4 |
| WV-31012 | 28.89 | 2.38 | 4 |
| WV-31013 | 89.17 | 0.91 | 3 |
| WV-31014 | 36.41 | 3.02 | 3 |
| WV-31015 | 47.85 | 10.51 | 4 |
| WV-31016 | 33.88 | 7.87 | 4 |
| WV-31017 | 30.16 | 0.33 | 3 |
| WV-31018 | 37.25 | 3.18 | 4 |
| WV-31019 | 27.78 | 1.32 | 4 |
| WV-31020 | 32.37 | 1.7 | 4 |
| WV-31021 | 36.42 | 4.74 | 4 |
| WV-31022 | 41.74 | 1.37 | 3 |
| WV-31023 | 34.88 | 1.27 | 3 |
| WV-31024 | 32.69 | 3.05 | 4 |
| WV-31025 | 48.32 | 1.13 | 4 |
| WV-31026 | 41.51 | 4.03 | 4 |
| WV-31027 | 27.14 | 0.39 | 3 |
| WV-31028 | 37.56 | 2.51 | 4 |
| WV-31029 | 82.9 | 4.07 | 3 |

TABLE 2A-continued

Activity of certain oligonucleotides/compositions. This Table shows % mRNA remaining (at 1 uM oligonucleotide treatment) relative to non-targeting control (e.g., WV-12891) treatment.

| ID | % MAPT remaining (1 uM) | SD | n |
|---|---|---|---|
| WV-31030 | 33.38 | 0.68 | 4 |
| WV-31031 | 58.43 | 1.4 | 4 |
| WV-31032 | 30.75 | 8.5 | 4 |
| WV-31033 | 29.84 | 5.26 | 4 |
| WV-31034 | 41.98 | 0.81 | 3 |
| WV-31035 | 26.89 | 2.52 | 4 |
| WV-31036 | 28.97 | 1.38 | 4 |
| WV-31037 | 56.75 | 6.18 | 4 |
| WV-31038 | 93.86 | 3.15 | 4 |
| WV-31039 | 51.19 | 0.93 | 3 |
| WV-31040 | 64.52 | 12.97 | 4 |
| WV-31041 | 87.04 | 7.68 | 4 |
| WV-31042 | 59.22 | 1.77 | 4 |
| WV-31043 | 57.13 | 2.31 | 4 |
| WV-31044 | 40.3 | 1.81 | 4 |
| WV-31045 | 91.84 | 2.17 | 4 |
| WV-31046 | 66.42 | 0.71 | 3 |
| WV-31048 | 50.57 | 13.61 | 4 |
| WV-31049 | 49.42 | 5.05 | 4 |
| WV-31050 | 52.95 | 2.73 | 4 |
| WV-31051 | 52.96 | 2.29 | 4 |
| WV-31052 | 55.26 | 0.43 | 3 |
| WV-33008 | 64.6 | 3.48 | 3 |
| WV-33009 | 71.61 | 1.49 | 3 |
| WV-33011 | 45.54 | 6.09 | 4 |
| WV-33012 | 83.5 | 11.62 | 4 |
| WV-33013 | 59.65 | 7.58 | 4 |
| WV-33014 | 68.75 | 9.32 | 4 |
| WV-33015 | 59.45 | 16.54 | 4 |
| WV-33016 | 60.75 | 3.52 | 4 |
| WV-33017 | 87.45 | 7.8 | 4 |
| WV-33018 | 53.61 | 10.56 | 4 |
| WV-33019 | 92.34 | 14.86 | 4 |
| WV-33020 | 54.32 | 20.35 | 4 |
| WV-33021 | 102.03 | 12.51 | 4 |
| WV-33022 | 64.06 | 6.26 | 4 |
| WV-33023 | 102.51 | 3.29 | 3 |
| WV-33024 | 90.38 | 9.69 | 4 |
| WV-33025 | 94.92 | 3.54 | 4 |
| WV-33026 | 91.73 | 5.2 | 4 |
| WV-33027 | 68.1 | 4.41 | 4 |
| WV-33028 | 63.71 | 6.08 | 4 |
| WV-33029 | 66.47 | 4.25 | 4 |
| WV-33030 | 64.15 | 8.94 | 4 |
| WV-33031 | 49.57 | 2.86 | 3 |
| WV-33032 | 54.28 | 0.81 | 3 |
| WV-33033 | 30 | 0.42 | 3 |
| WV-33034 | 30.22 | 1.59 | 4 |
| WV-33035 | 44.55 | 7.68 | 4 |
| WV-33036 | 72.35 | 6.24 | 4 |
| WV-33037 | 17.34 | 4.72 | 4 |
| WV-33038 | 40.09 | 2.95 | 4 |
| WV-33039 | 23.34 | 0.17 | 3 |
| WV-33040 | 33.44 | 7.46 | 4 |
| WV-33041 | 9.97 | 2.03 | 4 |
| WV-33042 | 16.54 | 0.22 | 3 |
| WV-33043 | 26.66 | 2.71 | 4 |
| WV-33044 | 30.72 | 1.06 | 3 |
| WV-33045 | 15.09 | 1.35 | 4 |
| WV-33046 | 15.8 | 2.53 | 4 |
| WV-33047 | 11.97 | 1.85 | 4 |
| WV-33048 | 42.65 | 2.07 | 4 |
| WV-33049 | 10.8 | 0.47 | 4 |
| WV-33050 | 3.12 | 0.2 | 8 |
| WV-33051 | 71.88 | 4.25 | 4 |
| WV-33052 | 16.85 | 1.85 | 4 |
| WV-33053 | 31.19 | 3.99 | 4 |
| WV-33054 | 23 | 4 | 4 |
| WV-33056 | 17.83 | 2.17 | 4 |
| WV-33057 | 9.42 | 1.81 | 4 |
| WV-33058 | 11.6 | 1.5 | 4 |

TABLE 2A-continued

Activity of certain oligonucleotides/compositions. This Table shows % mRNA remaining (at 1 uM oligonucleotide treatment) relative to non-targeting control (e.g., WV-12891) treatment.

| ID | % MAPT remaining (1 uM) | SD | n |
|---|---|---|---|
| WV-33059 | 5.33 | 1.12 | 4 |
| WV-33060 | 6.54 | 1.19 | 4 |
| WV-33061 | 4.15 | 0.4 | 4 |
| WV-33062 | 4.89 | 0.04 | 3 |
| WV-33063 | 18.53 | 0.31 | 3 |
| WV-33064 | 12.24 | 1.3 | 4 |
| WV-33065 | 6.38 | 0.53 | 4 |
| WV-33066 | 7.34 | 0.66 | 4 |
| WV-33067 | 61.03 | 5.05 | 4 |
| WV-33068 | 10.4 | 2.46 | 4 |
| WV-33069 | 26.69 | 2.91 | 4 |
| WV-33070 | 8.48 | 1.08 | 4 |
| WV-33071 | 4.86 | 0.37 | 4 |
| WV-33072 | 7.72 | 1.2 | 4 |
| WV-33073 | 3.52 | 0.33 | 4 |
| WV-33074 | 5.98 | 0.73 | 4 |
| WV-33075 | 37.71 | 5.09 | 4 |
| WV-33076 | 83.19 | 9.84 | 4 |
| WV-33077 | 12.14 | 0.66 | 4 |
| WV-33078 | 42.53 | 5.68 | 4 |
| WV-33079 | 68.09 | 8.54 | 4 |
| WV-33080 | 34.18 | 2.68 | 4 |
| WV-33081 | 26.45 | 4.3 | 4 |
| WV-33082 | 17.63 | 2.2 | 4 |
| WV-33083 | 89.29 | 2.7 | 4 |
| WV-33084 | 41.48 | 1.32 | 3 |
| WV-33085 | 34.5 | 4.27 | 4 |
| WV-33086 | 30.8 | 4.38 | 4 |
| WV-33087 | 14.73 | 1.12 | 4 |
| WV-33088 | 18.25 | 2.37 | 4 |
| WV-33089 | 12.27 | 1.16 | 4 |
| WV-33090 | 20.49 | 3.7 | 4 |
| WV-37497 | 39.77 | 1.80 | 4 |
| WV-37498 | 7.11 | 2.33 | 4 |
| WV-37499 | 12.91 | 1.96 | 4 |
| WV-37500 | 9.71 | 1.70 | 4 |
| WV-37501 | 8.82 | 3.11 | 4 |
| WV-37502 | 11.53 | 2.74 | 4 |
| WV-37503 | 9.28 | 2.78 | 4 |
| WV-37504 | 75.28 | 10.15 | 4 |
| WV-37505 | 23.69 | 0.69 | 3 |
| WV-37506 | 33.27 | 5.21 | 4 |
| WV-37507 | 12.05 | 1.61 | 4 |
| WV-37508 | 14.43 | 1.24 | 4 |
| WV-37509 | 18.90 | 2.36 | 4 |
| WV-37510 | 24.24 | 1.30 | 3 |
| WV-37511 | 44.05 | 1.05 | 3 |
| WV-37512 | 6.64 | 1.83 | 4 |
| WV-37513 | 11.26 | 1.18 | 4 |
| WV-37514 | 9.79 | 0.90 | 4 |
| WV-37515 | 7.59 | 1.87 | 4 |
| WV-37516 | 8.27 | 0.68 | 4 |
| WV-37517 | 7.86 | 0.88 | 4 |
| WV-37518 | 65.92 | 11.45 | 4 |
| WV-37519 | 24.38 | 2.76 | 4 |
| WV-37520 | 30.54 | 2.59 | 4 |
| WV-37521 | 12.04 | 1.42 | 4 |
| WV-37522 | 15.46 | 1.74 | 4 |
| WV-37523 | 18.44 | 1.96 | 4 |
| WV-37524 | 22.38 | 0.87 | 3 |

SD: standard deviation.
n: number of animals.

TABLE 2B

IC50 of certain oligonucleotides/compositions.

This Table shows IC50 values (e.g., determined by four parameter curve fitting of oligonucleotide concentration vs. % mRNA remaining). CI: Confidence interval. For example, a 95% confidence interval is a range of values that one can be 95% certain contains the true value.

| ID | in vitro IC50 (UM) | 95% CI (uM) |
|---|---|---|
| WV-26758 | 0.138 | 0.119 to 0.16 |
| WV-26759 | 0.223 | 0.163 to 0.288 |
| WV-29875 | 0.169 | 0.137 to 0.211 |
| WV-29876 | 0.049 | 0.031 to 0.064 |
| WV-29877 | 0.073 | 0.042 to 0.131 |
| WV-29878 | 0.084 | 0.068 to 0.106 |
| WV-29879 | 0.12 | 0.09 to 0.158 |
| WV-29880 | 0.109 | 0.085 to 0.14 |
| WV-29881 | 0.13 | 0.094 to 0.182 |
| WV-29882 | 0.1 | 0.091 to 0.11 |
| WV-29883 | 0.032 | 0.022 to 0.04 |
| WV-29884 | 0.062 | 0.031 to 0.121 |
| WV-29885 | 0.095 | 0.058 to 0.162 |
| WV-29886 | 0.069 | 0.051 to 0.096 |
| WV-29887 | 0.088 | 0.055 to 0.138 |
| WV-29888 | 0.149 | 0.113 to 0.199 |
| WV-30672 | 0.205 | 0.143 to 0.269 |
| WV-30674 | 0.108 | 0.14 to 0.222 |
| WV-32808 | 0.141 | 0.086 to 0.233 |
| WV-32809 | 0.139 | 0.103 to 0.195 |
| WV-32810 | 0.208 | 0.16 to 0.273 |
| WV-32811 | 0.134 | 0.111 to 0.163 |
| WV-32813 | 0.107 | 0.085 to 0.136 |
| WV-32814 | 0.103 | 0.079 to 0.135 |
| WV-32815 | 0.121 | 0.09 to 0.167 |
| WV-32816 | 0.083 | 0.065 to 0.105 |
| WV-32817 | 0.083 | 0.066 to 0.106 |
| WV-32818 | 0.123 | 0.083 to 0.176 |
| WV-32819 | 0.131 | 0.097 to 0.175 |
| WV-32820 | 0.143 | 0.124 to 0.166 |
| WV-32821 | 0.126 | 0.104 to 0.154 |
| WV-32822 | 0.15 | 0.114 to 0.203 |
| WV-32823 | 0.043 | 0.032 to 0.059 |
| WV-32824 | 0.052 | 0.043 to 0.064 |
| WV-32825 | 0.095 | 0.072 to 0.126 |
| WV-32826 | 0.054 | 0.043 to 0.07 |
| WV-32827 | 0.094 | 0.075 to 0.12 |
| WV-36875 | 0.107 | 0.076 to 0.153 |
| WV-36876 | 0.135 | 0.101 to 0.183 |
| WV-36877 | 0.111 | 0.086 to 0.144 |
| WV-37299 | 2.043 | 1.245 to 6.066 |
| WV-37300 | 0.818 | 0.52 to 1.53 |
| WV-37301 | 0.781 | 0.565 to 1.13 |
| WV-37302 | 0.47 | 0.354 to 0.653 |
| WV-37303 | 0.608 | 0.484 to 0.786 |
| WV-37304 | 0.717 | 0.491 to 1.15 |
| WV-37305 | 0.542 | 0.375 to 0.851 |
| WV-37499 | 0.276 | 0.206 to 0.371 |
| WV-37500 | 0.202 | 0.136 to 0.301 |
| WV-37501 | 0.215 | 0.141 to 0.33 |
| WV-37502 | 0.213 | 0.165 to 0.277 |
| WV-37503 | 0.232 | 0.192 to 0.282 |
| WV-37511 | 1.193 | 0.192 to 7.414 |
| WV-37512 | 0.143 | 0.104 to 0.197 |
| WV-37513 | 0.226 | 0.146 to 0.351 |
| WV-37514 | 0.209 | 0.162 to 0.271 |
| WV-37515 | 0.2 | 0.159 to 0.251 |
| WV-37516 | 0.153 | 0.129 to 0.184 |
| WV-37517 | 0.164 | 0.125 to 0.217 |
| WV-38924 | 0.034 | 0.021 to 0.056 |
| WV-38925 | 0.036 | 0.024 to 0.054 |
| WV-38926 | 0.046 | 0.028 to 0.078 |
| WV-38927 | 0.084 | 0.054 to 0.132 |
| WV-38928 | 0.049 | 0.036 to 0.066 |
| WV-38929 | 0.043 | 0.034 to 0.055 |
| WV-38930 | 0.086 | 0.071 to 0.106 |
| WV-38931 | 0.104 | 0.078 to 0.14 |
| WV-40376 | 0.103 | 0.087 to 0.124 |
| WV-40377 | 0.105 | 0.092 to 0.121 |
| WV-40378 | 0.123 | 0.096 to 0.158 |
| WV-40379 | 0.105 | 0.082 to 0.135 |
| WV-40380 | 0.08 | 0.067 to 0.095 |
| WV-40381 | 0.078 | 0.058 to 0.105 |

Example 3. Provided Oligonucleotides and Compositions are Active In Vivo

Among other things, the present disclosure demonstrated that provided oligonucleotides and compositions are active in vivo. In the present Example, animal procedures were performed under IACUC guidelines at Biomere (Worcester, MA, USA). The transgenic human wild type MAPT (hTau) mouse contains the full human intronic, exonic, 5' and 3' UTR MAPT sequence on a tau-null background. Mixed sex hTau mice aged 3-4 months were dosed with 2.5 μL at desired oligonucleotide concentration which included 100 μg on Day 1 via intracerebroventricular (ICV) administration. Animals were euthanized by $CO_2$ asphyxiation followed by cardiac perfusion with saline, and tissue samples were harvested and flash-frozen in dry ice. Total RNA were extracted using Direct-zol 96 RNA Kit (Zymo). cDNA production from RNA samples was performed using High-Capacity cDNA Reverse Transcription kit (Thermo Fisher) following manufacturer's instructions and qPCR analysis performed in CFX System using iQ Multiplex Powermix (Bio-Rad) (as appreciated by those skilled in the art, commercial probes may be utilized, e.g., MAPT Hs00213484_m1 FAM and Tubb3 Mm00727586_s1 VIC PL (Thermo Fisher)). mRNA knockdown levels were calculated as % mRNA remaining relative to PBS treatment (ΔΔCt). As confirmed, provided technologies can provide reduction of MAPT product levels and/or activities for about or at least about 4, 8, 12, 18 or 24 weeks.

Results are shown in Tables 3A-3B. Table 3A shows % MAPT Remaining at the indicated time points in hippocampus. For each time point, data is normalized to a PBS treated group. N=8 mice per group. Table 3B shows % MAPT Remaining at the indicated time points in cortex. For each time point, data is normalized to a PBS treated group. N=8 mice per group. Negative controls were PBS (phosphate-buffered saline).

TABLE 3A

% MAPT Remaining at the indicated time points in hippocampus.

| | PBS: 4 wk | WV-14104: 4 wk | WV-29875: 4 wk | WV-29877: 4 wk | WV-29878: 4 wk |
|---|---|---|---|---|---|
| Mean | 1.00 | 0.19 | 0.07 | 0.11 | 0.06 |
| Std. Deviation | 0.11 | 0.10 | 0.03 | 0.15 | 0.02 |

TABLE 3A-continued

% MAPT Remaining at the indicated time points in hippocampus.

| | PBS: 8 wk | WV-14104: 8 wk | WV-29875: 8 wk | WV-29877: 8 wk | WV-29878: 8 wk |
|---|---|---|---|---|---|
| Mean | 1.00 | 0.19 | 0.18 | 0.08 | 0.09 |
| Std. Deviation | 0.11 | 0.11 | 0.17 | 0.12 | 0.11 |
| | PBS: 12 wk | WV-14104: 12 wk | WV-29875: 12 wk | WV-29877: 12 wk | WV-29878: 12 wk |
| Mean | 1.00 | 0.32 | 0.17 | 0.08 | 0.11 |
| Std. Deviation | 0.14 | 0.19 | 0.13 | 0.04 | 0.06 |
| | PBS: 18 wk | WV-14104: 18 wk | WV-29875: 18 wk | WV-29877: 18 wk | WV-29878: 18 wk |
| Mean | 1.00 | 0.67 | 0.65 | 0.40 | 0.69 |
| Std. Deviation | 0.20 | 0.21 | 0.23 | 0.29 | 0.29 |
| | PBS: 24 wk | WV-14104: 24 wk | WV-29875: 24 wk | WV-29877: 24 wk | WV-29878: 24 wk |
| Mean | 1.03 | 0.61 | 0.66 | 0.73 | 0.56 |
| Std. Deviation | 0.20 | 0.13 | 0.15 | 0.39 | 0.18 |

TABLE 3B

% MAPT Remaining at the indicated time points in cortex.

| | PBS: 4 wk | WV-14104: 4 wk | WV-29875: 4 wk | WV-29877: 4 wk | WV-29878: 4 wk |
|---|---|---|---|---|---|
| Mean | 1.00 | 0.35 | 0.21 | 0.27 | 0.14 |
| Std. Deviation | 0.15 | 0.19 | 0.10 | 0.23 | 0.04 |
| | PBS: 8 wk | WV-14104: 8 wk | WV-29875: 8 wk | WV-29877: 8 wk | WV-29878: 8 wk |
| Mean | 1.00 | 0.29 | 0.31 | 0.12 | 0.26 |
| Std. Deviation | 0.14 | 0.13 | 0.20 | 0.04 | 0.22 |
| | PBS: 12 wk | WV-14104: 12 wk | WV-29875: 12 wk | WV-29877: 12 wk | WV-29878: 12 wk |
| Mean | 1.00 | 0.44 | 0.36 | 0.16 | 0.23 |
| Std. Deviation | 0.26 | 0.15 | 0.17 | 0.08 | 0.10 |
| | PBS: 18 wk | WV-14104: 18 wk | WV-29875: 18 wk | WV-29877: 18 wk | WV-29878: 18 wk |
| Mean | 1.00 | 0.88 | 0.91 | 0.56 | 0.84 |
| Std. Deviation | 0.11 | 0.30 | 0.18 | 0.31 | 0.28 |
| | PBS: 24 wk | WV-14104: 24 wk | WV-29875: 24 wk | WV-29877: 24 wk | WV-29878: 24 wk |
| Mean | 1.00 | 0.75 | 0.74 | 0.66 | 0.64 |
| Std. Deviation | 0.15 | 0.19 | 0.10 | 0.16 | 0.23 |

Activities of provided technologies were also confirmed in non-human primate animals. In some embodiments, Cynomolgus monkeys aged 2 to 4 years were treated intrathecally with a single dose of 12 mg WV-29878 (n=6). Animals were sacrificed 11 or 29 days after dosing. In the present Example, animal procedures were performed under IACUC, USA National Research Council, and the Canadian Council on Animal Care guidelines at Charles River Laboratories (Senneville, QC Canada). Multiple regions of the brain and spinal cord tissue were dissected and flash frozen in liquid nitrogen. Total RNA was extracted using the RiboPure Kit (Life Technologies). cDNA production from RNA samples was performed using the Superscript IV VILO Master Mix Kit (Invitrogen) following manufacturer's instructions and qPCR analysis performed in the QuantStudio 7 Flex Real-Time PCR System using Taqman Gene Expression Master Mic (Thermo Fisher) (as appreciated by those skilled in the art, commercial probes may be utilized, e.g., MAPT Mf00902189_m1 FAM and ARL1 Mf02795431_ml VIC PL (Thermo Fisher)). mRNA knockdown levels were calculated as % mRNA remaining relative to untreated animals (ΔΔCt).

Certain results are shown in Table 4. Table 4 shows % MAPT Remaining at day 29 post-dose in various brain and spinal cord regions. For each time point, data is normalized to the untreated group. As confirmed, provided technologies can provide activities, e.g., for about or at least about 29 days or 1 month post dose.

TABLE 4

% MAPT remaining 29 days post-dose in cynomolgus monkey.

| | Control | Hippocampus | Brain Cortex | Cervical Spinal Cord | Thoracic Spinal Cord | Lumbar Spinal Cord |
|---|---|---|---|---|---|---|
| Mean | 100 | 11.5 | 7.848 | 31.08 | 21.36 | 5.967 |
| Std. Deviation | 12.22 | 0.9978 | 3.504 | 16.92 | 11.8 | 2.961 |

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations may depend upon the specific application or applications for which the teachings of the present disclosure is/are used. Those skilled in the art will recognize, or be able to ascertain using no more than routine experimentation, many equivalents to the embodiments of the present disclosure. It is, therefore, to be understood that the foregoing embodiments are presented by way of example only and that, within the scope ofthe appended claims and equivalents thereto, claimed technologies may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. An oligonucleotide, wherein the oligonucleotide is:

Geo*STeon001RGeoTeon001RTeo*SC*SC*SA*SC*RT*SA*ST*SC*RC*ST*SmC*SmC*SmU*SmU*SmC (SEQ ID NO: 29) or a pharmaceutically acceptable salt thereof, wherein:

m represents a 2'-OMe modification to a nucleoside;

eo represents a 2'-O-methoxyethyl modification to a nucleoside;

*R represents a phosphorothioate internucleotidic linkage in the Rp configuration;

*S represents a phosphorothioate internucleotidic linkage in the Sp configuration; and n001R represents a n001 linkage in the Rp configuration, wherein a n001 linkage has the structure of

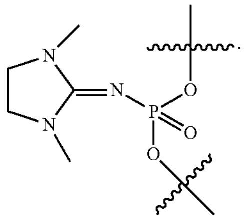 [SMILES: *OP(=O)(N=C1N(C)CCN1C)O*]

2. The oligonucleotide of claim 1, wherein the oligonucleotide is a pharmaceutically acceptable salt.

3. The oligonucleotide of claim 2, wherein the oligonucleotide is a sodium salt.

4. The oligonucleotide of claim 3, wherein the number of sodium ions in the sodium salt equals the total number of phosphorothioate and phosphate linkages in the oligonucleotide.

5. A chirally controlled oligonucleotide composition of an oligonucleotide of claim 1, wherein each chiral internucleotidic linkage of the oligonucleotide independently has a diastereopurity of at least 90%.

6. The composition of claim 5, wherein each chiral internucleotidic linkage of the oligonucleotide independently has a diastereopurity of at least 95%.

7. The composition of claim 6, wherein each chiral internucleotidic linkage of the oligonucleotide independently has a diastereopurity of at least 98%.

8. A pharmaceutical composition, comprising an oligonucleotide of claim 1 and a pharmaceutically acceptable carrier.

9. The composition of claim 8, wherein the pharmaceutically acceptable carrier is a pharmaceutically acceptable diluent or excipient.

10. The composition of claim 8, wherein the pharmaceutically acceptable carrier is a pH buffered solution.

11. An oligonucleotide, wherein the oligonucleotide is:

Geo*STeon001RGeoTeon001RTeo*SC*SC*SA*SC*RT*SA*ST*SC*RC*ST*SmCn00 1RmC*SmU*SmU*SmC (SEQ ID NO: 30) or a pharmaceutically acceptable salt thereof, wherein:

m represents a 2'-OMe modification to a nucleoside;

eo represents a 2'-O-methoxyethyl modification to a nucleoside;

*R represents a phosphorothioate internucleotidic linkage in the Rp configuration;

*S represents a phosphorothioate internucleotidic linkage in the Sp configuration; and n001R represents a n001 linkage in the Rp configuration, wherein a n001 linkage has the structure of

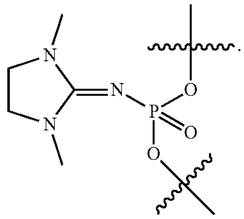 [SMILES: *OP(=O)(N=C1N(C)CCN1C)O*]

.

12. The oligonucleotide of claim 11, wherein the oligonucleotide is a pharmaceutically acceptable salt.

13. The oligonucleotide of claim 12, wherein the oligonucleotide is a sodium salt.

14. The oligonucleotide of claim 13, wherein the number of sodium ions in the sodium salt equals the total number of phosphorothioate and phosphate linkages in the oligonucleotide.

15. A chirally controlled oligonucleotide composition of an oligonucleotide of claim 11, wherein each chiral internucleotidic linkage of the oligonucleotide independently has a diastereopurity of at least 90%.

16. The composition of claim 15, wherein each chiral internucleotidic linkage of the oligonucleotide independently has a diastereopurity of at least 95%.

17. The composition of claim 16, wherein each chiral internucleotidic linkage of the oligonucleotide independently has a diastereopurity of at least 98%.

18. A pharmaceutical composition, comprising an oligonucleotide of claim 11 and a pharmaceutically acceptable carrier.

19. The composition of claim 18, wherein the pharmaceutically acceptable carrier is a pharmaceutically acceptable diluent or excipient.

20. The composition of claim 18, wherein the pharmaceutically acceptable carrier is a pH buffered solution.

* * * * *